US012653894B2

(12) United States Patent
Gray et al.

(10) Patent No.: US 12,653,894 B2
(45) Date of Patent: Jun. 16, 2026

(54) DEGRADATION OF FAK OR FAK AND ALK BY CONJUGATION OF FAK AND ALK INHIBITORS WITH E3 LIGASE LIGANDS AND METHODS OF USE

(71) Applicant: DANA-FARBER CANCER INSTITUTE, INC., Boston, MA (US)

(72) Inventors: Nathanael S. Gray, Boston, MA (US); Baishan Jiang, Brookline, MA (US); Behnam Nabet, Boston, MA (US); Tinghu Zhang, Brookline, MA (US); Mingfeng Hao, Hefei (CN)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 1045 days.

(21) Appl. No.: 17/279,752

(22) PCT Filed: Sep. 26, 2019

(86) PCT No.: PCT/US2019/053139

§ 371 (c)(1),
(2) Date: Mar. 25, 2021

(87) PCT Pub. No.: WO2020/069117

PCT Pub. Date: Apr. 2, 2020

(65) Prior Publication Data

US 2022/0040317 A1 Feb. 10, 2022

Related U.S. Application Data

(60) Provisional application No. 62/737,542, filed on Sep. 27, 2018.

(51) Int. Cl.

| | |
|---|---|
| ***C07D 401/12*** | (2006.01) |
| ***A61K 47/54*** | (2017.01) |
| ***A61K 47/55*** | (2017.01) |
| ***C07D 401/14*** | (2006.01) |
| ***C07D 417/14*** | (2006.01) |

(52) U.S. Cl.

CPC ............ *A61K 47/55* (2017.08); *A61K 47/545* (2017.08); *C07D 401/12* (2013.01); *C07D 401/14* (2013.01); *C07D 417/14* (2013.01)

(58) Field of Classification Search

CPC ... C07D 401/12; C07D 401/14; C07D 417/14
See application file for complete search history.

(56) References Cited

U.S. PATENT DOCUMENTS

| | | | |
|---|---|---|---|
| 2009/0054395 | A1 | 2/2009 | Luzzio et al. |
| 2010/0113475 | A1 | 5/2010 | Adams et al. |
| 2012/0083488 | A1 | 4/2012 | Kinoshita et al. |
| 2017/0065719 | A1 | 3/2017 | Qian et al. |

FOREIGN PATENT DOCUMENTS

| | | | |
|---|---|---|---|
| WO | 2004/080980 | A1 | 9/2004 |
| WO | 2008/115369 | A2 | 9/2008 |
| WO | 2013075167 | A1 | 5/2013 |
| WO | 2017079267 | A1 | 5/2017 |
| WO | 2017/211924 | A1 | 12/2017 |
| WO | 2018/033556 | A1 | 2/2018 |
| WO | 2018064589 | A1 | 4/2018 |
| WO | 2018/148440 | A1 | 8/2018 |
| WO | 2019/018666 | A1 | 1/2019 |
| WO | 2019114770 | A1 | 6/2019 |

OTHER PUBLICATIONS

Huang, H. T. et al., "A Chemoproteomic Approach to Query the Degradable Kinome Using a Multi-kinase Degrader," Cell Chem. Biol., Feb. 18, 2018; 25(1):88-99.e6. doi: 10.1016/j.chembiol.2017.10.005. Epub Nov. 9, 2017. PMID: 29129717; PMCID: PMC6427047.

Powell et al., "Supporting Information—Chemically Induced Degradation of Anaplastic Lymphoma Kinase (ALK)," J. Med. Chem, May 10, 2018; 61(9):4249-4255. doi: 10.1021/acs.jmedchem.7b01655. Epub Apr. 24, 2018. PMID: 29660984; PMCID: PMC6294449.

Russell et al., "An integrated flow and microwave approach to a broad spectrum protein kinase inhibitor," RSC Advances, vol. 5, No. 113, pp. 93433-93437, XP055950285, DOI: 10.1039/C5RA09426G (2015).

Yoon et al., "Understanding the roles of FAK in cancer: inhibitors, genetic models, and new insights," J. Histochem. Cytochem., vol. 63(2), pp. 114-128, DOI: 10.1369/0022155414561498 (2015).

Heuckmann et al., "Differential Protein Stability and ALK Inhibitor Sensitivity of EML4-ALK Fusion Variants", Clinical Cancer Research, 2012, vol. 18, No. 17, pp. 4682-4690.

Lovly et al., "Rationale for Co-Targeting IGF-1R and ALK in ALK Fusion-Positive Lung Cancer", Clinical Cancer Research, 2014, vol. 20, No. 9, pp. 1027-1034.

Ott et al., "Discovery of Clinical Candidate CEP-37440, a Selective Inhibitor of Focal Adhesion Kinase (FAK) and Anaplastic Lymphoma Kinase (ALK)", Journal of Medicinal Chemistry, 2016, vol. 59, pp. 7478-7496.

Powell et al., "Chemically Induced Degradation of Anaplastic Lymphoma Kinase (ALK)", Journal of Medicinal Chemistry, 2018, vol. 61, pp. 4249-4255.

Richards et al., "Crystal Structure of EML 1 reveals the basis for Hsp90 Dependence of Oncogenic EML4-ALK by Disruption of an ATypical β-Propeller Domain", PNAS, 2014, vol. 111, No. 14, pp. 5195-5200.

(Continued)

*Primary Examiner* — Brian E Mcdowell

(74) *Attorney, Agent, or Firm* — ArentFox Schiff LLP; Daniel W. Clarke; Shawn P. Foley

(57) ABSTRACT

Disclosed are bifunctional compounds (degraders) that target FAK or FAK and ALK for degradation. Also disclosed are pharmaceutical compositions containing the degraders and methods of using the compounds to treat disease.

14 Claims, 9 Drawing Sheets

(56) References Cited

OTHER PUBLICATIONS

Taipale et al., "Quantitative Analysis of Hsp90-Client Interactions Reveals Principles of Substrate Recognition", Cell, 2012, vol. 150, No. 5, pp. 987-1001.
Yan et al., "Discovery of ax PROTAC Targeting ALK with in Vivo Activity", European Journal of Medicinal Chemistry, 2020, pp. 1-29.
Zhang et al., "Proteolysis TargetingChimeras (PROTACs) of Anaplastic Lymphoma Kinase (ALK)", European Journal of Medicinal Chemistry, 2018, vol. 151, pp. 304-314.

FIG. 4
DMSO
Compound 13 (nM)
1 10 100 1000
Compound 1 (nM)
1 10 100 1000
Compound 9 (nM)
1 10 100 1000
FAK
α-Tubulin

Compound 13

VS-4718

DEGRADATION OF FAK OR FAK AND ALK BY CONJUGATION OF FAK AND ALK INHIBITORS WITH E3 LIGASE LIGANDS AND METHODS OF USE

RELATED APPLICATIONS

This application is a national stage application, filed under 35 U.S.C. § 371, of International Application No. PCT/US2019/053139, filed Sep. 26, 2019, which claims the benefit of priority under 35 U.S.C. § 119 (e) to U.S. Provisional Application No. 62/737,542, filed on Sep. 27, 2018, each of which is incorporated herein by reference in its entirety.

BACKGROUND OF THE INVENTION

Focal adhesion kinase (FAK) and proline-rich tyrosine kinase 2 (PYK2) are non-receptor tyrosine kinases that constitute the FAK subfamily and play a vital role in many oncogenic pathways (Parsons et al., Clin. Can. Res. 14(3): 627-32 (2008)). FAK protein levels are commonly upregulated in many cancers including pancreatic adenocarcinoma, ovarian cancer, and breast cancer, (Sulzmaier et al., Nat. Rev. Cancer 14(9):598-610 (2014)) and recent pan-cancer cell line screening efforts identified FAK as a significant dependency (Tsherniak et al., Cell 170(3):564-576 e16 (2017)), highlighting FAK as a tractable cancer drug target. FAK regulates diverse signaling pathways including PI3K-AKT and integrin signaling, has kinase-independent scaffolding and nuclear functions, and mediates cancer cell transformation, proliferation, survival and migration (Sulzmaier et al., Nat. Rev. Cancer 14(9):598-610 (2014)). FAK inhibitors such as VS-4718 are currently under clinical evaluation.

SUMMARY OF THE INVENTION

A first aspect of the present invention is directed to a bifunctional compound (also referred to herein as a "degrader" or "PROTAC"), which has a structure represented by formula (I):

(I)

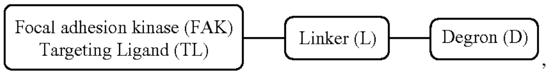

, wherein the targeting ligand represents a moiety that binds FAK, the degron is a thalidomide analog that binds cereblon (CRBN) or a moiety that binds von Hippel Landau tumor suppressor (VHL), and the linker represents a moiety that covalently connects the degron and the targeting ligand, or a pharmaceutically acceptable salt or stereoisomer thereof.

Another aspect of the present invention is directed to a pharmaceutical composition including a therapeutically effective amount of a bifunctional compound of the present invention, or a pharmaceutically acceptable salt or stereoisomer thereof, and a pharmaceutically acceptable carrier. Bifunctional compounds of the present invention may be water-soluble; hence, they may be advantageously and conveniently formulated for parenteral or oral administration, whereupon they permeate membranes of cells harboring proteins to which the bifunctional compounds bind (via the targeting ligand) resulting in degradation of FAK. In some embodiments, the bifunctional compounds of the present invention degrade FAK and anaplastic lymphoma kinase (ALK).

Another aspect of the present invention is directed to a compound which has a structure represented by formula (II):

(II)

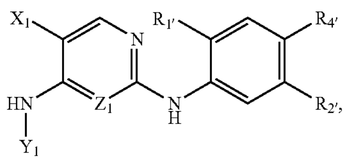

wherein $X_1$ is halo, $CF_3$, methyl, ethyl or cyclopropyl;

$Y_1$ is

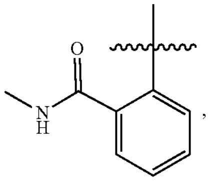
,

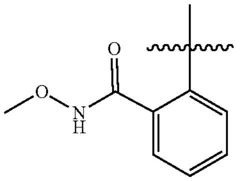
,

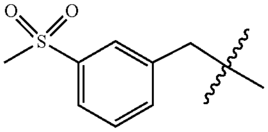
, or

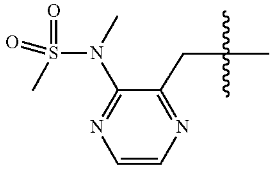

$Z_1$ is N or CH;

$R_{1'}$ is H or $OR_{3'}$, wherein $R_{3'}$ is H, optionally substituted $C_1$-$C_4$ alkyl or cyclopropyl; $R_{2'}$ is optionally substituted $C_1$-$C_4$ alkyl; and $R_{4'}$ is

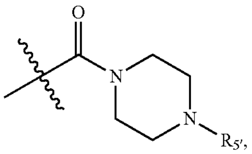

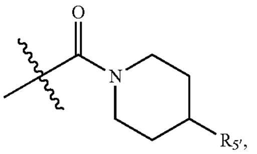

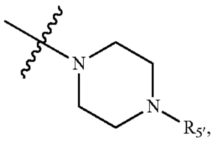

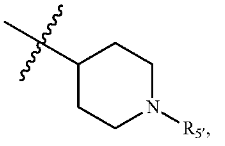

-continued

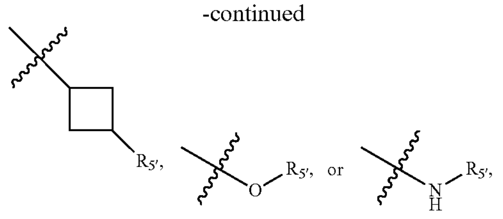

wherein $R_{5'}$ is H, optionally substituted $C_1$-$C_4$ alkyl, optionally substituted $C_3$-$C_6$ carbocyclic, or optionally substituted $C_3$-$C_6$ heterocyclic, or a pharmaceutically acceptable salt or stereoisomer thereof.

Another aspect of the present invention is directed to a pharmaceutical composition that includes a therapeutically effective amount of a compound of formula (II) or a pharmaceutically acceptable salt or stereoisomer thereof, and a pharmaceutically acceptable carrier.

Yet another aspect of the present invention is directed to methods of making the compounds of the present invention.

A further aspect of the present invention is directed to methods of treating diseases or disorders involving aberrant FAK or FAK and ALK activity, that entails administration of a therapeutically effective amount of a bifunctional compound of formula (I) and/or the compound of formula (II) to a subject in need thereof.

In some embodiments, the disease or disorder is cancer, a non-cancerous proliferative disease or a neurodegenerative disease. In some embodiments, the cancer is a solid tumor.

Without intending to be bound by any particular theory of operation, the bifunctional compounds of the present invention are believed to degrade aberrant FAK and ALK proteins that are involved in the genesis and/or progression of disease via the cell's ubiquitin/proteasome system, whose function is to routinely identify and remove damaged proteins. The bifunctional compounds of the present invention tag FAK or FAK and ALK (which is bound by the targeting ligand functionality) for ubiquitination and degradation via the Cul3-based E3-ubiquitin ligase complex. After destruction of a FAK molecule or FAK and ALK molecules, the degrader is released and continues to be active. Thus, by engaging and exploiting the body's own natural protein disposal system, the bifunctional compounds of the present invention may represent a potential improvement over traditional small molecule inhibitors of aberrant proteins in the treatment of cancers and other disease that have proven difficult to treat.

As demonstrated in the working examples, compounds of formula (II) exhibited increased inhibition of FAK and ALK compared to known potent FAK inhibitor, VS-4718 (also known as PND-1186), and may overcome limitations associated with the use of the known FAK inhibitor. Importantly, compounds of formula (II) displayed significantly improved kinome selectivity compared to VS-4718, providing a more optimal scaffold suited for degrader development.

DETAILED DESCRIPTION

Figure 1A:
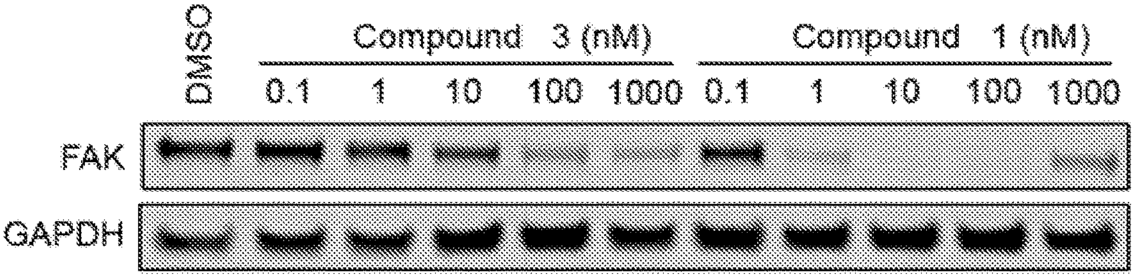
FIG. 1A-FIG. 1B are immunoblots that show the degradation of focal adhesion kinase (FAK) in PA-TU-8988T cells after being treated with 0.1 nM to 1000 nM of inventive compounds 1 and 3-6 for 4 hours.

Unless defined otherwise, all technical and scientific terms used herein have the same meaning as is commonly understood by one of skill in the art to which the subject matter herein belongs. As used in the specification and the appended claims, unless specified to the contrary, the following terms have the meaning indicated in order to facilitate the understanding of the present invention.

As used in the description and the appended claims, the singular forms "a", "an", and "the" include plural referents unless the context clearly dictates otherwise. Thus, for example, reference to "a composition" includes mixtures of two or more such compositions, reference to "an inhibitor" includes mixtures of two or more such inhibitors, and the like.

Unless stated otherwise, the term "about" means within 10% (e.g., within 5%, 2% or 1%) of the particular value modified by the term "about."

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

With respect to compounds of the present invention, and to the extent the following terms are used herein to further describe them, the following definitions apply.

As used herein, the term "alkyl" refers to a saturated linear or branched-chain monovalent hydrocarbon radical. In one embodiment, the alkyl radical is a $C_1$-$C_{18}$ group. In other embodiments, the alkyl radical is a $C_0$-$C_6$, $C_0$-$C_5$, $C_0$-$C_3$, $C_1$-$C_{12}$, $C_1$-$C_5$, $C_1$-$C_6$, $C_1$-$C_5$, $C_1$-$C_4$ or $C_1$-$C_3$ group (wherein $C_0$ alkyl refers to a bond). Examples of alkyl groups include methyl, ethyl, 1-propyl, 2-propyl, i-propyl, 1-butyl, 2-methyl-1-propyl, 2-butyl, 2-methyl-2-propyl, 1-pentyl, n-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, heptyl, octyl, nonyl, decyl, undecyl and dodecyl. In some embodiments, an alkyl group is a $C_1$-$C_3$ alkyl group. In some embodiments, an alkyl group is a $C_1$-$C_2$ alkyl group.

As used herein, the term "alkylene" refers to a straight or branched divalent hydrocarbon chain linking the rest of the molecule to a radical group, consisting solely of carbon and hydrogen, containing no unsaturation and having from one to 12 carbon atoms, for example, methylene, ethylene, propylene, n-butylene, and the like. The alkylene chain may be attached to the rest of the molecule through a single bond and to the radical group through a single bond. In some embodiments, the alkylene group contains one to 8 carbon atoms ($C_1$-$C_8$ alkylene). In other embodiments, an alkylene group contains one to 5 carbon atoms ($C_1$-$C_5$ alkylene). In other embodiments, an alkylene group contains one to 4 carbon atoms ($C_1$-$C_4$ alkylene). In other embodiments, an alkylene contains one to three carbon atoms ($C_1$-$C_3$ alkylene). In other embodiments, an alkylene group contains one to two carbon atoms ($C_1$-$C_2$ alkylene). In other embodiments, an alkylene group contains one carbon atom ($C_1$ alkylene).

The terms "alkoxyl" or "alkoxy" as used herein refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl.

As used herein, the term "halogen" (or "halo" or "halide") refers to fluorine, chlorine, bromine, or iodine.

As used herein, the term "cyclic group" broadly refers to any group that used alone or as part of a larger moiety, contains a saturated, partially saturated or aromatic ring system e.g., carbocyclic (cycloalkyl, cycloalkenyl), heterocyclic (heterocycloalkyl, heterocycloalkenyl), aryl and heteroaryl groups. Cyclic groups may have one or more (e.g., fused) ring systems. Thus, for example, a cyclic group can contain one or more carbocyclic, heterocyclic, aryl or heteroaryl groups.

As used herein, the term "carbocyclic" (also "carbocyclyl") refers to a group that used alone or as part of a larger moiety, contains a saturated, partially unsaturated, or aromatic ring system having 3 to 20 carbon atoms, that is alone or part of a larger moiety (e.g., an alkcarbocyclic group). The term carbocyclyl includes mono-, bi-, tri-, fused, bridged, and spiro-ring systems, and combinations thereof. In one embodiment, carbocyclyl includes 3 to 15 carbon atoms ($C_3$-$C_{15}$). In one embodiment, carbocyclyl includes 3 to 12 carbon atoms ($C_3$-$C_{12}$). In another embodiment, carbocyclyl includes $C_3$-$C_5$, $C_3$-$C_{10}$ or $C_5$-$C_{10}$. In another embodiment, carbocyclyl, as a monocycle, includes $C_3$-$C_8$, $C_3$-$C_6$ or $C_5$-$C_6$. In some embodiments, carbocyclyl, as a bicycle, includes $C_7$-$C_{12}$. In another embodiment, carbocyclyl, as a spiro system, includes $C_5$-$C_{12}$. Representative examples of monocyclic carbocyclyls include cyclopropyl, cyclobutyl, cyclopentyl, 1-cyclopent-1-enyl, 1-cyclopent-2-enyl, 1-cyclopent-3-enyl, cyclohexyl, perdeuteriocyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, phenyl, and cyclododecyl; bicyclic carbocyclyls having 7 to 12 ring atoms include [4,3], [4,4], [4,5], [5,5], [5,6] or [6,6] ring systems, such as for example bicyclo[2.2.1]heptane, bicyclo[2.2.2]octane, naphthalene, and bicyclo[3.2.2]nonane. Representative examples of spiro carbocyclyls include spiro[2.2]pentane, spiro[2.3]hexane, spiro[2.4]heptane, spiro[2.5]octane and spiro[4.5]decane. The term carbocyclyl includes aryl ring systems as defined herein. The term carbocycyl also includes cycloalkyl rings (e.g., saturated or partially unsaturated mono-, bi-, or spiro-carbocycles). The term carbocyclic group also includes a carbocyclic ring fused to one or more (e.g., 1, 2 or 3) different cyclic groups (e.g., aryl or heterocyclic rings), where the radical or point of attachment is on the carbocyclic ring.

Thus, the term carbocyclic also embraces carbocyclylalkyl groups which as used herein refer to a group of the formula —$R^c$-carbocyclyl where $R^c$ is an alkylene chain. The term carbocyclic also embraces carbocyclylalkoxy groups which as used herein refer to a group bonded through an oxygen atom of the formula —O—$R^c$-carbocyclyl where $R^c$ is an alkylene chain.

As used herein, the term "heterocyclyl" refers to a "carbocyclyl" that used alone or as part of a larger moiety, contains a saturated, partially unsaturated or aromatic ring system, wherein one or more (e.g., 1, 2, 3, or 4) carbon atoms have been replaced with a heteroatom (e.g., O, N, N(O), S, S(O), or $S(O)_2$). The term heterocyclyl includes mono-, bi-, tri-, fused, bridged, and spiro-ring systems, and combinations thereof. In some embodiments, a heterocyclyl refers to a 3 to 15 membered heterocyclyl ring system. In some embodiments, a heterocyclyl refers to a 3 to 12 membered heterocyclyl ring system. In some embodiments, a heterocyclyl refers to a saturated ring system, such as a 3 to 12 membered saturated heterocyclyl ring system. In some embodiments, a heterocyclyl refers to a heteroaryl ring system, such as a 5 to 14 membered heteroaryl ring system. The term heterocyclyl also includes $C_3$-$C_8$ heterocycloalkyl, which is a saturated or partially unsaturated mono-, bi-, or spiro-ring system containing 3-8 carbons and one or more (1, 2, 3 or 4) heteroatoms.

In some embodiments, a heterocyclyl group includes 3-12 ring atoms and includes monocycles, bicycles, tricycles and Spiro ring systems, wherein the ring atoms are carbon, and one to 5 ring atoms is a heteroatom such as nitrogen, sulfur or oxygen. In some embodiments, heterocyclyl includes 3- to 7-membered monocycles having one or more heteroatoms selected from nitrogen, sulfur or oxygen. In some embodiments, heterocyclyl includes 4- to 6-membered monocycles having one or more heteroatoms selected from nitrogen, sulfur or oxygen. In some embodiments, heterocyclyl includes 3-membered monocycles. In some embodiments, heterocyclyl includes 4-membered monocycles. In some embodiments, heterocyclyl includes 5-6 membered monocycles. In some embodiments, the heterocyclyl group includes 0 to 3 double bonds. In any of the foregoing embodiments, heterocyclyl includes 1, 2, 3 or 4 heteroatoms. Any nitrogen or sulfur heteroatom may optionally be oxidized (e.g., NO, SO, $SO_2$), and any nitrogen heteroatom may optionally be quaternized (e.g., $[NR_4]^+Cl^-$, $[NR_4]^+OH^-$).

Representative examples of heterocyclyls include oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydropyranyl, dihydrothienyl, tetrahydrothienyl, imidazolidinyl, piperidinyl, piperazinyl, morpholinyl, thiomorpholinyl, 1,1-dioxo-thiomorpholinyl, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, 1,1-dioxoisothiazolidinonyl, oxazolidinonyl, imidazolidinonyl, 4,5,6,7-tetrahydro[2H]indazolyl, tetrahydrobenzoimidazolyl, 4,5,6,7-tetrahydrobenzo[d]imidazolyl, 1,6-dihydroimidazol[4,5-d]pyrrolo[2,3-b]pyridinyl, thiazinyl, thiophenyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, 1-pyrrolinyl, 2-pyrrolinyl, 3-pyrrolinyl, indolinyl, thiapyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinylimidazolinyl, 3-azabicyclo[3.1.0]hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl, azabicyclo[2.2.2]hexanyl, 2-azabicyclo[3.2.1]octanyl, 8-azabicyclo[3.2.1]octanyl, 2-azabicyclo[2.2.2]octanyl, 8-azabicyclo[2.2.2]octanyl, 7-oxabicyclo[2.2.1]heptane, azaspiro[3.5]nonanyl, azaspiro[2.5]octanyl, azaspiro[4.5]decanyl, 1-azaspiro[4.5]decan-2-only, azaspiro[5.5]undecanyl, tetrahydroindolyl, octahydroindolyl, tetrahydroisoindolyl, tetrahydroindazolyl, 1,1-dioxohexahydrothiopyranyl. Examples of 5-membered heterocyclyls containing a sulfur or oxygen atom and one to three nitrogen atoms are thiazolyl, including thiazol-2-yl and thiazol-2-yl N-oxide, thiadiazolyl, including 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Example 5-membered ring heterocyclyls containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Representative examples of benzo-fused 5-membered heterocyclyls are benzoxazol-2-yl, benzthiazol-2-yl and benzimidazol-2-yl. Example 6-membered heterocyclyls contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are yet other examples of heterocyclyl groups. In some embodiments, a heterocyclic group includes a heterocyclic ring fused to one or more (e.g., 1, 2 or 3) different cyclic groups (e.g., carbocyclic rings or heterocyclic rings), where the radical or point of attachment is on the heterocyclic ring, and in some embodiments wherein the point of attachment is a heteroatom contained in the heterocyclic ring.

Thus, the term heterocyclic embraces N-heterocyclyl groups which as used herein refer to a heterocyclyl group containing at least one nitrogen and where the point of attachment of the heterocyclyl group to the rest of the molecule is through a nitrogen atom in the heterocyclyl group. Representative examples of N-heterocyclyl groups include 1-morpholinyl, 1-piperidinyl, 1-piperazinyl, 1-pyrrolidinyl, pyrazolidinyl, imidazolinyl and imidazolidinyl. The term heterocyclic also embraces C-heterocyclyl groups which as used herein refer to a heterocyclyl group containing at least one heteroatom and where the point of attachment of the heterocyclyl group to the rest of the molecule is through a carbon atom in the heterocyclyl group. Representative examples of C-heterocyclyl radicals include 2-morpholinyl, 2- or 3- or 4-piperidinyl, 2-piperazinyl, and 2- or 3-pyrrolidinyl. The term heterocyclic also embraces heterocyclylalkyl groups which as disclosed above refer to a group of the formula —R-heterocyclyl where $R^c$ is an alkylene chain. The term heterocyclic also embraces heterocyclylalkoxy groups which as used herein refer to a radical bonded through an oxygen atom of the formula —O—$R^c$-heterocyclyl where $R^c$ is an alkylene chain.

As used herein, the term "aryl" used alone or as part of a larger moiety (e.g., "aralkyl", wherein the terminal carbon atom on the alkyl group is the point of attachment, e.g., a benzyl group), "aralkoxy" wherein the oxygen atom is the point of attachment, or "aroxyalkyl" wherein the point of attachment is on the aryl group) refers to a group that includes monocyclic, bicyclic or tricyclic, carbon ring system, that includes fused rings, wherein at least one ring in the system is aromatic. In some embodiments, the aralkoxy group is a benzoxy group. The term "aryl" may be used interchangeably with the term "aryl ring". In one embodiment, aryl includes groups having 6-18 carbon atoms. In another embodiment, aryl includes groups having 6-10 carbon atoms. Examples of aryl groups include phenyl, naphthyl, anthracyl, biphenyl, phenanthrenyl, naphthacenyl, 1,2,3,4-tetrahydronaphthalenyl, 1H-indenyl, 2,3-dihydro-1H-indenyl, naphthyridinyl, and the like, which may be substituted or independently substituted by one or more substituents described herein. A particular aryl is phenyl. In some embodiments, an aryl group includes an aryl ring fused to one or more (e.g., 1, 2 or 3) different cyclic groups (e.g., carbocyclic rings or heterocyclic rings), where the radical or point of attachment is on the aryl ring.

Thus, the term aryl embraces aralkyl groups (e.g., benzyl) which as disclosed above refer to a group of the formula —$R^c$-aryl where $R^c$ is an alkylene chain such as methylene or ethylene.

In some embodiments, the aralkyl group is an optionally substituted benzyl group. The term aryl also embraces aralkoxy groups which as used herein refer to a group bonded through an oxygen atom of the formula —O—$R^c$-aryl where $R^c$ is an alkylene chain such as methylene or ethylene.

As used herein, the term "heteroaryl" used alone or as part of a larger moiety (e.g., "heteroarylalkyl" (also "heteroaralkyl"), or "heteroarylalkoxy" (also "heteroaralkoxy"), refers to a monocyclic, bicyclic or tricyclic ring system having 5 to 14 ring atoms, wherein at least one ring is aromatic and contains at least one heteroatom. In one embodiment, heteroaryl includes 4-6 membered monocyclic aromatic groups where one or more ring atoms is nitrogen, sulfur or oxygen that is independently optionally substituted. In another embodiment, heteroaryl includes 5-6 membered monocyclic aromatic groups where one or more ring atoms is nitrogen, sulfur or oxygen. Representative examples of heteroaryl groups include thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, imidazopyridyl, pyrazinyl, pyridazinyl, triazinyl, tetrazinyl, tetrazolo[1,5-b]pyridazinyl, purinyl, deazapurinyl, benzoxazolyl, benzofuryl, benzothiazolyl, benzothiadiazolyl, benzotriazolyl, benzoimidazolyl, indolyl, 1,3-thiazol-2-yl, 1,3,4-triazol-5-yl, 1,3-oxazol-2-yl, 1,3,4-oxadiazol-5-yl, 1,2,4-oxadiazol-5-yl, 1,3,4-thiadiazol-5-yl, 1H-tetrazol-5-yl, 1,2,3-triazol-5-yl, and pyrid-2-yl N-oxide. The term "heteroaryl" also includes groups in which a heteroaryl is fused to one or more cyclic (e.g., carbocyclyl, or heterocyclyl) rings, where the radical or point of attachment is on the heteroaryl ring. Nonlimiting examples include indolyl, indolizinyl, isoindolyl, benzothienyl, benzothiophenyl, methylenedioxyphenyl, benzofuranyl, dibenzofuranyl, indazolyl, benzimidazolyl, benzodioxazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl and pyrido[2,3-b]-1,4-oxazin-3(4H)-one. A heteroaryl group may be mono-, bi- or tri-cyclic. In some embodiments, a heteroaryl group includes a heteroaryl ring fused to one or more (e.g., 1, 2 or 3) different cyclic groups (e.g., carbocyclic rings or heterocyclic rings), where the radical or point of attachment is on the heteroaryl ring, and in some embodiments wherein the point of attachment is a heteroatom contained in the heterocyclic ring.

Thus, the term heteroaryl embraces N-heteroaryl groups which as used herein refer to a heteroaryl group as defined above containing at least one nitrogen and where the point of attachment of the heteroaryl group to the rest of the molecule is through a nitrogen atom in the heteroaryl group. The term heteroaryl also embraces C-heteroaryl groups which as used herein refer to a heteroaryl group as defined above and where the point of attachment of the heteroaryl group to the rest of the molecule is through a carbon atom in the heteroaryl group. The term heteroaryl also embraces heteroarylalkyl groups which as disclosed above refer to a group of the formula —$R^c$-heteroaryl, where $R^c$ is an alkylene chain as defined above. The term heteroaryl also embraces heteroaralkoxy (or heteroarylalkoxy) groups which as used herein refer to a group bonded through an oxygen atom of the formula —O—$R^c$-heteroaryl, where $R^c$ is an alkylene group as defined above.

Any of the groups described herein may be substituted or unsubstituted. As used herein, the term "substituted" broadly refers to all permissible substituents with the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc. Representative substituents include halogens, hydroxyl groups, and any other organic groupings containing any number of carbon atoms, e.g., 1-14 carbon atoms, and which may include one or more (e.g., 1 2 3, or 4) heteroatoms such as oxygen, sulfur, and nitrogen grouped in a linear, branched, or cyclic structural format.

Representative examples of substituents may thus include alkyl, substituted alkyl (e.g., C1-C6, C1-5, C1-4, C1-3, C1-2, C1), alkoxy (e.g., C1-C6, C1-5, C1-4, C1-3, C1-2, C1), substituted alkoxy (e.g., C1-C6, C1-5, C1-4, C1-3, C1-2, C1), alkenyl (e.g., C2-C6, C2-5, C2-4, C2-3, C2), substituted alkenyl (e.g., C2-C6, C2-5, C2-4, C2-3, C2), alkynyl (e.g., C2-C6, C2-5, C2-4, C2-3, C2), substituted alkynyl (e.g., C2-C6, C2-5, C2-4, C2-3, C2), cyclic (e.g., C3-C12, C5-C6), substituted cyclic (e.g., C3-C12, C5-C6), carbocyclic (e.g., C3-C12, C5-C6), substituted carbocyclic (e.g., C3-C12, C5-C6), heterocyclic (e.g., C3-C12, C5-C6), substituted heterocyclic (e.g., C3-C12, C5-C6), aryl (e.g., benzyl and phenyl), substituted aryl (e.g., substituted benzyl or phenyl), heteroaryl (e.g., pyridyl or pyrimidyl), substituted heteroaryl (e.g., substituted pyridyl or pyrimidyl), aralkyl (e.g., benzyl), substituted aralkyl (e.g., substituted benzyl), halo, hydroxyl, aryloxy (e.g., C6-C12, C6), substituted aryloxy (e.g., C6-C12, C6), alkylthio (e.g., C1-C6), substituted alkylthio (e.g., C1-C6), arylthio (e.g., C6-C12, C6), substituted arylthio (e.g., C6-C12, C6), cyano, carbonyl, substituted carbonyl, carboxyl, substituted carboxyl, amino, substituted amino, amido, substituted amido, sulfonyl, substituted sulfonyl, amino acid, and peptide groups.

The term "binding" as it relates to interaction between the targeting ligand and focal adhesion kinase (FAK) and anaplastic lymphoma kinase (ALK), typically refers to an inter-molecular interaction that may be preferential or substantially specific (also referred to herein as "selective") in that binding of the targeting ligand with any other proteins present in the cell is functionally insignificant and/or does not lead to degradation. The present bifunctional compounds may preferentially bind and recruit FAK or FAK and ALK, leading to FAK or FAK and ALK degradation.

The term "binding" as it relates to interaction between the degron and the E3 ubiquitin ligase, typically refers to an inter-molecular interaction that may or may not exhibit an affinity level that equals or exceeds that affinity between the targeting ligand and the target protein, but nonetheless wherein the affinity is sufficient to achieve recruitment of the ligase to the targeted degradation and the selective degradation of the targeted protein.

Broadly, the bifunctional compound of the present invention has a structure represented by formula (I):

(I)

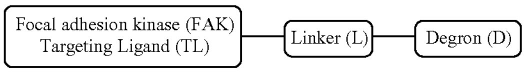

wherein the targeting ligand represents a moiety that binds FAK, the degron is a thalidomide analog, or a moiety that binds von Hippel Landau tumor suppressor (VHL), and the linker represents a moiety that covalently connects the degron and the targeting ligand, or a pharmaceutically acceptable salt or stereoisomer thereof.

In some embodiments, the compound of formula (I) degrades FAK and anaplastic lymphoma kinase (ALK).

Targeting Ligands

In some embodiments, the FAK-ALK targeting ligand is represented by structure (TL):

(TL)

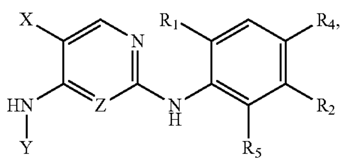

wherein

X is halo, $CF_3$, methyl, ethyl or cyclopropyl;

Y is

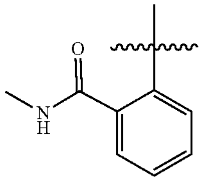

,

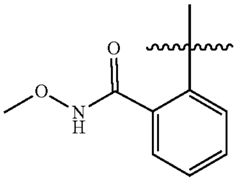

,

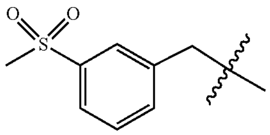

,

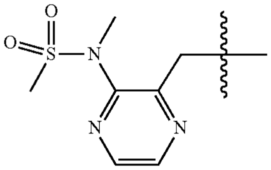

or

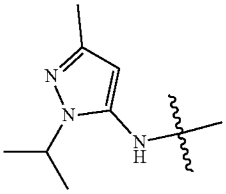

;

Z is N or CH;

$R_1$ is H or $OR_3$, wherein $R_3$ is H, optionally substituted $C_1$-$C_4$ alkyl (e.g., methyl, ethyl and isopropyl) or cyclopropyl;

$R_2$ is H or optionally substituted $C_1$-$C_4$ alkyl (e.g., methyl, ethyl and isopropyl);

$R_4$ is H

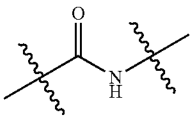

,

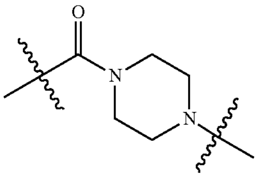

,

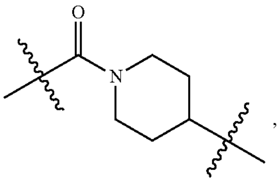

,

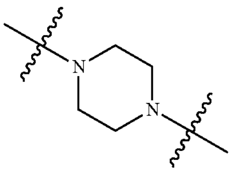

,

-continued

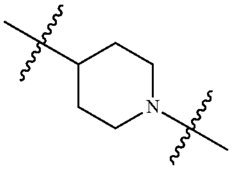

or

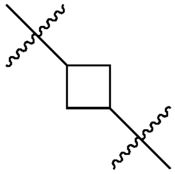

;

and $R_5$ is H, $OR_3$, wherein $R_3$ is H, optionally substituted $C_1$-$C_4$ alkyl (e.g., methyl, ethyl and isopropyl) or cyclopropyl,

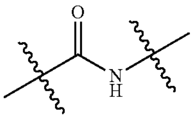

,

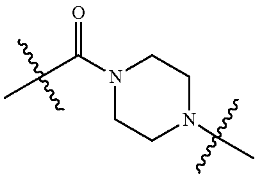

,

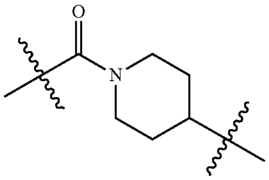

,

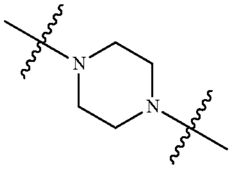

,

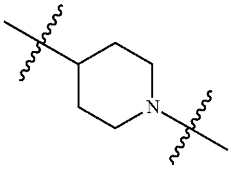

or

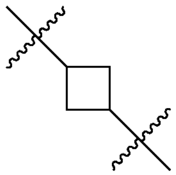

.

Thus in some embodiments, the bifunctional compounds are represented by structure (Ia):

(Ia)

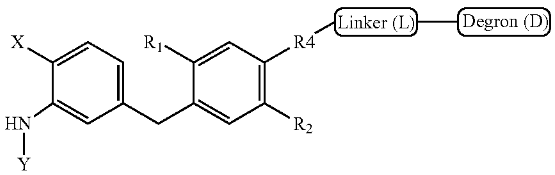

, or a pharmaceutically acceptable salt or stereoisomer thereof.

The targeting ligand represented by structure (TL) embraces various moieties disclosed hereinbelow that may be used as TLs in the bifunctional compounds.

In some embodiments, the targeting ligand is a VS-4718 (formerly PND-1186) analog. Thus, referring to structure TL, in some embodiments wherein X is $CF_3$; Y is

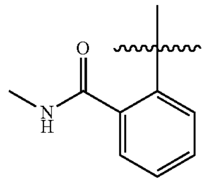

;

Z is CH, $R_1$ is $OR_3$, wherein $R_3$ is methyl or isopropyl; $R_2$ is H or methyl; $R_4$ is

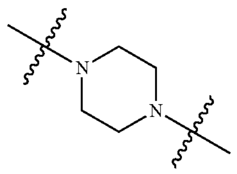

or

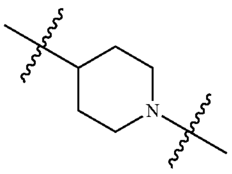

;

and $R_5$ is H, the targeting ligand is represented by structure (TL1a) or (TL1b).

-continued (TL1b)

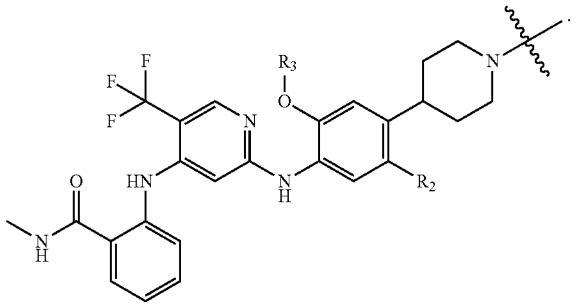

.

Other analogs of VS-4718 that bind FAK and which may be useful as targeting ligands are described in International Publication WO 2008/115369.

Thus, in some embodiments, the bifunctional compounds are represented by structure (Ia-1a) or (Ia-1b):

(Ia-1a)

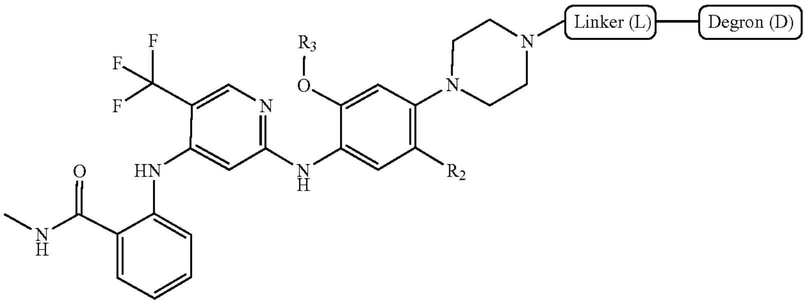

or (Ia-1b)

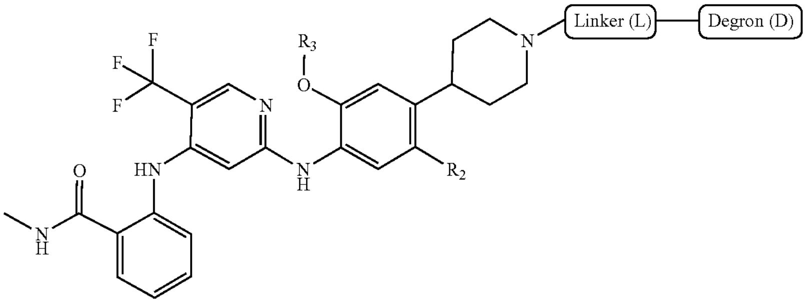

.

(TL1a)

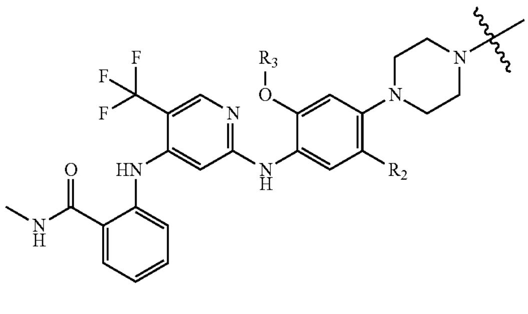

or or a pharmaceutically acceptable salt or stereoisomer thereof.

In some embodiments, the targeting ligand is derived from defactinib or an analog thereof. Defactinib, also known as VS-6063, and analogs thereof that bind FAK and which may be useful as targeting ligands are described in U.S. Pat. Nos. 7,928,109 and 9,962,385.

Thus, referring to structure TL, in some embodiments wherein X is $CF_3$; Y is

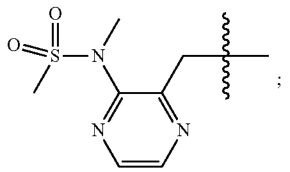 [SMILES: *Cc1nccnc1N(C)S(C)(=O)=O]

Z is N, $R_1$ and $R_2$ are H; $R_4$ is

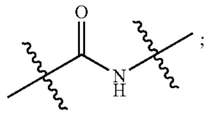 [SMILES: *NC(*)=O]

and $R_5$ is H, the targeting ligand is represented by structure (TL2a):

(TL2a)

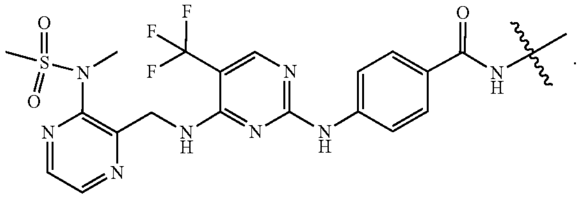

Thus, in some embodiments, the bifunctional compounds are represented by structure (Ia-2a):

(Ia-2a)

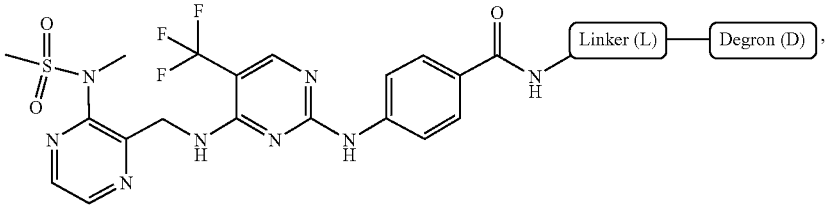

or a pharmaceutically acceptable salt or stereoisomer thereof.

In some embodiments, the targeting ligand is a PF-573228 analog. Thus, referring to structure TL, in some embodiments wherein X is $CF_3$; Y is

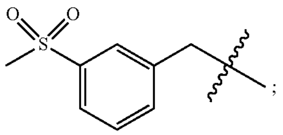 [SMILES: *Cc1cccc(S(C)(=O)=O)c1]

Z is N, $R_1$ and $R_2$ are H; $R_4$ is

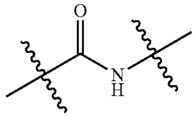

or

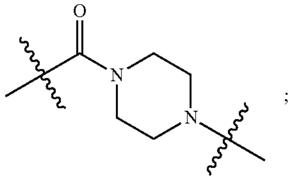

and $R_5$ is H, the targeting ligand is represented by structure (TL2b1) or (TL2b2):

(TL2b1)

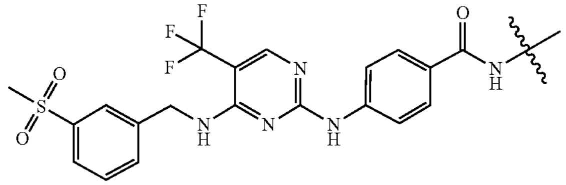

(TL2b2)

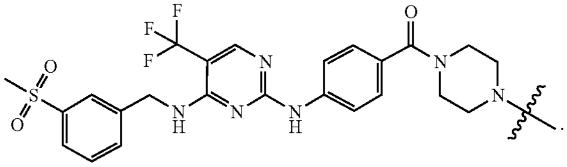

Thus, in some embodiments, the bifunctional compounds are represented by structure (Ia-2b1) or (Ia-2b2):

(Ia-2b1)

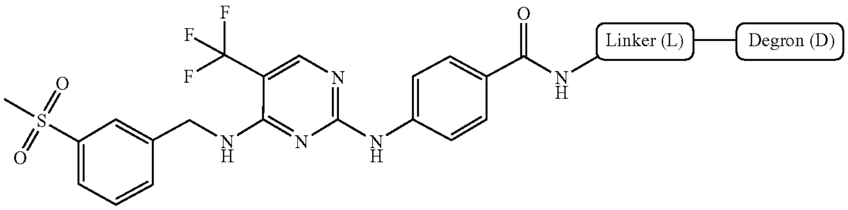

or (Ia-2b2)

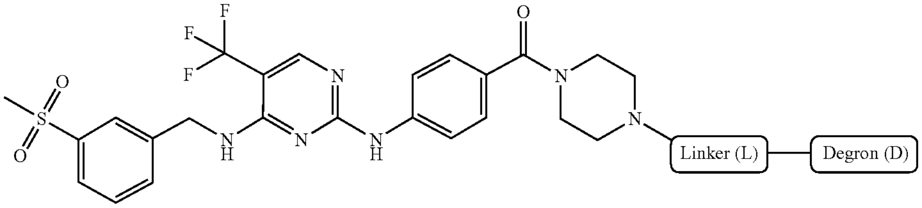

, or a pharmaceutically acceptable salt or stereoisomer thereof.

In some embodiments, the FAK-ALK targeting ligand is a TAE-226 analog. Thus, referring to structure TL, in some embodiments wherein X is Cl; Y is

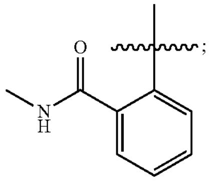 [SMILES: *c1ccccc1C(=O)NC]

Z is N, $R_1$ and $R_2$ are H; $R_4$ is or

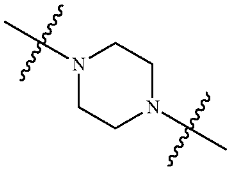

or

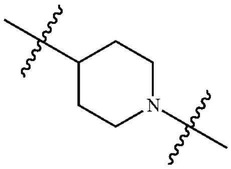

;

and $R_5$ is $OR_3$, wherein $R_3$ is methyl, the targeting ligand is represented by structure (TL3a) or (TL3b):

(TL3a)

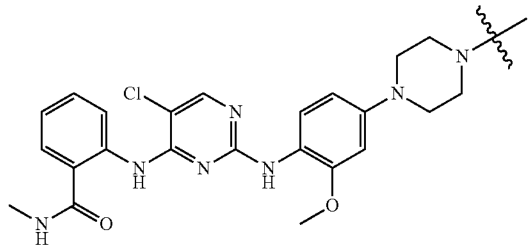

or (TL3b)

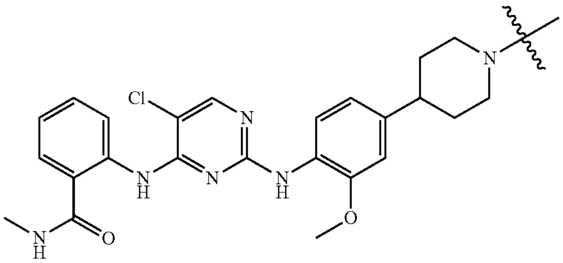

Other TAE-226 analogs thereof that bind FAK-ALK and which may be useful as targeting ligands are described in U.S. Patent Application Publication 2013/0017194 A1.

Thus, in some embodiments, the bifunctional compounds are represented by structure (Ia-3a) or (Ia-3b):

(Ia-3a)

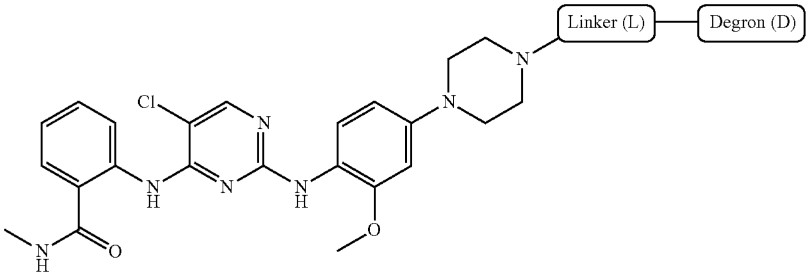

or

-continued (Ia-3b)

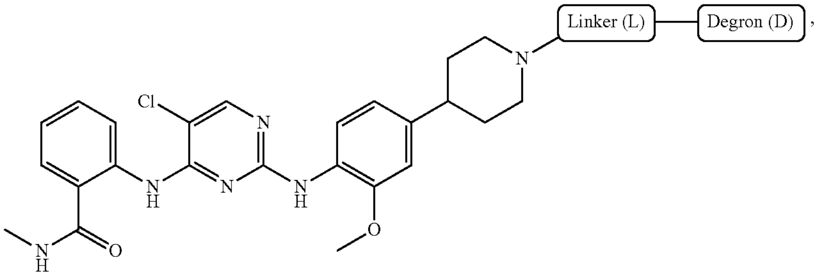

or a pharmaceutically acceptable salt or stereoisomer thereof.

In some embodiments, the targeting ligand is a GSK2256098 analog. Thus, referring to structure TL, in some embodiments, wherein X is Cl; Y is

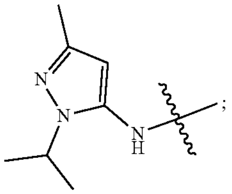 [SMILES: *Nc1cc(C)nn1C(C)C]

Z is CH; $R_1$, $R_2$ and $R_4$ are H; $R_5$ is

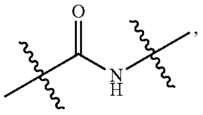 [SMILES: *NC(*)=O]

and $R_3$ is methyl, the targeting is represented by structure (TL4):

(TL4)

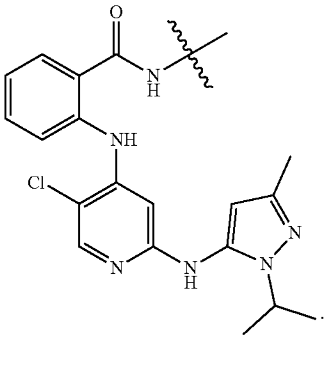

Other GSK2256098 analogs thereof that bind FAK and which may be useful as targeting ligands are described in U.S. Patent Application Publication 2011/0269774 A1.

Thus, in some embodiments, the bifunctional compounds are represented by structure (Ia-4):

(Ia-4)

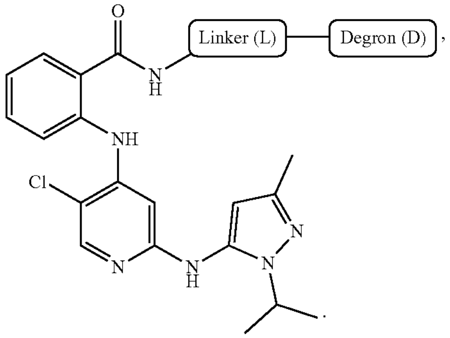

or a pharmaceutically acceptable salt or stereoisomer thereof.

Further representative compounds that may be useful as FAK-ALK targeting ligands are described in U.S. Pat. No. 7,235,562, U.S. Patent Application Publications 2011/0269774 A1 and 2013/0017194 A1, and Sulzmaier, et al., Nat. Rev. Cancer 14(9):598-610 (2104).

Linkers

The linker ("L") provides a covalent attachment the targeting ligand and the degron. The structure of linker may not be critical, provided it does not substantially interfere with the activity of the targeting ligand or the degron. In some embodiments, the linker is an alkylene chain (e.g., having 1-10 alkylene units). In other embodiments, the linker may be an alkylene chain or a bivalent alkylene chain, either of which may be interrupted by, and/or terminate (at either or both termini) at least one of —O—, —S—, —N(R")—, —C(O)—, —C(O)O—, —OC(O)—, —OC(O)O—, —C(NOR")—, —C(O)N(R")—, —C(O)N(R")C(O)—, —C(O)N(R")C(O)N(R")—, —N(R")C(O)—, —N(R")C(O)N(R")—, —N(R")C(O)O—, —OC(O)N(R")—, —C(NR")—, —N(R')C(NR")—, —C(NR")N(R")—, —N(R")C(NR")N(R")—, $—S(O)_2—$, —OS(O)—, —S(O)O—, —S(O)—, $—OS(O)_2—$, $—S(O)_2O—$, $—N(R")S(O)_2—$, $—S(O)_2N(R")—$, —N(R")S(O)—, —S(O)N(R")—, $—N(R")S(O)_2N(R")—$, —N(R')S(O)N(R')—, $C_{3-12}$ carbocyclene, 3- to 12-membered heterocyclene, 5- to 12-membered heteroarylene or any combination thereof, wherein R" is H or $C_1$-$C_6$ alkyl, wherein the one or both terminating groups may be the same or different.

In some embodiments the linker may be $C_1$-$C_{10}$ alkylene chain terminating in NH-group wherein the nitrogen is also bound to the degron.

In certain embodiments, the linker is an alkylene chain having 1-10 alkylene units and interrupted by or terminating in

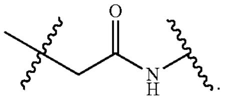 [SMILES: *CC(=O)N*]

In other embodiments, the linker is a polyethylene glycol chain having 2-8 PEG units and terminating in

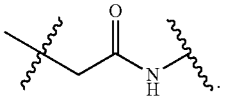 [SMILES: *CC(=O)N*]

“Carbocyclene” refers to a bivalent carbocycle radical, which is optionally substituted.

“Heterocyclene” refers to a bivalent heterocyclyl radical which may be optionally substituted.

“Heteroarylene” refers to a bivalent heteroaryl radical which may be optionally substituted.

Representative examples of linkers that may be suitable for use in the present invention include alkylene chains, e.g.:

(L1)

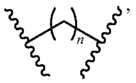

wherein n is an integer from 1-10 (“from” meaning inclusive), e.g., 1-9, 1-8, 1-7, 1-6, 1-5, 1-4, 1-3, 1-2, 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, 9-10 and 1, 2, 3, 4, 5, 6, 7, 8, 9 and 10, examples of which include:

(L1-a)

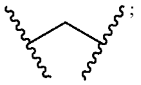

(L1-b)

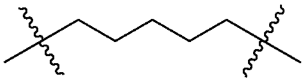

(L1-c)

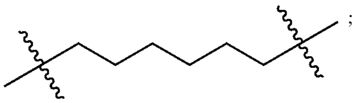

(L1-d)

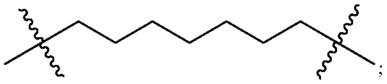

and (L1-e)

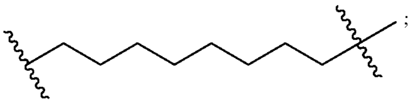

alkylene chains terminating in various functional groups (as described above), examples of which are as follows:

(L2-a)

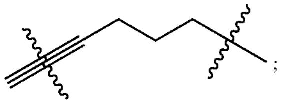

(L2-b)

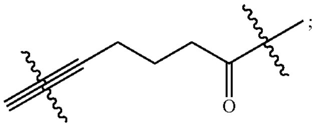

(L2-c)

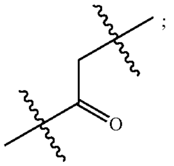

(L2-d)

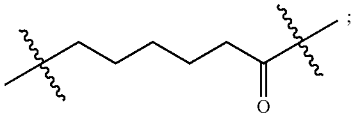

(L2-e)

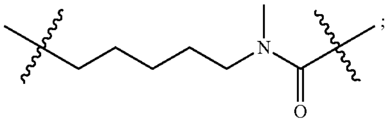

(L2-f)

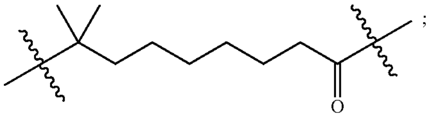

and (L2-g)

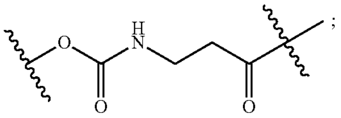

alkylene chains interrupted with various functional groups (as described above), examples of which are as follows:

(L3-a)

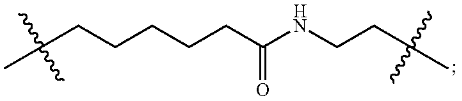

(L3-b)

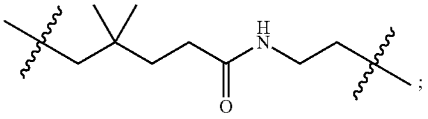

(L3-c)

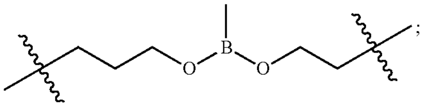

and

-continued (L3-d)

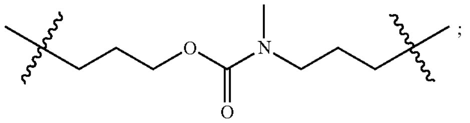

alkylene chains interrupted or terminating with heterocyclene groups, e.g., (L4)

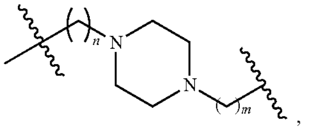

wherein m and n are independently integers from 0-10, examples of which include:

(L4-a)

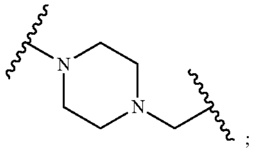

(L4-b)

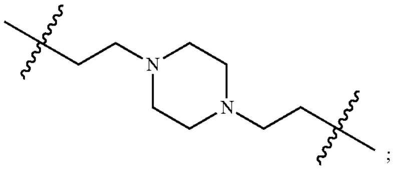

(L4-c)

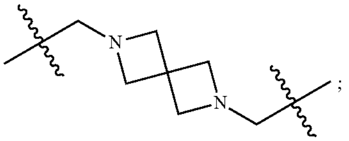

(L4-d)

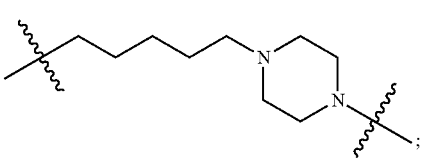

and (L4-e)

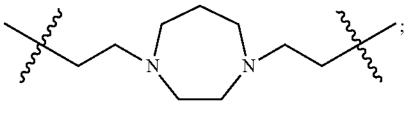

alkylene chains interrupted by amide, heterocyclene and/or aryl groups, examples of which include:

(L5-a)

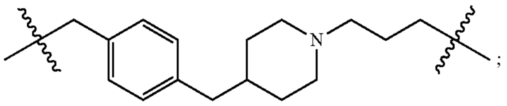

and (L5-b)

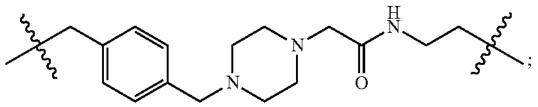

alkylene chains interrupted by heterocyclene and aryl groups, and a heteroatom, examples of which include:

(L6-a)

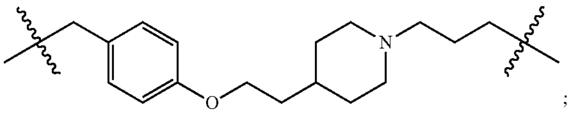

(L6-b)

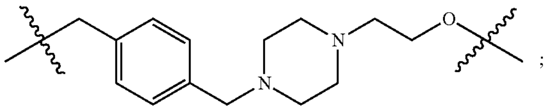

and (L6-c)

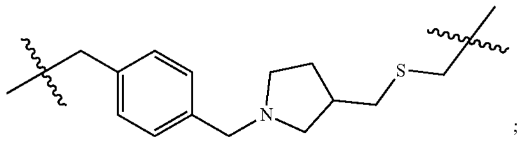

alkylene chains interrupted by or terminating in a heteroatom such as N, O or B, e.g., (L7)

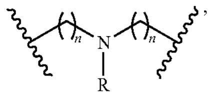

wherein each n independently is an integer from 1-10, e.g., 1-9, 1-8, 1-7, 1-6, 1-5, 1-4, 1-3, 1-2, 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, 9-10, and 1, 2, 3, 4, 5, 6, 7, 8, 9 and 10, and R is H, or $C_1$ to $C_4$ alkyl, an example of which is (L7-a)

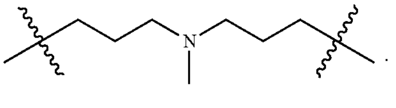

In some embodiments, the linker is a polyethylene glycol chain, examples of which include:

(L8)

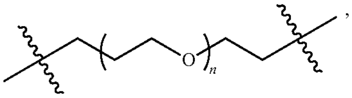

wherein n is an integer from 2-10, examples of which include:

(L8-a)

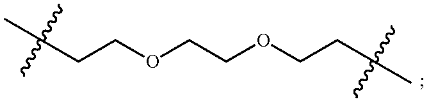

(L8-b)

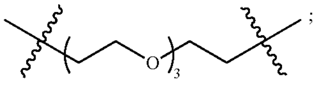

(L8-c)

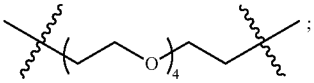

and (L8-d)

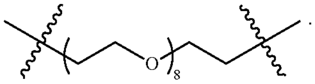

In some embodiments, the polyethylene glycol chain may terminate in a functional group, examples of which are as follows:

(L9-a)

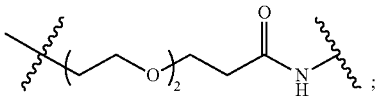

(L9-b)

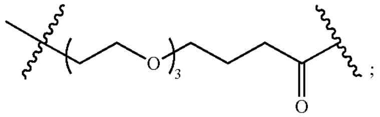

(L9-c)

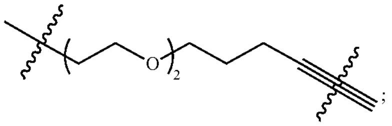

-continued (L9-d)

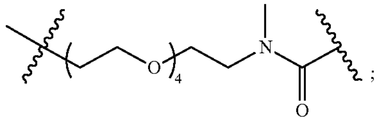

and (L9-e)

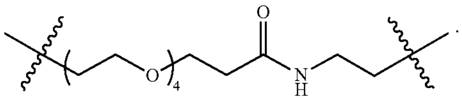

In some embodiments, the bifunctional compound of formula (I) includes a linker that is represented by any one of the following structures:

(L10-a)

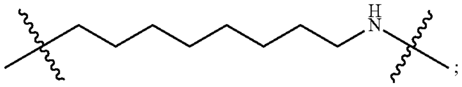

(L10-b)

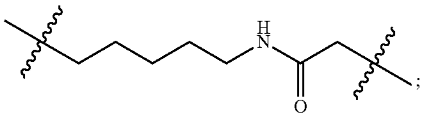

(L10-c)

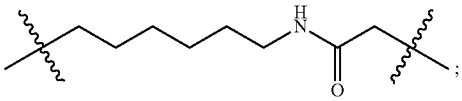

(L10-d)

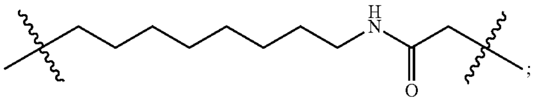

(L10-e)

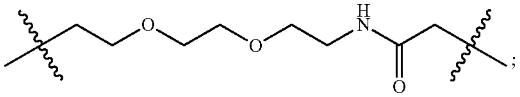

and (L10-f)

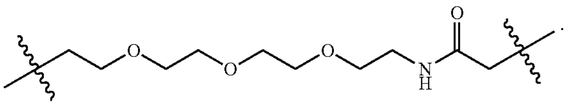

Thus, in some embodiments, the bifunctional compounds of the present invention may be represented by any of the following structures.

(I-L10a)

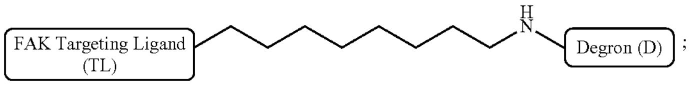

(I-L10b)

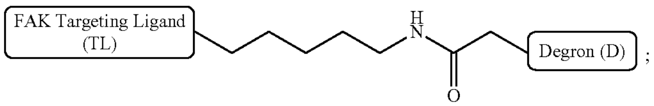

-continued
(I-L10c)
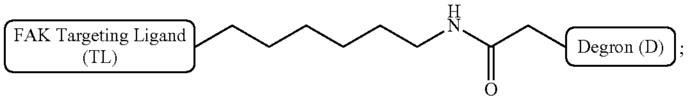
(I-L10d)
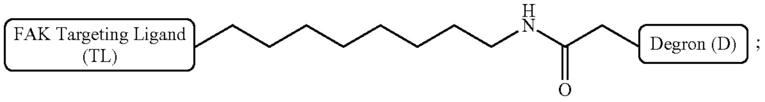
(I-L10-e)
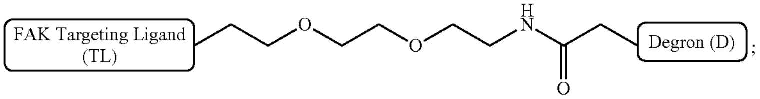
and
(I-L10f)
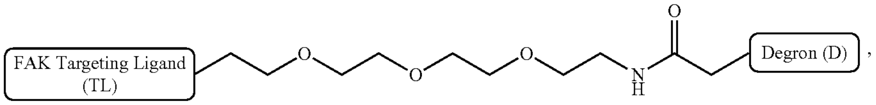
or a pharmaceutically acceptable salt or stereoisomer thereof.
In some embodiments, the bifunctional compounds of the present invention are represented by any of the following structures:
(TL-L10a)
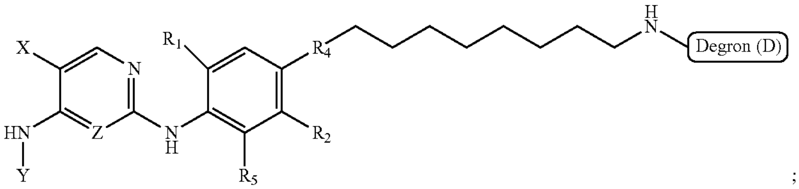
;
(TL-L10b)
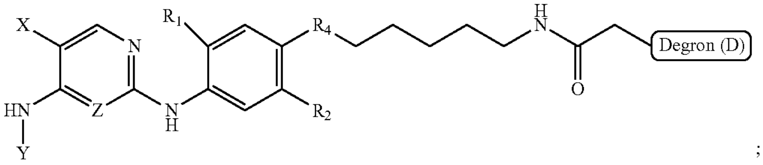
;
(TL-L10c)
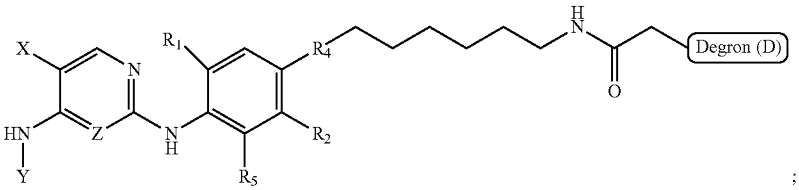
;
(TL-L10d)
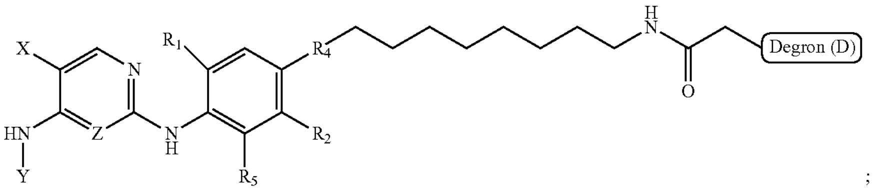
;

-continued
(TL-L10e)
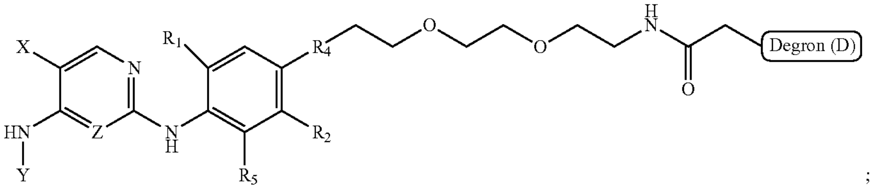
;
(TL-L10f)
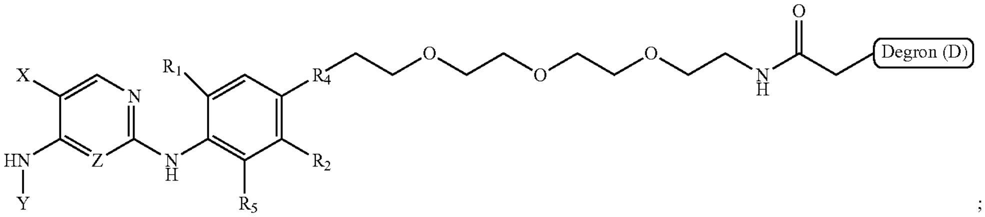
;
(TL1a-L10a)
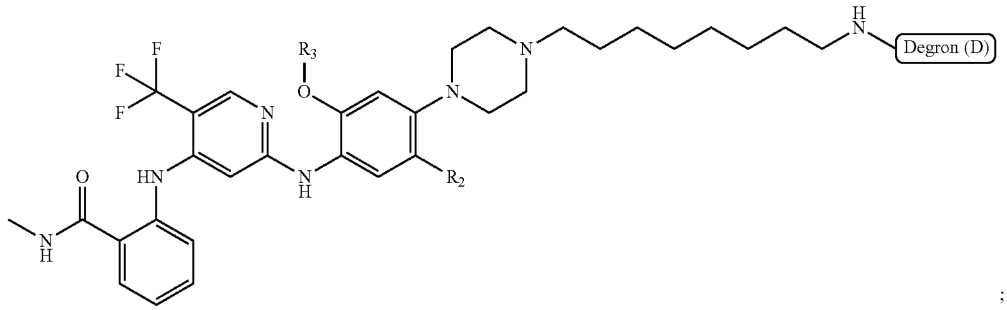
;
(TL1a-L10b)
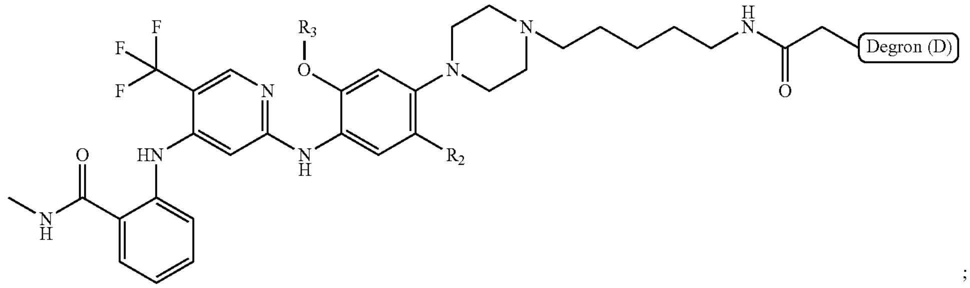
;
(TL1a-10c)
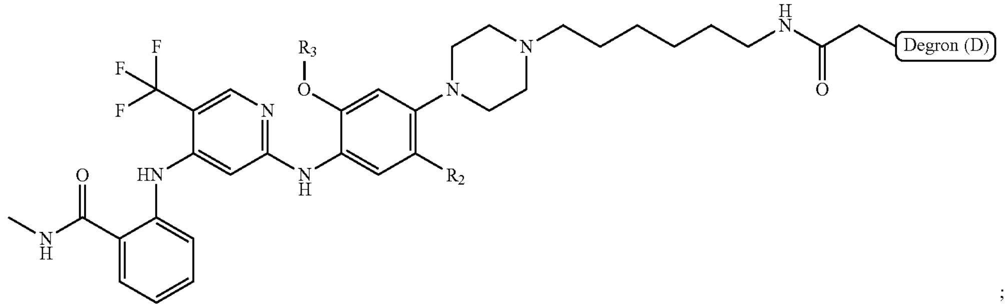
;

-continued
(TL1a-L10d)
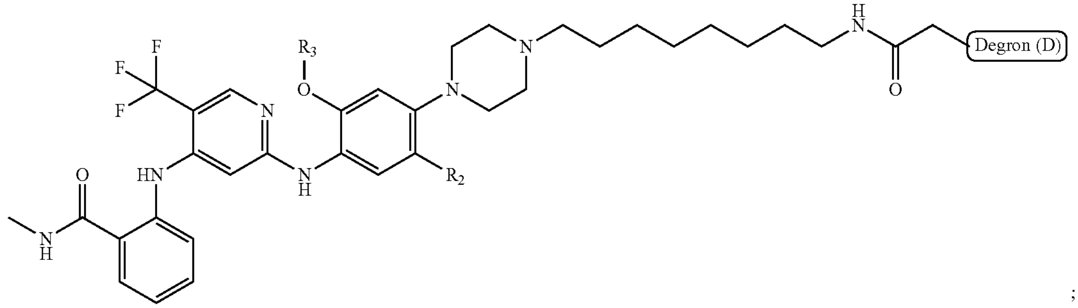
;
(TL1a-L10e)
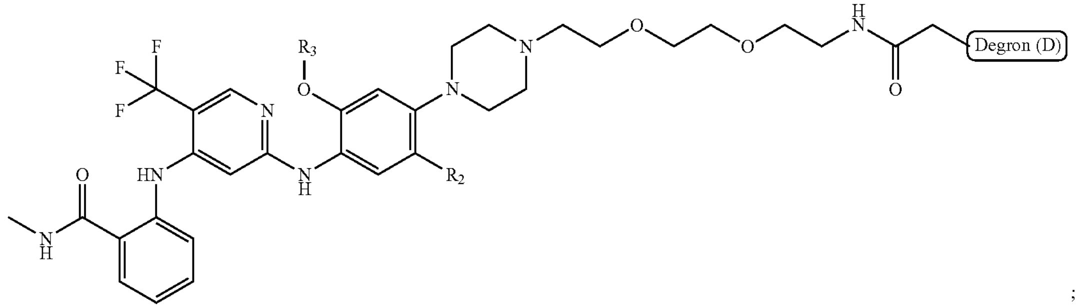
;
(TL1a-L10f)
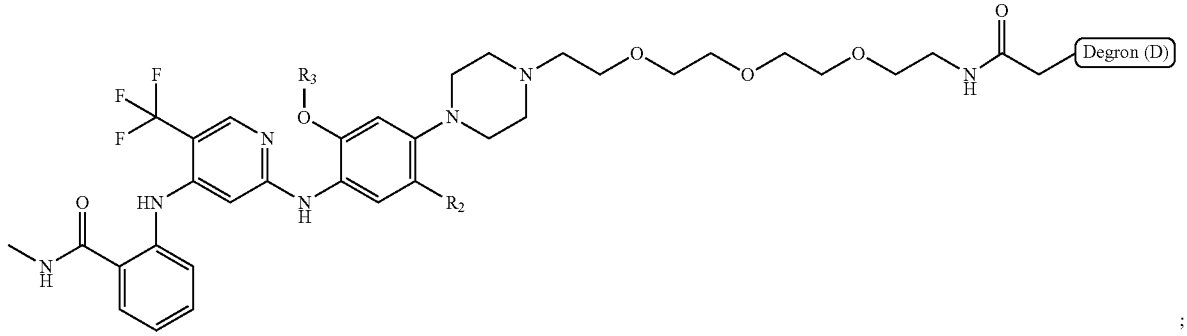
;
(TL1b-L10a)
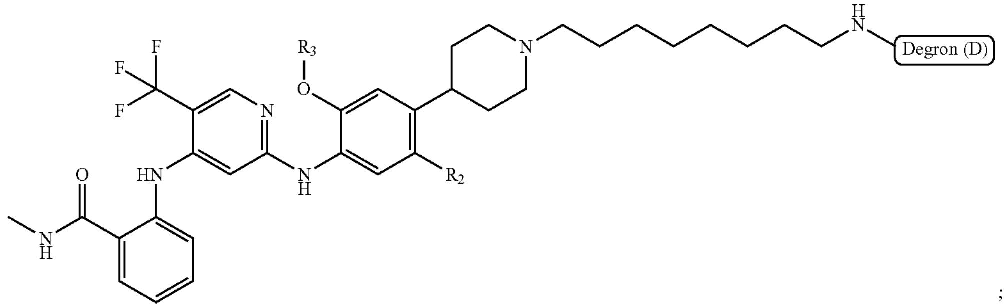
;
(TL1b-L10b)
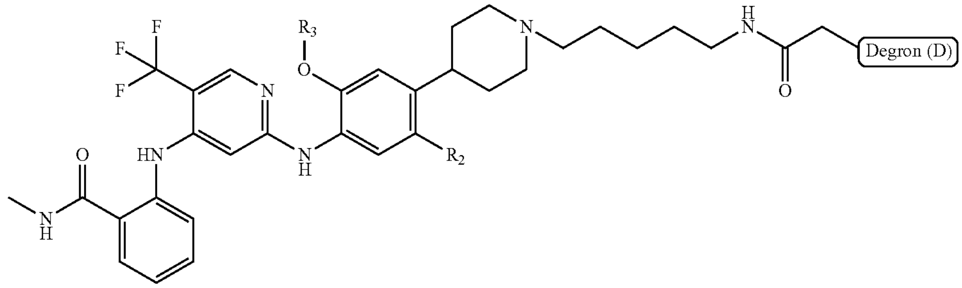
;

-continued
(TL1b-L10c)
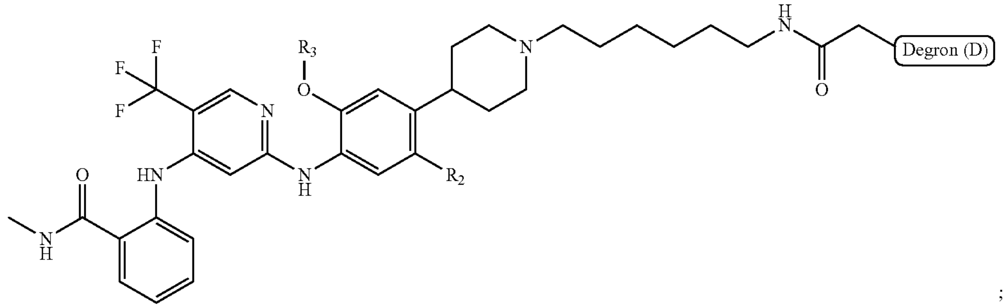
;
(TL1b-L10d)
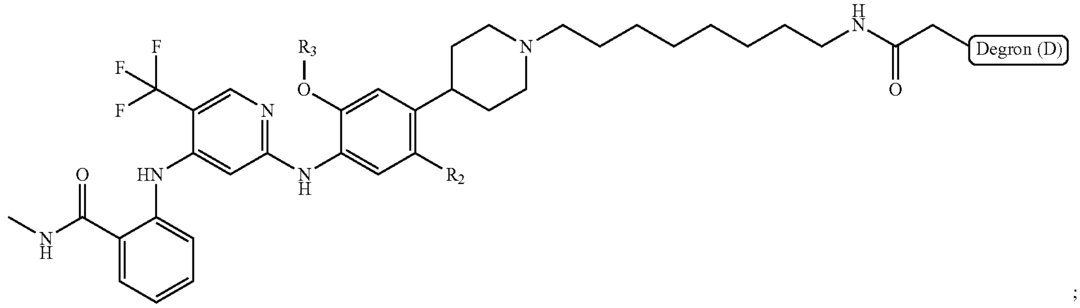
;
(TL1b-L10e)
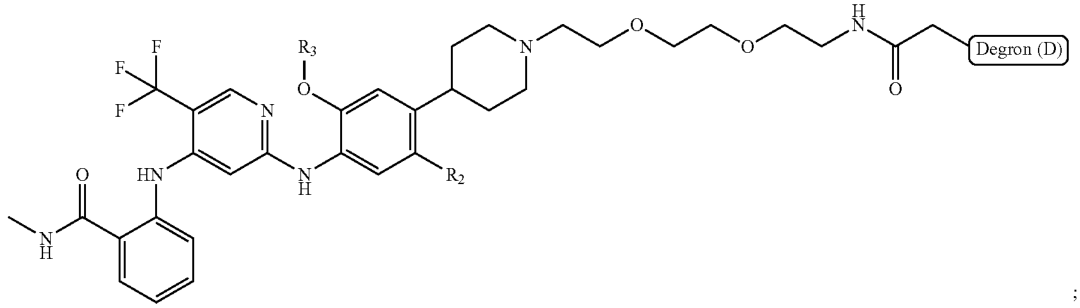
;
(TL1b-L10f)
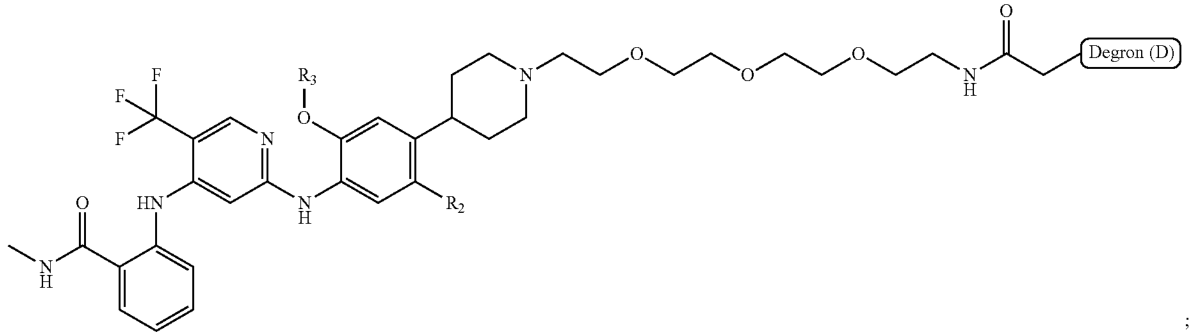
;
(TL2a-L10a)
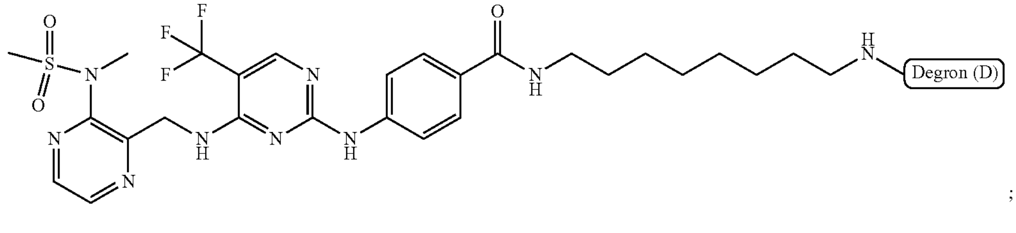
;

-continued
(TL2a-L10b)
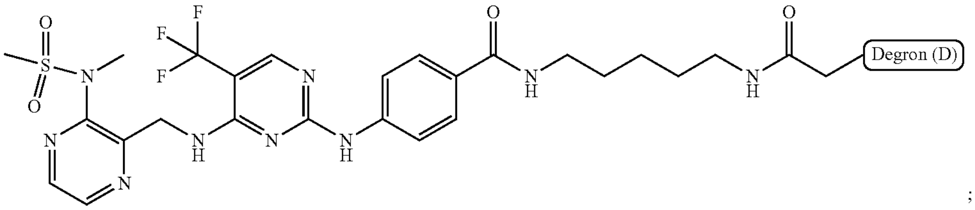
;
(TL2a-L10c)
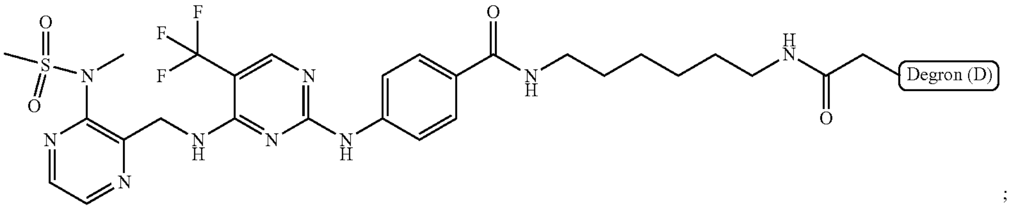
;
(TL2a-L10d)
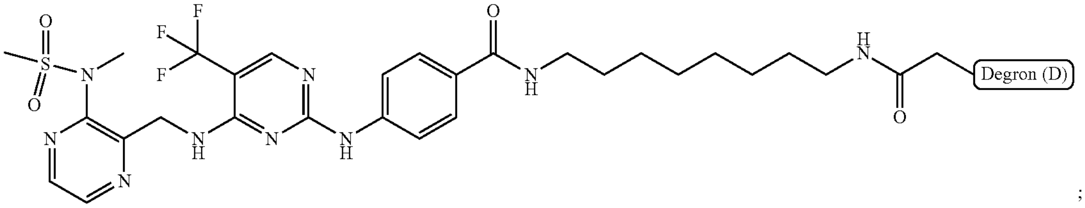
;
(TL2a-L10e)
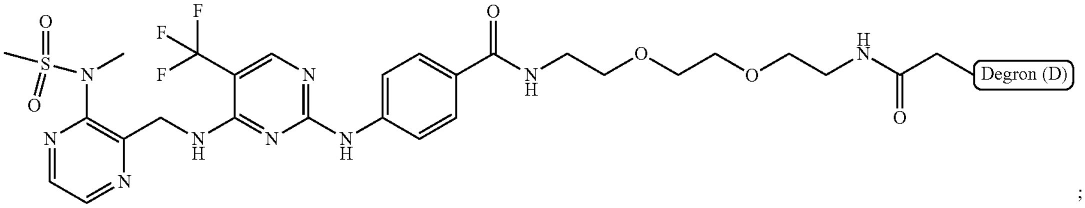
;
;
(TL2a-L10f)
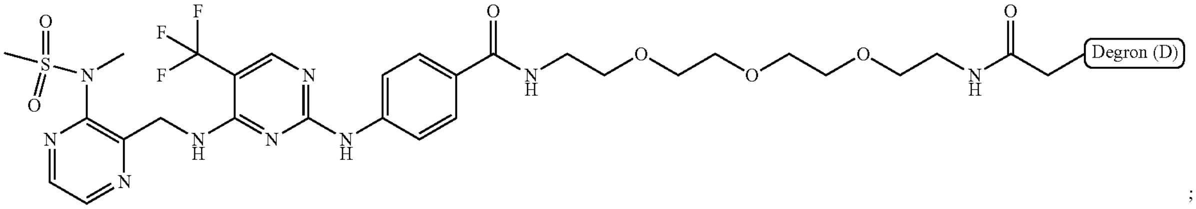
;
(TL2b1-L10a)
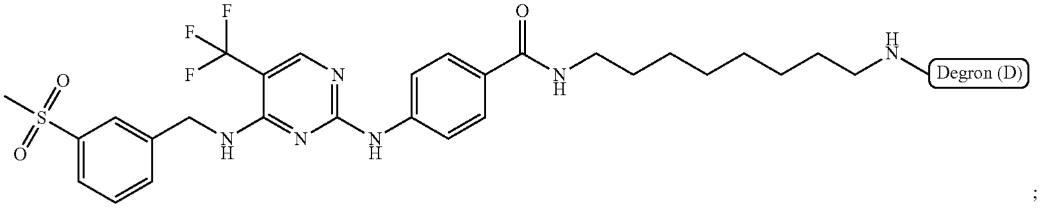
;
(TL2b1-L10b)
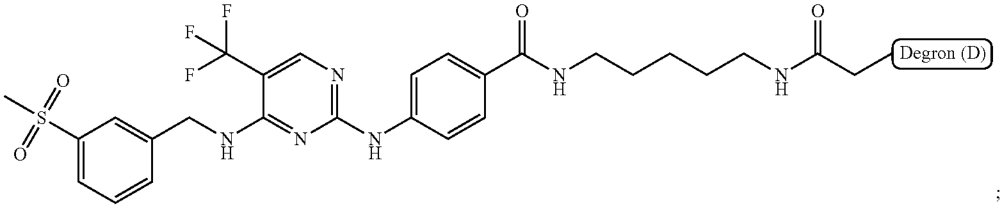
;

-continued
(TL2b1-L10c)
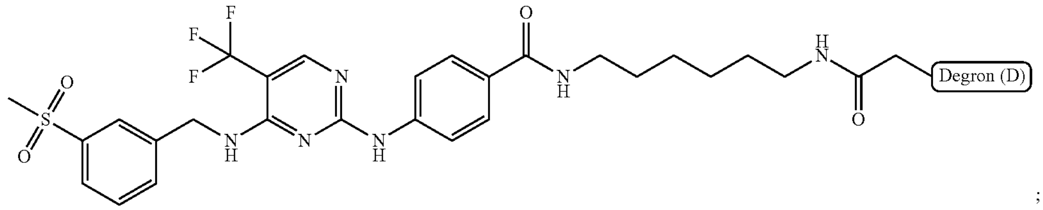
;
(TL2b1-L10d)
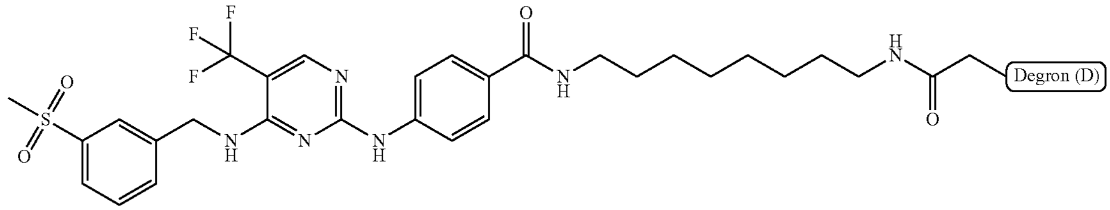
;
(TL2b1-L10e)
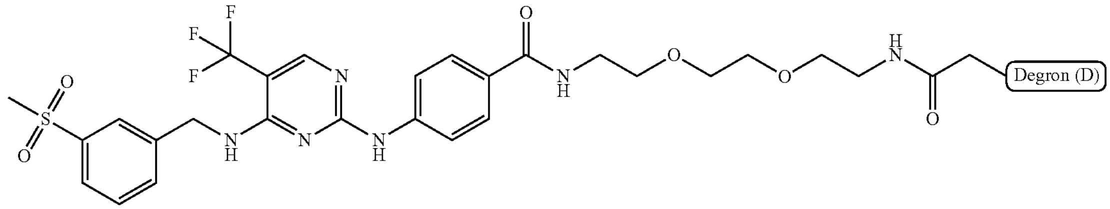
;
(TL2b1-L10f)
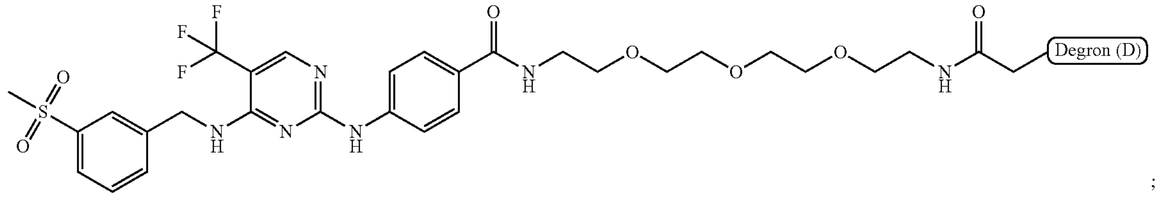
;
(TL2b2-L10a)
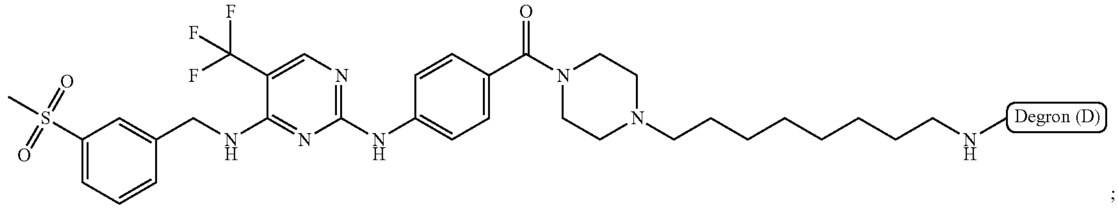
;
(TL2b2-L10b)
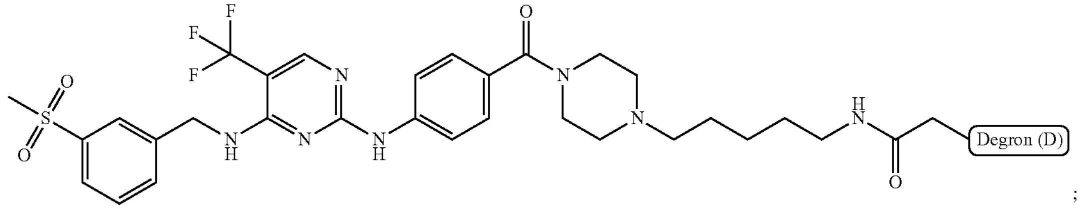
;
(TL2b2-L10c)
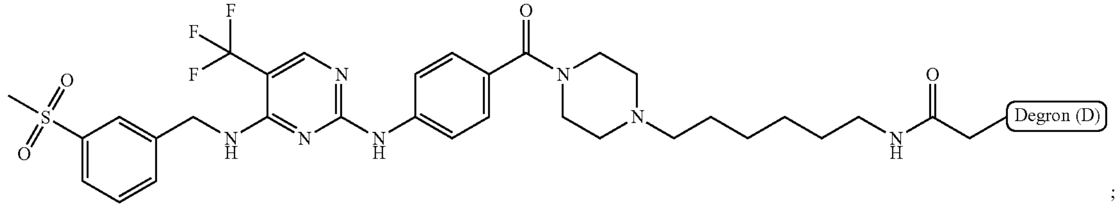
;

-continued
(TL2b2-L10d)
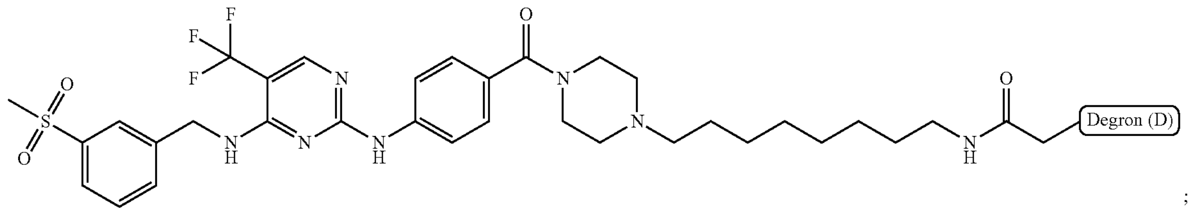
;
(TL2b2-L10e)
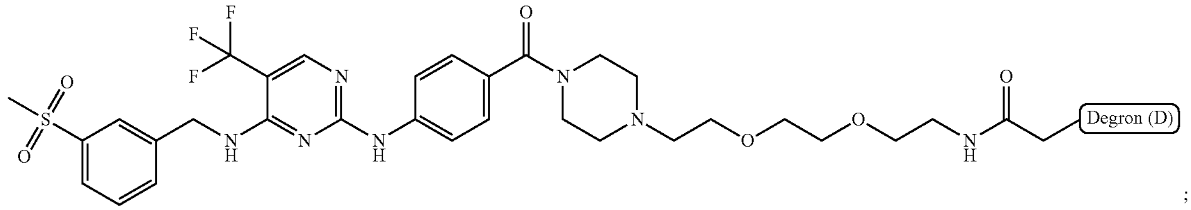
;
(TL2b2-L10f)
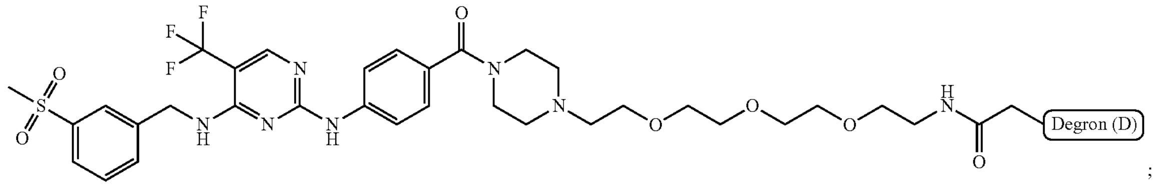
;
(TL3a-L10a)
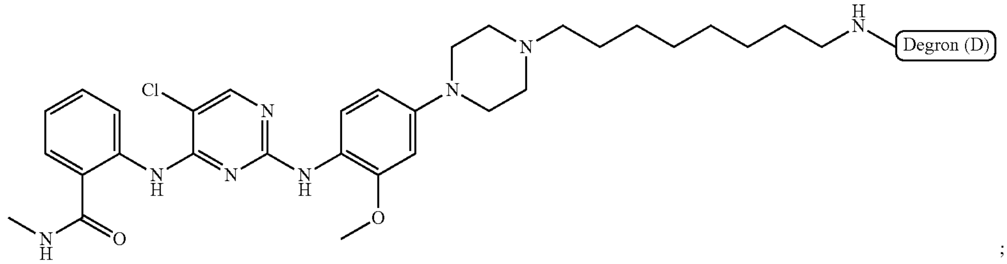
;
(TL3a-L10b)
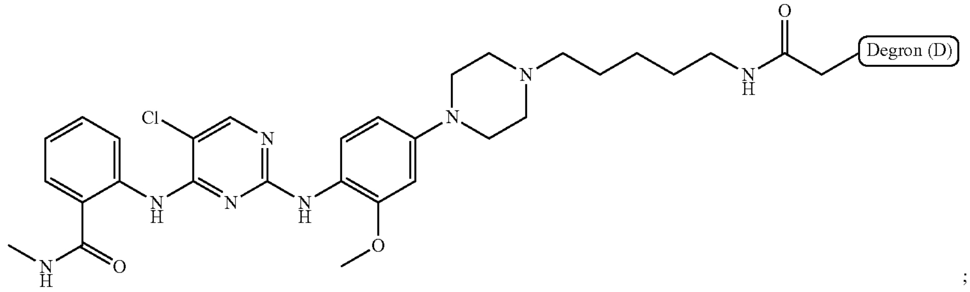
;
(TL3a-L10c)
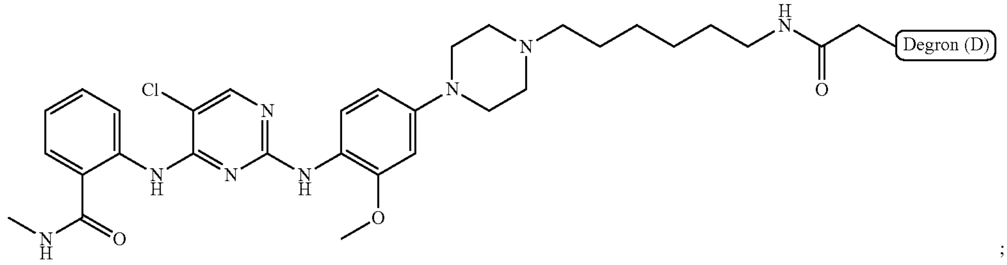
;

-continued
(TL3a-L10d)
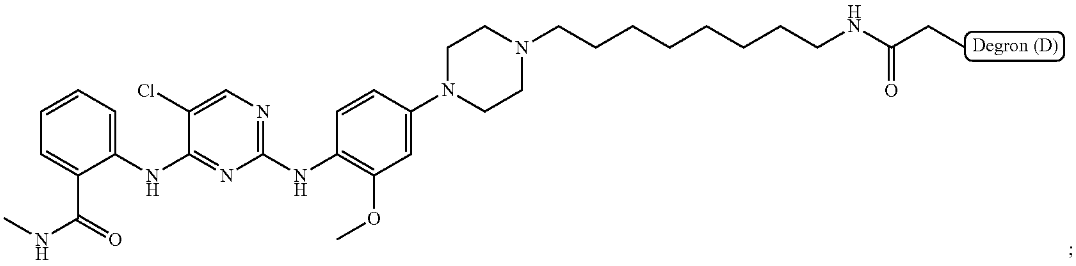
;
(TL3a-L10e)
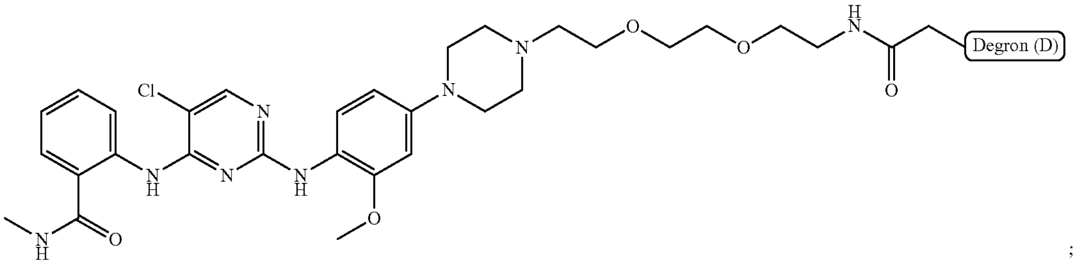
;
(TL3a-L10f)
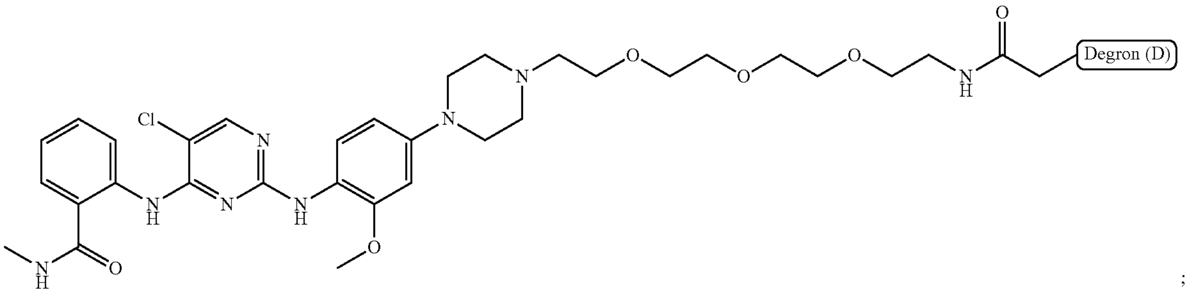
;
(TL3b-L10a)
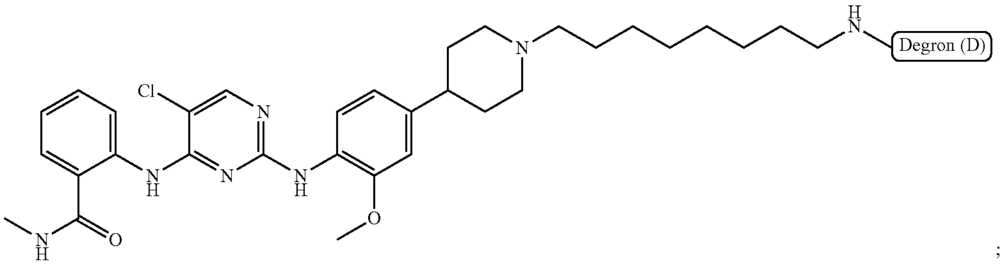
;
(TL3b-L10b)
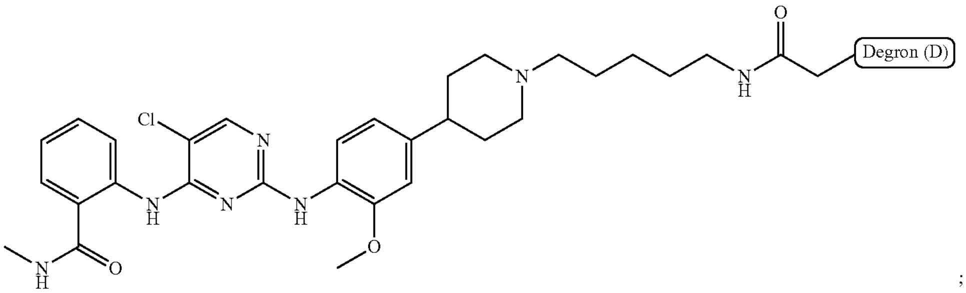
;

-continued
(TL3b-L10c)
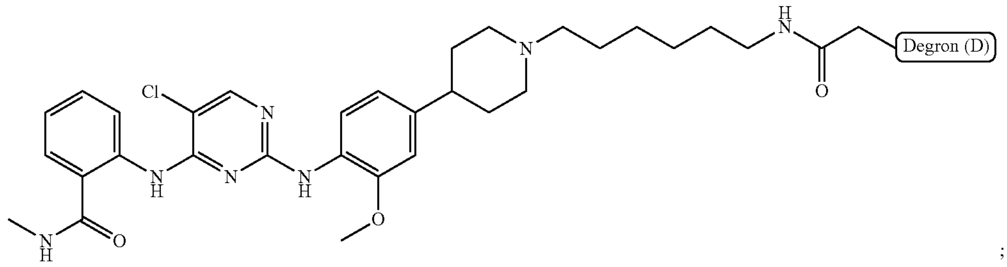
;
(TL3b-L10d)
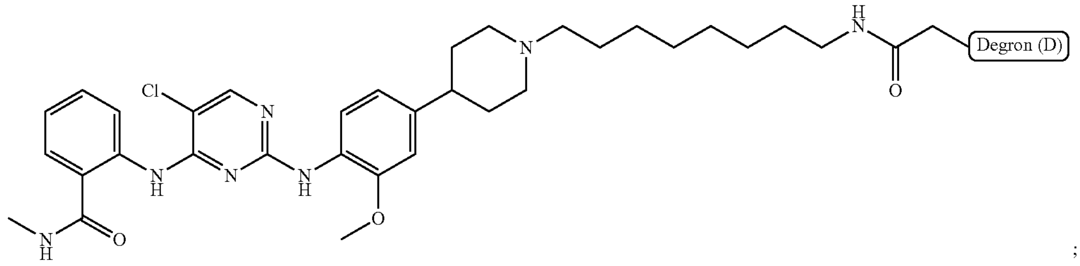
;
(TL3b-L10e)
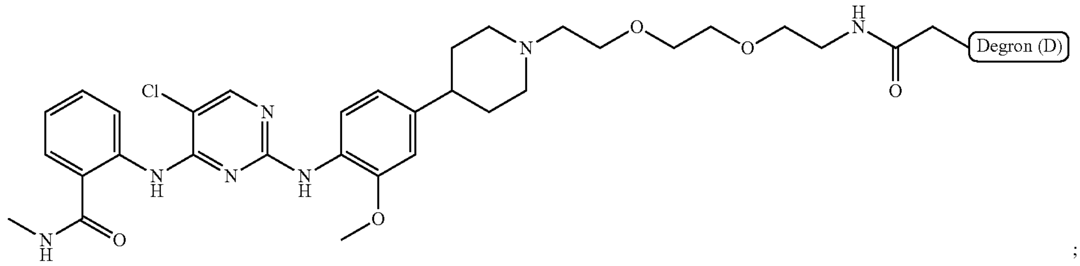
;
(TL3b-L10f)
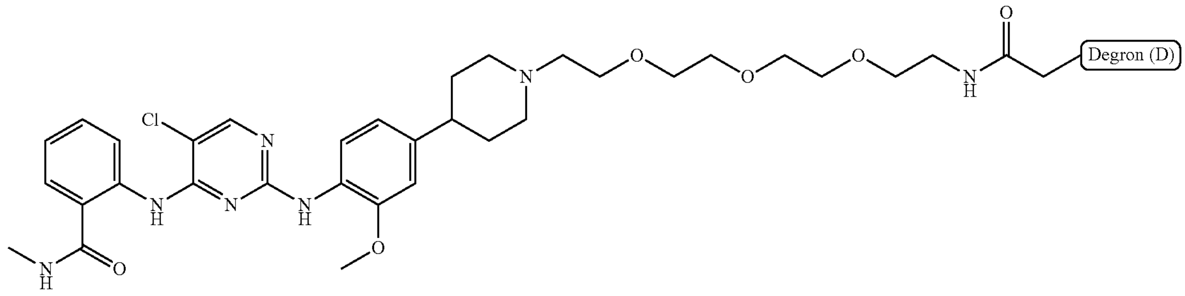
(TL4-L10a)
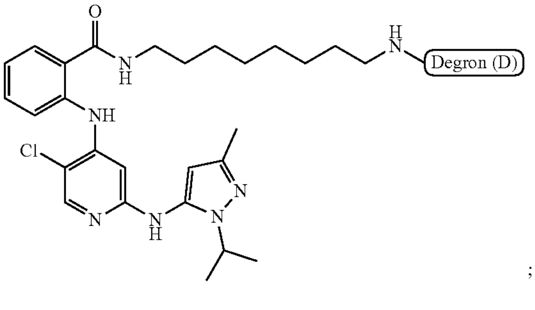
;
(TL4-L10b)
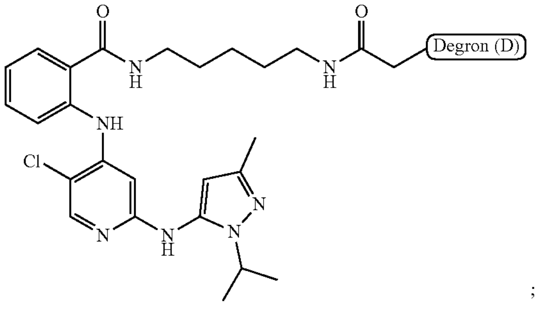
;

-continued (TL4-L10c)

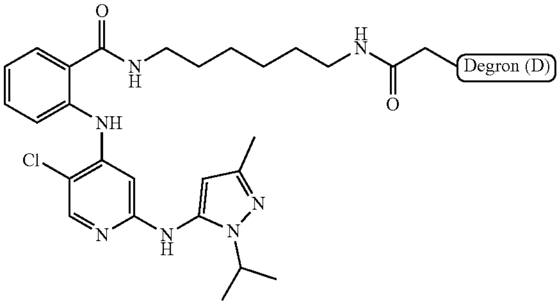

;

(TL4-L10d)

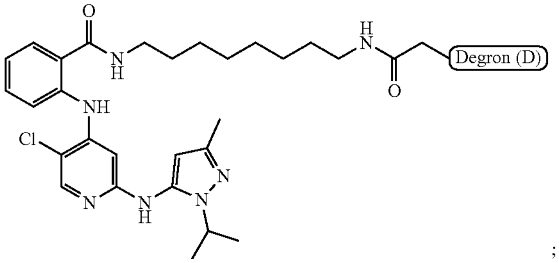

;

(TL4-L10e)

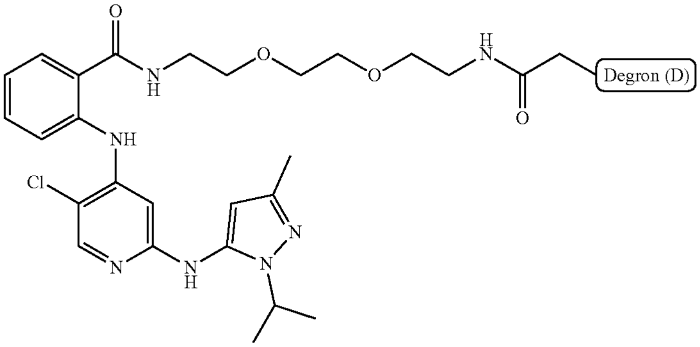

;

(TL4-L10f)

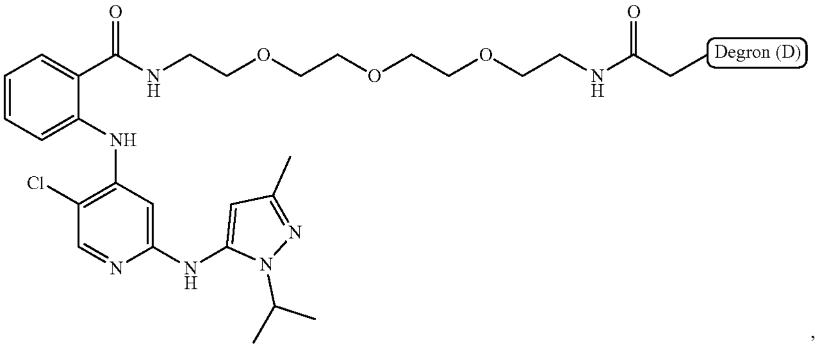

, or a pharmaceutically acceptable salt or stereoisomer thereof.

Degrons

The Ubiquitin-Proteasome Pathway (UPP) is a critical cellular pathway that regulates key regulator proteins and degrades misfolded or abnormal proteins. UPP is central to multiple cellular processes. The covalent attachment of ubiquitin to specific protein substrates is achieved through the action of E3 ubiquitin ligases. These ligases include over 500 different proteins and are categorized into multiple classes defined by the structural element of their E3 functional activity.

The degron ("D") is a functional moiety that binds cereblon (CRBN) or von Hippel Landau tumor suppressor (VHL). In some embodiments, the bifunctional compound of formula (I) includes as the degron, a thalidomide analog that binds cereblon. Representative examples of thalidomide analogs that bind cereblon are described in U.S. Patent Application Publication 2018/0015087 A1 (e.g., the indolinones such as isoindolinones and isoindoline-1,3-diones embraced by formulae IA ad IA' therein, and the bridged cycloalkyl compounds embraced by formulae IB and IB' therein) and in U.S. Application Publication 2018/0085465 A1 (e.g., the compounds of formulae D-D3 as described therein).

In some embodiments, the thalidomide analog that binds cereblon (CRBN) is represented by any one of the following structures:

(D1-a)

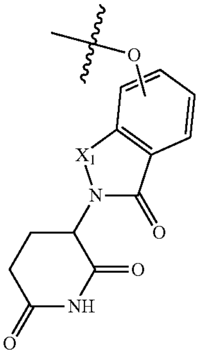

;

-continued (D1-b)

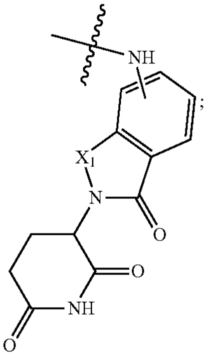

;

(D1-c)

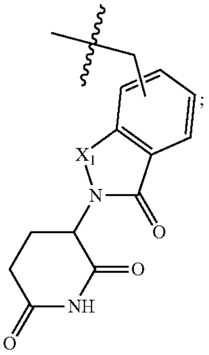

; and (D1-d)

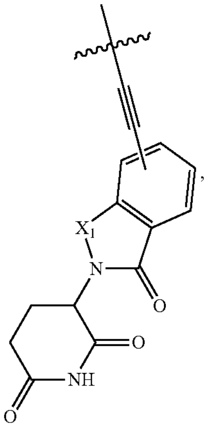

, wherein $X_1$ is $CH_2$ or CO.

Thus, in some embodiments, the bifunctional compounds of the present invention may have a structure as represented by any one of formulae (Ib) to (I-6):

(Ib)

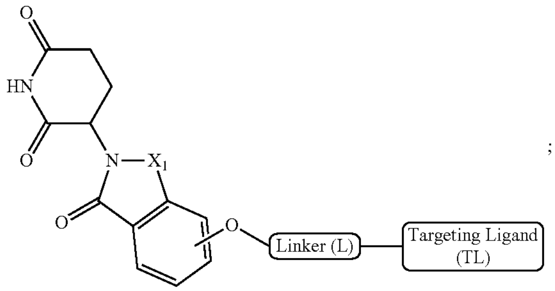

;

(Ic)

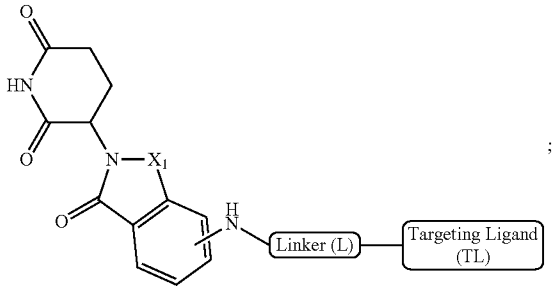

;

(Id)

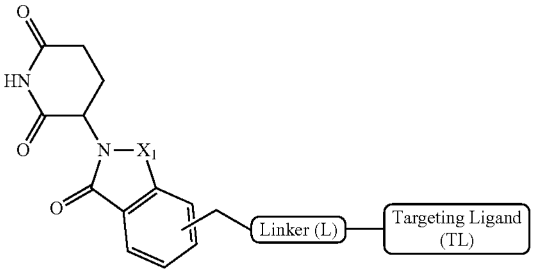

; and (Ie)

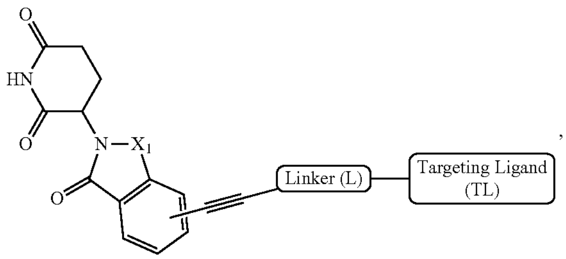

, wherein $X_1$ is $CH_2$ or CO, or a pharmaceutically acceptable salt or stereoisomer thereof.

In some embodiments, the bifunctional compounds of formula (I) are represented by any of the following structures:

(Ib-1)
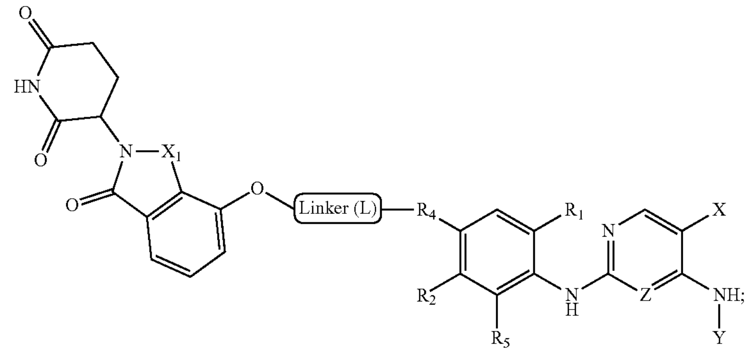
(Ib-1a1)
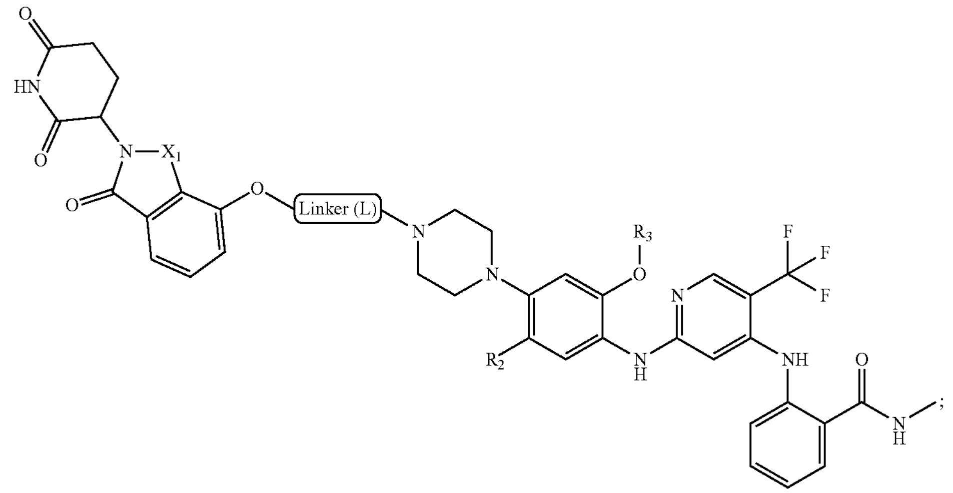
(Ib-1a2)
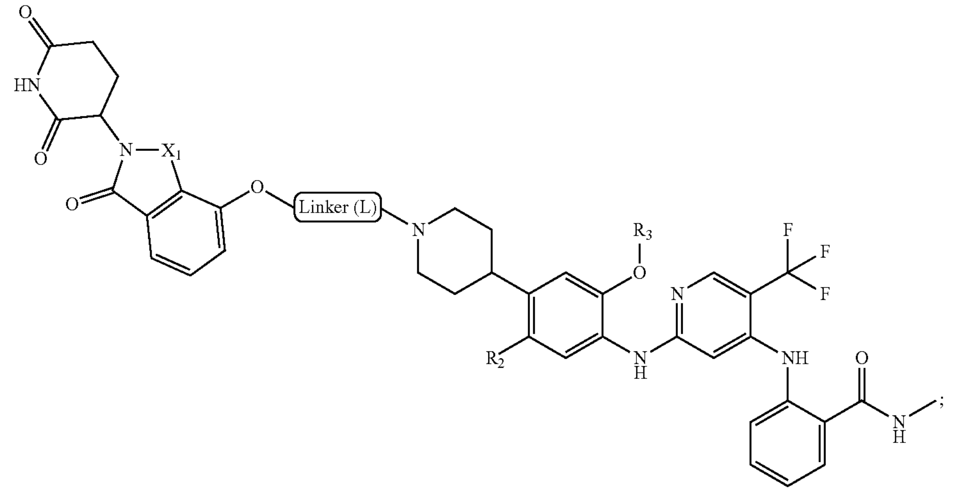

-continued
(Ib-1b)
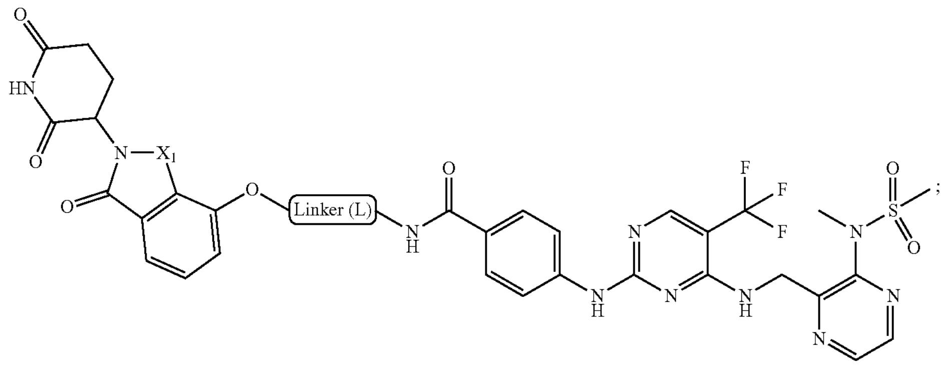
(Ib-1c)
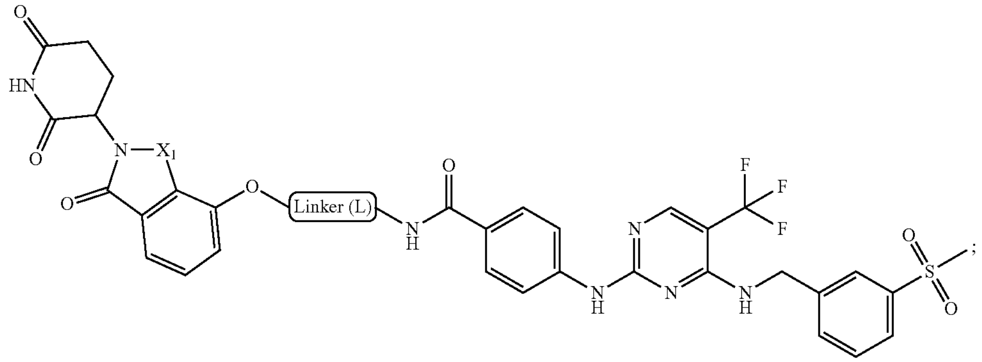
(Ib-1d)
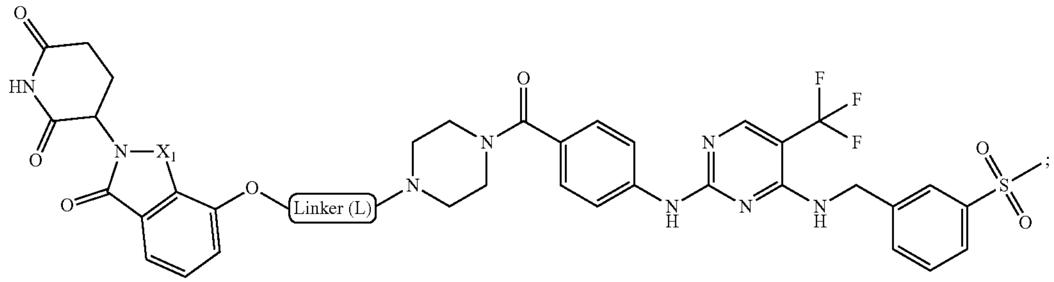
(Ib-1e1)
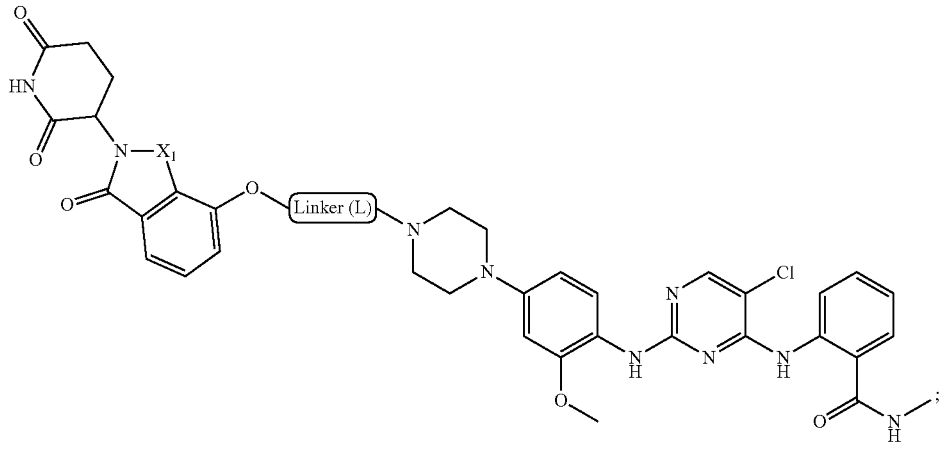

-continued
(Ib-1e2)
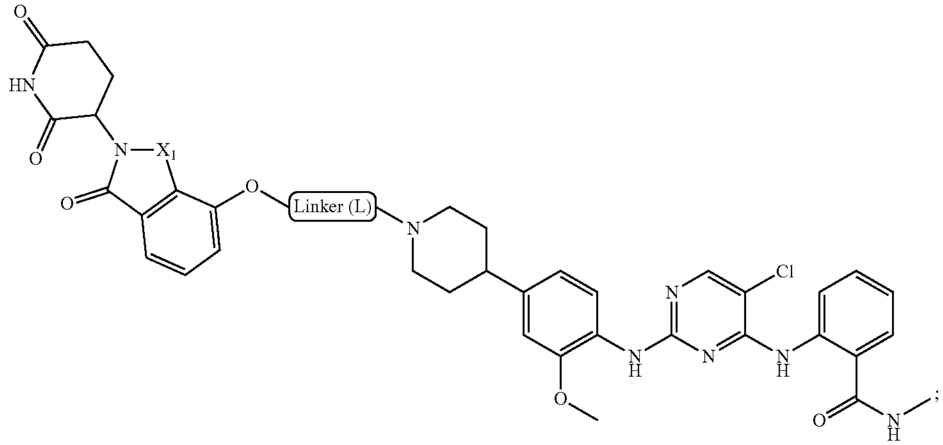
(Ib-1f)
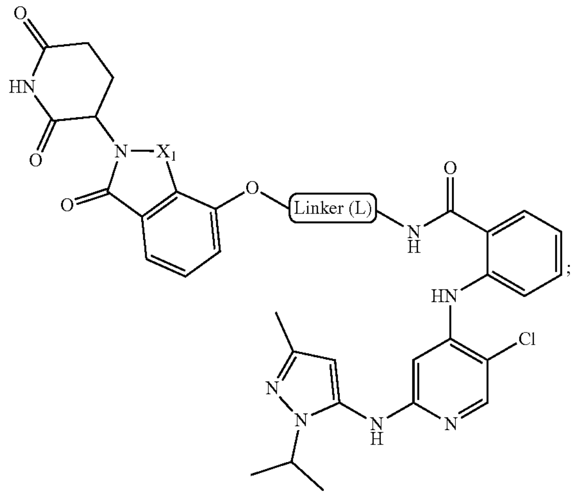
(Ic-1)
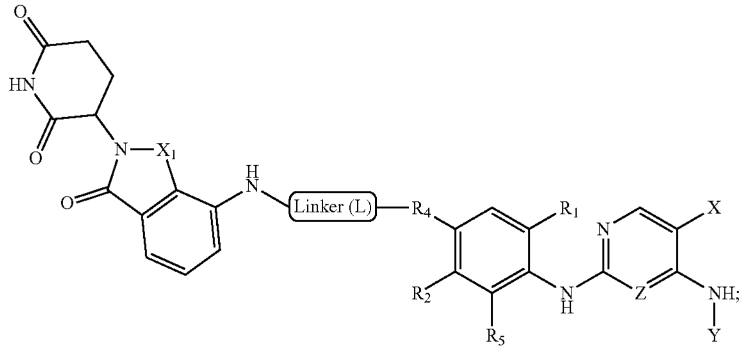

-continued
(Ic-1a1)
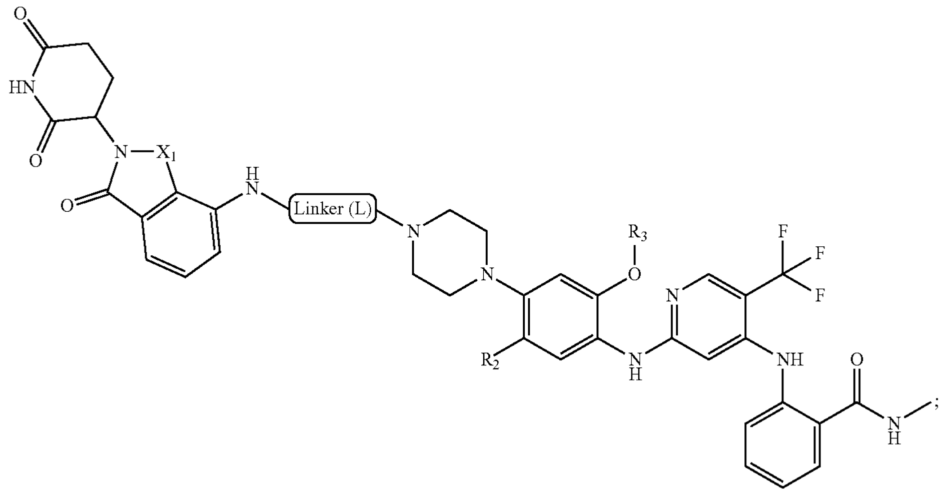
(Ic-1a2)
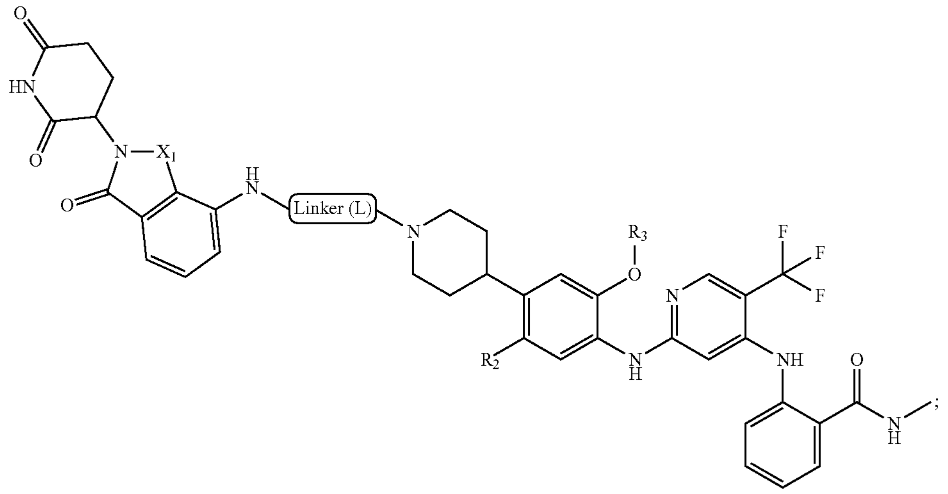
(Ic-1b)
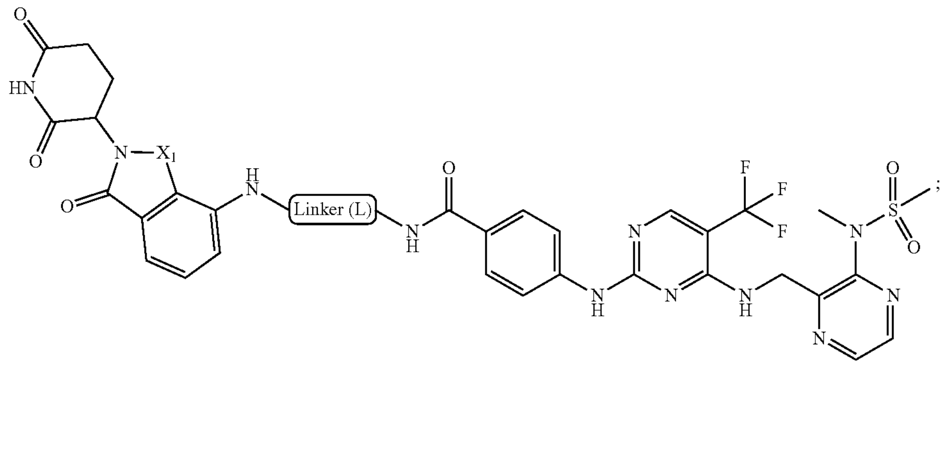

-continued
(Ic-1c)
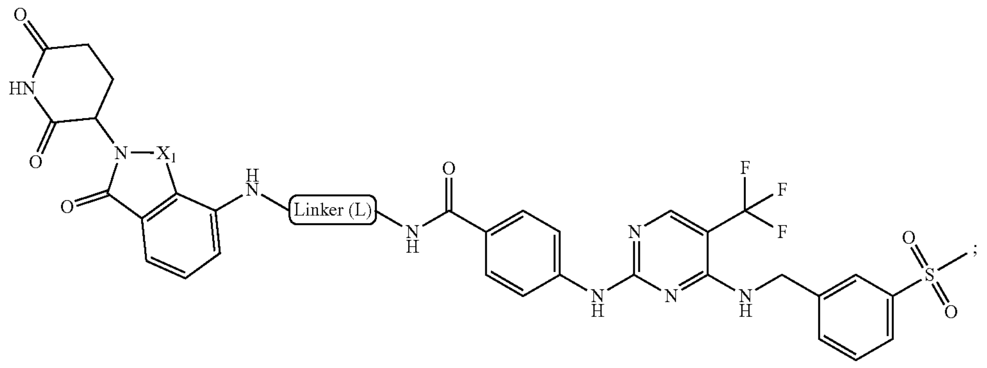
(Ic-1d)
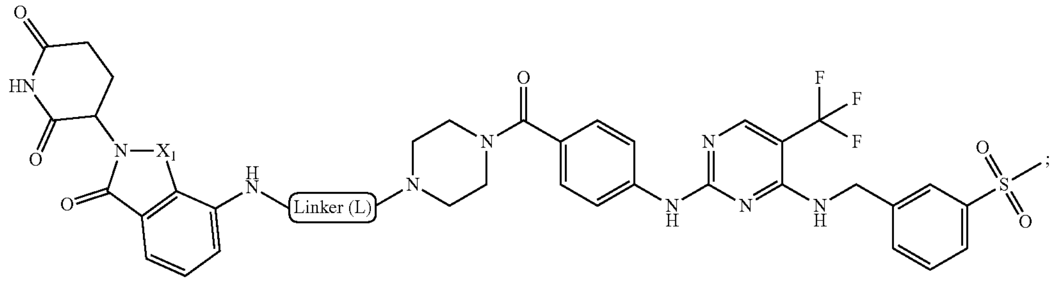
(Ic-1e1)
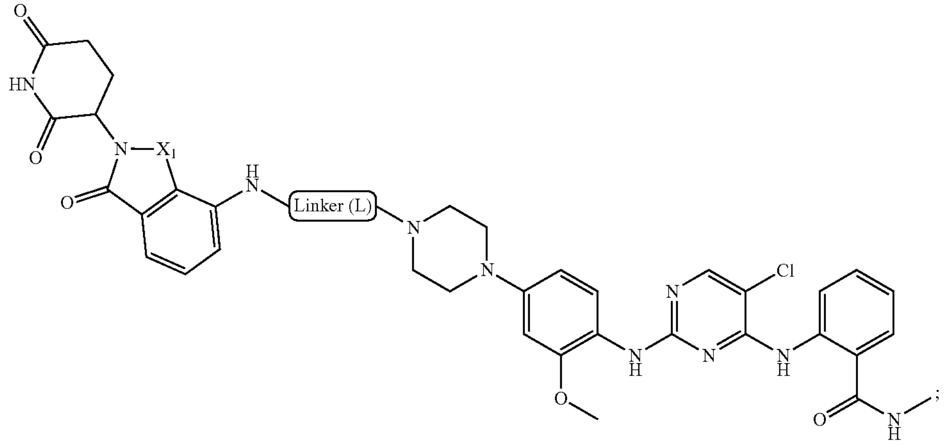
(Ic-1e2)
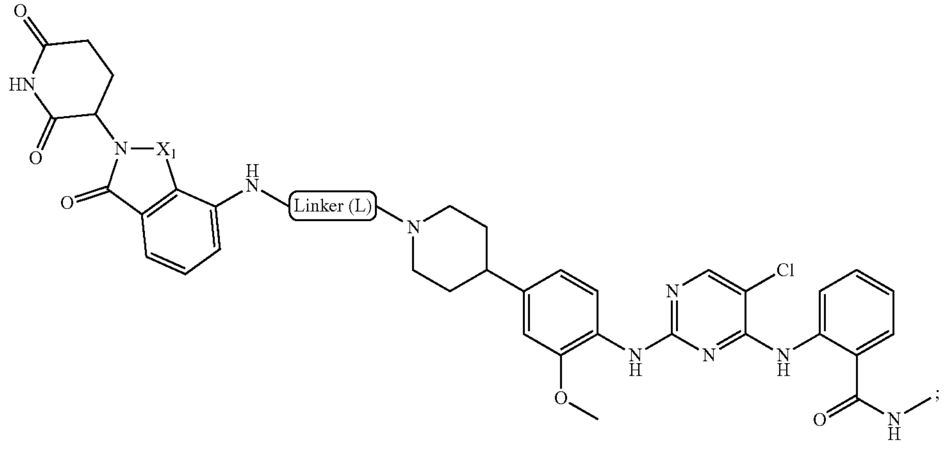

-continued
(Ic-1f)
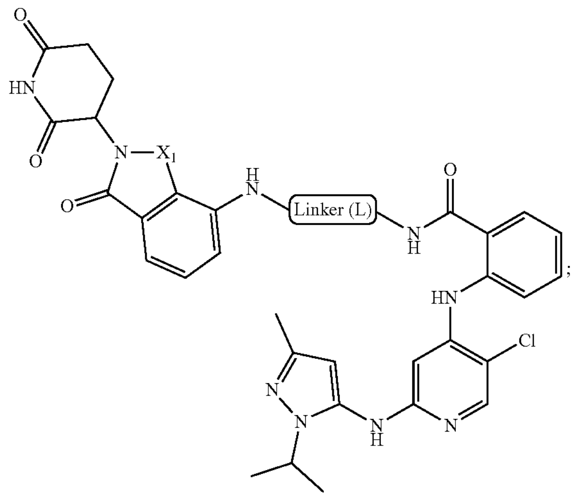
(Id-1)
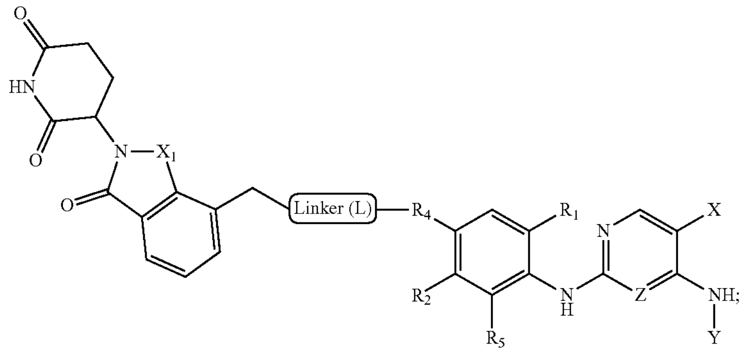
(Id-1a1)
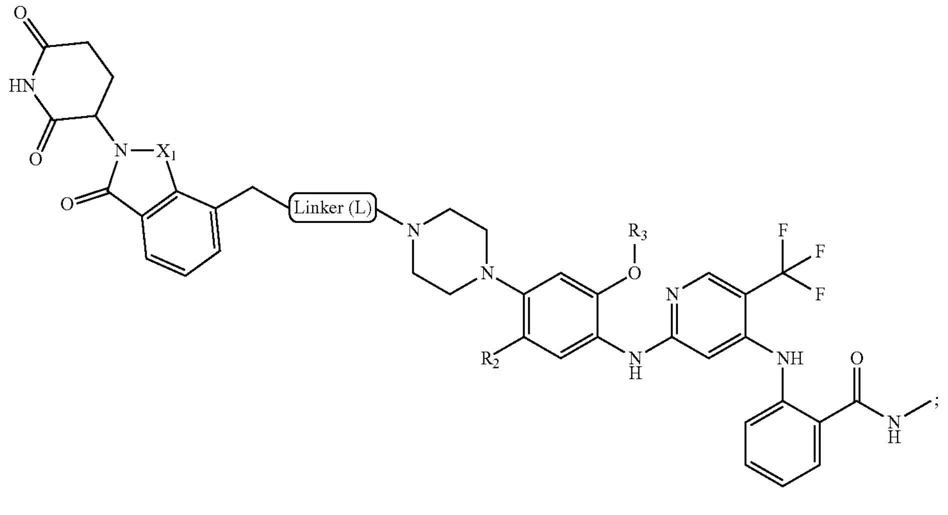

-continued
(Id-1a2)
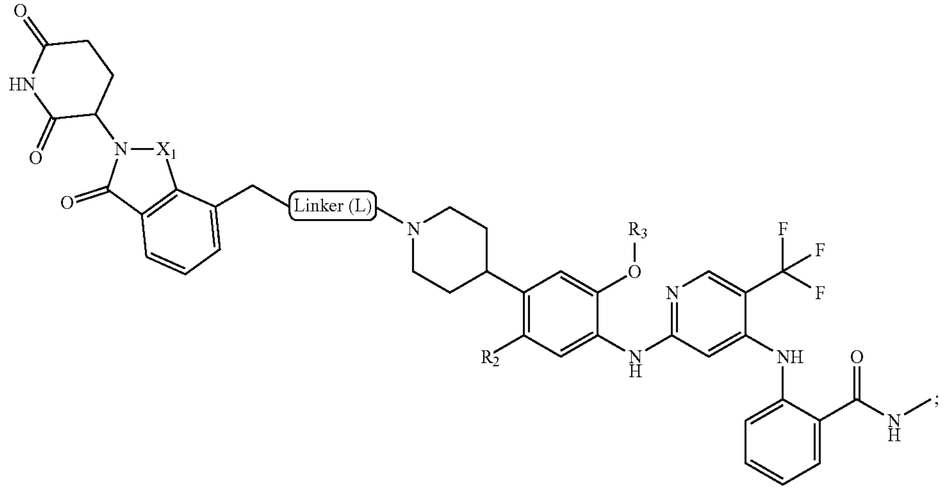
(Id-1b)
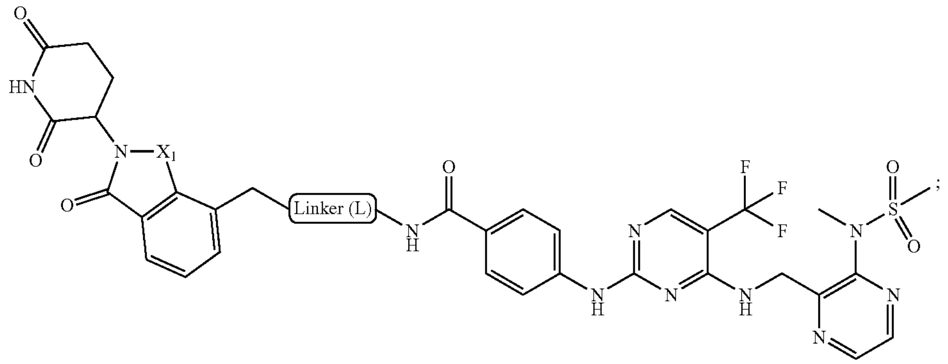
(Id-1c)
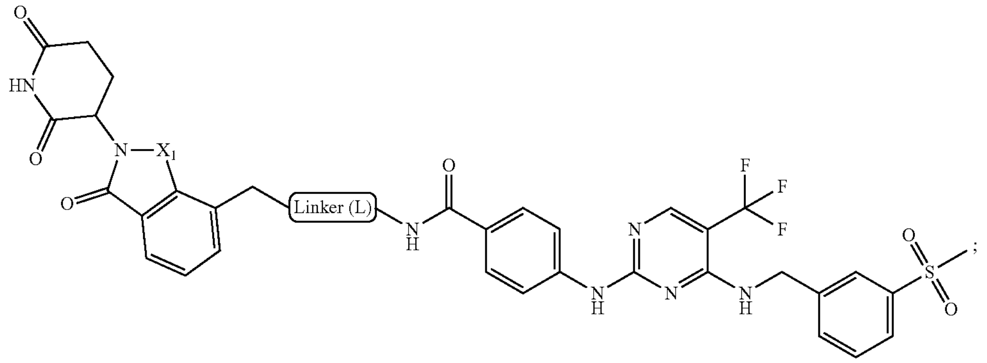
(Id-1d)
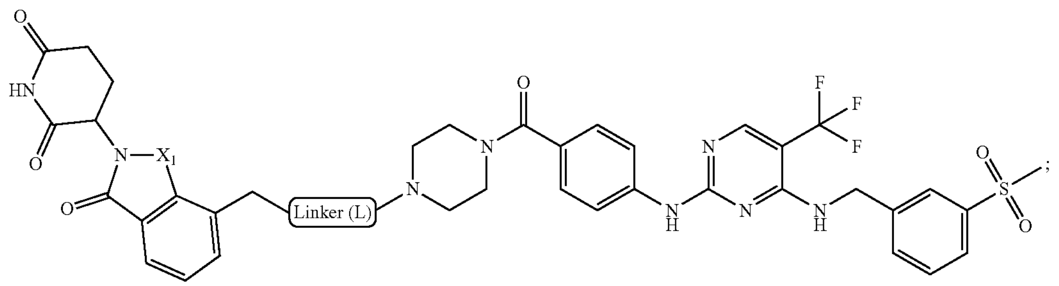

-continued
(Id-1e1)
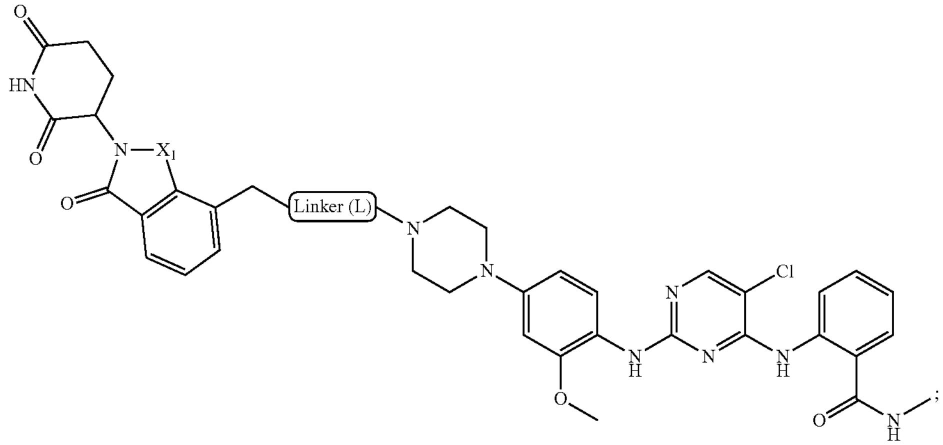
(Id-1e2)
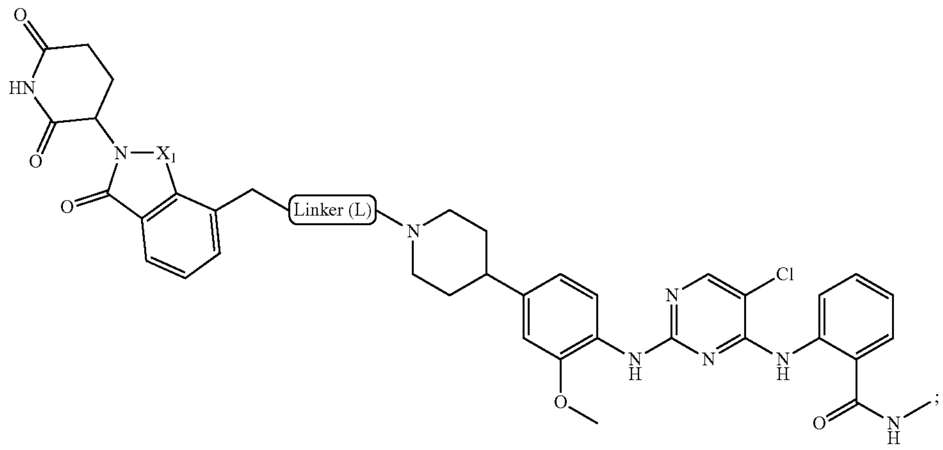
(Id-1f)
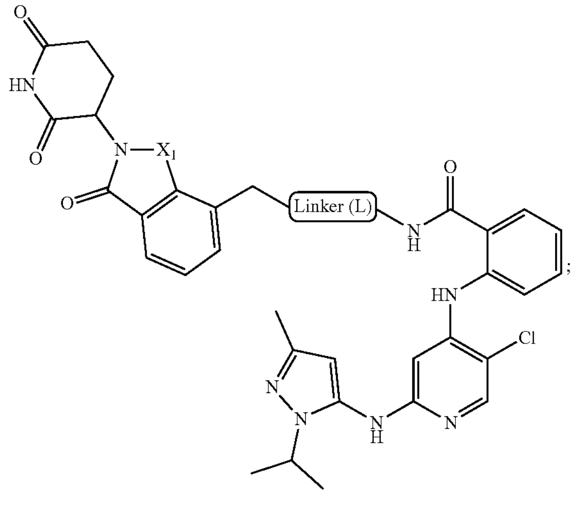

-continued
(Ie-1)
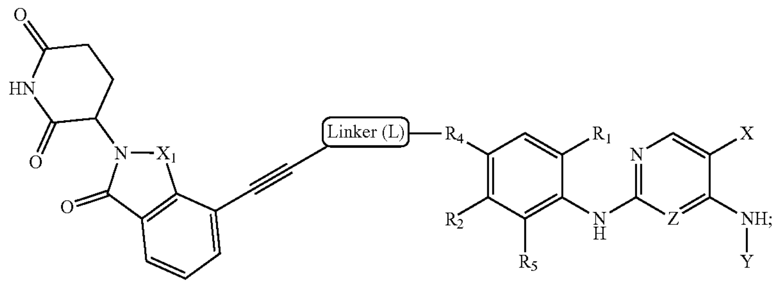
(Ie-1a1)
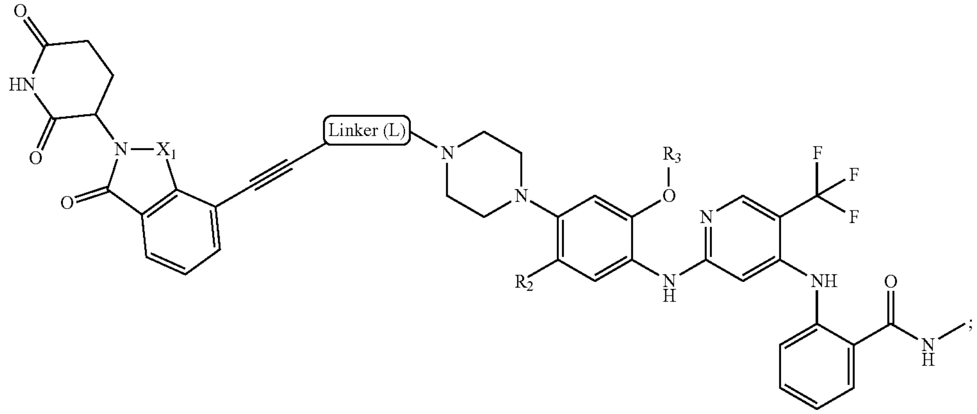
(Ie-1a2)
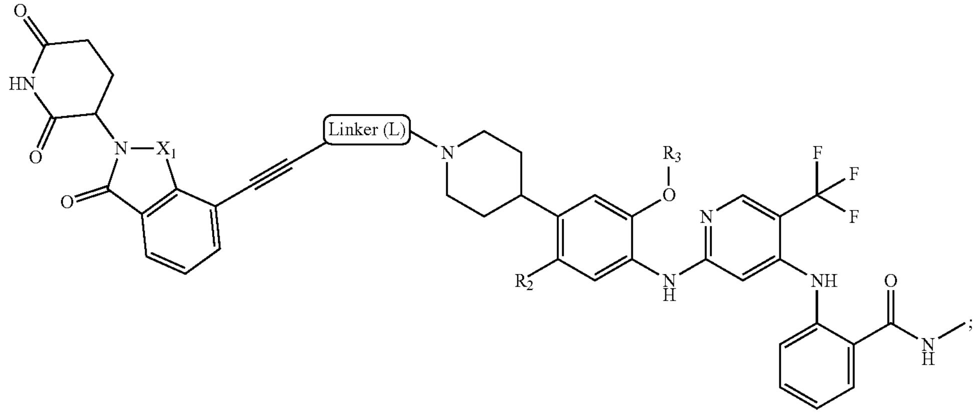
(Ie-1b)
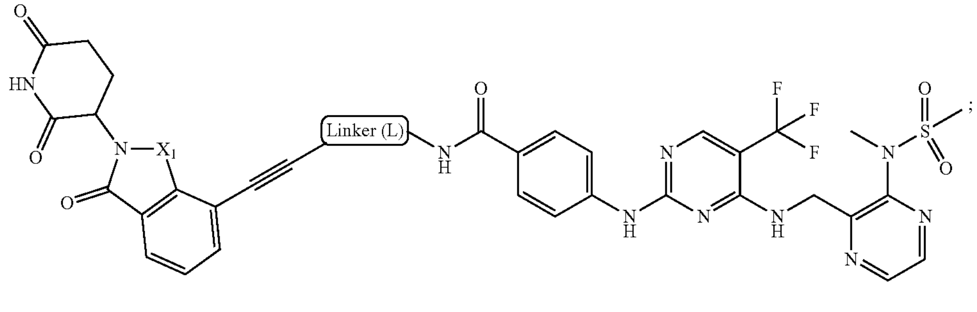

-continued
(Ie-1c)
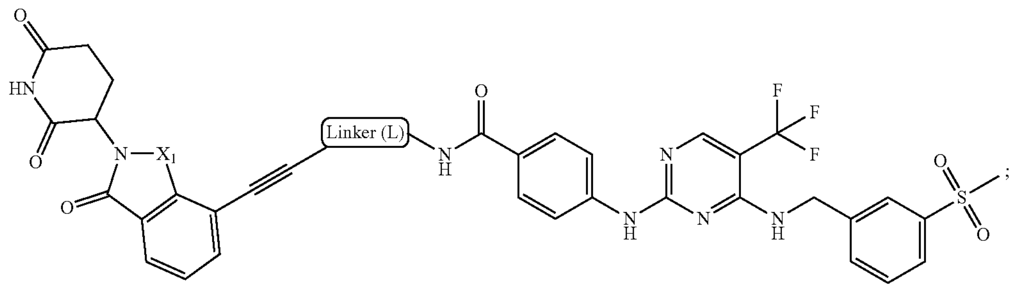
(Ie-1d)
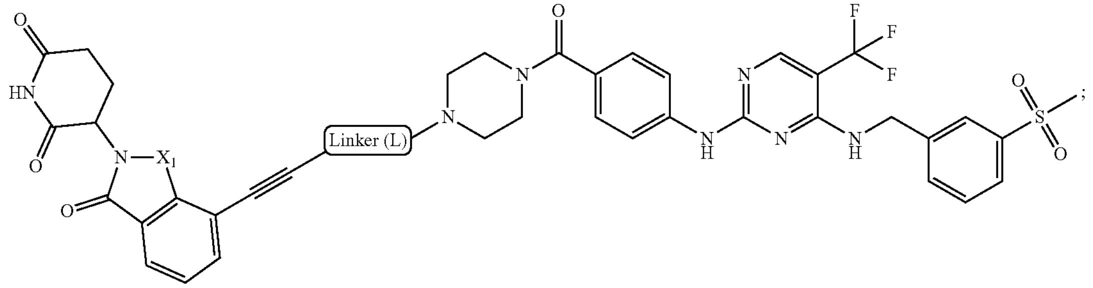
(Ie-1e1)
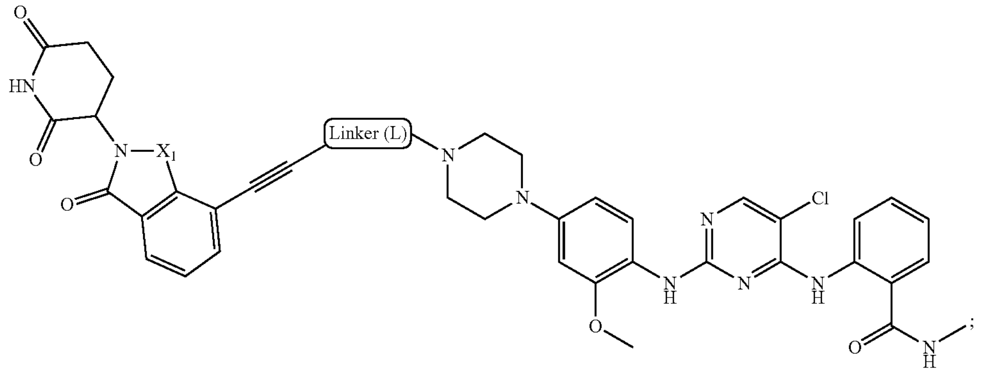
(Ie-1e2)
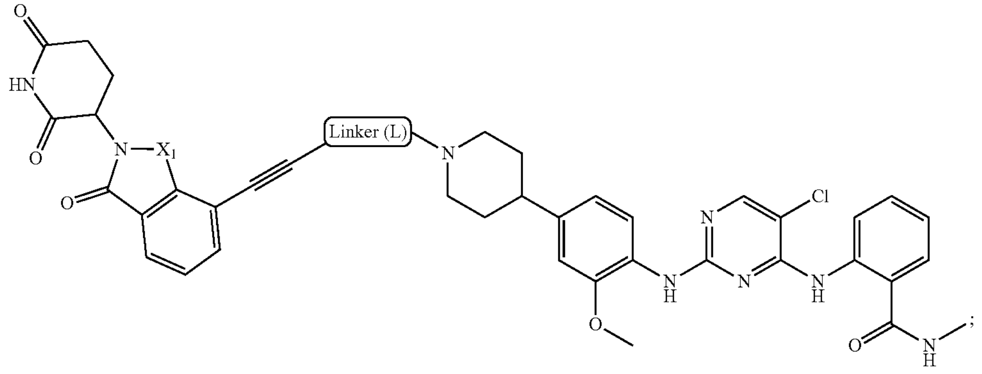
and -continued
(Ie-1f)
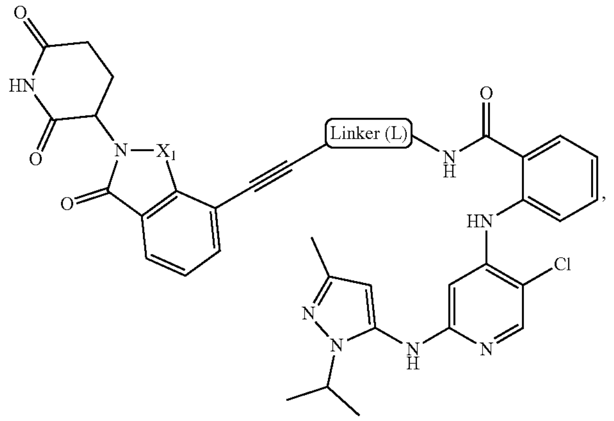
or a pharmaceutically acceptable salt or stereoisomer thereof.
In some embodiments, the E3 ubiquitin ligase that is bound by the degron is the von Hippel-Lindau (VHL) tumor suppressor. See, Iwai et al., Proc. Nat'l. Acad. Sci. USA 96:12436-41(1999).
Representative examples of degrons that bind VHL are as follows:
(D2-a)
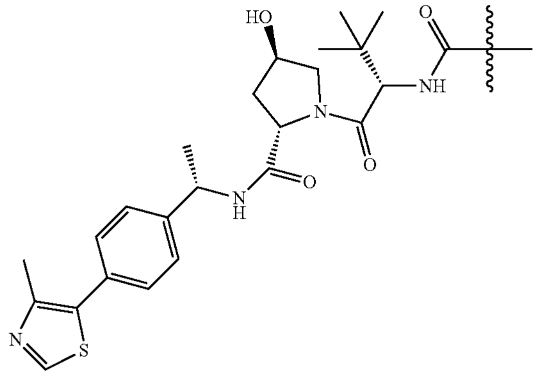
;
(D2-b)
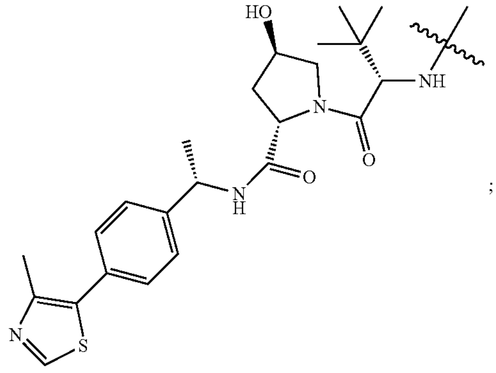
;
-continued
(D2-c)
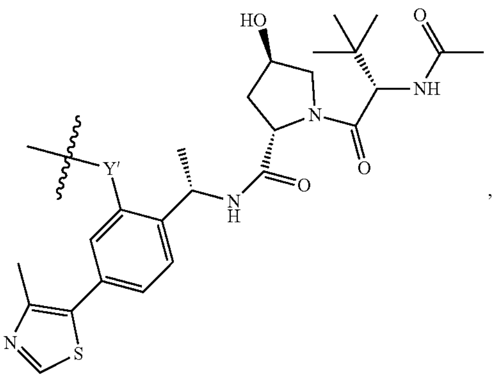
,
wherein Y' is a bond, N, O or C;
(D2-d)
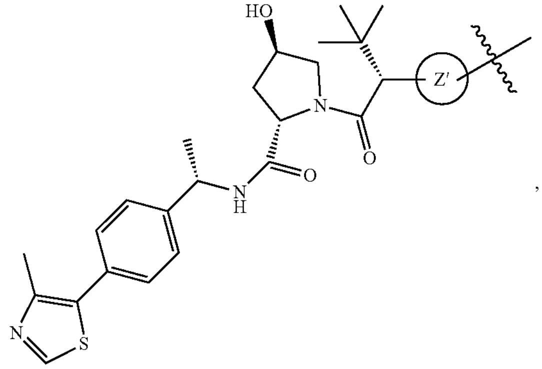
, wherein Z' is a $C_5$-$C_6$ carbocyclic or heterocyclic group, and
(D2-e)
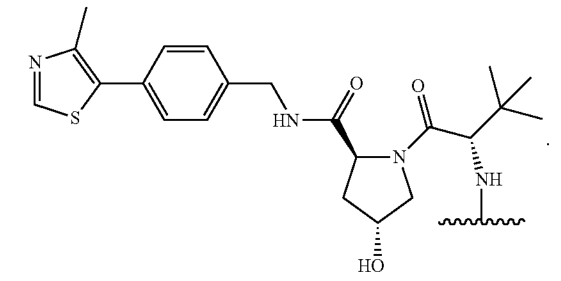
Thus, in some embodiments, the bifunctional compounds of the present invention are represented by any of the following structures:
(If)
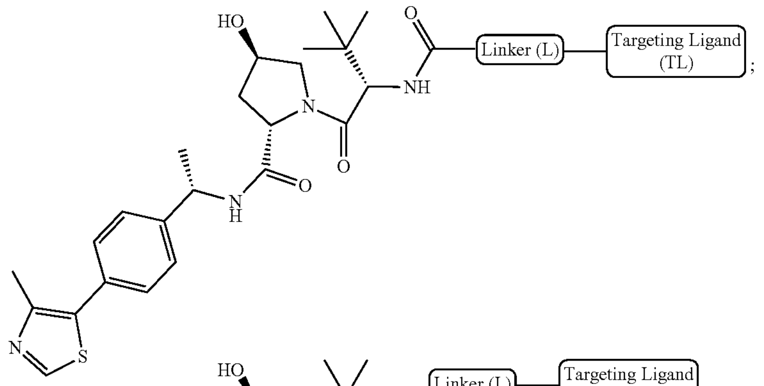
(Ig)
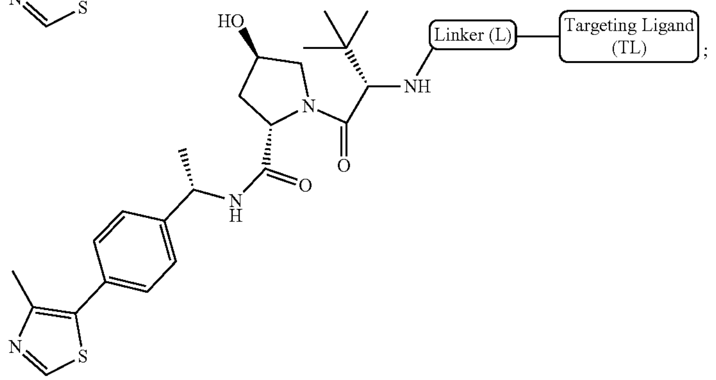
(Ih)
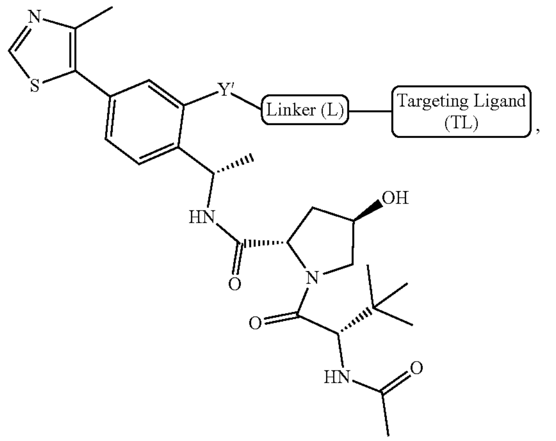

wherein Y' is a bond, N, O or C;
(Ii)
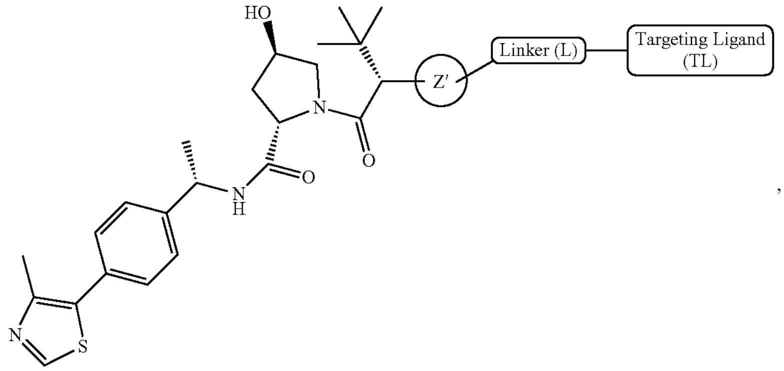
,
wherein Z' is a $C_5$-$C_6$ carbocyclic or heterocyclic group; and
(Ij)
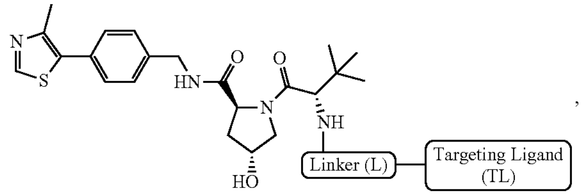
,
or a pharmaceutically acceptable salt or stereoisomer thereof.
In some embodiments, the bifunctional compounds of the present invention are represented by any of the following structures:
(If-1)
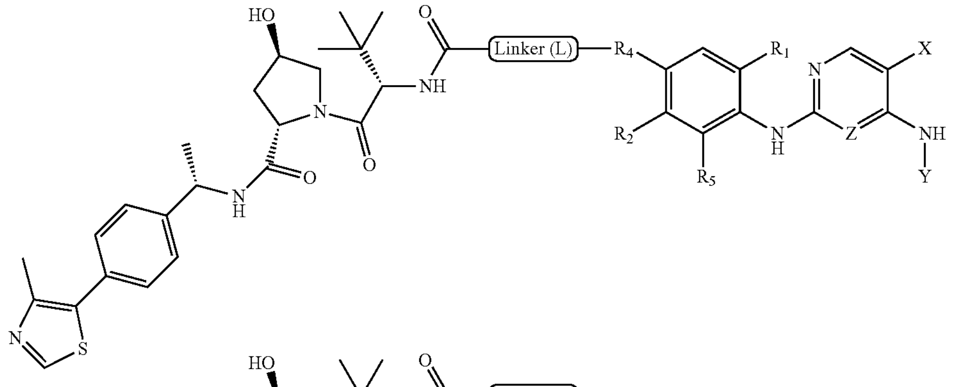
(If-1a1)
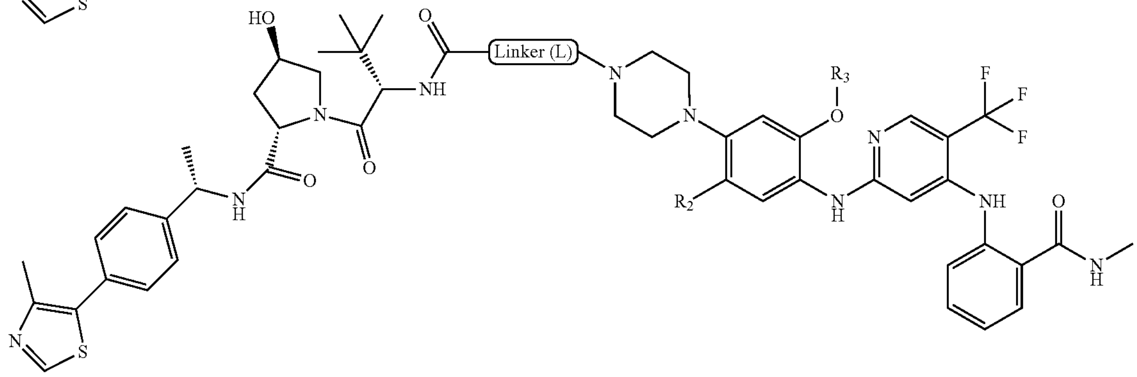
;

-continued
(If-1a2)
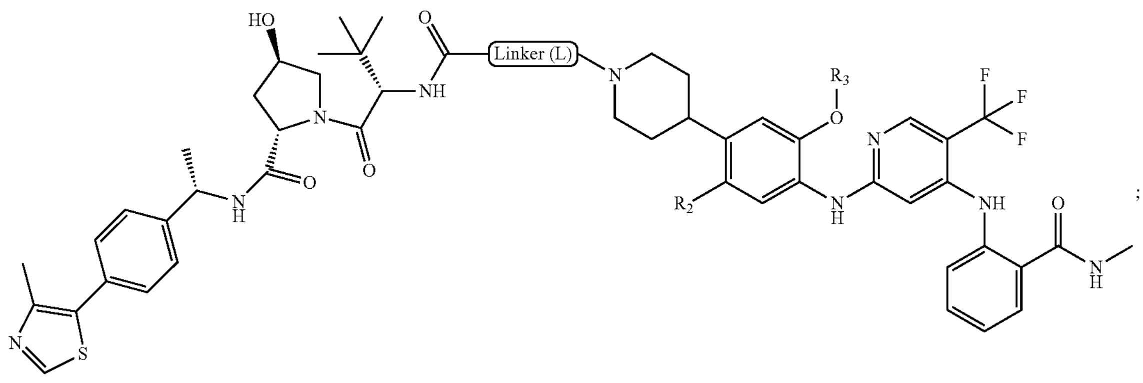
;
(If-1b)
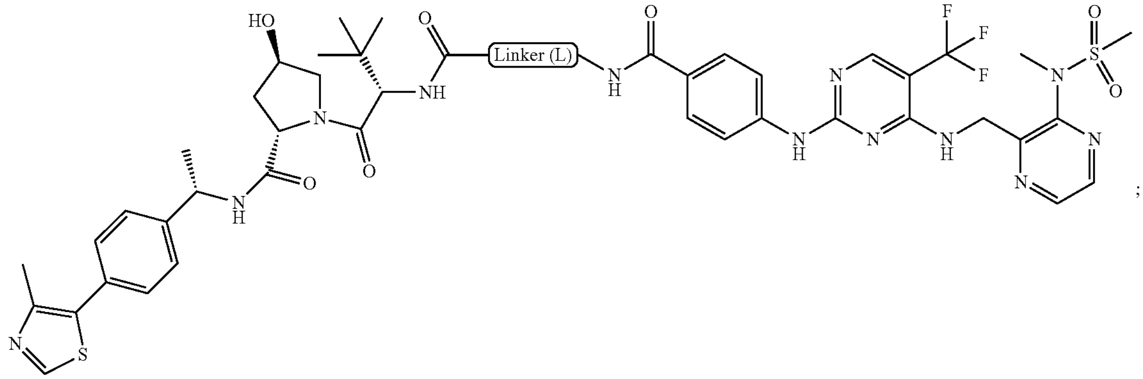
;
(If-1c)
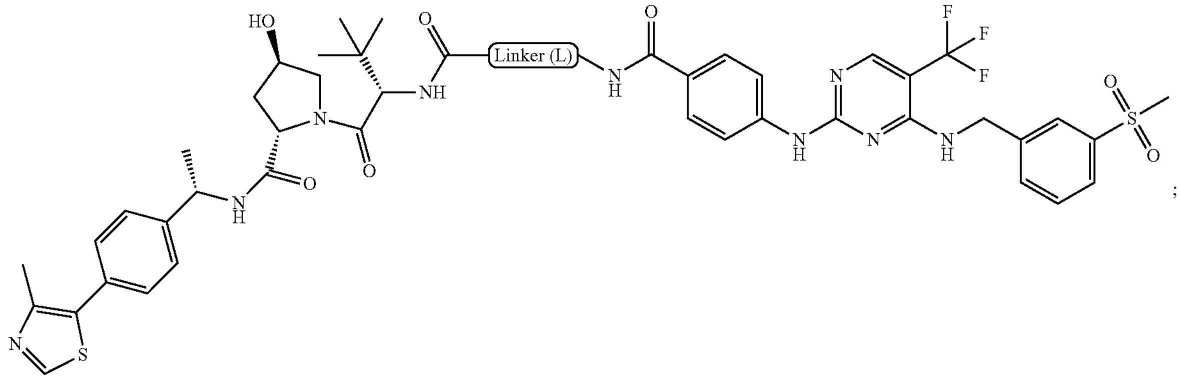
;
(If-1d)
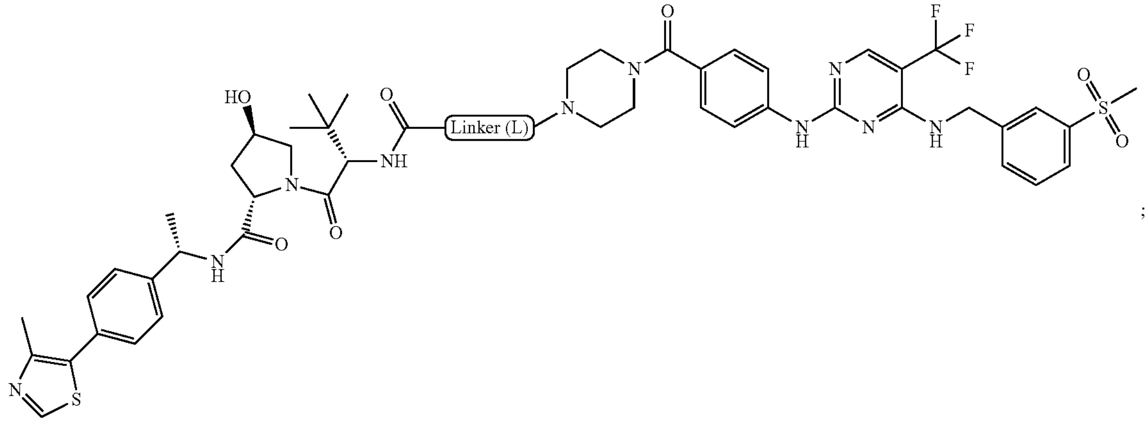
;

-continued
(If-1e1)
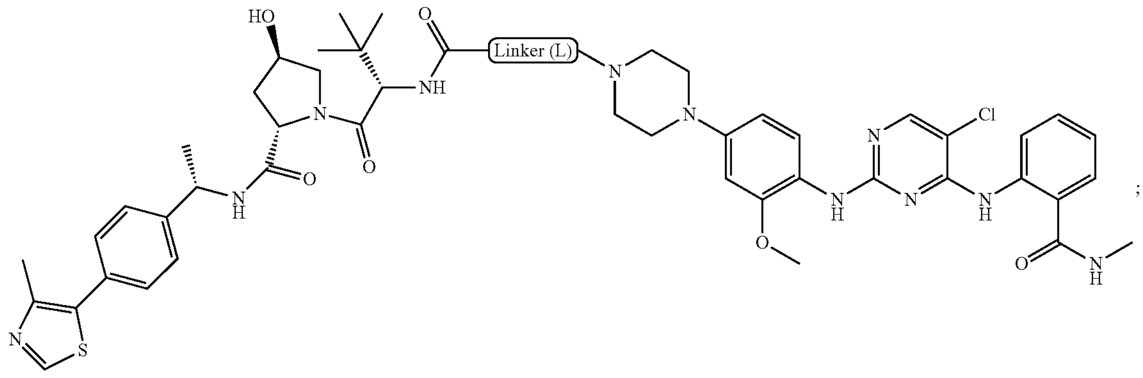
;
(If-1e2)
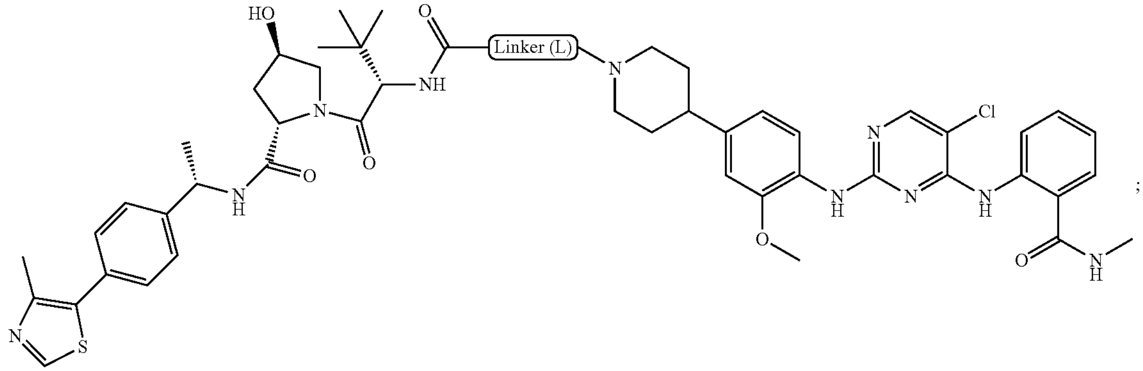
;
(If-1f)
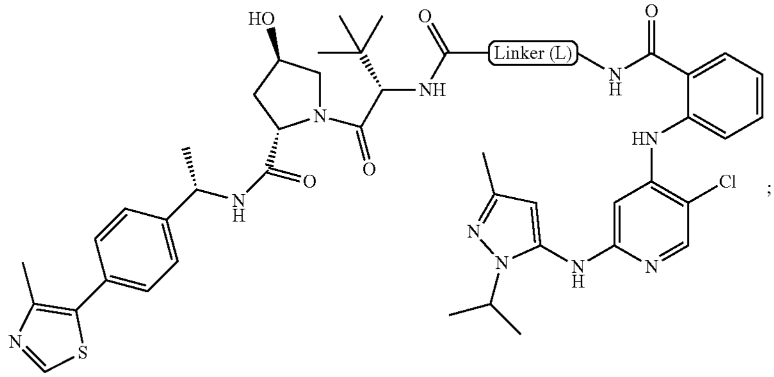
;
(Ig-1)
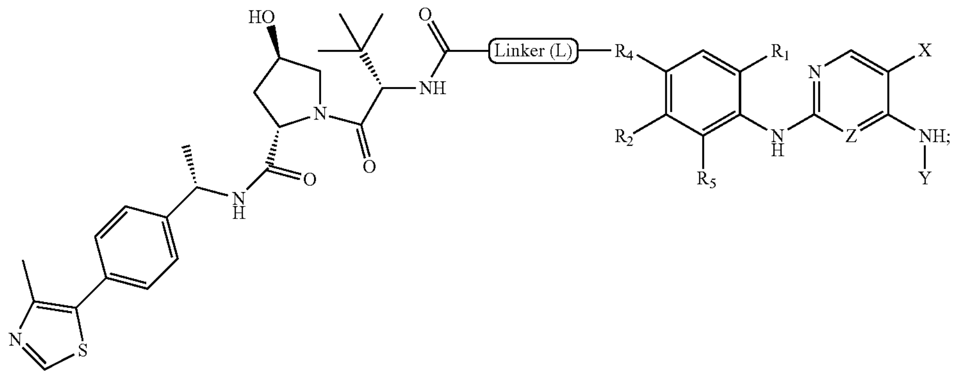

-continued
(Ig-1a1)
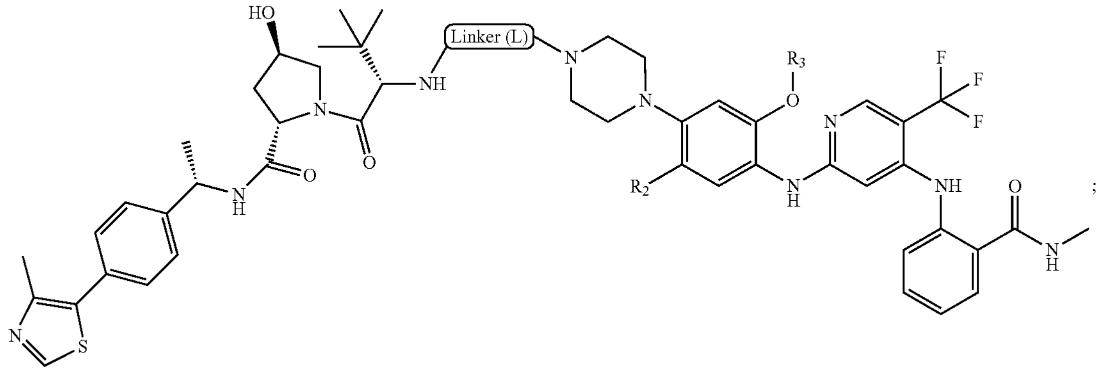
;
(Ig-1a2)
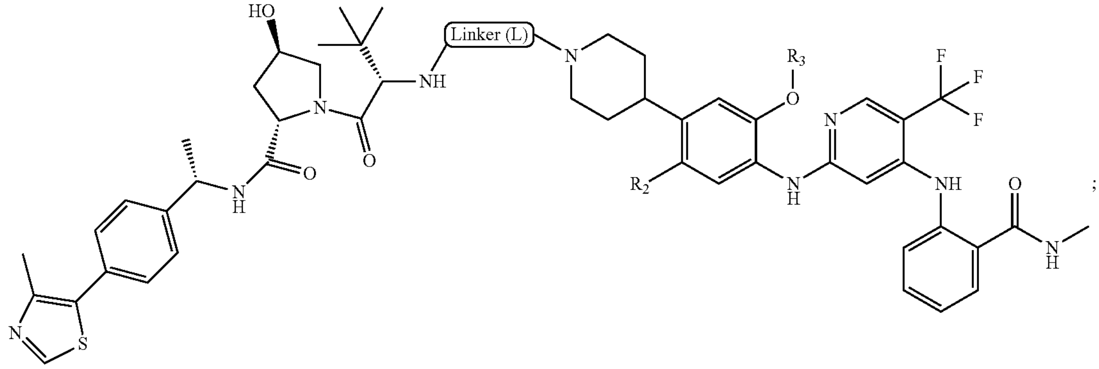
;
(Ig-1b)
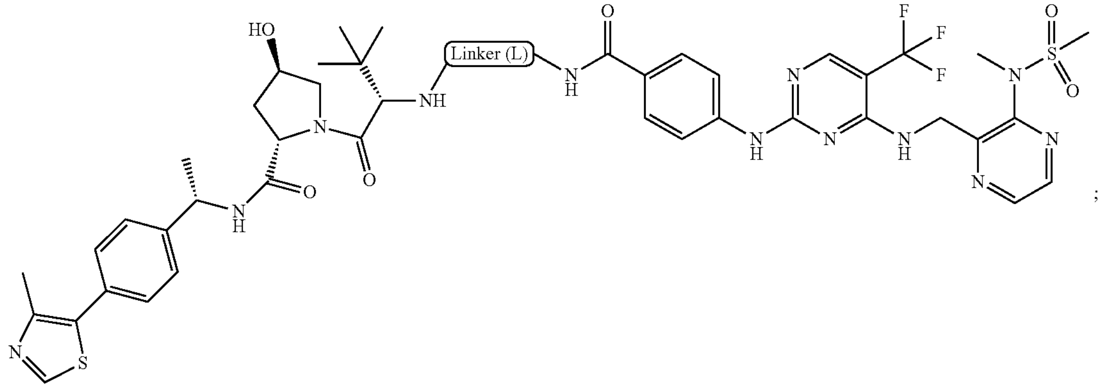
;
(Ig-1c)
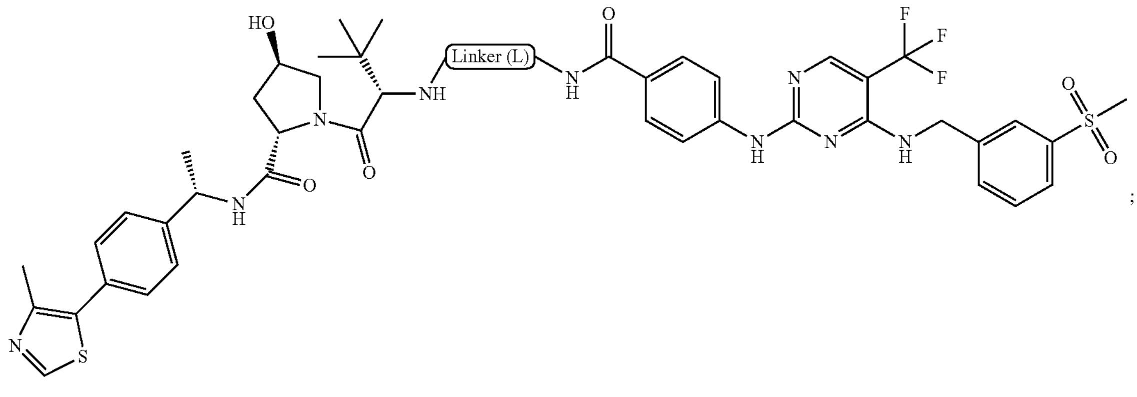
;

-continued
(Ig-1d)
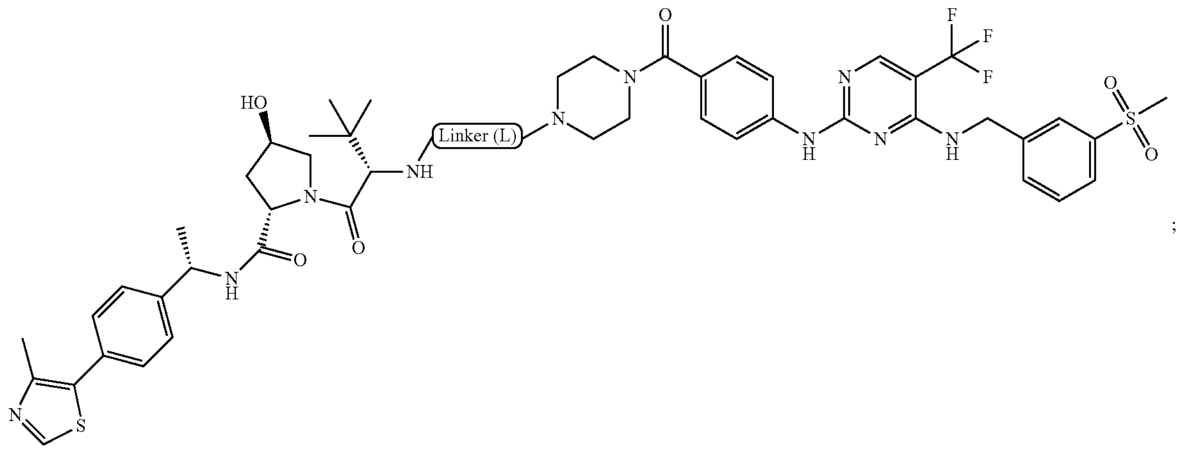
;
(Ig-1e1)
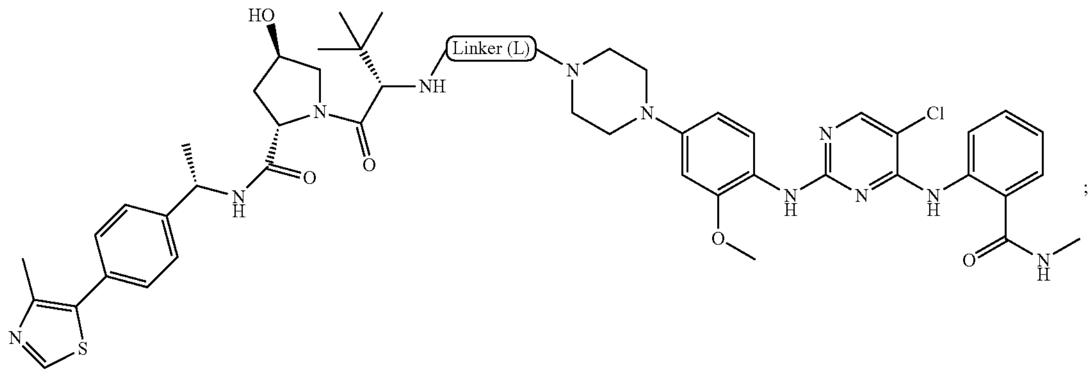
;
(Ig-1e2)
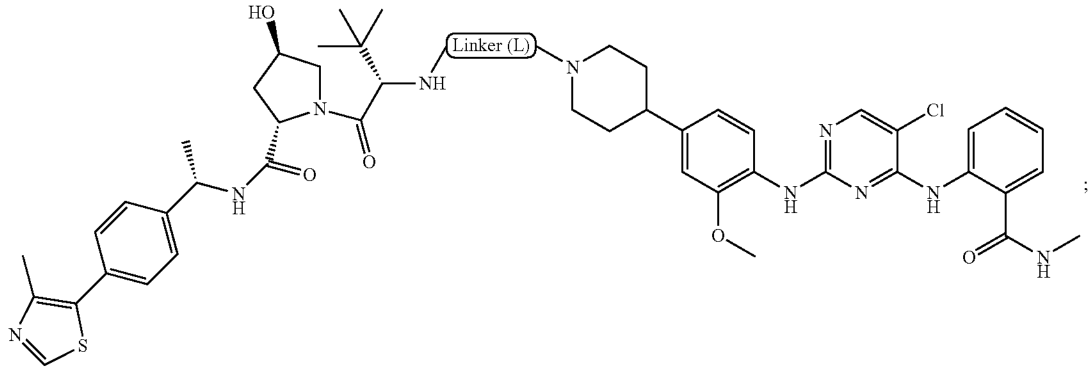
;
(Ig-1f)
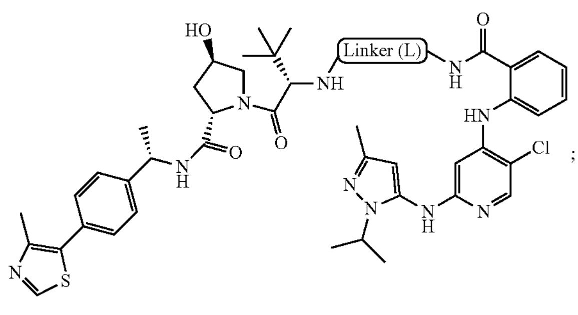
;
(Ih-1)
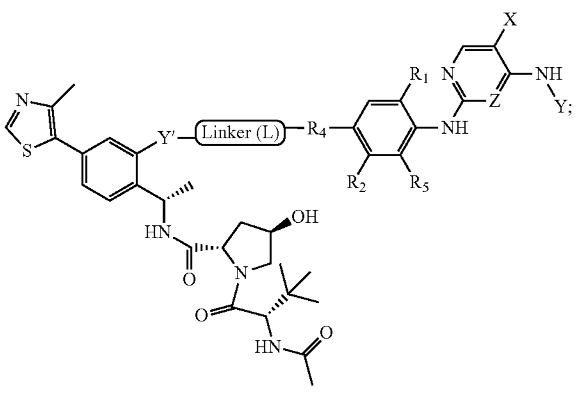

-continued
(Ih-1a1)
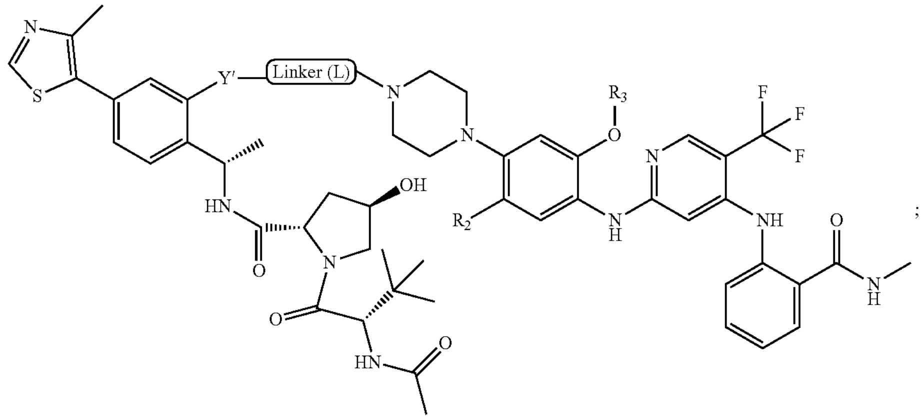
;
(Ih-1a2)
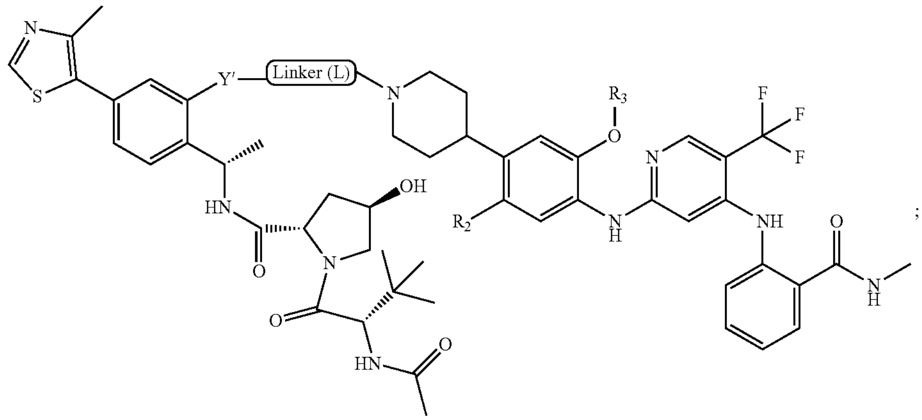
;
(Ih-1b)
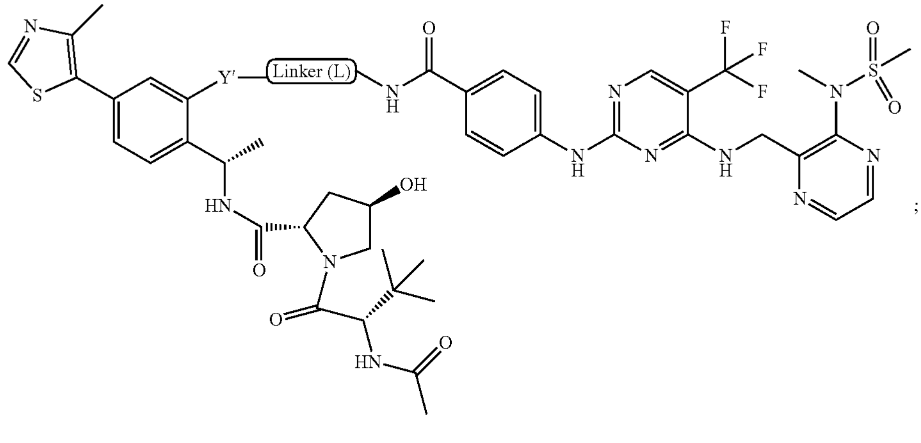
;

-continued
(Ih-1c)
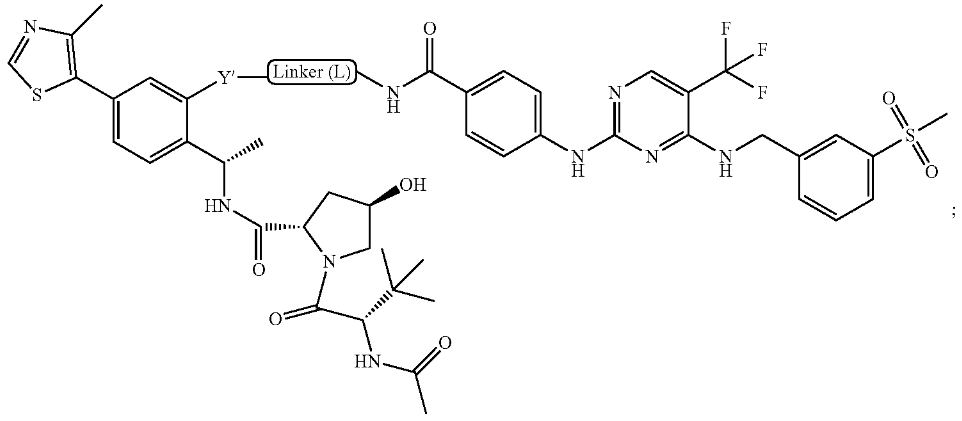
;
(Ih-1d)
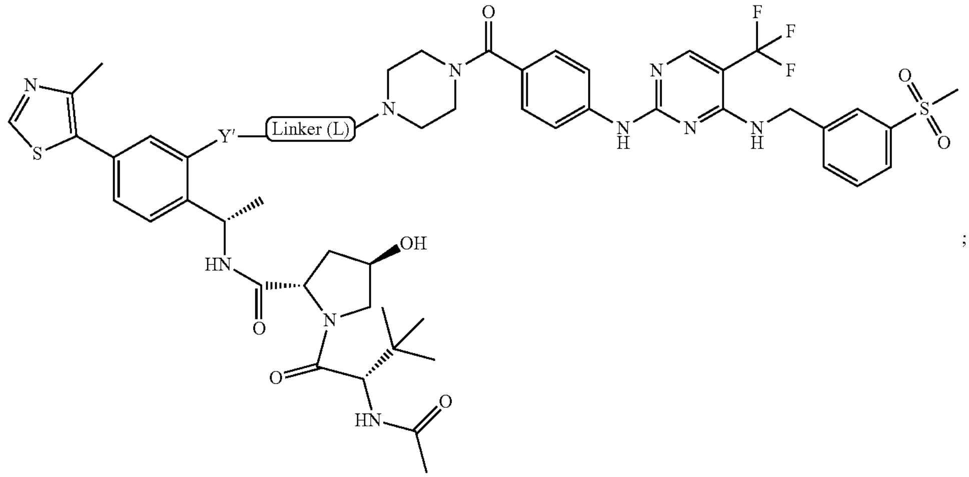
;
(Ih-1e1)
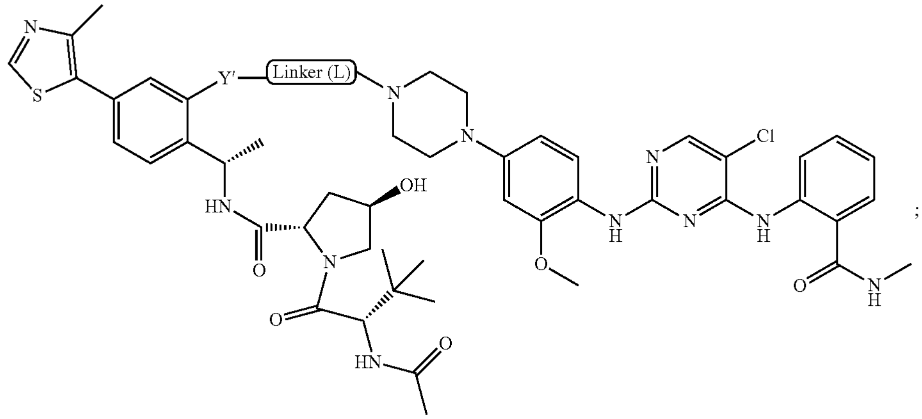
;

-continued
(Ih-1e2)
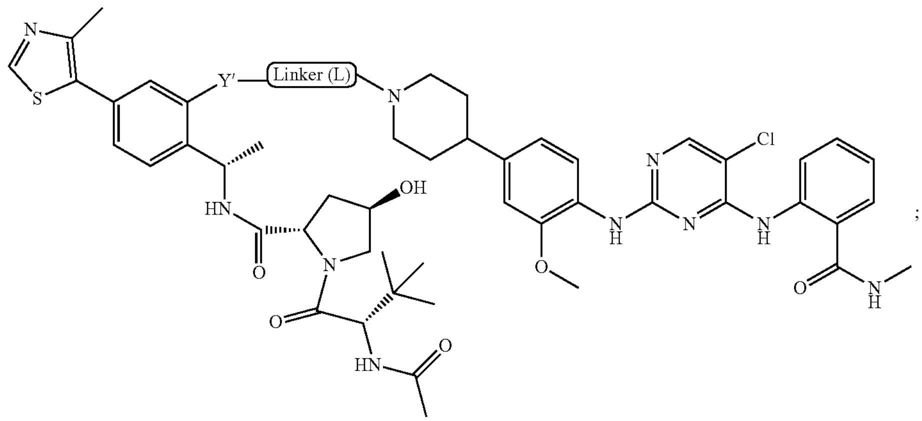
;
(Ih-1f)
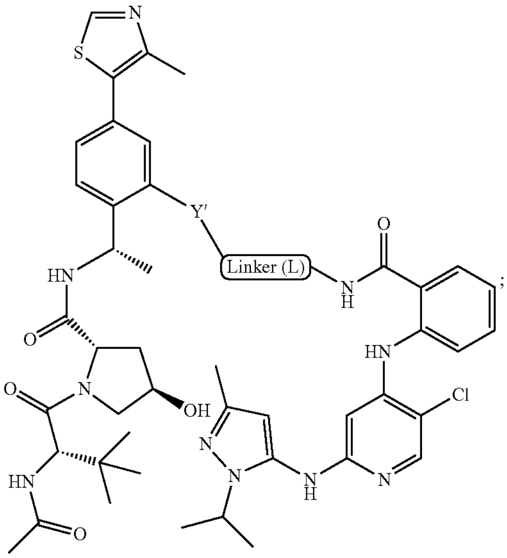
;
(Ii-1)
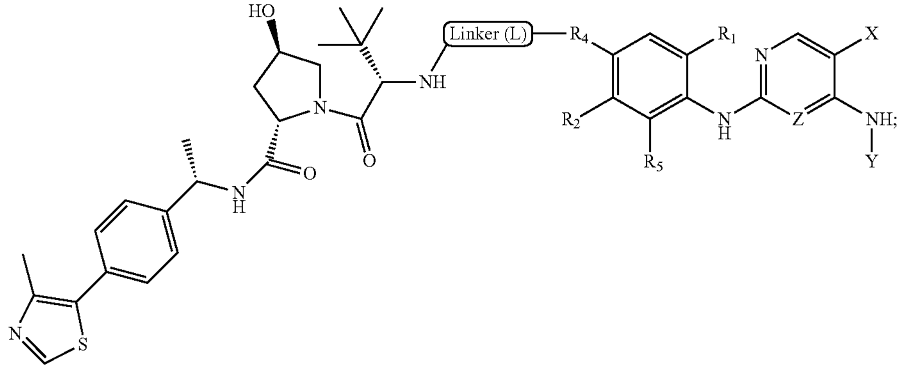
;

-continued
(Ii-1a1)
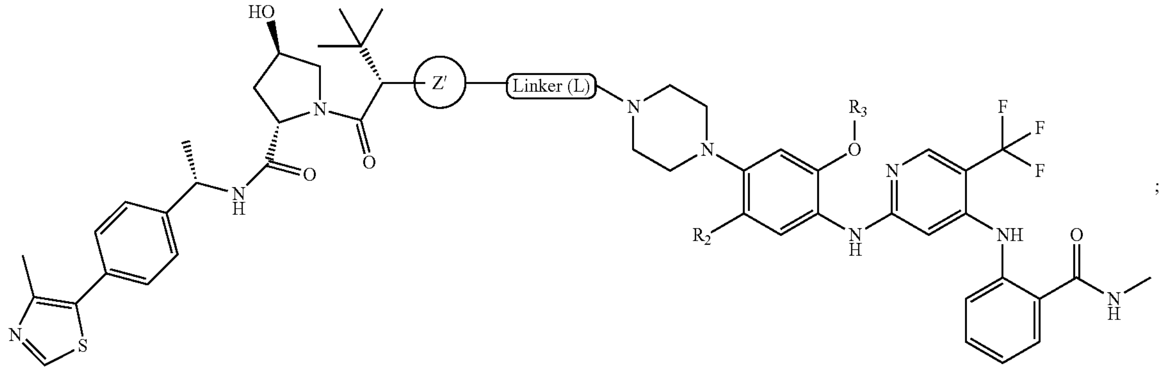
;
(Ii--1a2)
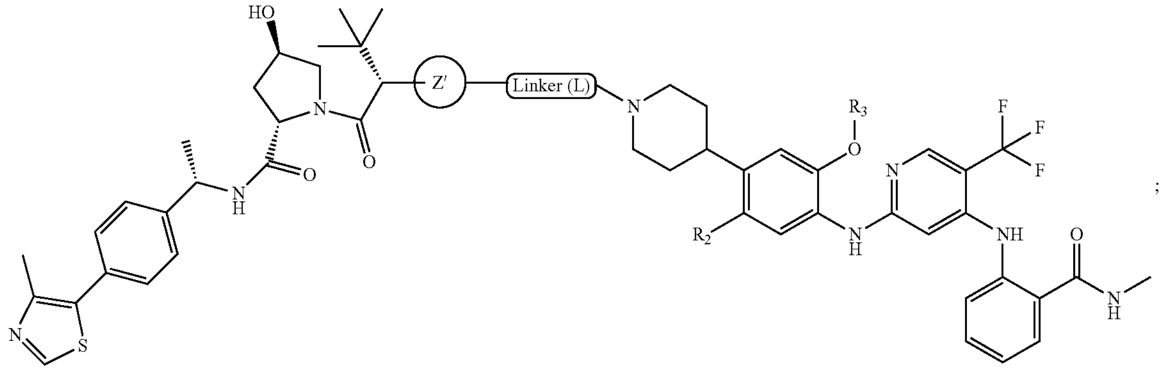
;
(Ii-1b)
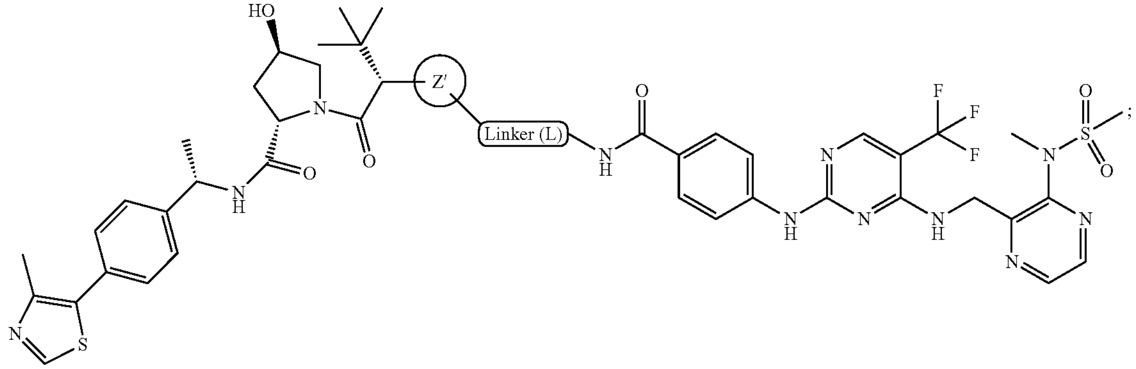
;
(Ii--1c)
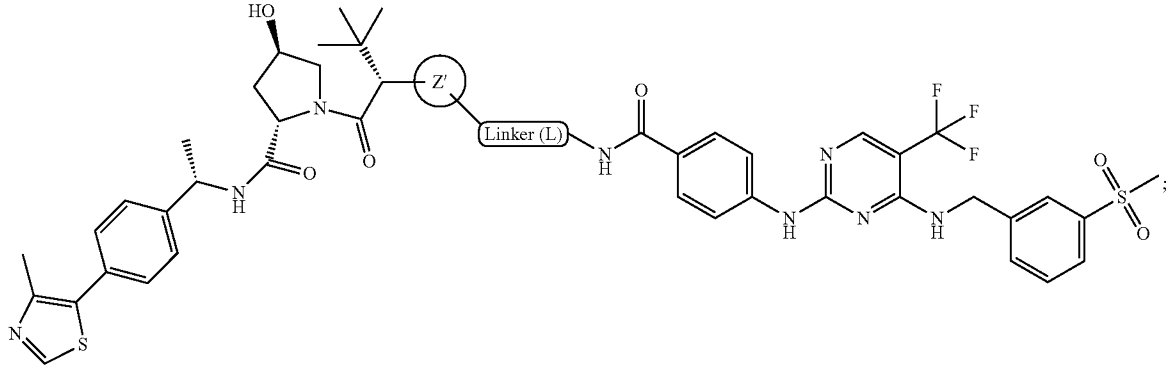
;

-continued
(Ii-1d)
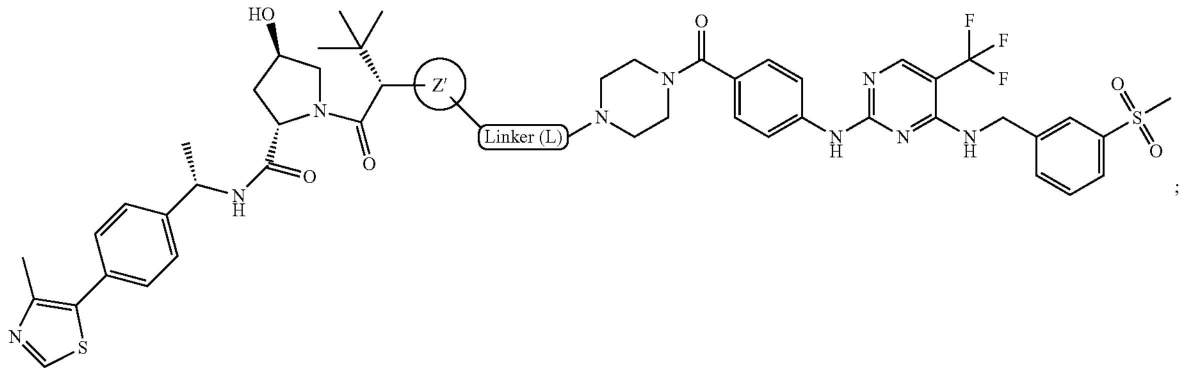
;
(Ii-1e1)
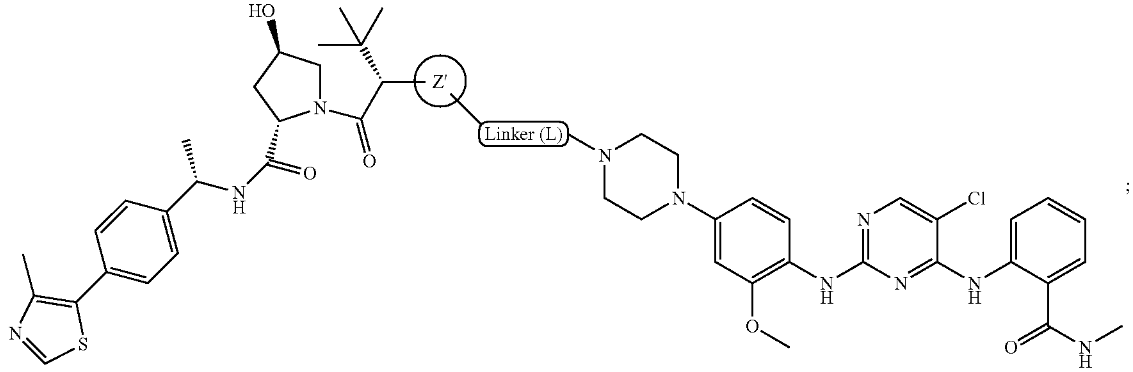
;
(Ii-1e2)
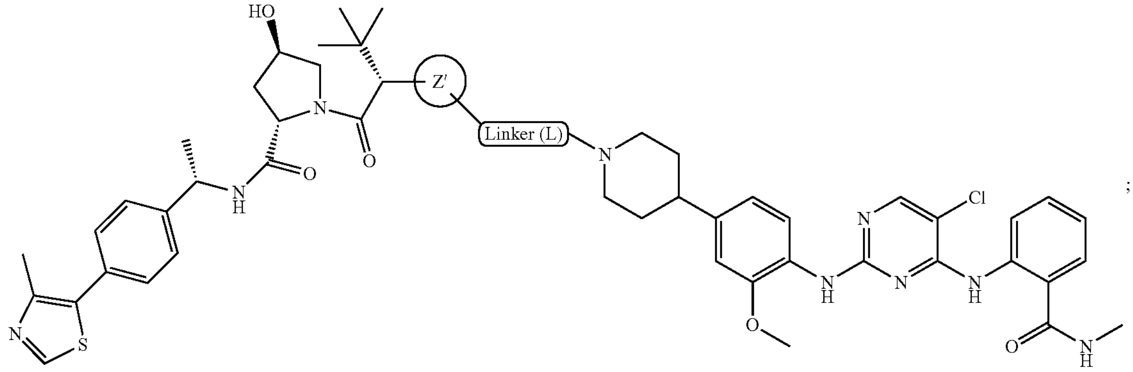
;
(Ii-1f)
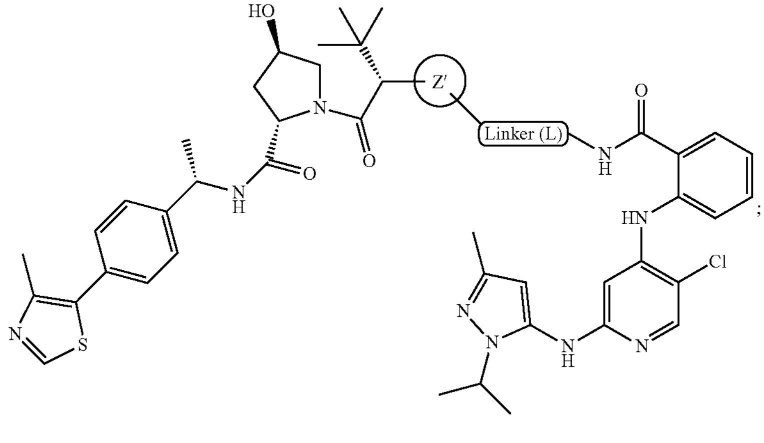
;

-continued
(Ij-1)
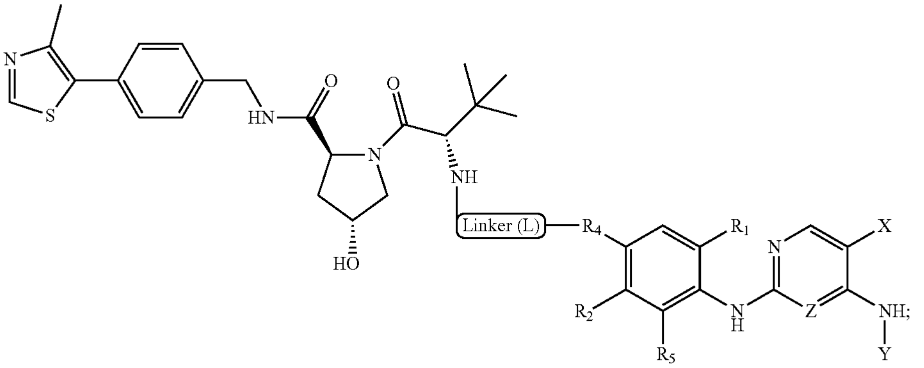
(Ij-1a1)
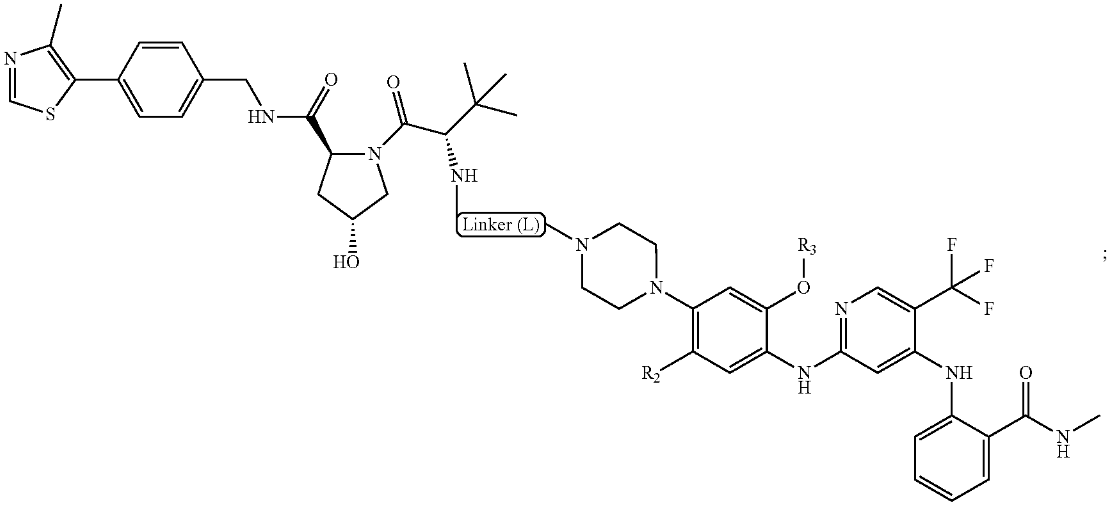
;
(Ij-1a2)
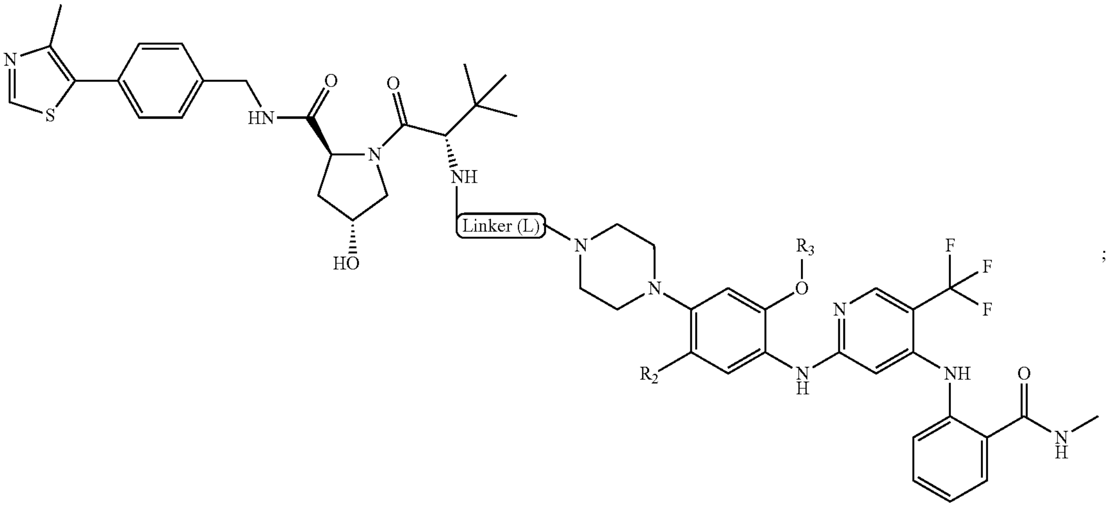
;

-continued
(Ij-1b)
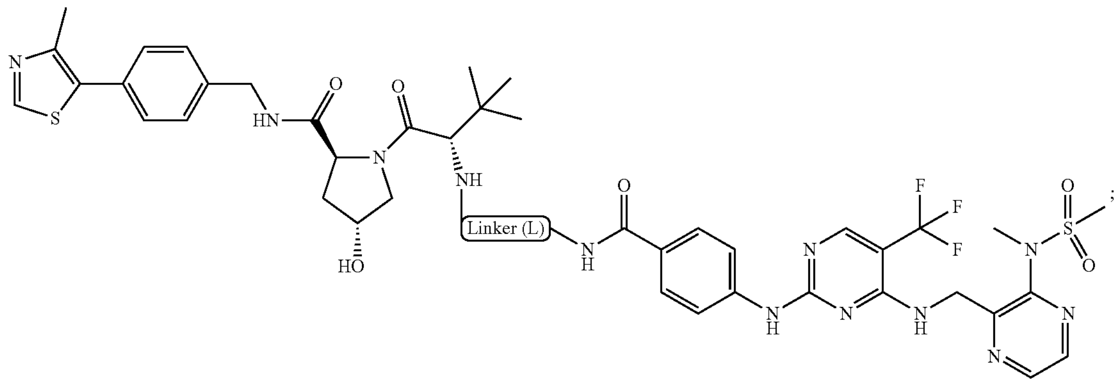
;
(Ij-1c)
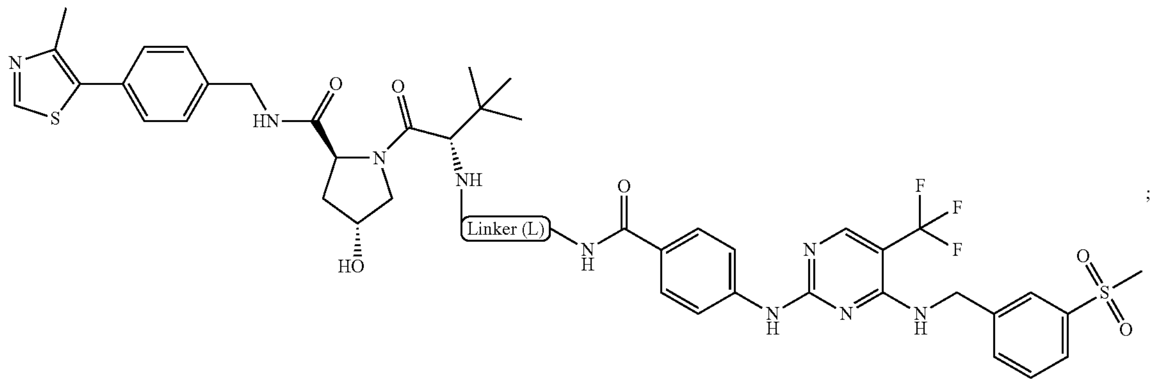
;
(Ij-1d)
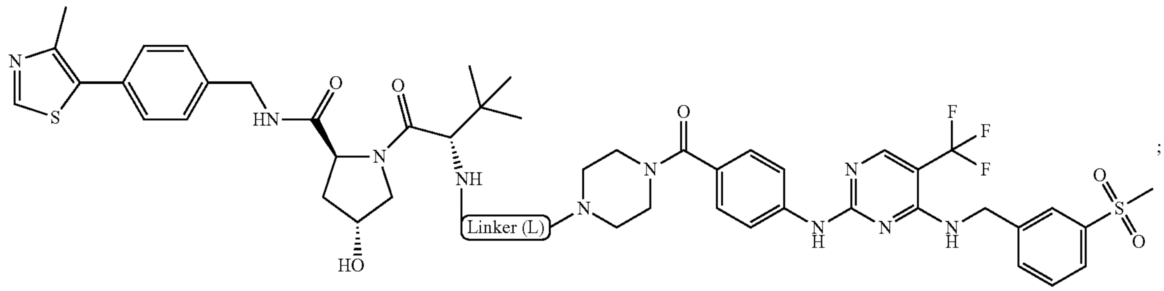
;
(Ij-1e1)
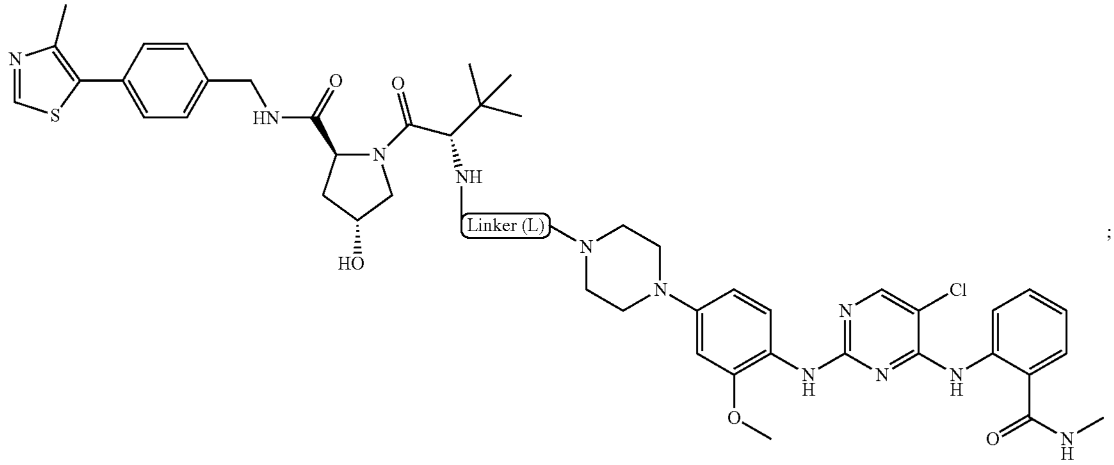
;

-continued (Ij-1e2)

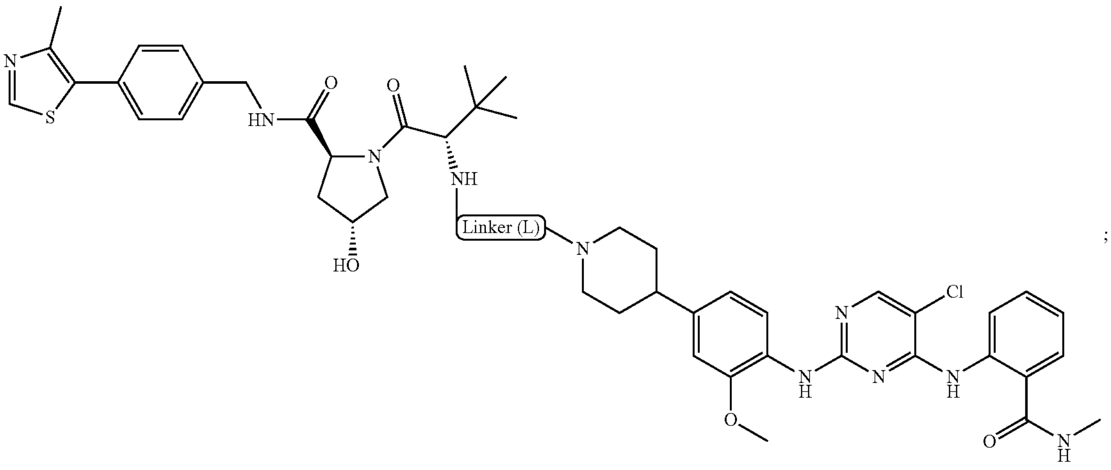

; and (Ij-1f)

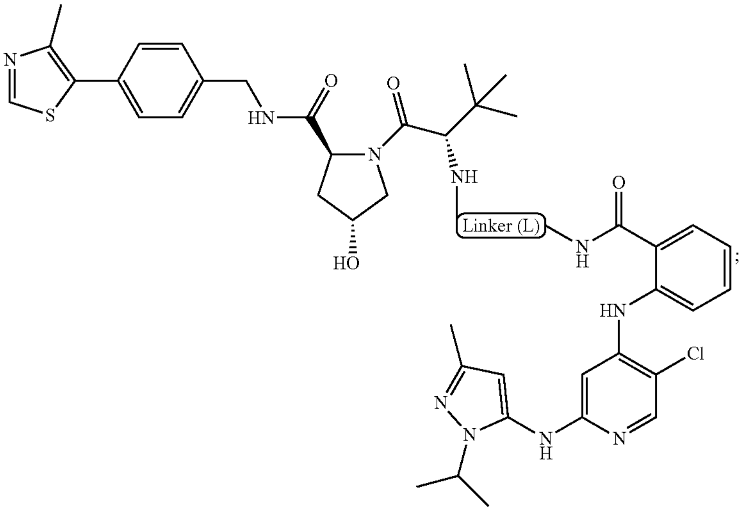

;

wherein Y' is a bond, N, O or C and Z' is a $C_5$-$C_6$ carbocyclic or heterocyclic group, or a pharmaceutically acceptable salt or stereoisomer thereof.

Yet other degrons that bind VHL and which may be suitable for use in the present invention are disclosed in U.S. Patent Application Publication 2017/0121321 A1.

Thus, in some embodiments, the bifunctional compounds of this invention are represented by any structures generated by the combination of structures TL to TL4, L1 to L10, and the structures of the degrons described herein, including D1-a to D1-d and D2a to D2-e, or a pharmaceutically acceptable salt or stereoisomer thereof.

In some embodiments, the bifunctional compounds of the present invention are represented by any of the following structures:

(1)
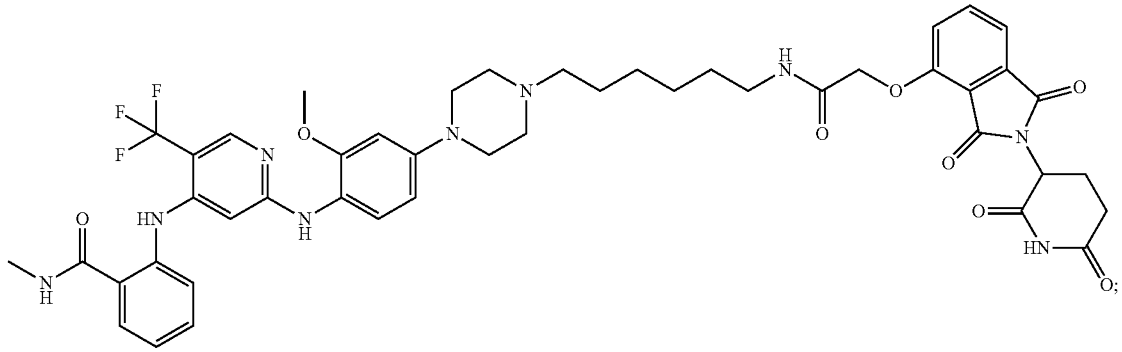
(3)
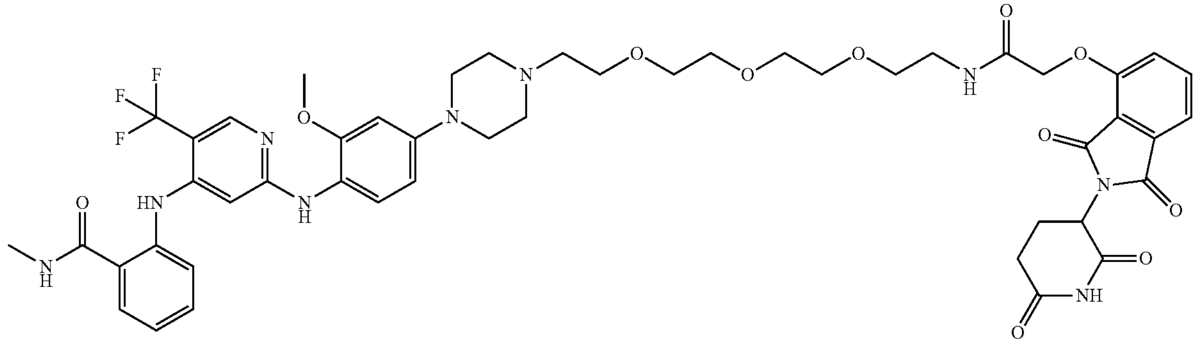
(4)
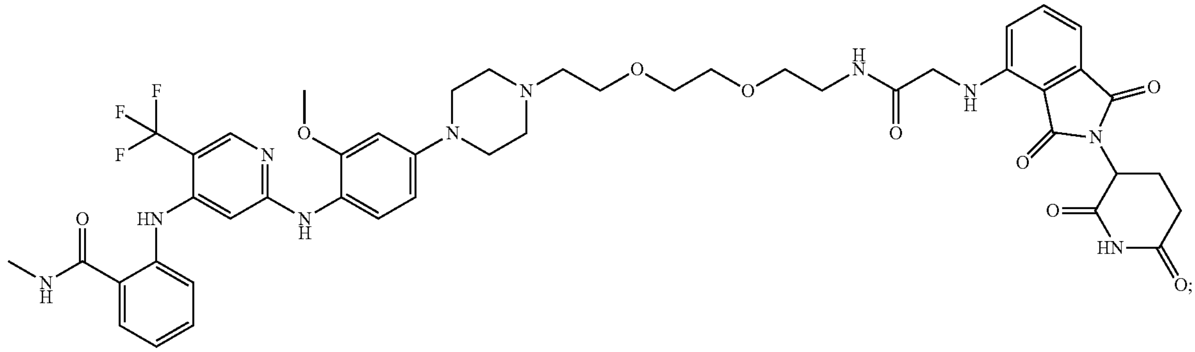
(5)
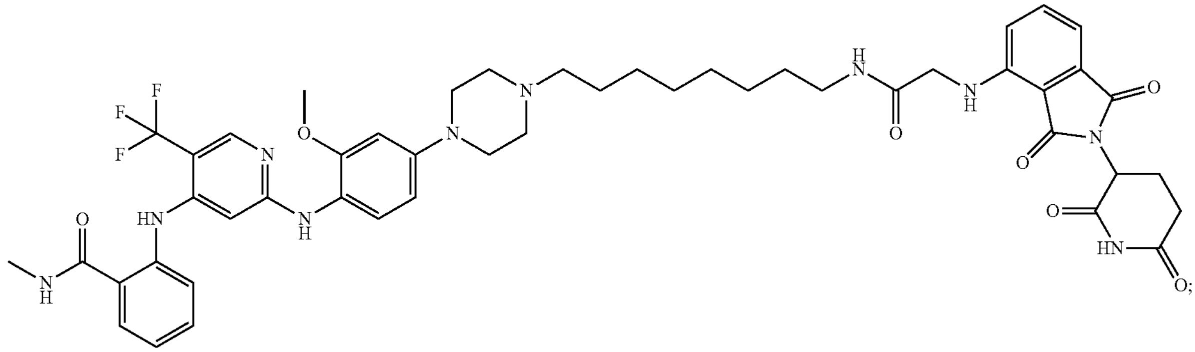

-continued
(6)
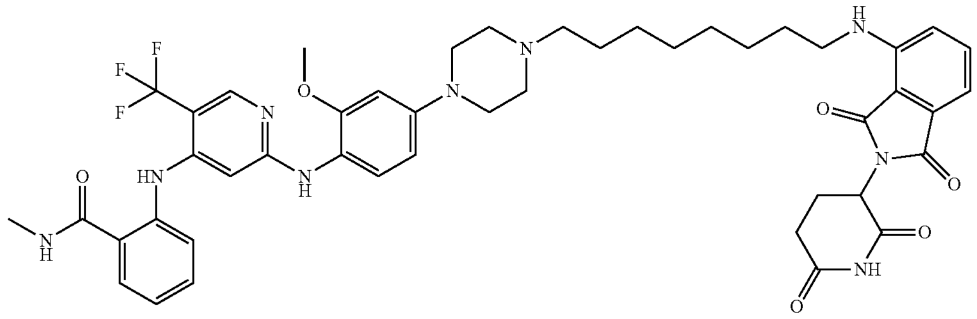
;
(7)
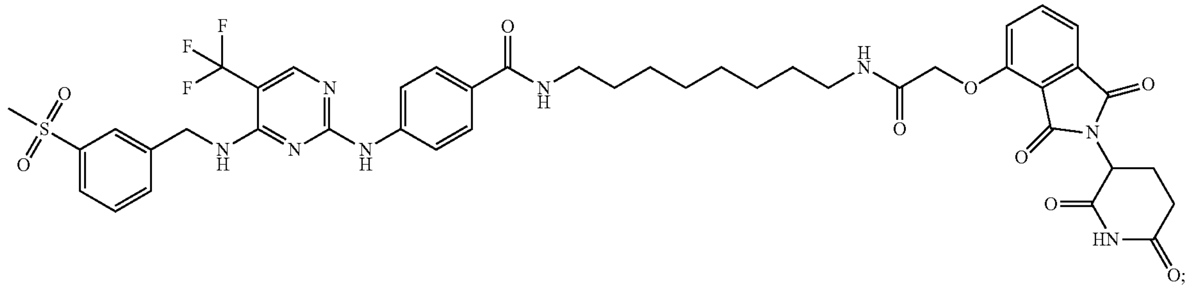
;
(8)
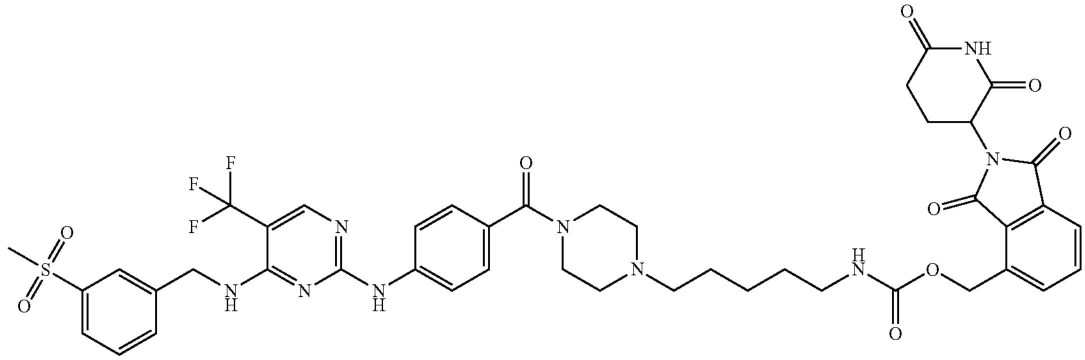
;
(9)
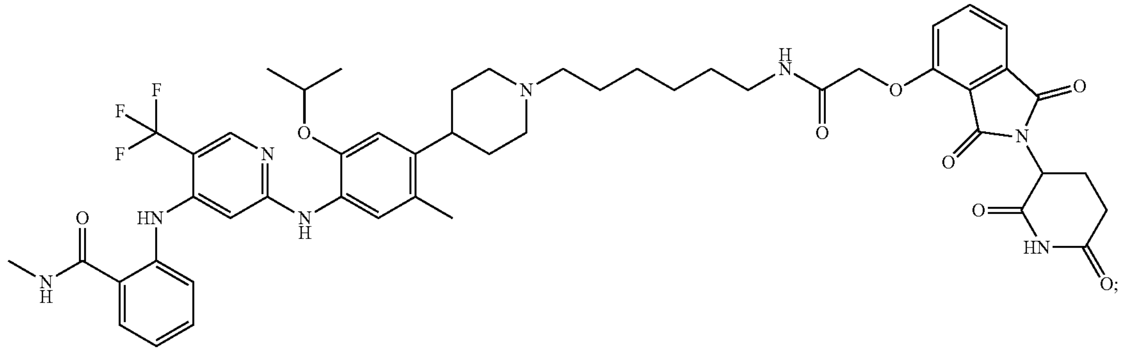
;

-continued
(10)
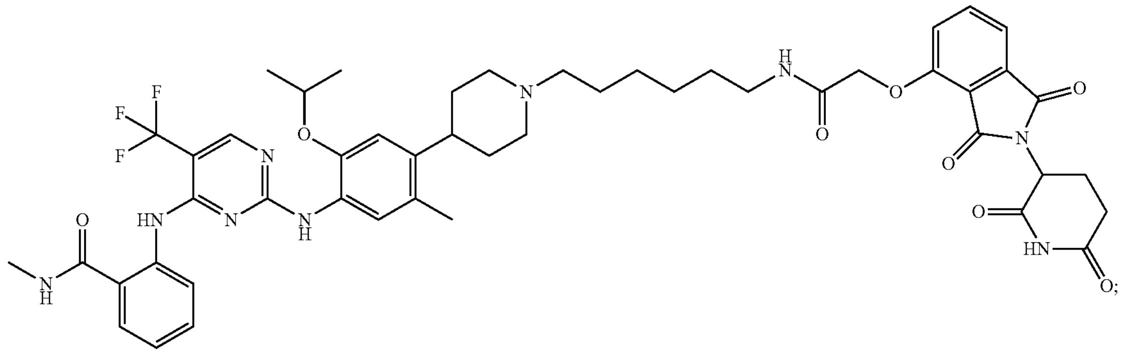
(11)
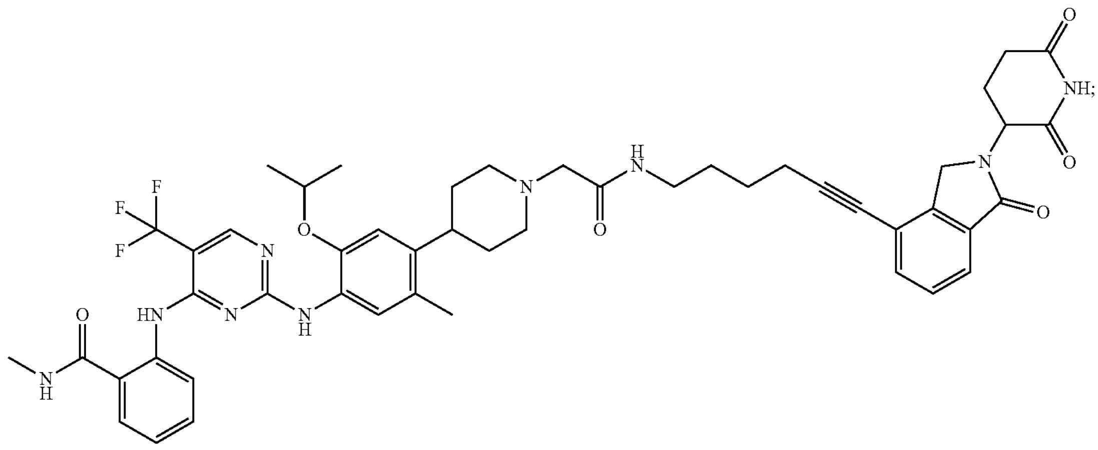
and
(12)
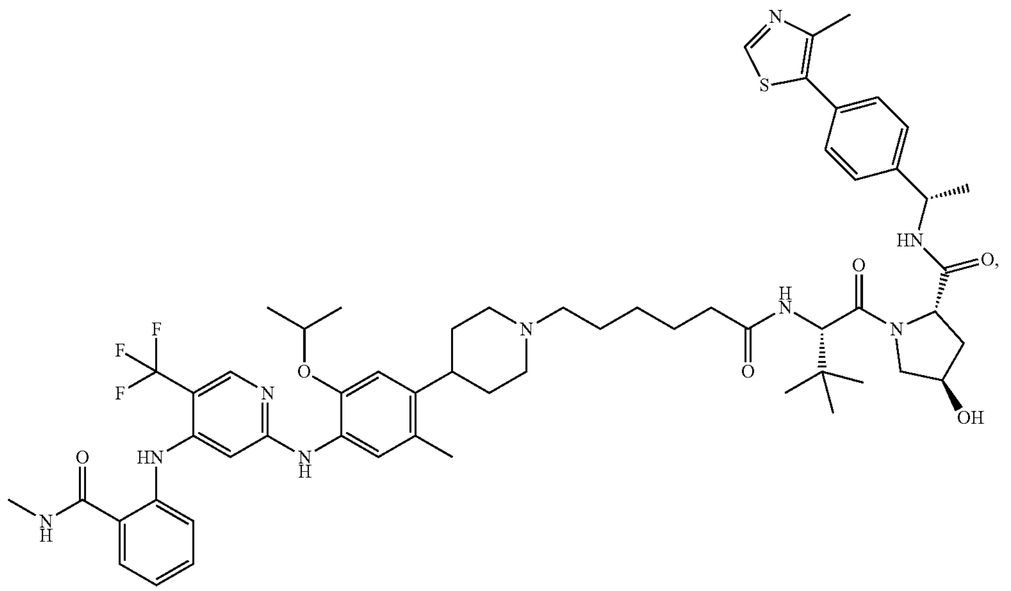
65
or pharmaceutically acceptable salts and stereoisomers thereof.

In another aspect, the present invention is directed to compounds that are selective inhibitors of FAK and ALK, and which have a structure represented by formula (II):

(II)

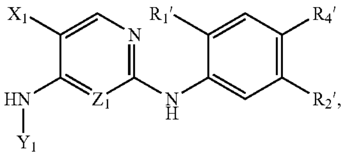

wherein $X_1$ is halo, $CF_3$, methyl, ethyl or cyclopropyl;

$Y_1$ is

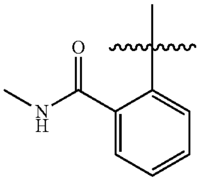,

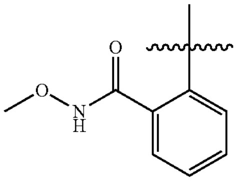,

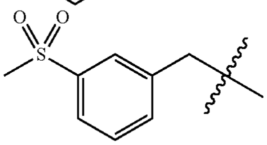, or

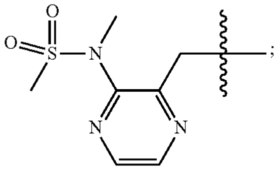;

$Z_1$ is N or CH;

$R_{1'}$ is H or $OR_{3'}$, wherein $R_{3'}$ is H, optionally substituted $C_1$-$C_4$ alkyl or cyclopropyl;

$R_{2'}$ is optionally substituted $C_1$-$C_4$ alkyl; and $R_{4'}$ is

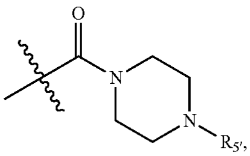

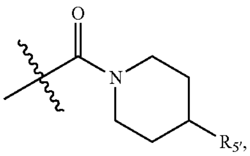

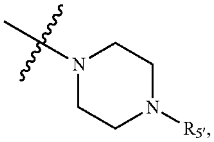

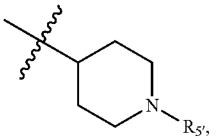

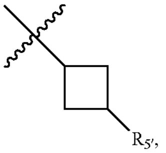

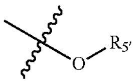, or

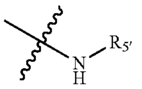, wherein $R_{5'}$ is H, optionally substituted $C_1$-$C_4$ alkyl, optionally substituted $C_3$-$C_6$ carbocyclic, or optionally substituted $C_3$-$C_6$ heterocyclic, or a pharmaceutically acceptable salt or stereoisomer thereof.

In some embodiments, wherein $X_1$ is $CF_3$; $Y_1$ is

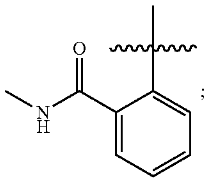;

$Z_1$ is CH; $R_{1'}$ is $OR_{3'}$, wherein $R_{3'}$ is methyl or isopropyl; $R_{2'}$ is methyl; $R_{4'}$ is

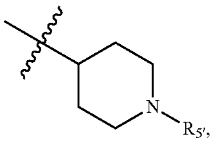

and the FAK-ALK inhibitor is represented by structure (II-1):

(II-1)

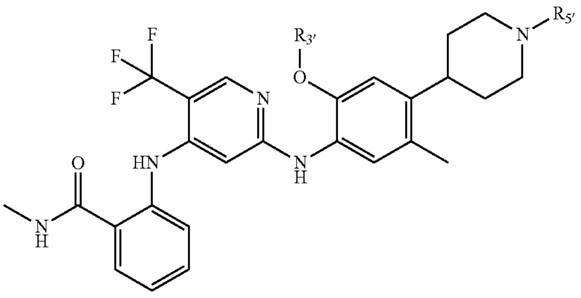

or a pharmaceutically acceptable salt or stereoisomer thereof.

In some embodiments, the selective FAK-ALK inhibitor has structure (Int-12 or compound 13):

(Int-12 or 13)

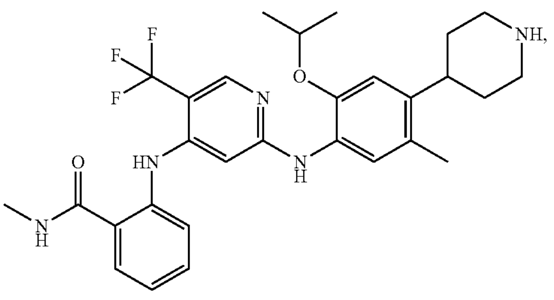

or a pharmaceutically acceptable salt stereoisomer thereof.

Compounds of the present invention (bifunctional compounds of formula (I) and compounds of formula (II) and their respective stereoisomers) may be in the form of a free acid or free base, or a pharmaceutically acceptable salt. As used herein, the term "pharmaceutically acceptable" in the context of a salt refers to a salt of the compound that does not abrogate the biological activity or properties of the compound, and is relatively non-toxic, i.e., the compound in salt form may be administered to a subject without causing undesirable biological effects (such as dizziness or gastric upset) or interacting in a deleterious manner with any of the other components of the composition in which it is contained. The term "pharmaceutically acceptable salt" refers to a product obtained by reaction of the compound of the present invention with a suitable acid or a base. Examples of pharmaceutically acceptable salts of the compounds of this invention include those derived from suitable inorganic bases such as Li, Na, K, Ca, Mg, Fe, Cu, Al, Zn and Mn salts. Examples of pharmaceutically acceptable, nontoxic acid addition salts are salts of an amino group formed with inorganic acids such as hydrochloride, hydrobromide, hydroiodide, nitrate, sulfate, bisulfate, phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, 4-methylbenzenesulfonate or p-toluenesulfonate salts and the like. Certain compounds of the invention can form pharmaceutically acceptable salts with various organic bases such as lysine, arginine, guanidine, diethanolamine or metformin.

In some embodiments, the bifunctional compound of formula (I) or the compound of formula (II) is an isotopic derivative in that it has at least one desired isotopic substitution of an atom, at an amount above the natural abundance of the isotope, i.e., enriched. In one embodiment, the compound includes deuterium or multiple deuterium atoms. Substitution with heavier isotopes such as deuterium, i.e. $^2$H, may afford certain therapeutic advantages resulting from greater metabolic stability, for example, increased in vivo half-life or reduced dosage requirements, and thus may be advantageous in some circumstances.

Compounds of the present invention may have at least one chiral center and thus may be in the form of a stereoisomer, which as used herein, embraces all isomers of individual compounds that differ only in the orientation of their atoms in space. The term stereoisomer includes mirror image isomers (enantiomers which include the (R-) or (S-) configurations of the compounds), mixtures of mirror image isomers (physical mixtures of the enantiomers, and racemates or racemic mixtures) of compounds, geometric (cis/trans or E/Z, R/S) isomers of compounds and isomers of compounds with more than one chiral center that are not mirror images of one another (diastereoisomers). The chiral centers of the compounds may undergo epimerization in vivo; thus, for these compounds, administration of the compound in its (R-) form is considered equivalent to administration of the compound in its (S-) form. Accordingly, the compounds of the present invention may be made and used in the form of individual isomers and substantially free of other isomers, or in the form of a mixture of various isomers, e.g., racemic mixtures of stereoisomers.

In addition, compounds of the present invention embrace the use of N-oxides, crystalline forms (also known as polymorphs), active metabolites of the compounds having the same type of activity, tautomers, and unsolvated as well as solvated forms with pharmaceutically acceptable solvents such as water, ethanol, and the like, of the compounds. The solvated forms of the conjugates presented herein are also considered to be disclosed herein.

Methods of Synthesis

In another aspect, the present invention is directed to methods for making the compounds of the present invention, or pharmaceutically acceptable salts or stereoisomers thereof. Broadly, the inventive compounds or pharmaceutically-acceptable salts or stereoisomers thereof may be prepared by any process known to be applicable to the preparation of chemically related compounds. The compounds of the present invention will be better understood in connection with the synthetic schemes that described in various working examples and which illustrate non-limiting methods by which the compounds of the invention may be prepared.

Pharmaceutical Compositions

Another aspect of the present invention is directed to a pharmaceutical composition that includes a therapeutically effective amount of a compound of the present invention or a pharmaceutically acceptable salt or stereoisomer thereof, and a pharmaceutically acceptable carrier. The term "pharmaceutically acceptable carrier," as known in the art, refers to a pharmaceutically acceptable material, composition or vehicle, suitable for administering compounds of the present invention to mammals. Suitable carriers may include, for example, liquids (both aqueous and non-aqueous alike, and combinations thereof), solids, encapsulating materials, gases, and combinations thereof (e.g., semi-solids), and gases, that function to carry or transport the compound from one organ, or portion of the body, to another organ, or portion of the body. A carrier is "acceptable" in the sense of being physiologically inert to and compatible with the other ingredients of the formulation and not injurious to the subject or patient. Depending on the type of formulation, the composition may include one or more pharmaceutically acceptable excipients.

Broadly, compounds of the present invention may be formulated into a given type of composition in accordance with conventional pharmaceutical practice such as conventional mixing, dissolving, granulating, dragee-making, levigating, emulsifying, encapsulating, entrapping and compression processes (see, e.g., Remington: *The Science and Practice of Pharmacy* (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York). The type of formulation depends on the mode of administration which may include enteral (e.g., oral, buccal, sublingual and rectal), parenteral (e.g., subcutaneous (s.c.), intravenous (i.v.), intramuscular (i.m.), and intrasternal injection, or infusion techniques, intra-ocular, intra-arterial, intramedullary, intrathecal, intraventricular, transdermal, interdermal, intravaginal, intraperitoneal, mucosal, nasal, intratracheal instillation, bronchial instillation, and inhalation) and topical (e.g., transdermal). In general, the most appropriate route of administration will depend upon a variety of factors including, for example, the nature of the agent (e.g., its stability in the environment of the gastrointestinal tract), and/or the condition of the subject (e.g., whether the subject is able to tolerate oral administration). For example, parenteral (e.g., intravenous) administration may also be advantageous in that the compound may be administered relatively quickly such as in the case of a single-dose treatment and/or an acute condition.

In some embodiments, the compounds of the present invention are formulated for oral or intravenous administration (e.g., systemic intravenous injection).

Accordingly, compounds of the present invention may be formulated into solid compositions (e.g., powders, tablets, dispersible granules, capsules, cachets, and suppositories), liquid compositions (e.g., solutions in which the compound is dissolved, suspensions in which solid particles of the compound are dispersed, emulsions, and solutions containing liposomes, micelles, or nanoparticles, syrups and elixirs); semi-solid compositions (e.g., gels, suspensions and creams); and gases (e.g., propellants for aerosol compositions). Compounds may also be formulated for rapid, intermediate or extended release.

Solid dosage forms for oral administration include capsules, tablets, pills, powders, and granules. In such solid dosage forms, the active compound is mixed with a carrier such as sodium citrate or dicalcium phosphate and an additional carrier or excipient such as a) fillers or extenders such as starches, lactose, sucrose, glucose, mannitol, and silicic acid, b) binders such as, for example, methylcellulose, microcrystalline cellulose, hydroxypropylmethylcellulose, carboxymethylcellulose, sodium carboxymethylcellulose, alginates, gelatin, polyvinylpyrrolidinone, sucrose, and acacia, c) humectants such as glycerol, d) disintegrating agents such as crosslinked polymers (e.g., crosslinked polyvinylpyrrolidone (crospovidone), crosslinked sodium carboxymethyl cellulose (croscarmellose sodium), sodium starch glycolate, agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also include buffering agents. Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings. They may further contain an opacifying agent.

In some embodiments, compounds of the present invention are formulated in a hard or soft gelatin capsule. Representative excipients that may be used include pregelatinized starch, magnesium stearate, mannitol, sodium stearyl fumarate, lactose anhydrous, microcrystalline cellulose and croscarmellose sodium. Gelatin shells may include gelatin, titanium dioxide, iron oxides and colorants.

Liquid dosage forms for oral administration include solutions, suspensions, emulsions, micro-emulsions, syrups and elixirs. In addition to the compound, the liquid dosage forms may contain an aqueous or non-aqueous carrier (depending upon the solubility of the compounds) commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Oral compositions may also include an excipients such as wetting agents, suspending agents, coloring, sweetening, flavoring, and perfuming agents.

Injectable preparations may include sterile aqueous solutions or oleaginous suspensions. They may be formulated according to standard techniques using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. The effect of the compound may be prolonged by slowing its absorption, which may be accomplished by the use of a liquid suspension or crystalline or amorphous material with poor water solubility. Prolonged absorption of the compound from a parenterally administered formulation may also be accomplished by suspending the compound in an oily vehicle.

In certain embodiments, compounds of the present invention may be administered in a local rather than systemic manner, for example, via injection of the conjugate directly into an organ, often in a depot preparation or sustained release formulation. In specific embodiments, long acting formulations are administered by implantation (for example subcutaneously or intramuscularly) or by intramuscular injection. Injectable depot forms are made by forming microencapsule matrices of the compound in a biodegradable polymer, e.g., polylactide-polyglycolides, poly(orthoesters) and poly(anhydrides). The rate of release of the compound may be controlled by varying the ratio of compound to polymer and the nature of the particular polymer employed. Depot injectable formulations are also prepared by entrapping the compound in liposomes or microemulsions that are compatible with body tissues. Furthermore, in other embodiments, the compound is delivered in a targeted drug delivery system, for example, in a liposome coated with organ-specific antibody. In such embodiments, the liposomes are targeted to and taken up selectively by the organ.

Compounds of the present invention may be formulated for buccal or sublingual administration, examples of which include tablets, lozenges and gels.

The bifunctional compounds of formula (I) and compounds of formula (II) may be formulated for administration by inhalation. Various forms suitable for administration by inhalation include aerosols, mists or powders. Pharmaceutical compositions may be delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In some embodiments, the dosage unit of a pressurized aerosol may be determined by providing a valve to deliver a metered amount. In some embodiments, capsules and cartridges including gelatin, for example, for use in an inhaler or insufflator, may be formulated containing a powder mix of the compound and a suitable powder base such as lactose or starch.

Compounds of the present invention may be formulated for topical administration which as used herein, refers to administration intradermally by application of the formulation to the epidermis. These types of compositions are typically in the form of ointments, pastes, creams, lotions, gels, solutions and sprays.

Representative examples of carriers useful in formulating the bifunctional compounds for topical application include solvents (e.g., alcohols, poly alcohols, water), creams, lotions, ointments, oils, plasters, liposomes, powders, emulsions, microemulsions, and buffered solutions (e.g., hypotonic or buffered saline). Creams, for example, may be formulated using saturated or unsaturated fatty acids such as stearic acid, palmitic acid, oleic acid, palmito-oleic acid, cetyl, or oleyl alcohols. Creams may also contain a non-ionic surfactant such as polyoxy-40-stearate.

In some embodiments, the topical formulations may also include an excipient, an example of which is a penetration enhancing agent. These agents are capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, *Percutaneous Penetration Enhancers*, Maibach H. I. and Smith H. E. (eds.), CRC Press, Inc., Boca Raton, Fla. (1995), which surveys the use and testing of various skin penetration enhancers, and Buyuktimkin et al., *Chemical Means of Transdermal Drug Permeation Enhancement in Transdermal and Topical Drug Delivery Systems*, Gosh T. K., Pfister W. R., Yum S. I. (Eds.), Interpharm Press Inc., Buffalo Grove, Ill. (1997). Representative examples of penetration enhancing agents include triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate), and N-methylpyrrolidone.

Representative examples of yet other excipients that may be included in topical as well as in other types of formulations (to the extent they are compatible), include preservatives, antioxidants, moisturizers, emollients, buffering agents, solubilizing agents, skin protectants, and surfactants. Suitable preservatives include alcohols, quaternary amines, organic acids, parabens, and phenols. Suitable antioxidants include ascorbic acid and its esters, sodium bisulfite, butylated hydroxytoluene, butylated hydroxyanisole, tocopherols, and chelating agents like EDTA and citric acid. Suitable moisturizers include glycerine, sorbitol, polyethylene glycols, urea, and propylene glycol. Suitable buffering agents include citric, hydrochloric, and lactic acid buffers. Suitable solubilizing agents include quaternary ammonium chlorides, cyclodextrins, benzyl benzoate, lecithin, and polysorbates. Suitable skin protectants include vitamin E oil, allatoin, dimethicone, glycerin, petrolatum, and zinc oxide.

Transdermal formulations typically employ transdermal delivery devices and transdermal delivery patches wherein the compound is formulated in lipophilic emulsions or buffered, aqueous solutions, dissolved and/or dispersed in a polymer or an adhesive. Patches may be constructed for continuous, pulsatile, or on demand delivery of pharmaceutical agents. Transdermal delivery of the compounds may be accomplished by means of an iontophoretic patch. Transdermal patches may provide controlled delivery of the compounds wherein the rate of absorption is slowed by using rate-controlling membranes or by trapping the compound within a polymer matrix or gel. Absorption enhancers may be used to increase absorption, examples of which include absorbable pharmaceutically acceptable solvents that assist passage through the skin.

Ophthalmic formulations include eye drops.

Formulations for rectal administration include enemas, rectal gels, rectal foams, rectal aerosols, and retention enemas, which may contain conventional suppository bases such as cocoa butter or other glycerides, as well as synthetic polymers such as polyvinylpyrrolidone, PEG, and the like. Compositions for rectal or vaginal administration may also be formulated as suppositories which can be prepared by mixing the bifunctional compound of formula (I) or compound of formula (II) with suitable non-irritating carriers and excipients such as cocoa butter, mixtures of fatty acid glycerides, polyethylene glycol, suppository waxes, and combinations thereof, all of which are solid at ambient temperature but liquid at body temperature and therefore melt in the rectum or vaginal cavity and release the compound.

Dosage Amounts

As used herein, the term, "therapeutically effective amount" refers to an amount of a bifunctional compound of formula (I) or compound of formula (II), or a pharmaceutically acceptable salt or a stereoisomer thereof, that is effective in producing the desired therapeutic response in a particular patient suffering from a disease or disorder mediated by aberrant FAK or FAK and ALK activity. The term "therapeutically effective amount" thus includes the amount of the compound of the invention or a pharmaceutically acceptable salt or a stereoisomer thereof, that when administered, induces a positive modification in the disease or disorder to be treated (e.g., to selectively inhibit/degrade FAK or FAK and ALK), or is sufficient to prevent development or progression of the disease or disorder, or alleviate to some extent, one or more of the symptoms of the disease or disorder being treated in a subject, or which simply kills or inhibits the growth of diseased (e.g., cancer) cells, or reduces the amounts of FAK or FAK and ALK in diseased cells.

The total daily dosage of the compounds and usage thereof may be decided in accordance with standard medical practice, e.g., by the attending physician using sound medical judgment. The specific therapeutically effective dose for any particular subject will depend upon a variety of factors including the disease or disorder being treated and the severity thereof (e.g., its present status); the activity of the specific compound employed; the specific composition employed; the age, body weight, general health, sex and diet of the subject; the time of administration, route of administration, and rate of excretion of the specific compound employed; the duration of the treatment; drugs used in combination or coincidental with the specific compound employed; and like factors well known in the medical arts (see, for example, *Goodman and Gilman's The Pharmacological Basis of Therapeutics,* 10th Edition, A. Gilman, J. Hardman and L. Limbird, eds., McGraw-Hill Press, 155-173, 2001).

Bifunctional compounds of formula (I) and compounds of formula (II) and their pharmaceutically acceptable salts and stereoisomers may be effective over a wide dosage range. In some embodiments, the total daily dosage (e.g., for adult humans) may range from about 0.001 to about 1600 mg, from 0.01 to about 1600 mg, from 0.01 to about 500 mg, from about 0.01 to about 100 mg, from about 0.5 to about 100 mg, from 1 to about 100-400 mg per day, from about 1 to about 50 mg per day, from about 5 to about 40 mg per day, and in yet other embodiments from about 10 to about 30 mg per day. Individual dosages may be formulated to contain the desired dosage amount depending upon the number of times the compound is administered per day. By way of example, capsules may be formulated with from about 1 to about 200 mg of compound (e.g., 1, 2, 2.5, 3, 4, 5, 10, 15, 20, 25, 50, 100, 150, and 200 mg). In some embodiments, the compound may be administered at a dose in range from about 0.01 mg to about 200 mg/kg of body weight per day. In some embodiments, a dose of from 0.1 to 100, e.g., from 1 to 30 mg/kg per day in one or more dosages per day may be effective By way of example, a suitable dose for oral administration may be in the range of 1-30 mg/kg of body weight per day, and a suitable dose for intravenous administration may be in the range of 1-10 ng/kg of body weight per day.

Methods of Use

Methods of the present invention are directed to treating diseases or disorders involving aberrant (e.g., dysfunctional or dysregulated) FAK or FAK and ALK activity, and include administration of a therapeutically effective amount of a bifunctional compound of formula (I) or a compound of formula (II) or a pharmaceutically acceptable salt or stereoisomer thereof, to a subject in need thereof.

The diseases or disorders are characterized or mediated by aberrant FAK or FAK and ALK activity (e.g., elevated levels of protein(s) or otherwise functionally abnormal protein activity/activities relative to a non-pathological state). A "disease" is generally regarded as a state of health of a subject wherein the subject cannot maintain homeostasis, and wherein if the disease is not ameliorated then the subject's health continues to deteriorate. In contrast, a "disorder" in a subject is a state of health in which the subject is able to maintain homeostasis, but in which the subject's state of health is less favorable than it would be in the absence of the disorder. Left untreated, a disorder does not necessarily cause a further decrease in the animal's state of health. In some embodiments, bifunctional compounds of formula (I) and compounds of formula (II) may be useful in the treatment of cell proliferative diseases and disorders (e.g., cancer or benign neoplasms). As used herein, the term "cell proliferative disease or disorder" refers to the conditions characterized by aberrant cell growth, or both, including noncancerous conditions such as neoplasms, precancerous conditions, benign tumors, and cancer.

The term "subject" (or "patient") as used herein includes all members of the animal kingdom prone to or suffering from the indicated disease or disorder. In some embodiments, the subject is a mammal, e.g., a human or a non-human mammal. The methods are also applicable to companion animals such as dogs and cats as well as livestock such as cows, horses, sheep, goats, pigs, and other domesticated and wild animals. A subject "in need of" the treatment may be suffering from or suspected of suffering from a specific disease or disorder may have been positively diagnosed or otherwise presents with a sufficient number of risk factors or a sufficient number or combination of signs or symptoms such that a medical professional could diagnose or suspect that the subject was suffering from the disease or disorder. Thus, subjects suffering from, and suspected of suffering from, a specific disease or disorder are not necessarily two distinct groups.

The modes of administration (e.g., oral, parenteral) may also be determined in accordance with the standard medical practice.

Exemplary types of non-cancerous (e.g., cell proliferative) diseases or disorders that may be amenable to treatment with the compounds of the present invention include inflammatory diseases and conditions, autoimmune diseases, neurodegenerative diseases, heart diseases, viral diseases, chronic and acute kidney diseases or injuries, metabolic diseases, and allergic and genetic diseases.

In some embodiments, the compounds of the present invention may be useful in the treatment of neurodegenerative diseases and disorders. As used herein, the term "neurodegenerative diseases and disorders" refers to conditions (which are non-cancerous in nature) characterized by progressive degeneration or death of nerve cells, or both, including problems with movement (ataxias), or mental functioning (dementias). Representative examples of such diseases and disorders include Alzheimer's disease (AD) and AD-related dementias, Parkinson's disease (PD) and PD-related dementias, prion disease, motor neuron diseases (MND), Huntington's disease (HD), Pick's syndrome, spinocerebellar ataxia (SCA), spinal muscular atrophy (SMA), primary progressive aphasia (PPA), amyotrophic lateral sclerosis (ALS), traumatic brain injury (TBI), multiple sclerosis (MS), dementias (e.g., vascular dementia (VaD), Lewy body dementia (LBD), semantic dementia, and frontotemporal lobar dementia (FTD).

In some embodiments, the bifunctional compounds may be useful in the treatment of autoimmune diseases and disorders. As used herein, the term "autoimmune disease" refers to the condition where the immune system produces antibodies that attack normal body tissues. Representative examples of such diseases include Sjogren's syndrome, Hashimoto thyroiditis, rheumatoid arthritis, juvenile (type 1) diabetes, polymyositis, scleroderma, Addison disease, lupus including systemic lupus erythematosus, vitiligo, pernicious anemia, glomerulonephritis, pulmonary fibrosis, celiac disease, polymyalgia rheumatica, multiple sclerosis, ankylosing spondylitis, alopecia areata, vasculitis, and temporal arteritis.

In some embodiments, the methods are directed to treating subjects having cancer. Broadly, the compounds of the present invention may be effective in the treatment of carcinomas (solid tumors including both primary and metastatic tumors), sarcomas, melanomas, and hematological cancers (cancers affecting blood including lymphocytes, bone marrow and/or lymph nodes) such as leukemia, lymphoma and multiple myeloma. Adult tumors/cancers and pediatric tumors/cancers are included. The cancers may be vascularized, or not yet substantially vascularized, or non-vascularized tumors.

Representative examples of cancers includes adenocortical carcinoma, AIDS-related cancers (e.g., Kaposi's and AIDS-related lymphoma), appendix cancer, childhood cancers (e.g., childhood cerebellar astrocytoma, childhood cerebral astrocytoma), basal cell carcinoma, skin cancer (non-melanoma), biliary cancer, extrahepatic bile duct cancer, intrahepatic bile duct cancer, bladder cancer, urinary bladder cancer, brain cancer (e.g., gliomas and glioblastomas such as brain stem glioma, gestational trophoblastic tumor glioma, cerebellar astrocytoma, cerebral astrocytoma/malignant glioma, ependymoma, medulloblastoma, supratentorial primitive neuroectodeimal tumors, visual pathway and hypothalamic glioma), breast cancer, bronchial adenomas/carcinoids, carcinoid tumor, nervous system cancer (e.g., central nervous system cancer, central nervous system lymphoma), cervical cancer, chronic myeloproliferative disorders, colorectal cancer (e.g., colon cancer, rectal cancer), lymphoid neoplasm, mycosis fungoids, Sezary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastrointestinal cancer (e.g., stomach cancer, small intestine cancer, gastrointestinal carcinoid tumor, gastrointestinal stromal tumor (GIST)), cholangiocarcinoma, germ cell tumor, ovarian germ cell tumor, head and neck cancer, neuroendocrine tumors, Hodgkin's lymphoma, Ann Arbor stage III and stage IV childhood Non-Hodgkin's lymphoma, ROS1-positive refractory Non-Hodgkin's lymphoma, leukemia, lymphoma, multiple myeloma, hypopharyngeal cancer, intraocular melanoma, ocular cancer, islet cell tumors (endocrine pancreas), renal cancer (e.g., Wilm's Tumor, renal cell carcinoma), liver cancer, lung cancer (e.g., non-small cell lung cancer and small cell lung cancer), ALK-positive anaplastic large cell lymphoma, ALK-positive advanced malignant solid neoplasm, Waldenstrom's macroglobulinema, melanoma, intraocular (eye) melanoma, merkel cell carcinoma, mesothelioma, metastatic squamous neck cancer with occult primary, multiple endocrine neoplasia (MEN), myelodysplastic syndromes, myelodyplastic/myeloproliferative diseases, nasopharyngeal cancer, neuroblastoma, oral cancer (e.g., mouth cancer, lip cancer, oral cavity cancer, tongue cancer, oropharyngeal cancer, throat cancer, laryngeal cancer), ovarian cancer (e.g., ovarian epithelial cancer, ovarian germ cell tumor, ovarian low malignant potential tumor), pancreatic cancer, islet cell pancreatic cancer, paranasal sinus and nasal cavity cancer, parathyroid cancer, penile cancer, pharyngeal cancer, pheochromocytoma, pineoblastoma, metastatic anaplastic thyroid cancer, undifferentiated thyroid cancer, papillary thyroid cancer, pituitary tumor, plasma cell neoplasm/multiple myeloma, pleuropulmonary blastoma, prostate cancer, retinoblastoma, rhabdomyosarcoma, salivary gland cancer, uterine cancer (e.g., endometrial uterine cancer, uterine sarcoma, uterine corpus cancer), squamous cell carcinoma, testicular cancer, thymoma, thymic carcinoma, thyroid cancer, juvenile xanthogranuloma, transitional cell cancer of the renal pelvis and ureter and other urinary organs, urethral cancer, gestational trophoblastic tumor, vaginal cancer, vulvar cancer, hepatoblastoma, rhabdoid tumor, and Wilms tumor.

Sarcomas that may be treatable with compounds of the present invention include both soft tissue and bone cancers alike, representative examples of which include osteosarcoma or osteogenic sarcoma (bone) (e.g., Ewing's sarcoma), chondrosarcoma (cartilage), leiomyosarcoma (smooth muscle), rhabdomyosarcoma (skeletal muscle), mesothelial sarcoma or mesothelioma (membranous lining of body cavities), fibrosarcoma (fibrous tissue), angiosarcoma or hemangioendothelioma (blood vessels), liposarcoma (adipose tissue), glioma or astrocytoma (neurogenic connective tissue found in the brain), myxosarcoma (primitive embryonic connective tissue), mesenchymous or mixed mesodermal tumor (mixed connective tissue types), and histiocytic sarcoma (immune cancer).

In some embodiments, methods of the present invention entail treatment of subjects having cell proliferative diseases or disorders of the hematological system, liver (hepatocellular), brain, lung, colorectal (e.g., colon), pancreas, prostate, ovary, breast, skin (e.g., melanoma), and endometrium.

As used herein, "cell proliferative diseases or disorders of the hematologic system" include lymphoma, leukemia, myeloid neoplasms, mast cell neoplasms, myelodysplasia, benign monoclonal gammopathy, lymphomatoid papulosis, polycythemia vera, chronic myelocytic leukemia, agnogenic myeloid metaplasia, and essential thrombocythemia. Representative examples of hematologic cancers may thus include multiple myeloma, lymphoma (including T-cell lymphoma, Hodgkin's lymphoma, non-Hodgkin's lymphoma (diffuse large B-cell lymphoma (DLBCL), follicular lymphoma (FL), mantle cell lymphoma (MCL) and ALK+ anaplastic large cell lymphoma (e.g., B-cell non-Hodgkin's lymphoma selected from diffuse large B-cell lymphoma (e.g., germinal center B-cell-like diffuse large B-cell lymphoma or activated B-cell-like diffuse large B-cell lymphoma), Burkitt's lymphoma/leukemia, mantle cell lymphoma, mediastinal (thymic) large B-cell lymphoma, follicular lymphoma, marginal zone lymphoma, lymphoplasmacytic lymphoma/Waldenstrom macroglobulinemia, metastatic pancreatic adenocarcinoma, refractory B-cell non-Hodgkin's lymphoma, and relapsed B-cell non-Hodgkin's lymphoma, childhood lymphomas, and lymphomas of lymphocytic and cutaneous origin, e.g., small lymphocytic lymphoma, leukemia, including childhood leukemia, hairy-cell leukemia, acute lymphocytic leukemia, acute myelocytic leukemia, acute myeloid leukemia (e.g., acute monocytic leukemia), chronic lymphocytic leukemia, small lymphocytic leukemia, chronic myelocytic leukemia, chronic myelogenous leukemia, and mast cell leukemia, myeloid neoplasms and mast cell neoplasms.

As used herein, "cell proliferative diseases or disorders of the liver" include all forms of cell proliferative disorders affecting the liver. Cell proliferative disorders of the liver may include liver cancer (e.g., hepatocellular carcinoma, intrahepatic cholangiocarcinoma and hepatoblastoma), a precancer or precancerous condition of the liver, benign growths or lesions of the liver, and malignant growths or lesions of the liver, and metastatic lesions in tissue and organs in the body other than the liver. Cell proliferative disorders of the brain may include hyperplasia, metaplasia, and dysplasia of the liver.

As used herein, "cell proliferative diseases or disorders of the brain" include all forms of cell proliferative disorders affecting the brain. Cell proliferative disorders of the brain may include brain cancer (e.g., gliomas, glioblastomas, meningiomas, pituitary adenomas, vestibular schwannomas, and primitive neuroectodermal tumors (medulloblastomas)), a precancer or precancerous condition of the brain, benign growths or lesions of the brain, and malignant growths or lesions of the brain, and metastatic lesions in tissue and organs in the body other than the brain. Cell proliferative disorders of the brain may include hyperplasia, metaplasia, and dysplasia of the brain.

As used herein, "cell proliferative diseases or disorders of the lung" include all forms of cell proliferative disorders affecting lung cells. Cell proliferative disorders of the lung include lung cancer, precancer and precancerous conditions of the lung, benign growths or lesions of the lung, hyperplasia, metaplasia, and dysplasia of the lung, and metastatic lesions in the tissue and organs in the body other than the lung. Lung cancer includes all forms of cancer of the lung, e.g., malignant lung neoplasms, carcinoma in situ, typical carcinoid tumors, and atypical carcinoid tumors. Lung cancer includes small cell lung cancer ("SLCL"), non-small cell lung cancer ("NSCLC"), squamous cell carcinoma, adenocarcinoma, small cell carcinoma, large cell carcinoma, and mesothelioma. Lung cancer can include "scar carcinoma", bronchioveolar carcinoma, giant cell carcinoma, spindle cell carcinoma, and large cell neuroendocrine carcinoma. Lung cancer also includes lung neoplasms having histologic and ultrastructural heterogeneity (e.g., mixed cell types). In some embodiments, a compound of the present invention may be used to treat non-metastatic or metastatic lung cancer (e.g., NSCLC, ALK-positive NSCLC, NSCLC harboring ROS1 Rearrangement, Lung Adenocarcinoma, and squamous cell carcinoma).

As used herein, "cell proliferative diseases or disorders of the colon" include all forms of cell proliferative disorders affecting colon cells, including colon cancer, a precancer or precancerous conditions of the colon, adenomatous polyps of the colon and metachronous lesions of the colon. Colon cancer includes sporadic and hereditary colon cancer, malignant colon neoplasms, carcinoma in situ, typical carcinoid tumors, and atypical carcinoid tumors, adenocarcinoma, squamous cell carcinoma, and squamous cell carcinoma. Colon cancer can be associated with a hereditary syndrome such as hereditary nonpolyposis colorectal cancer, familiar adenomatous polyposis, MYH associated polyposis, Gardner's syndrome, Peutz-Jeghers syndrome, Turcot's syndrome and juvenile polyposis. Cell proliferative disorders of the colon may also be characterized by hyperplasia, metaplasia, or dysplasia of the colon.

As used herein, "cell proliferative diseases or disorders of the pancreas" include all forms of cell proliferative disorders affecting pancreatic cells. Cell proliferative disorders of the pancreas may include pancreatic cancer, a precancer or precancerous condition of the pancreas, hyperplasia of the pancreas, dysplasia of the pancreas, benign growths or lesions of the pancreas, and malignant growths or lesions of the pancreas, and metastatic lesions in tissue and organs in the body other than the pancreas. Pancreatic cancer includes all forms of cancer of the pancreas, including ductal adenocarcinoma, adenosquamous carcinoma, pleomorphic giant cell carcinoma, mucinous adenocarcinoma, osteoclast-like giant cell carcinoma, mucinous cystadenocarcinoma, acinar carcinoma, unclassified large cell carcinoma, small cell carcinoma, pancreatoblastoma, papillary neoplasm, mucinous cystadenoma, papillary cystic neoplasm, and serous cystadenoma, and pancreatic neoplasms having histologic and ultrastructural heterogeneity (e.g., mixed cell types).

As used herein, "cell proliferative diseases or disorders of the prostate" include all forms of cell proliferative disorders affecting the prostate. Cell proliferative disorders of the prostate may include prostate cancer, a precancer or precancerous condition of the prostate, benign growths or lesions of the prostate, and malignant growths or lesions of the prostate, and metastatic lesions in tissue and organs in the body other than the prostate. Cell proliferative disorders of the prostate may include hyperplasia, metaplasia, and dysplasia of the prostate.

As used herein, "cell proliferative diseases or disorders of the ovary" include all forms of cell proliferative disorders affecting cells of the ovary. Cell proliferative disorders of the ovary may include a precancer or precancerous condition of the ovary, benign growths or lesions of the ovary, ovarian cancer, and metastatic lesions in tissue and organs in the body other than the ovary. Cell proliferative disorders of the ovary may include hyperplasia, metaplasia, and dysplasia of the ovary.

As used herein, "cell proliferative diseases or disorders of the breast" include all forms of cell proliferative disorders affecting breast cells. Cell proliferative disorders of the breast may include breast cancer, a precancer or precancerous condition of the breast, benign growths or lesions of the breast, and metastatic lesions in tissue and organs in the body other than the breast. Cell proliferative disorders of the breast may include hyperplasia, metaplasia, and dysplasia of the breast.

As used herein, "cell proliferative diseases or disorders of the skin" include all forms of cell proliferative disorders affecting skin cells. Cell proliferative disorders of the skin may include a precancer or precancerous condition of the skin, benign growths or lesions of the skin, melanoma, malignant melanoma or other malignant growths or lesions of the skin, and metastatic lesions in tissue and organs in the body other than the skin. Cell proliferative disorders of the skin may include hyperplasia, metaplasia, and dysplasia of the skin.

As used herein, "cell proliferative diseases or disorders of the endometrium" include all forms of cell proliferative disorders affecting cells of the endometrium. Cell proliferative disorders of the endometrium may include a precancer or precancerous condition of the endometrium, benign growths or lesions of the endometrium, endometrial cancer, and metastatic lesions in tissue and organs in the body other than the endometrium. Cell proliferative disorders of the endometrium may include hyperplasia, metaplasia, and dysplasia of the endometrium.

The compounds of formula (I) and compounds of formula (II) may be administered to a patient, e.g., a cancer patient, as a monotherapy or by way of combination therapy. Therapy may be "front/first-line", i.e., as an initial treatment in patients who have undergone no prior anti-cancer treatment regimens, either alone or in combination with other treatments; or "second-line", as a treatment in patients who have undergone a prior anti-cancer treatment regimen, either alone or in combination with other treatments; or as "third-line", "fourth-line", etc. treatments, either alone or in combination with other treatments. Therapy may also be given to patients who have had previous treatments which have been partially successful but became intolerant to the particular treatment. Therapy may also be given as an adjuvant treatment, i.e., to prevent reoccurrence of cancer in patients with no currently detectable disease or after surgical removal of a tumor. Thus, in some embodiments, the compound may be administered to a patient who has received another therapy, such as chemotherapy, radioimmunotherapy, surgical therapy, immunotherapy, radiation therapy, targeted therapy or any combination thereof.

The methods of the present invention may entail administration of compounds of the invention or pharmaceutical compositions thereof to the patient in a single dose or in multiple doses (e.g., 1, 2, 3, 4, 5, 6, 7, 8, 10, 15, 20, or more doses). For example, the frequency of administration may range from once a day up to about once every eight weeks. In some embodiments, the frequency of administration ranges from about once a day for 1, 2, 3, 4, 5, or 6 weeks, and in other embodiments entails a 28-day cycle which includes daily administration for 3 weeks (21 days). In other embodiments, the bifunctional compound may be dosed twice a day (BID) over the course of two and a half days (for a total of 5 doses) or once a day (QD) over the course of two days (for a total of 2 doses). In other embodiments, the bifunctional compound may be dosed once a day (QD) over the course of five days.

Combination Therapy

The compounds of the present invention and their pharmaceutically acceptable salts and stereoisomers may be used in combination or concurrently with at least one other active agent, e.g., anti-cancer agent or regimen, in treating diseases and disorders. The terms "in combination" and "concurrently in this context mean that the agents are co-administered, which includes substantially contemporaneous administration, by way of the same or separate dosage forms, and by the same or different modes of administration, or sequentially, e.g., as part of the same treatment regimen, or by way of successive treatment regimens. Thus, if given sequentially, at the onset of administration of the second compound, the first of the two compounds is in some cases still detectable at effective concentrations at the site of treatment. The sequence and time interval may be determined such that they can act together (e.g., synergistically to provide an increased benefit than if they were administered otherwise). For example, the therapeutics may be administered at the same time or sequentially in any order at different points in time; however, if not administered at the same time, they may be administered sufficiently close in time so as to provide the desired therapeutic effect, which may be in a synergistic fashion. Thus, the terms are not limited to the administration of the active agents at exactly the same time.

The dosage of the additional anticancer therapeutic may be the same or even lower than known or recommended doses. See, Hardman et al., eds., *Goodman & Gilman's The Pharmacological Basis Of Basis Of Therapeutics,* 10th ed., McGraw-Hill, New York, 2001*; Physician's Desk Reference* 60th ed., 2006. For example, anti-cancer agents that may be used in combination with the inventive compounds are known in the art. See, e.g., U.S. Pat. No. 9,101,622 (Section 5.2 thereof) and U.S. Pat. No. 9,345,705 B2 (Columns 12-18 thereof). Representative examples of additional active agents and treatment regimens include radiation therapy, chemotherapeutics (e.g., mitotic inhibitors, angiogenesis inhibitors, anti-hormones, autophagy inhibitors, alkylating agents, intercalating antibiotics, growth factor inhibitors, anti-androgens, signal transduction pathway inhibitors, anti-microtubule agents, platinum coordination complexes, HDAC inhibitors, proteasome inhibitors, and topoisomerase inhibitors), immunomodulators, therapeutic antibodies (e.g., mono-specific and bispecific antibodies) and CAR-T therapy.

In some embodiments, the bifunctional compound of formula (I) or compound formula (II) and the additional anticancer therapeutic may be administered less than 5 minutes apart, less than 30 minutes apart, less than 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. The two or more anticancer therapeutics may be administered within the same patient visit.

In some embodiments involving cancer treatment, the bifunctional compound of formula (I) or the compound of formula (II) and the additional anti-cancer or therapeutic are cyclically administered. Cycling therapy involves the administration of one anticancer therapeutic for a period of time, followed by the administration of a second anti-cancer therapeutic for a period of time and repeating this sequential administration, i.e., the cycle, in order to reduce the development of resistance to one or both of the anticancer therapeutics, to avoid or reduce the side effects of one or both of the anticancer therapeutics, and/or to improve the efficacy of the therapies. In one example, cycling therapy involves the administration of a first anticancer therapeutic for a period of time, followed by the administration of a second anticancer therapeutic for a period of time, optionally, followed by the administration of a third anticancer therapeutic for a period of time and so forth, and repeating this sequential administration, i.e., the cycle in order to reduce the development of resistance to one of the anticancer therapeutics, to avoid or reduce the side effects of one of the anticancer therapeutics, and/or to improve the efficacy of the anticancer therapeutics.

In some embodiments, a compound of the present invention may be used in combination other anti-cancer agents, representative examples of which include Trametinib (e.g., for cancer), Vismodegib (e.g., for intracranial meningioma and recurrent meningioma), Nab-Paclitaxel and Gemcitabine (e.g., for pancreatic cancer), Pembrolizumab and Gemcitabine (e.g., for advanced solid tumors and pancreatic cancer), Pembrolizumab (e.g., for carcinoma, non-small cell lung cancer (NSCLC), and pancreatic neoplasms), Paclitaxel (e.g., for ovarian cancer), Avelumab (e.g., for epithelial ovarian cancer), and Paclitaxel and Carboplatin (e.g., for ovarian cancer).

Pharmaceutical Kits

The present compositions may be assembled into kits or pharmaceutical systems. Kits or pharmaceutical systems according to this aspect of the invention include a carrier or package such as a box, carton, tube or the like, having in close confinement therein one or more containers, such as vials, tubes, ampoules, or bottles, which contain a compound of the present invention or a pharmaceutical composition thereof. The kits or pharmaceutical systems of the invention may also include printed instructions for using the compounds and compositions.

These and other aspects of the present invention will be further appreciated upon consideration of the following working examples, which are intended to illustrate certain particular embodiments of the invention but are not intended to limit its scope, as defined by the claims.

EXAMPLES

Example 1: Synthesis of 2-((2-((4-(4-(6-(2-((2-(2,6-dioxopiperidin-3-yl)-1,3-dioxoisoindolin-4-yl)oxy)acetamido)hexyl)piperazin-1-yl)-2-methoxyphenyl)amino)-5-(trifluoromethyl)pyridin-4-yl)amino)-N-methylbenzamide (1)

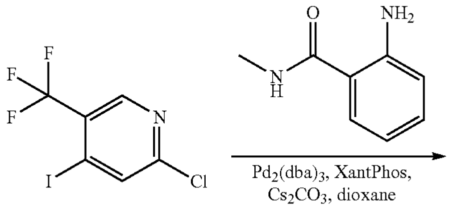

-continued

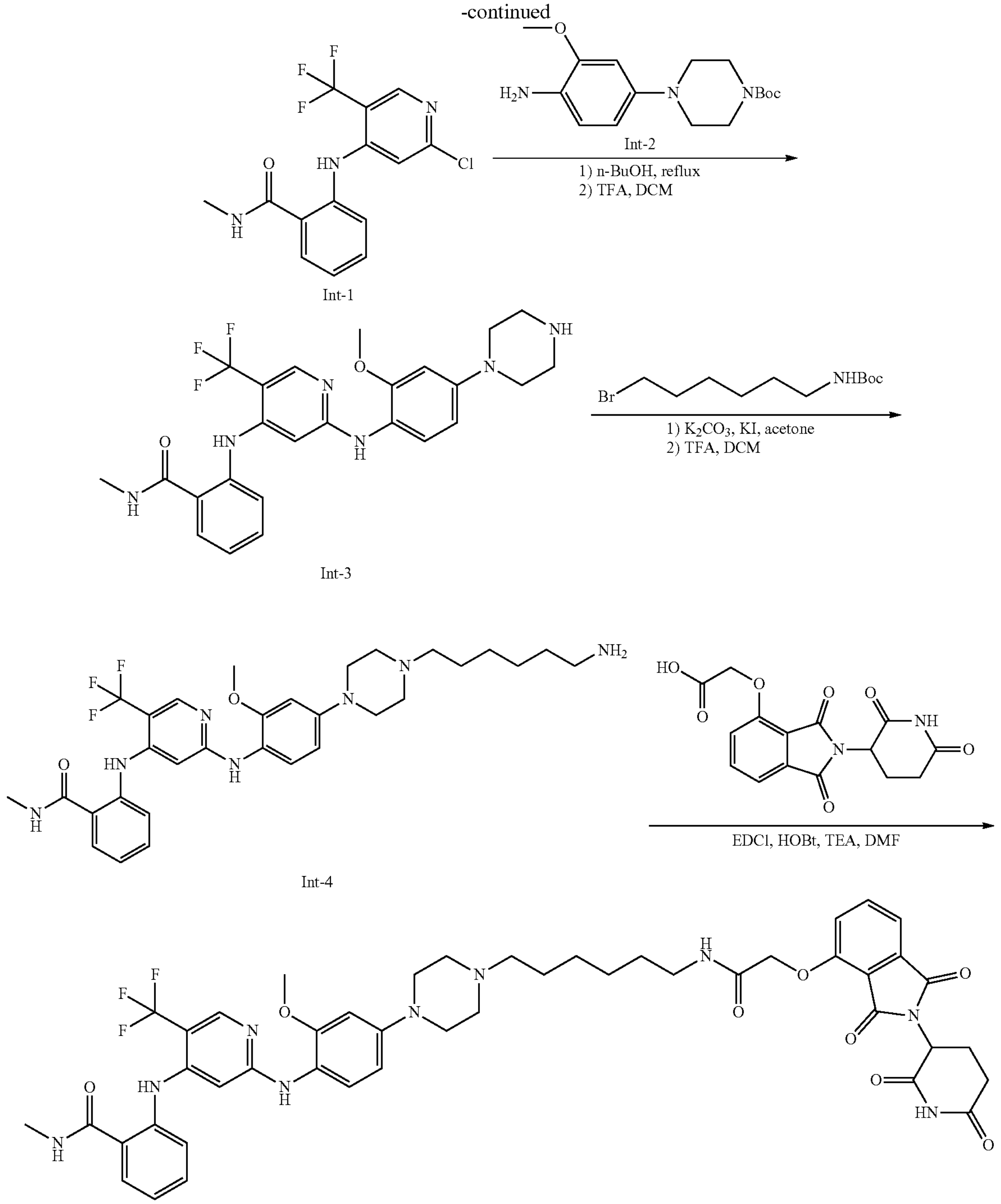

1

To a mixture of 2-chloro-4-iodo-5-(trifluoromethyl)pyridine (6.5 mmol, 978 mg), 2-amino-N-methylbenzamide (6.5 mmol, 2.0 g), $Cs_2CO_3$ (9.7 mmol, 3.7 g), $Pd_2(dba)_3$ (0.52 mmol, 476 mg) and XantPhos (4,5-Bis(diphenylphosphino)-9,9-dimethylxanthene) (0.78 mmol, 451 mg) in a 25 mL vial, 10 mL of dioxane was added under N2. The reaction was stirred and heated at 90° C. for 24 h. The reaction mixture was cooled to room temperature and filtered through a pad of Celite®. The filtrate was washed with brine. The organic layer was dried over anhydrous $Na_2SO_4$ and evaporated under reduced pressure. The crude product was purified by silica gel column chromatography with 0-40% hexane in ethyl acetate to give compound Int-1 as a gray solid (1.84 g, 86%).

LCMS: m/z 330.1 $[M+H]^+$.

To a suspension of Int-1 (3 mmol, 1.0 g) in 10 mL of n-BuOH was added Int-2 (3.3 mmol, 1 g). The mixture was stirred and heated to reflux under N2 for 3 days. The reaction was allowed to cool to room temperature and the solvent was evaporated under reduced pressure to give a yellowish residue which was then dissolved in 10 mL of dichloromethane (DCM), followed by the slow addition of trifluoroacetic acid (TFA) (5 mL) at 0° C. The resulting solution mixture was allowed to warm to room temperature and stirred overnight. The reaction mixture was evaporated to give a brown residue which was purified by reverse phase HPLC (0-100% MeOH in $H_2O$) to give Int-3 as a light brown solid (1.17 g, 78% over two steps).

LCMS: m/z 501.2 $[M+H]^+$.

To a solution of Int-3 (22.5 mg, 0.045 mmol) in acetone (0.5 mL) was added tert-butyl (6-bromohexyl)carbamate (19 mg, 0.068 mmol), followed by $K_2CO_3$ (12.3 mg, 0.09 mmol) and KI (11.3 mg, 0.068 mmol). The mixture was then heated to reflux and kept stirring for 24 h. The mixture was diluted with ethyl acetate (EtOAc) and $H_2O$, and the organic layer was washed with brine. The organic layer was dried over anhydrous $Na_2SO_4$ and concentrated under reduced pressure. The crude was then dissolved in 1 mL of DCM, followed by the addition of 1 mL of TFA at 0° C. and kept stirring overnight at room temperature. The solvent was evaporated, and the residue was purified by reverse phase HPLC (0-100% MeOH in $H_2O$) to give Int-4 as a light brown oil (21.3 mg, 79% over two steps).

mixture was filtered and purified by reverse phase HPLC (0-100% MeOH in $H_2O$) to give compound 1 as a light brown solid (27.5 mg, 86%).

$^1$H NMR (500 MHz, DMSO-d6) δ 11.12 (s, 1H), 10.42 (s, 1H), 9.68 (s, 1H), 9.30 (s, 1H), 8.69 (q, J=4.6 Hz, 1H), 8.13 (s, 1H), 7.97 (t, J=5.8 Hz, 1H), 7.88-7.78 (m, 1H), 7.73 (d, J=7.8 Hz, 1H), 7.59-7.46 (m, 3H), 7.41 (d, J=8.5 Hz, 1H), 7.32 (d, J=8.6 Hz, 1H), 7.25-7.16 (m, 1H), 6.72 (d, J=2.6 Hz, 1H), 6.57 (dd, J=8.8, 2.5 Hz, 1H), 6.53 (s, 1H), 4.78 (s, 2H), 4.11-3.35 (m, 8H), 3.23-3.06 (m, 6H), 3.03-2.83 (m, 3H), 2.76 (d, J=4.6 Hz, 3H), 2.67-2.56 (m, 1H), 1.79-1.58 (m, 2H), 1.47 (q, J=6.9 Hz, 2H), 1.38-1.28 (m, 4H).

LCMS: m/z 914.4 $[M+H]^+$.

Example 2: Synthesis of 2-((2-((2-methoxy-4-(4-(6-(2-((2-(1-methyl-2,6-dioxopiperidin-3-yl)-1,3-dioxoisoindolin-4-yl)oxy)acetamido)hexyl)piperazin-1-yl)phenyl)amino)-5-(trifluoromethyl)pyridin-4-yl)amino)-N-methylbenzamide (2)

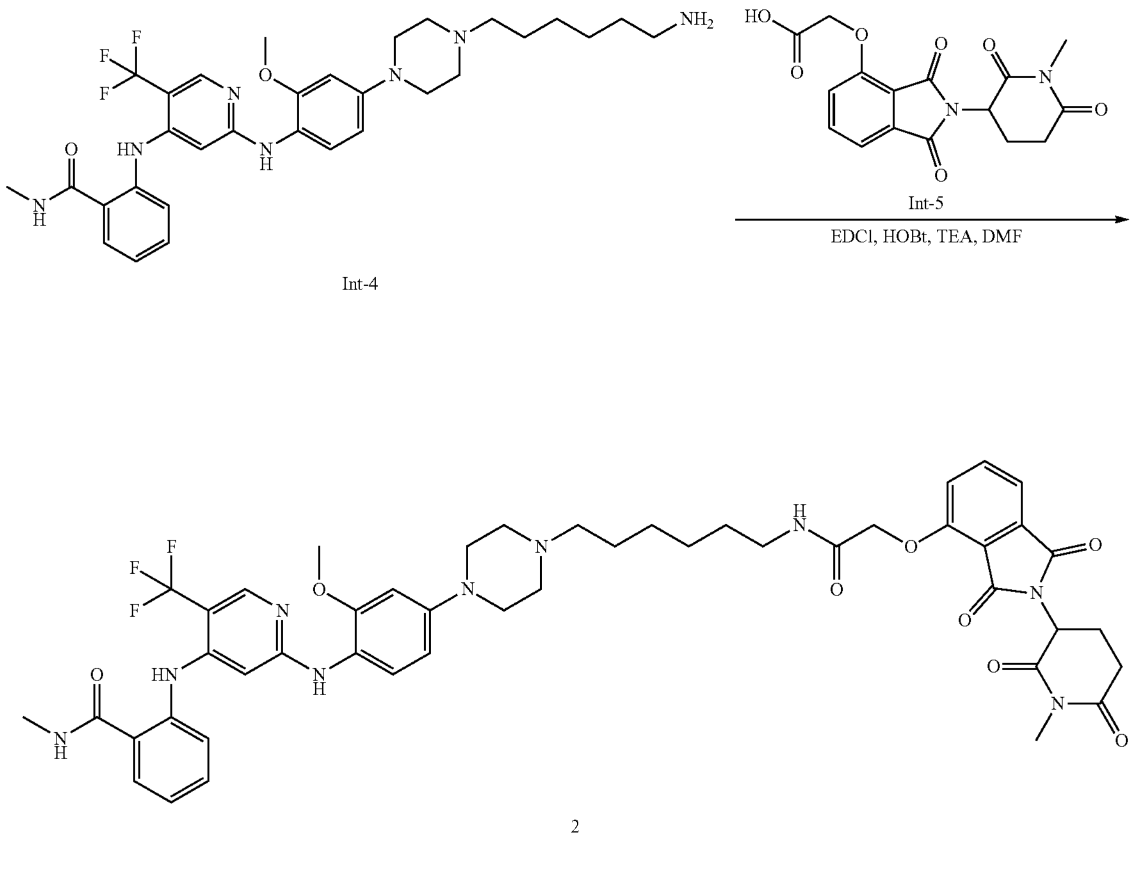

Int-4

2

LCMS: m/z 600.3 [M+1].

To a solution of Int-4 (0.035 mmol, 21 mg) and 2-(2-(2,6-dioxopiperidin-3-yl)-1,3-dioxoisoindolin-4-ylamino)acetic acid (11.6 mg, 0.035 mmol) in anhydrous dimethylformamide (DMF) (1 mL), 1-ethyl-3-(3-dimethylaminopropyl) carbodiimide (EDCI) (8.7 mg, 0.046 mmol), N-hydroxybenzotriazole (HOBt) (6.6 mg, 0.049 mmol), and triethylamine (TEA) (19 mg, 26 μL, 0.19 mmol) were added. The reaction was stirred at room temperature overnight. The To a solution of Int-4 (0.035 mmol, 21 mg) and Int-5 (12.5 mg, 0.035 mmol) in anhydrous DMF (1 mL), EDCI (8.7 mg, 0.046 mmol), HOBT (6.6 mg, 0.049 mmol), and TEA (19 mg, 26 μL, 0.19 mmol) were added. The reaction was stirred at room temperature overnight. The mixture was filtered and purified by reverse phase HPLC (0-100% MeOH in $H_2O$) to give compound 2 (26 mg, 80%).

LCMS: m/z 928.4 $[M+H]^+$.

Example 3: Synthesis of 2-((2-((4-(4-(1-((2-(2,6-dioxopiperidin-3-yl)-1,3-dioxoisoindolin-4-yl)oxy)-2-oxo-6,9,12-trioxa-3-azatetradecan-14-yl)piperazin-1-yl)-2-methoxyphenyl)amino)-5-(trifluoromethyl)pyridin-4-yl)amino)-N-methylbenzamide (3)

3

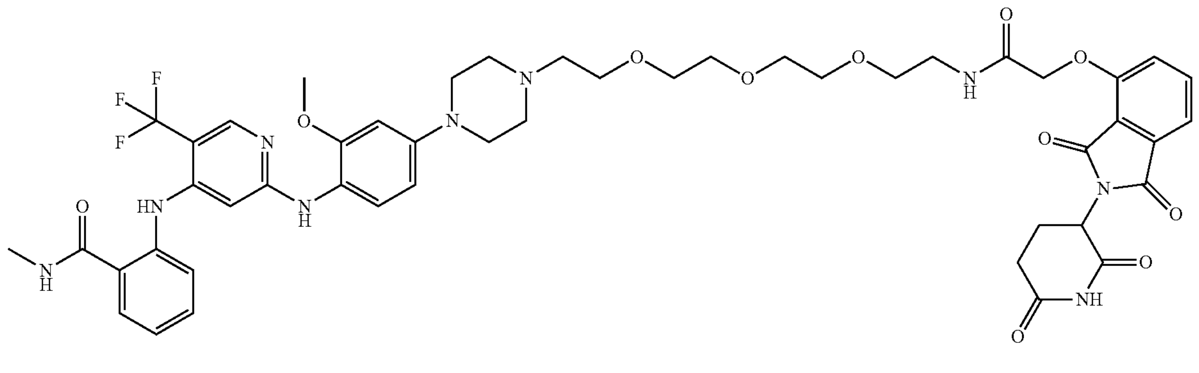

Compound 3 was prepared in an analogous manner to compound 1 from Int-3 (22.5 mg, 0.045 mmol), tert-butyl (2-(2-(2-(2-bromoethoxy)ethoxy)ethoxy)ethyl)carbamate (16 mg, 0.045 mmol) and 2-(2-(2,6-dioxopiperidin-3-yl)-1,3-dioxoisoindolin-4-ylamino)acetic acid (11.6 mg, 0.035 mmol). Compound 3 was obtained as a light brown solid (15.6 mg, 35% yield over 3 steps).

LC-MS: m/z 990.4 $[M+H]^+$.

Example 4: Synthesis of 2-((2-((4-(4-(2-(2-(2-(2-((2-(2,6-dioxopiperidin-3-yl)-1,3-dioxoisoindolin-4-yl)amino)acetamido)ethoxy)ethoxy)ethyl)piperazin-1-yl)-2-methoxyphenyl)amino)-5-(trifluoromethyl)pyridin-4-yl)amino)-N-methylbenzamide(4)

4

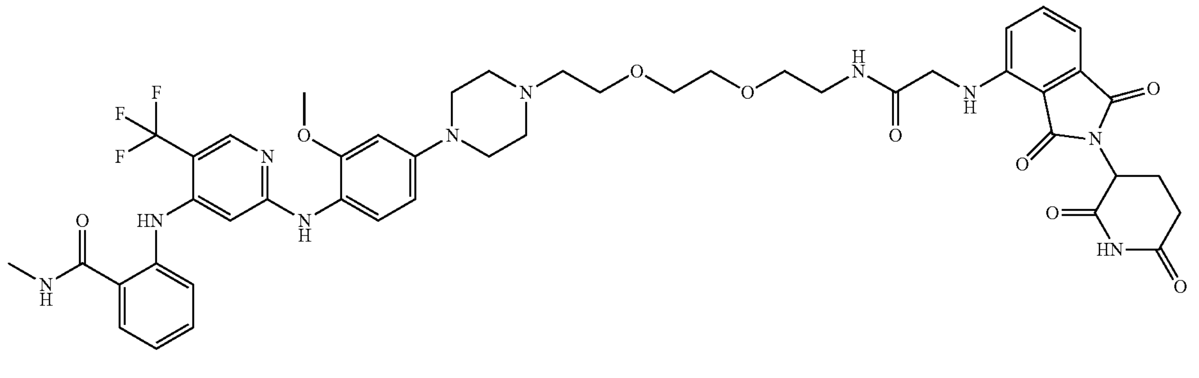

Compound 4 was prepared in an analogous manner to compound 1 from Int-3 (22.5 mg, 0.045 mmol), tert-butyl (2-(2-(2-bromoethoxy)ethoxy)ethyl)carbamate (14 mg, 0.045 mmol) and (2-(2,6-dioxopiperidin-3-yl)-1,3-dioxoisoindolin-4-yl)glycine (11.6 mg, 0.035 mmol). Compound 4 was obtained as a light brown solid (16.2 mg, 38% yield over 3 steps).

LC-MS: m/z 945.4 $[M+H]^+$.

Example 5: Synthesis of 2-((2-((4-(4-(8-(2-((2-(2,6-dioxopiperidin-3-yl)-1,3-dioxoisoindolin-4-yl)amino)acetamido)octyl)piperazin-1-yl)-2-methoxyphenyl)amino)-5-(trifluoromethyl)pyridin-4-yl)amino)-N-methylbenzamide (5)

5

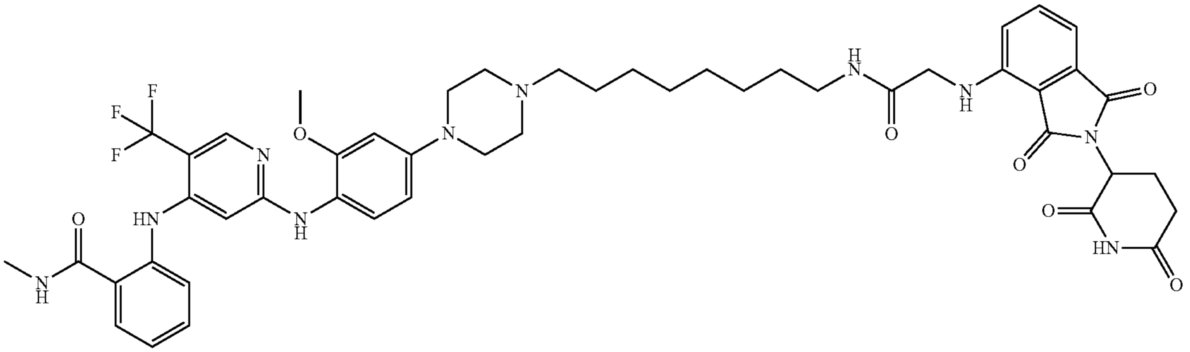

Compound 5 was prepared in an analogous manner to compound 1 from Int-3 (22.5 mg, 0.045 mmol), tert-butyl (8-bromooctyl)carbamate (14 mg, 0.045 mmol) and (2-(2,6-dioxopiperidin-3-yl)-1,3-dioxoisoindolin-4-yl)glycine (11.6 mg, 0.035 mmol). Compound 5 was obtained as light brown solid (13.1 mg, 31% yield over 3 steps).

LC-MS: m/z 941.4 $[M+H]^+$.

Example 6: Synthesis of 2-((2-((4-(4-(8-((2-(2,6-dioxopiperidin-3-yl)-1,3-dioxoisoindolin-4-yl)amino)octyl)piperazin-1-yl)-2-methoxyphenyl)amino)-5-(trifluoromethyl)pyridin-4-yl)amino)-N-methylbenzamide (6)

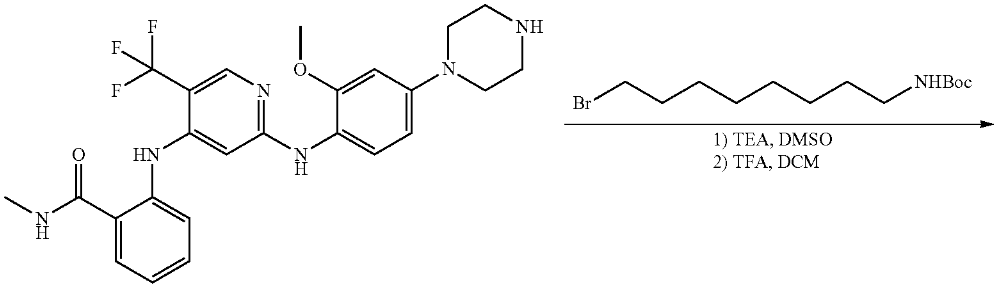

Int-3

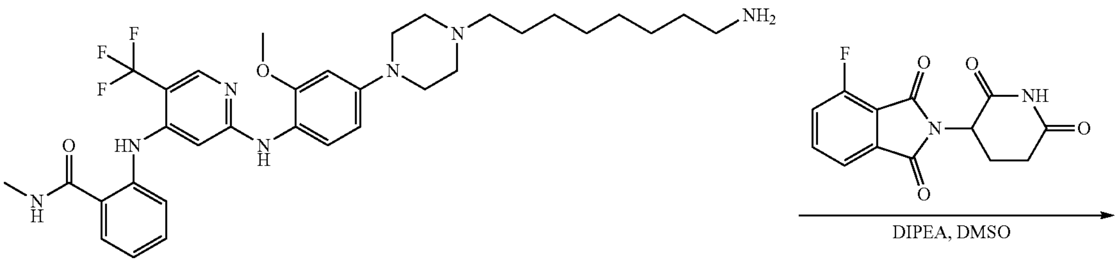

Int-6

-continued

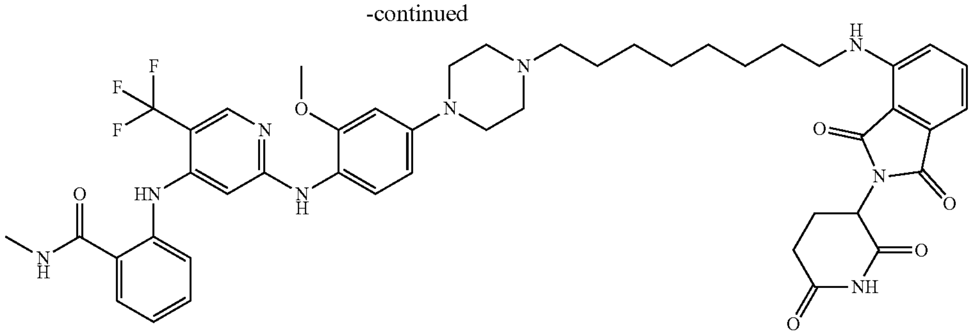

6

Int-6 was prepared in an analogous manner to Int-4 from Int-3 (22.5 mg, 0.045 mmol) and tert-butyl (8-bromooctyl) carbamate (14 mg, 0.045 mmol). Int-6 was obtained as light brown solid (22 mg, 78% yield over 2 steps).

LC-MS: m/z 628.4 $[M+H]^+$.

To a solution of Int-6 (22 mg, 0.035 mmol) in 1 mL of anhydrous dimethyl sulfoxide (DMSO) was added 2-(2,6-dioxopiperidin-3-yl)-4-fluoroisoindoline-1,3-dione (9.7 mg, 0.035 mmol) and N,N-diisopropylethylamine (DIPEA) (13.6 mg, 0.105 mmol). The reaction was stirred and heated at 90° C. for 2 h. The reaction mixture was cooled to room temperature and purified by reverse phase HPLC (0-100% MeOH in $H_2O$) to give compound 6 (12.4 mg, 40%).

LCMS: m/z 884.4 $[M+H]^+$.

Example 7: Synthesis of N-(8-(2-((2-(2,6-dioxopiperidin-3-yl)-1,3-dioxoisoindolin-4-yl)oxy)acetamido)octyl)-4-((4-((3-(methylsulfonyl)benzyl)amino)-5-(trifluoromethyl)pyrimidin-2-yl)amino)benzamide (7)

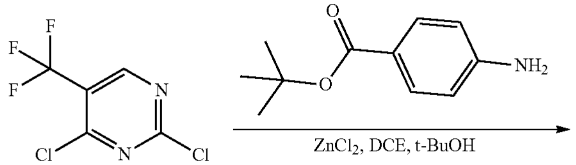

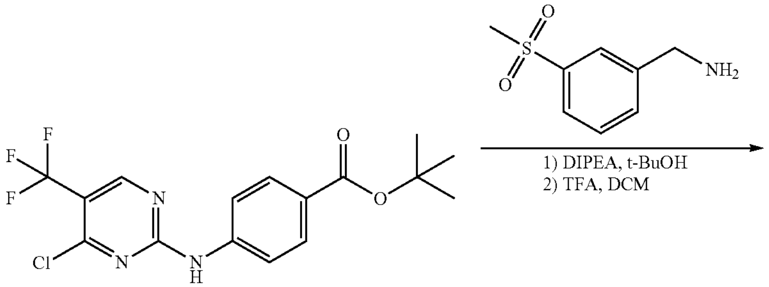

Int-7

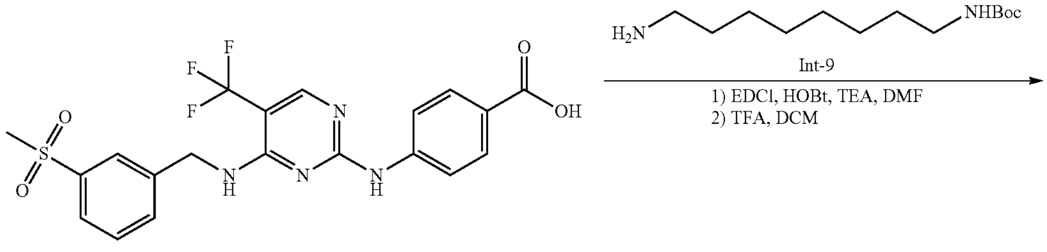

Int-8

-continued

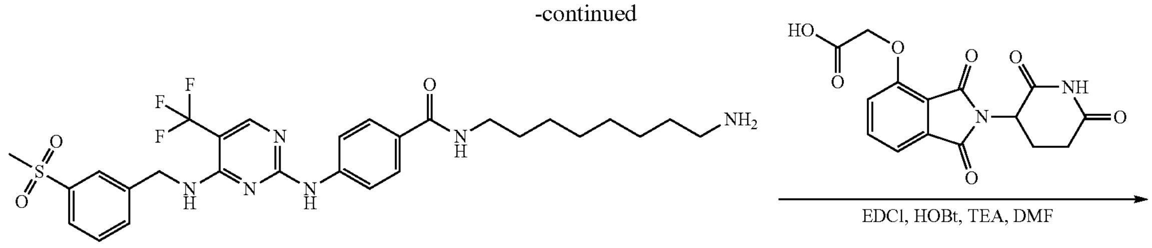

Int-10

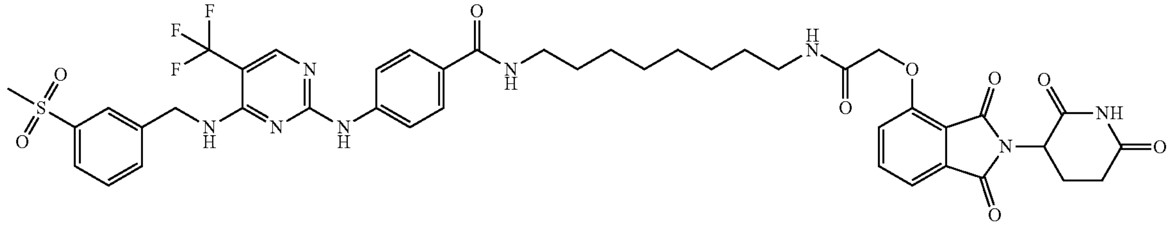

7

To a solution of 5-trifluoromethyl-2,4-dichloropyrimidine (2 g, 9.2 mmol) in 1:1 dichloroethane (DCE)/t-BuOH (80 mL) was added zinc chloride (11 mL of a 1M solution in ether, 1.2 eq) at 0° C. After 1 h, tert-butyl-4-aminobenzoate (1.8 g, 9.2 mmol) was added, followed by the dropwise addition of a solution of TEA (1.03 g, 10.1 mmol) in 10 mL of DCE/t-BuOH. After stirring for 1.5 h, the reaction was concentrated under reduced pressure. The residue was dissolved in 150 mL of ethyl acetate and washed with brine. The organic layer was dried over $Na_2SO_4$ and evaporated under reduced pressure to afford Int-7 as a yellow solid (2.7 g, 80%).

LCMS: m/z 374.1 $[M+H]^+$.

To a solution of Int-7 (2.7 g, 7.2 mmol) in 25 mL of t-BuOH was added (3-(methylsulfonyl)phenyl)methanamine (1.3 g, 7.2 mmol) and DIPEA (2.5 mL, 14.4 mmol). The mixture was stirred and heated at 80° C. for 24 h. The reaction mixture was then cooled to room temperature and the solvent was evaporated under reduced pressure. The residue was dissolved in 15 mL of DCM, followed by the addition of 7.5 mL of TFA at 0° C. The reaction was allowed to warm to room temperature and then stirred overnight. The mixture was concentrated under reduced pressure and the resulting residue was purified by column chromatography on silica gel (0-20% Methanol in DCM) to give Int-8 (2.45 g, 73% in two steps).

LCMS: m/z 467.1 $[M+H]^+$.

To a solution of Int-8 (16.3 mg, 0.035 mmol) and Int-9 (8.5 mg, 0.035 mmol) in 1 mL of anhydrous DMF, EDCI (8.7 mg, 0.046 mmol), HOBT (6.6 mg, 0.049 mmol), and TEA (19 mg, 26 μL, 0.19 mmol) were added. The mixture was stirred at room temperature overnight. The mixture was concentrated under reduced pressure and the resulting residue was dissolved in 1 mL of DCM, followed by the addition of 0.5 mL of TFA at 0° C. The reaction was stirred at room temperature overnight. The reaction mixture was evaporated under reduced pressure and purified by reverse phase HPLC (0-100% MeOH in $H_2O$) to give Int-10 (18.7 mg, 90% in two steps).

LCMS: m/z 593.2 $[M+H]^+$.

To a solution of Int-10 (18.7 mg, 0.032 mmol) and 2-(2-(2,6-dioxopiperidin-3-yl)-1,3-dioxoisoindolin-4-ylamino)acetic acid (12.5 mg, 0.035 mmol) in anhydrous DMF (1 mL), EDCI (8.7 mg, 0.046 mmol), HOBT (6.6 mg, 0.049 mmol), and TEA (19 mg, 26 μL, 0.19 mmol) were added. The mixture was stirred at room temperature overnight. The mixture was filtered and purified by reverse phase HPLC (0-100% MeOH in $H_2O$) to give compound 7 (29 mg, 89%).

LCMS: m/z 908.4 $[M+H]^+$.

Example 8: Synthesis of 2-((2-(2,6-dioxopiperidin-3-yl)-1,3-dioxoisoindolin-4-yl)oxy)-N-(5-(4-(4-((4-((3-(methylsulfonyl)benzyl)amino)-5-(trifluoromethyl)pyrimidin-2-yl)amino)benzoyl)piperazin-1-yl)pentyl)acetamide (8)

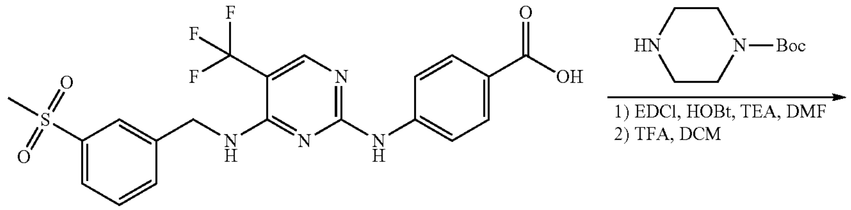

Int-8

-continued

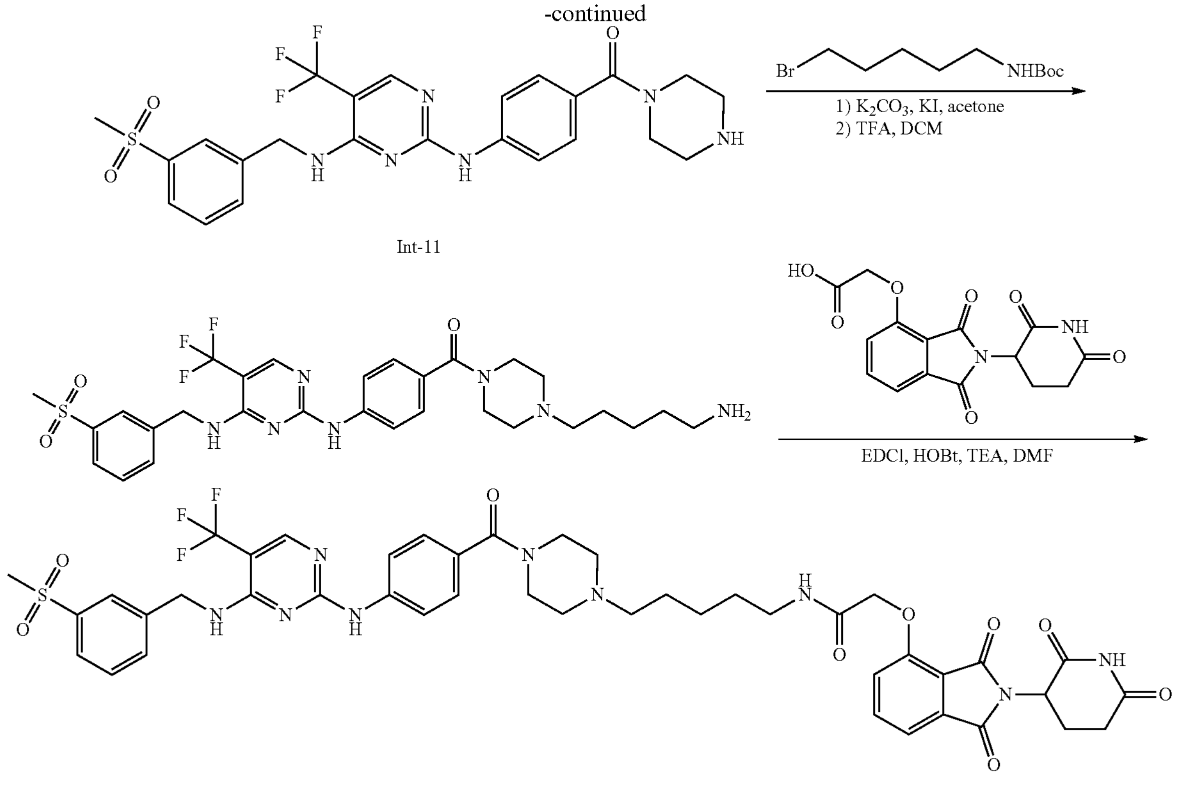

To a solution of Int-8 (32.6 mg, 0.07 mmol,) and 1-Boc-piperazine (13.0 mg, 0.07 mmol) in 1 mL of anhydrous DMF, EDCI (17.4 mg, 0.092 mmol), HOBT (13.2 mg, 0.097 mmol), and TEA (38 mg, 52 μL, 0.38 mmol) were added. The mixture was stirred at room temperature overnight. The mixture was concentrated under reduced pressure and the resulting residue was dissolved in 1 mL of DCM, followed by addition of 0.5 mL of TFA at 0° C. The reaction was stirred at room temperature overnight. The reaction mixture was evaporated under reduced pressure, and the resulting residue was purified by reverse phase HPLC (0-100% MeOH in $H_2O$) to give Int-11 (33 mg, 88% in two steps).

LCMS: m/z 535.2 [M+H]$^+$.

Compound 8 was synthesized in an analogous manner to compound 1 from intermediate Int-11 (22.5 mg, 0.045 mmol), tert-butyl (5-bromopentyl)carbamate (12 mg, 0.045 mmol) and 2-(2-(2,6-dioxopiperidin-3-yl)-1,3-dioxoisoindolin-4-ylamino)acetic acid (11.6 mg, 0.035 mmol). Compound 8 was obtained as a light brown solid (16.8 mg, 39% yield over 3 steps).

LCMS: m/z 935.4 [M+H]$^+$.

Example 9: Synthesis of 2-((2-((4-(1-(6-(2-((2-(2,6-dioxopiperidin-3-yl)-1,3-dioxoisoindolin-4-yl)oxy)acetamido)hexyl)piperidin-4-yl)-2-isopropoxy-5-methylphenyl)amino)-5-(trifluoromethyl)pyridin-4-yl)amino)-N-methylbenzamide (9)

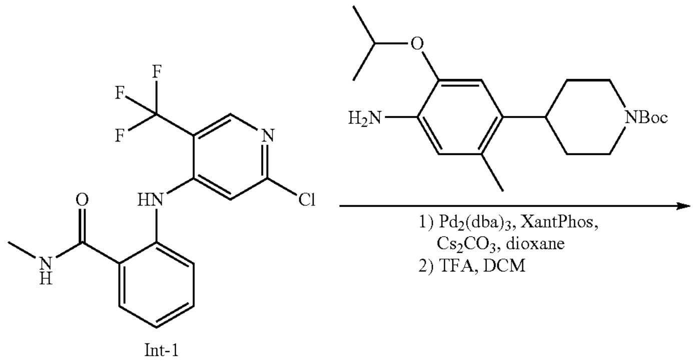

-continued

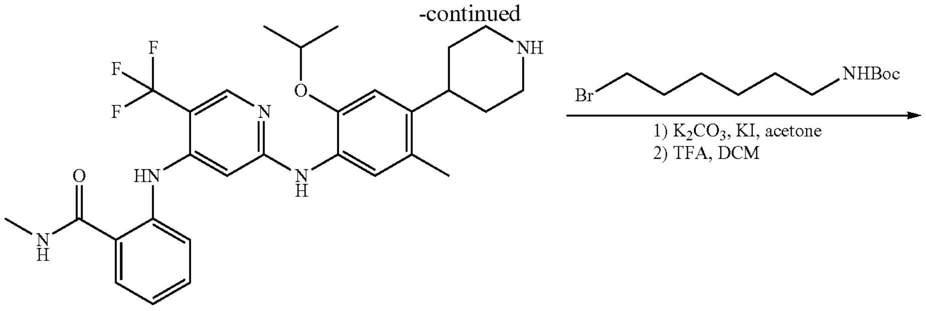

Int-12 (13)

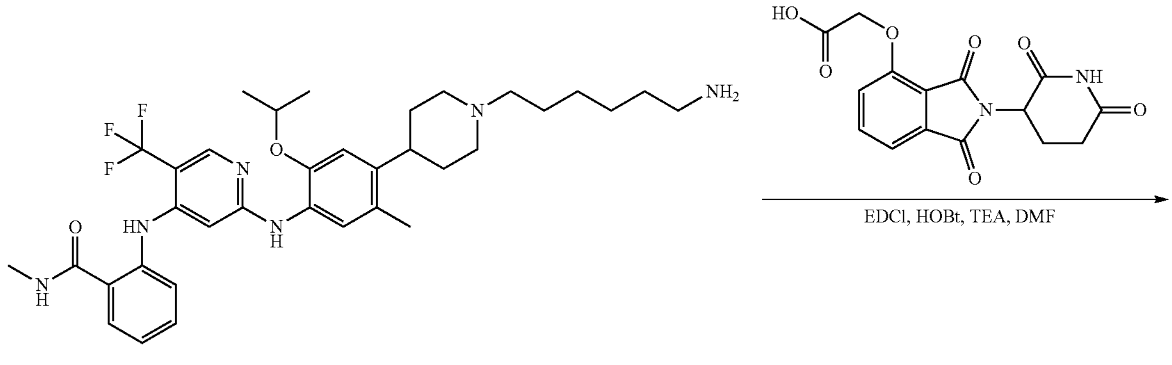

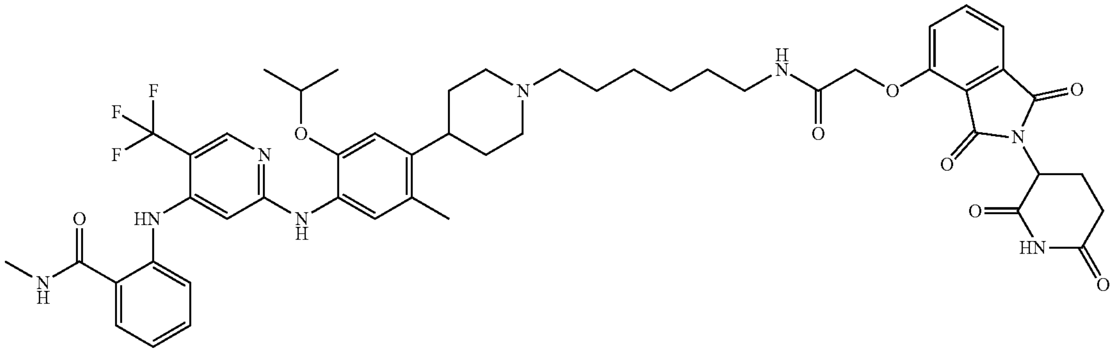

9

To a mixture of Int-1 (29.6 mg, 0.09 mmol), tert-butyl 4-(4-amino-5-isopropoxy-2-methylphenyl)piperidine-1-carboxylate (32 mg, 0.09 mmol), $Cs_2CO_3$ (68 mg, 0.18 mmol), $Pd_2(dba)_3$ (8.2 mg, 0.009 mmol) and XantPhos (5.2 mg, 0.009 mmol) in a 10 mL vial, 3 mL of dioxane was added under N2. The reaction was stirred and heated at 90° C. for 24 h. The reaction mixture was allowed to cool to room temperature and then filtered through a pad of Celite®. The filtrate was washed with brine. The organic layer was dried over anhydrous $Na_2SO_4$ and evaporated under reduced pressure. The crude product was dissolved in 2 mL of DCM, followed by the addition of 1 mL of TFA. The reaction was stirred overnight at room temperature. The mixture was then concentrated under reduced pressure and purified by reverse phase HPLC (0-100% MeOH in $H_2O$) to give Int-12, also described herein as 13, (24.4 mg, 50% in two steps).

LCMS: m/z 542.3 $[M+H]^+$.

Compound 9 was synthesized in an analogous manner to compound 1 from intermediate Int-12 (24.4 mg, 0.045 mmol), tert-butyl (6-bromohexyl)carbamate (12 mg, 0.045 mmol) and 2-(2-(2,6-dioxopiperidin-3-yl)-1,3-dioxoisoindolin-4-ylamino)acetic acid (11.6 mg, 0.035 mmol). Compound 9 was obtained as a light brown solid (13.8 mg, 32% yield over 3 steps).

$^1$H NMR (500 MHz, DMSO-d6) δ 11.12 (s, 1H), 10.45 (s, 1H), 9.40 (s, 1H), 9.06 (s, 1H), 8.68 (q, J=4.6 Hz, 1H), 8.22 (s, 1H), 7.97 (t, J=5.7 Hz, 1H), 7.88-7.77 (m, 1H), 7.73 (dd, J=7.9, 1.6 Hz, 1H), 7.60 (dd, J=8.2, 1.2 Hz, 1H), 7.50 (dd, J=9.0, 6.7 Hz, 2H), 7.41 (d, J=8.5 Hz, 1H), 7.33 (s, 1H), 7.20 (t, J=7.6 Hz, 1H), 6.79 (s, 1H), 6.67 (s, 1H), 4.78 (s, 2H), 3.56 (d, J=11.7 Hz, 2H), 3.17 (q, J=6.7 Hz, 2H), 2.76 (d, J=4.5 Hz, 3H), 2.69 (d, J=0.9 Hz, 4H), 2.54 (s, 4H), 2.25 (s, 3H), 2.17 (t, J=8.1 Hz, 4H), 1.95-1.83 (m, 3H), 1.66 (br, 2H), 1.47 (t, J=6.8 Hz, 2H), 1.33 (q, J=4.0, 3.5 Hz, 4H), 1.21 (s, 3H), 1.19 (s, 3H).

LCMS: m/z 955.4 $[M+H]^+$.

Example 10: Synthesis of 2-((2-((4-(1-(6-(2-((2-(2,6-dioxopiperidin-3-yl)-1,3-dioxoisoindolin-4-yl)oxy)acetamido)hexyl)piperidin-4-yl)-2-isopropoxy-5-methylphenyl)amino)-5-(trifluoromethyl)pyrimidin-4-yl)amino)-N-methylbenzamide(10)

(10)

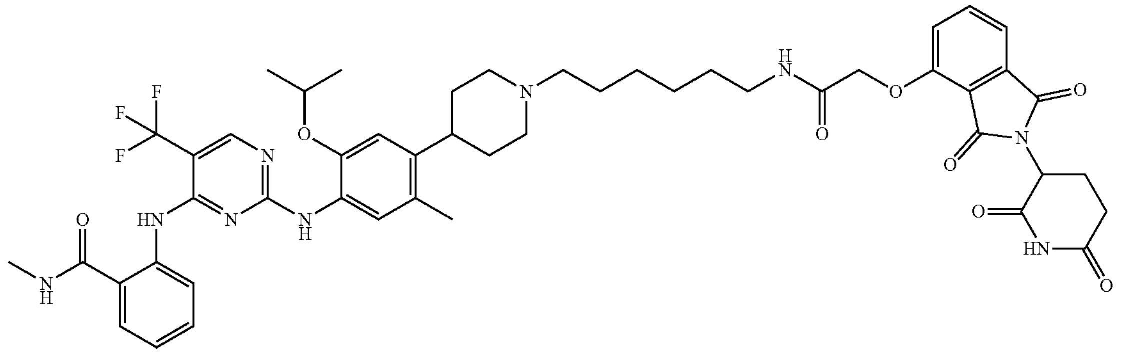

Compound 10 was synthesized in an analogous manner to compound 9 in example 9.

LCMS: m/z 957.0 $[M+H]^+$.

Example 11: Synthesis of 2-((2-((4-(1-(2-((6-(2-(2,6-dioxopiperidin-3-yl)-1-oxoisoindolin-4-yl)hex-5-yn-1-yl)amino)-2-oxoethyl)piperidin-4-yl)-2-isopropoxy-5-methylphenyl)amino)-5-(trifluoromethyl)pyrimidin-4-yl)amino)-N-methylbenzamide (11)

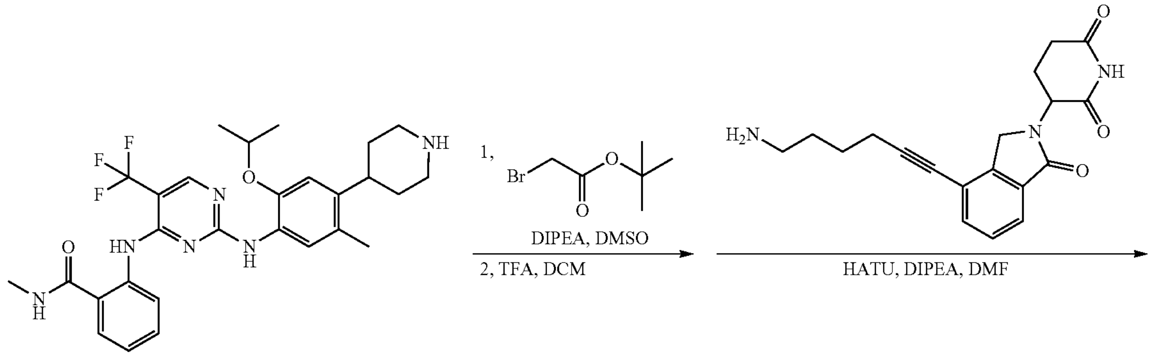

Int-12

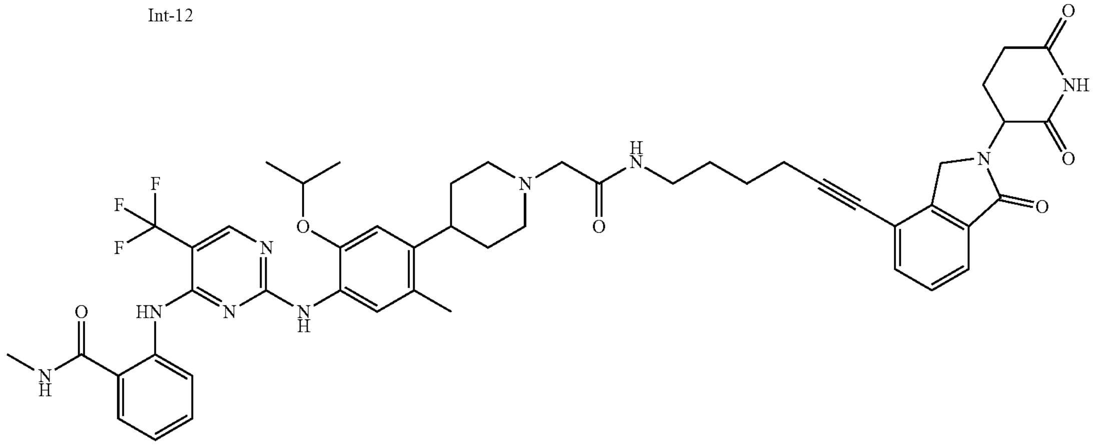

(11)

-continued

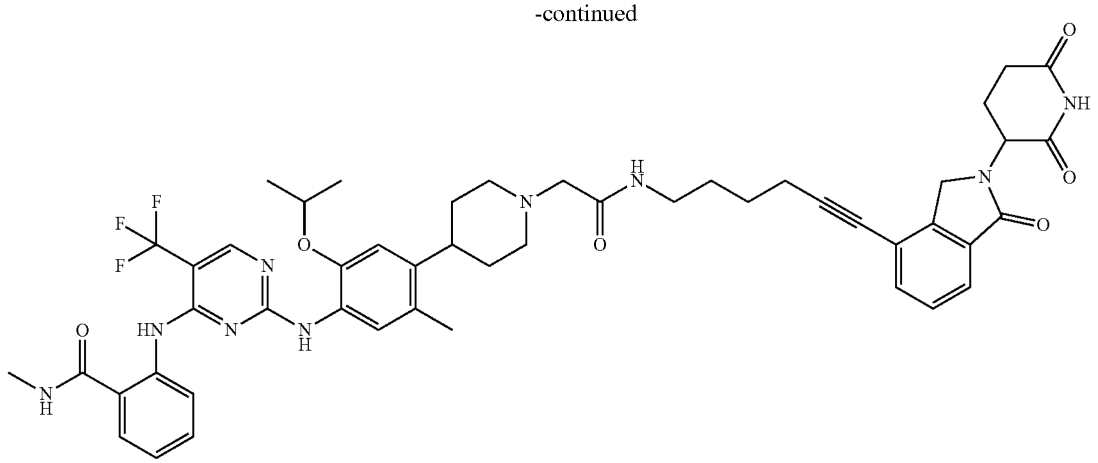

(11)

Compound 11 was synthesized in an analogous manner to compound 1 from intermediate Int-12 (24.4 mg, 0.045 mmol), tert-butyl 2-bromoacetate (18 mg, 0.09 mmol) and 3-(4-(6-aminohex-1-yn-1-yl)-1-oxoisoindolin-2-yl)piperidine-2,6-dione (15.3 mg, 0.045 mmol). Compound 11 was obtained as a light brown solid (16.6 mg, 40% yield over 3 steps).

LCMS: m/z 922.4 $[M+H]^+$.

Example 12: Synthesis of (2S,4R)-4-hydroxy-1-((S)-2-(7-(4-(5-isopropoxy-2-methyl-4-((4-((2-(methylcarbamoyl)phenyl)amino)-5-(trifluoromethyl)pyridin-2-yl)amino)phenyl)piperidin-1-yl) heptanamido)-3,3-dimethylbutanoyl)-N-((S)-1-(4-(4-methylthiazol-5-yl)phenyl)ethyl)pyrrolidine-2-carboxamide (12)

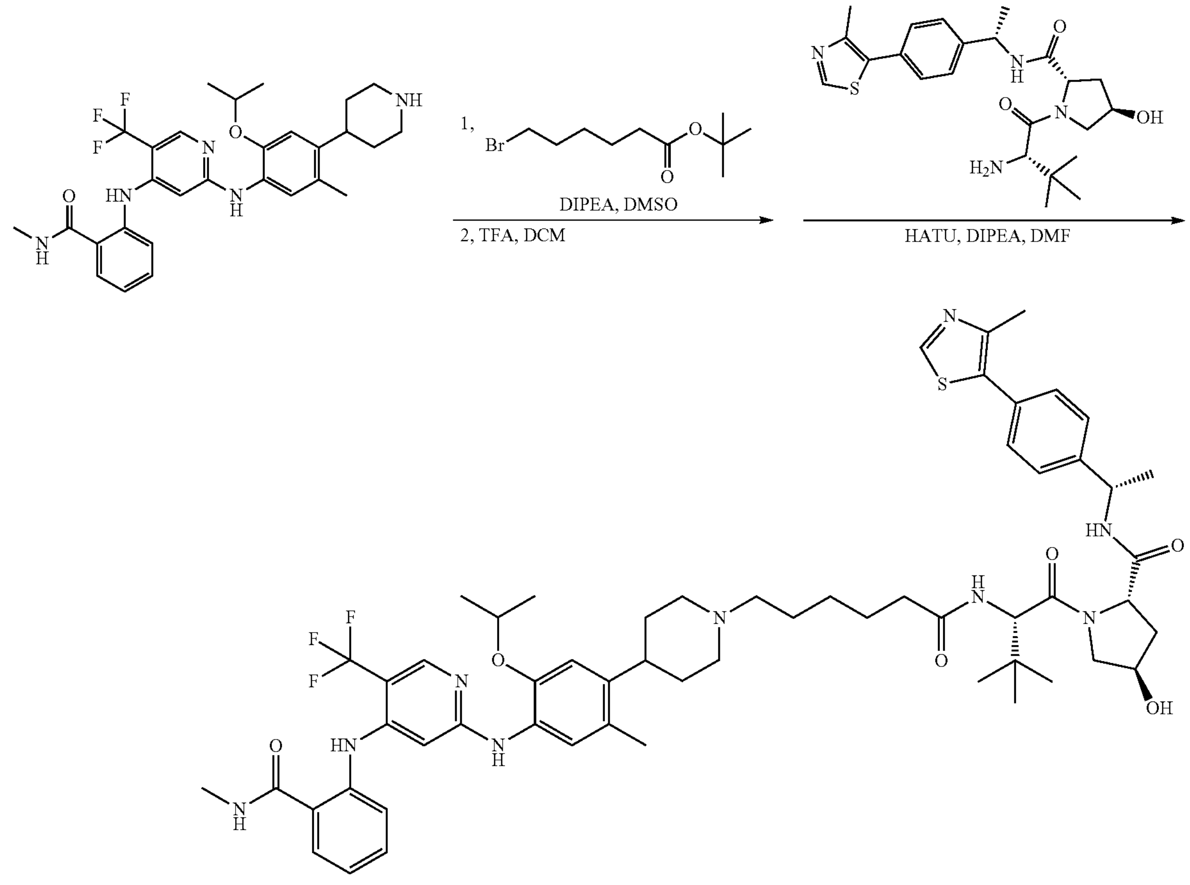

-continued

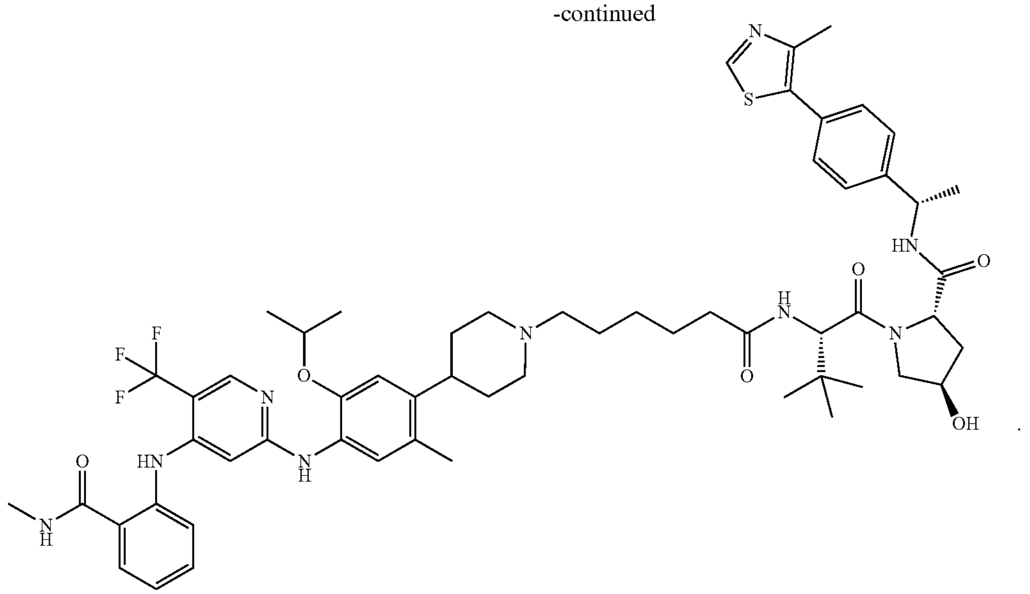

(12)

Compound 12 was synthesized in an analogous manner to compound 9 from intermediate Int-12 (24.4 mg, 0.045 mmol), tert-butyl 6-bromohexanoate (12 mg, 0.045 mmol) and (2S,4R)-1-((S)-2-amino-3,3-dimethylbutanoyl)-4-hydroxy-N-((S)-1-(4-(4-methylthiazol-5-yl)phenyl)ethyl)pyrrolidine-2-carboxamide (15.6 mg, 0.035 mmol). Compound 12 was obtained as a light brown solid (15.5 mg, 41% yield over 3 steps).

LCMS: m/z 1083.3 $[M+H]^+$.

Example 13: Cellular Degradation of Focal Adhesion Kinase (FAK) with Inventive Compounds PA-TU-8988T cells were treated with FAK degraders or indicated inhibitors for four hours at the indicated doses. After four hours, PA-TU-8988T cells were lysed in radioimmunoprecipitation assay (RIPA) buffer (Thermo Scientific™) on ice for 60 minutes and lysates were clarified by centrifugation. Immunoblotting for FAK was performed to evaluate changes in protein levels upon FAK degrader treatment. All samples were run with equal total protein content and immunoblotting was performed using antibodies that detect total FAK protein as well as GAPDH or α-Tubulin as a loading control. Fluorescently labelled infrared secondary antibodies that enable detection using an Odyssey® CLx Imager was employed to evaluate protein levels.

Figure 1B:
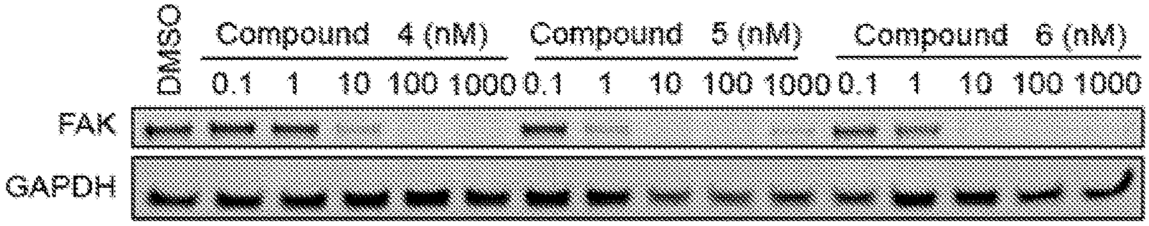

Treatment of PA-TU-8988T cells with inventive compounds 1 and 3-6 led to rapid and pronounced degradation of FAK protein (FIG. 1A and FIG. 1B). Treatment with compounds 1 and 5 led to the most pronounced degradation of FAK protein, with degradation evident at 1 nM and maximal degradation at 10 nM. Treatment with compounds 4 and 6 led to degradation of FAK protein at 10 nM and maximal degradation at 100 nM. Treatment with compound 3 led to modest degradation of FAK protein at 100 nM. These results indicate that FAK is a degradable kinase and compounds 1 and 5 are highly potent degraders of FAK protein.

Figure 2:
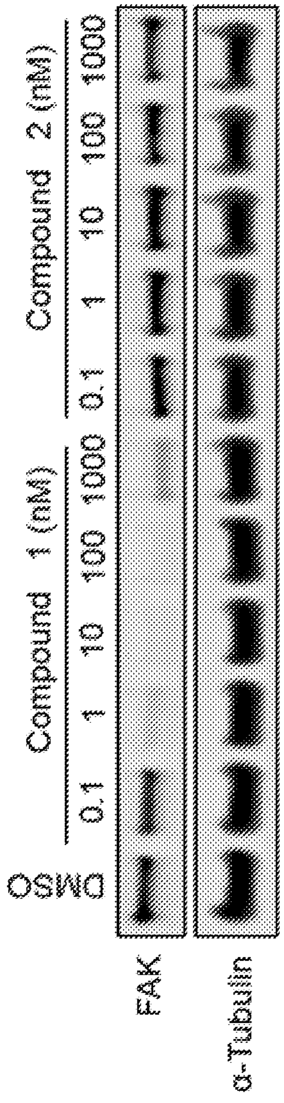
FIG. 2 is an immunoblot that shows the degradation of FAK in PA-TU-8988T cells after being treated with 0.1 nM to 1000 nM of inventive compound 1 and compound 2 (negative control) for 4 hours.

Treatment of PA-TU-8988T cells with inventive compound 1 led to rapid and pronounced degradation of FAK protein (FIG. 2). A negative control molecule, compound 2, which does not bind cereblon, did not induce degradation of FAK protein. These results indicate that compound 1 requires cereblon binding and recruitment to achieve potent degradation of FAK protein.

Figure 3:
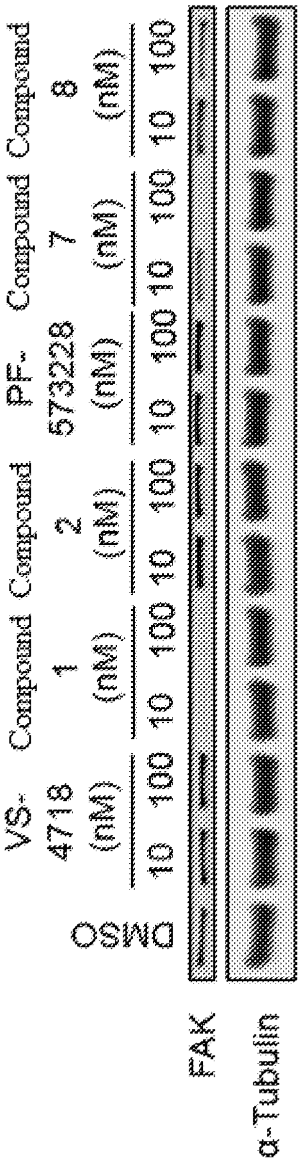
FIG. 3 is an immunoblot that shows the degradation of FAK in PA-TU-8988T cells after being treated with 0.1 nM to 1000 nM of inventive compounds 1, 7, and 8, compound 2, and inhibitors VS4718 and PF-573228 for 4 hours.

Treatment of PA-TU-8988T cells with inventive compound 1 led to rapid and pronounced degradation of FAK protein (FIG. 3). Treatment with compound 7 led to degradation of FAK protein at 10 nM and maximal degradation at 100 nM. Treatment with compound 8 led to modest degradation of FAK protein at 10 nM and maximal degradation at 100 nM. Treatment with the parent inhibitors (VS-4718 and PF-573228) and the negative control molecule, compound 2, did not induce degradation of FAK protein. These results indicate that FAK inhibitors do not induce degradation of FAK protein. This data further indicates that FAK protein is degradable in human pancreatic ductal adenocarcinoma cell lines.

Figure 4:
FIG. 4 is an immunoblot that shows the degradation of FAK in PA-TU-8988T cells after being treated with 1 nM to 1000 nM of inventive compounds 13 (parental inhibitor of compound 9), 1, and 9 for 4 hours.

Treatment of PA-TU-8988T cells with inventive compounds 1 and 9 led to rapid and pronounced degradation of FAK protein (FIG. 4). Treatment with the parent inhibitor of inventive compound 9, compound 13 (Int-12 in Example), did not induce degradation of FAK protein. These results further support the observations that FAK inhibitors do not induce degradation of FAK protein and that FAK protein is degradable in human pancreatic ductal adenocarcinoma cell lines.

Figure 5:
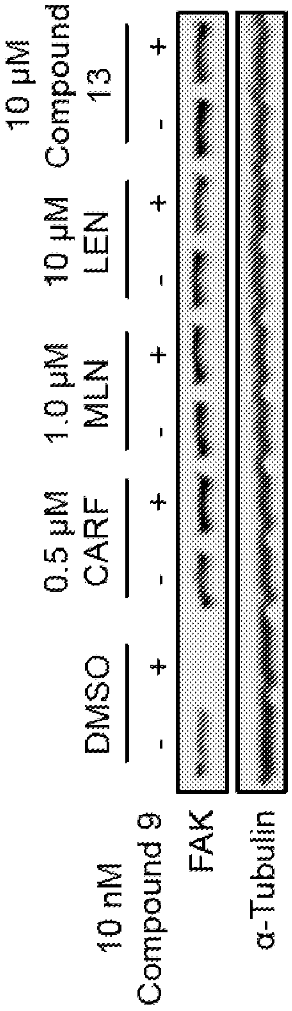
FIG. 5 is an immunoblot that shows the rescue of degradation of FAK in PA-TU-8988T cells after pre-treatment with DMSO, 0.5 μM carfilzomib (CARF), 1.0 μM MLN4924 (MLN), 10 μM lenalidomide (LEN) or 10 μM inventive compound 13 for two hours, followed by treatment with 10 nM of inventive compound 9 for four hours.

Treatment of PA-TU-8988T cells with carfilzomib, MLN4924, lenalidomide and inventive compound 13 rescued the degradation induced by compound 9 (FIG. 5). These results indicate that the proteasome (carfilzomib pretreatment) and activated E3 ligases (MLN4924 pre-treatment) are required for degradation induced by compound 13. These results also indicate that binding to CRBN (lenalidomide pre-treatment) and FAK (compound 13 pretreatment) are required for degradation induced by compound 9.

(13)

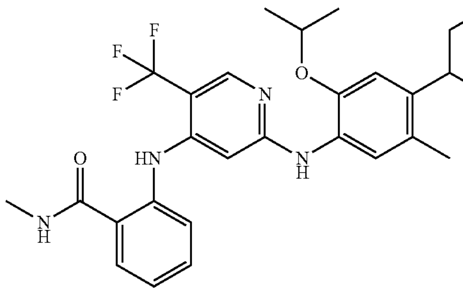

Figure 6A:
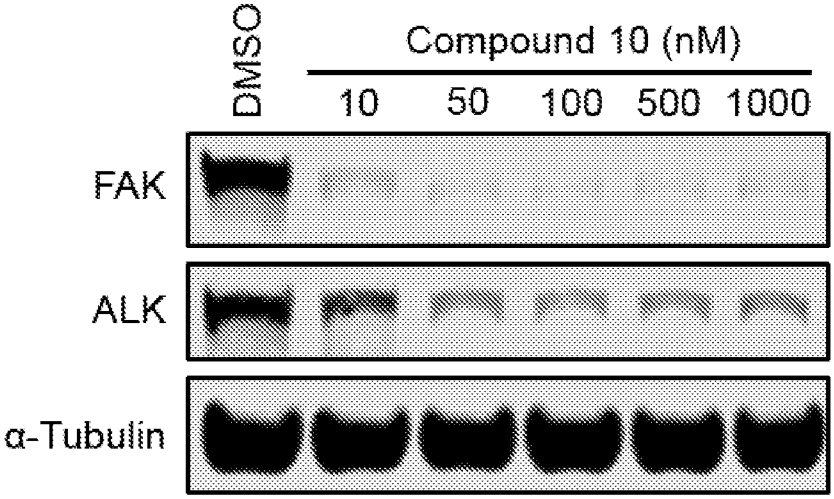
FIG. 6A is an immunoblot that shows the degradation of FAK and ALK in H3122 cells after being treated with 10 nM to 1000 nM of inventive compound 10 for 16 hours.
Figure 6B:
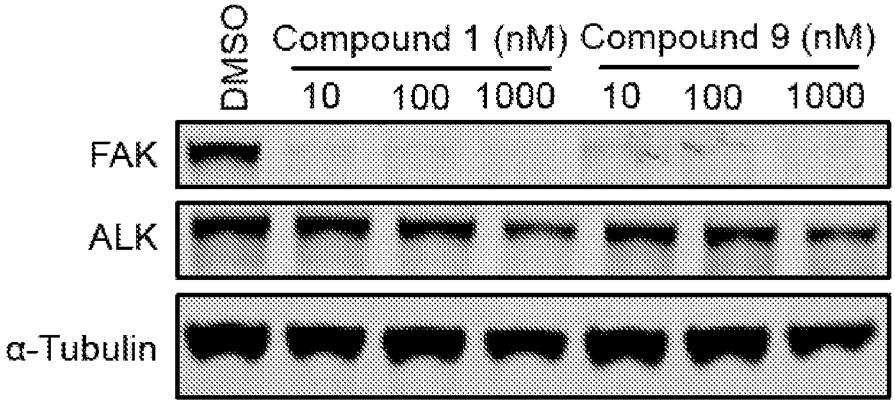
FIG. 6B is an immunoblot that shows the degradation of FAK in H3122 cells after being treated with 10 nM to 1000 nM of inventive compounds 1 and 9 for 24 hours. Inventive compounds 1 and 9 do not show degradation of ALK.

Treatment of $H_{3122}$ cells with inventive compounds 1, 9, and 10 led to pronounced degradation of FAK protein (FIG. 6A-FIG. 6B). Treatment with inventive compound 10 also led to degradation of ALK protein. These results support the observations that inventive compound 10 is a dual FAK and ALK degrader, while inventive compounds 1 and 9 are selective for FAK.

FAK degraders were evaluated in immunoblot assays to determine the effective dose required to achieve FAK protein loss. Immunoblots for FAK protein were normalized relative to the loading control and percent degradation was evaluated compared to DMSO treatment. Table 1 summarizes the percent FAK protein degradation that was achieved at 10 nM and 100 nM doses of FAK protein in this assay. Comparative evaluation of FAK degradation in PA-TU-8988T indicates that compounds 1, 5, 6 and 9 are the most potent FAK degraders, with greater than 90% degradation at 10 nM and 100 nM doses.

TABLE 1

Level of FAK degradation upon treatment with inventive compounds.

| Compound | Degradation at 10 nM | Degradation at 100 nM |
|---|---|---|
| 1 | ++++ | ++++ |
| 2 | – | – |
| 3 | ++ | ++++ |
| 4 | +++ | ++++ |
| 6 | ++++ | ++++ |
| 7 | + | ++++ |
| 8 | – | + |
| 9 | ++++ | ++++ |
| 13 | – | – |

Data is based on immunoblotting assessment of total FAX protein levels in PA-TU-8988T cells.
Key:
++++ is 85-100% degradation.
+++ is 70-84% degradation.
++ is 50-69% degradation.
+ is 25-49% degradation.
– is 0-24% degradation.

Table 1 shows a summary of the level of FAK degradation achieved upon treatment of PA-TU-8988T cells with the indicated compounds.

Example 14: In Vivo Degradation of Focal Adhesion Kinase (FAK) with Inventive Compounds PA-TU-8988T cells were implanted into the flanks of nude mice. After tumors had formed, mice were treated with indicated FAK degraders for three consecutive days via intraperitoneal administration and sacrificed 4 hours after the third and final treatment. Tumors and livers were harvested and lysed in RIPA on ice for 60 minutes and lysates were clarified by centrifugation. Immunoblotting for FAK was performed to evaluate changes in protein levels upon FAK degrader administration. All samples were run with equal total protein content and immunoblotting was performed using antibodies that detect total FAK protein as well as α-Tubulin as a loading control. Fluorescently labelled infrared secondary antibodies that enable detection using an Odyssey® CLx Imager was employed to evaluate protein levels.

Figure 7:
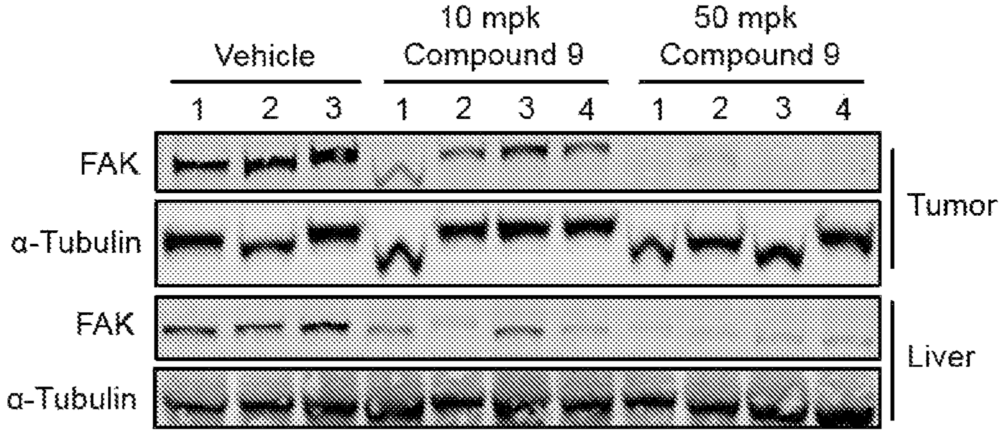
FIG. 7 is an immunoblot that shows the degradation of FAK in PA-TU-8988T tumor xenografts and mouse livers after being treated with 10 to 50 mg/mk (mpk) of inventive compound 9. Mice were treated for three consecutive days and assessments were performed 4 hours after the third and final treatment.

Treatment of mice implanted with PA-TU-8988T cells with inventive compound 9 led to pronounced degradation of FAK protein in the PA-TU-8988T xenograft tumors and mouse livers (FIG. 7). These results support the observation that compound 9 was a potent degrader of human and mouse FAK and depleted FAK protein in mouse models.

Example 15: Selectivity Profiling of Compound 13 and VS-4718

In vitro kinase assays with inventive compound 13 and VS-4718 were performed by Life Technologies™ in duplicate at an ATP concentration=Km for each indicated kinase. The results are summarized in Table 2 and indicate that inventive compound 13 maintained potent FAK activity, with improved activity on ALK as compared to VS-4718.

TABLE 2

$IC_{50}$ with inventive compound 13.

| | Biochemical $IC_{50}$ (nM) | |
|---|---|---|
| Compound ID | FAK | ALK |
| Compound 13 | 21 | 26.3 |
| VS-4718 | 20 | 41.1 |

Figure 8A:
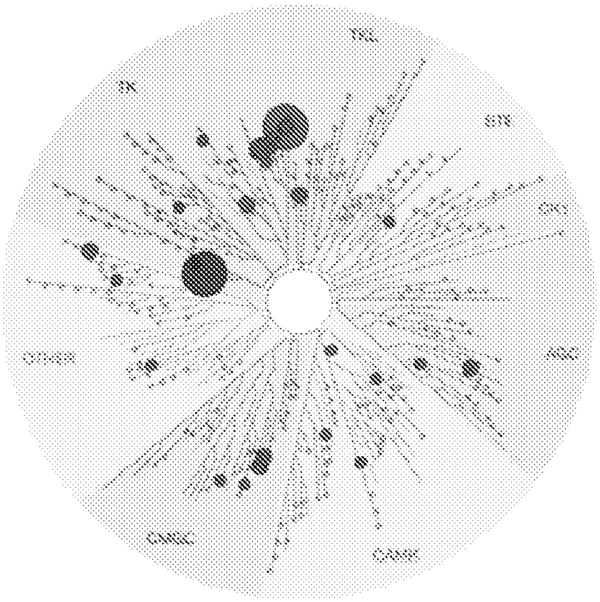
FIG. 8A-FIG. 8B is a set of diagrams that shows the results of KINOMEscan® competition binding assays with compound 13 (FIG. 8A) and VS4718 (FIG. 8B) at 1000 nM. FAK is noted in blue.
Figure 8B:
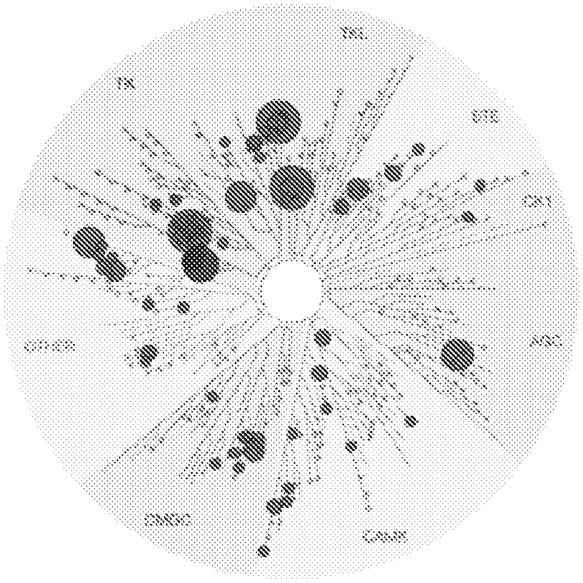

KINOMEscan® competition binding assays with inventive compound 13 and VS-4718 were performed by DiscovrX at 1000 nM. The results, illustrated in FIG. 8A-FIG. 8B, show an improved kinome-wide selectivity of inventive compound 13 compared to FAK inhibitor VS-4718. Additionally, despite the observed activity of compound 13 on ALK, degradation of ALK with compound 9 was not observed (FIG. 6B).

All patent publications and non-patent publications are indicative of the level of skill of those skilled in the art to which this invention pertains. All these publications are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A bifunctional compound which has a structure represented by formula (I):

(I)

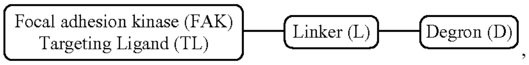

, wherein the FAK targeting ligand is represented by structure (TL):

(TL)

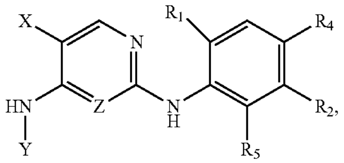

wherein

X is halo, $CF_3$, methyl, ethyl or cyclopropyl;

Y is

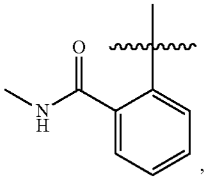 [SMILES: *c1ccccc1C(=O)NC]
,
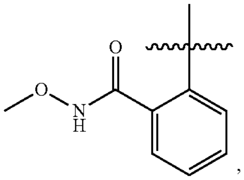
,
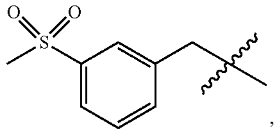
,
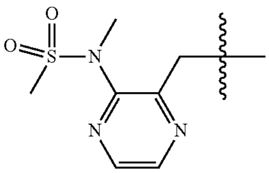
or
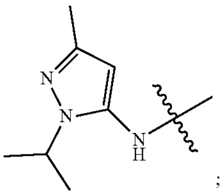
;

Z is CH;

$R_1$ is H or $OR_3$, wherein $R_3$ is H, optionally substituted $C_1$-$C_4$ alkyl or cyclopropyl;

$R_2$ is H or optionally substituted $C_1$-$C_4$ alkyl;

$R_4$ is

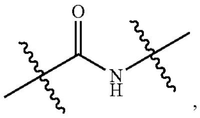
,
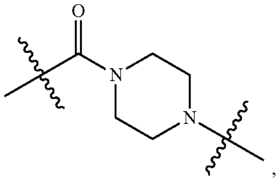
,

-continued

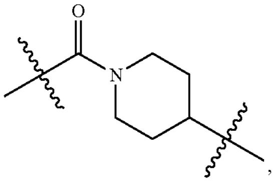
,
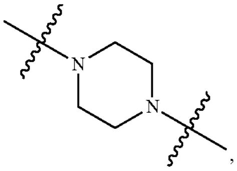
,
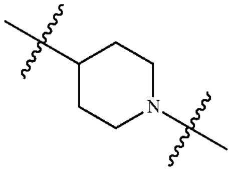
or
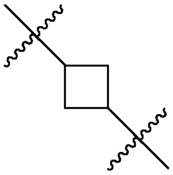
;

and $R_5$ is H or $OR_3$, wherein $R_3$ is H, optionally substituted $C_1$-$C_4$ alkyl or cyclopropyl;

wherein the degron is represented by any one of structures (D1-a) to (D1-d):

(D1-a)

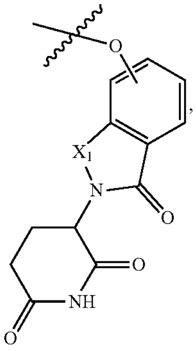
, (D1-b)

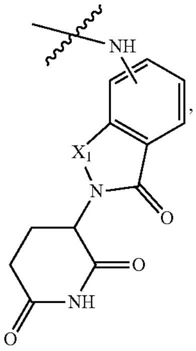
, (D1-c)

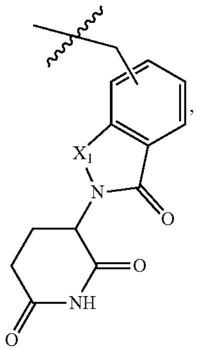
, and

-continued (D1-d)

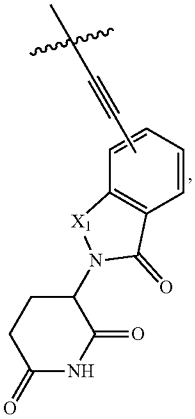

wherein $X_1$ is $CH_2$ or CO, or the degron has a structure represented by any one of structures (D2-a) to (D2-e):

(D2-a)

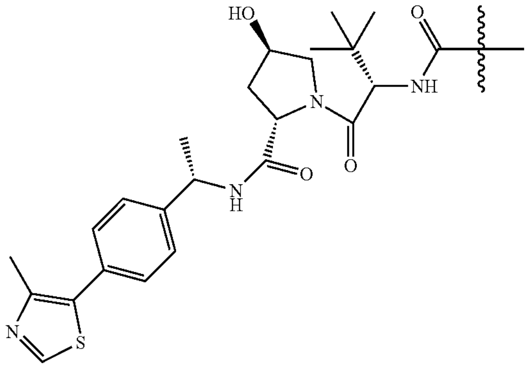

;

(D2-b)

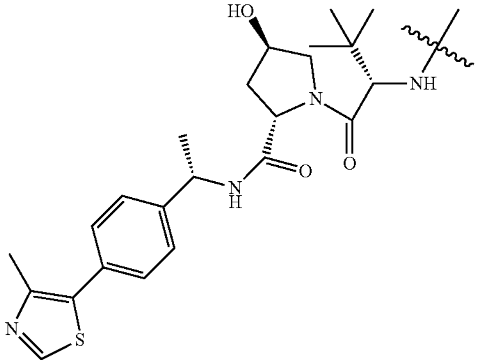

;

-continued (D2-c)

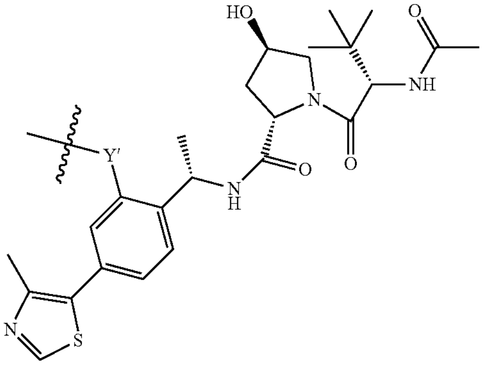

, wherein Y' is a bond or O;

(D2-d)

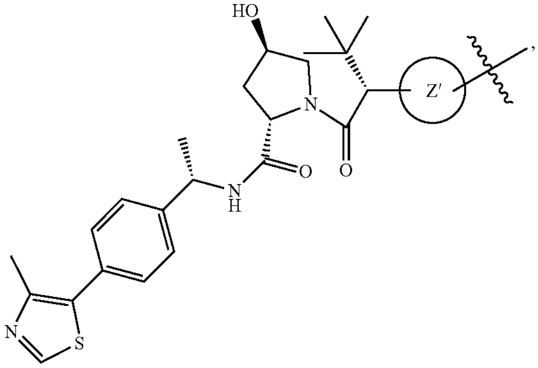

wherein Z' is a $C_5$-$C_6$ carbocyclic or heterocyclic group; and (D2-e)

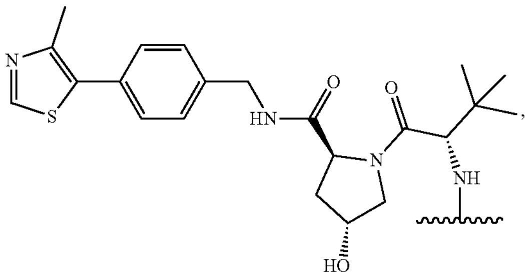

and the linker is an alkylene chain which may be interrupted by, and/or terminate (at either or both termini) at least one of —O—, —S—, —N(R")—, —C(O)—, —C(O)O—, —OC(O)—, —OC(O)O—, —C(NOR")—, —C(O) N(R")—, —C(O) N(R") C(O)—, —C(O) N(R") C(O) N(R")—, —N(R") C(O)—, —N(R") C(O) N(R")—, —N(R") C(O)O—, —OC(O) N(R")—, —C(NR")—, —N(R') C(NR")—, —C(NR") N(R")—, —N(R")C(NR")N (R")—, —$S(O)_2$—, —OS(O)—, —S(O)O—, —S(O)—, —$OS(O)_2$—, —$S(O)_2O$—, —N(R")$S(O)_2$—, —$S(O)_2$N (R")—, —N(R")S(O)—, —S(O)N(R")—, —N(R")$S(O)_2$N (R")—, —N(R')S(O)N(R')—, $C_{3-12}$ carbocyclene, 3- to 12-membered heterocyclene, 5- to 12-membered heteroarylene or any combination thereof, wherein R" is H or $C_1$-$C_6$ alkyl, wherein the one or both terminating groups may be the same or different, or a pharmaceutically acceptable salt or stereoisomer thereof.

2. The bifunctional compound of claim 1, wherein $R_2$ is methyl, ethyl or isopropyl.

3. The bifunctional compound of claim 1, wherein the bifunctional compound is represented by structure (Ia):

(Ia)

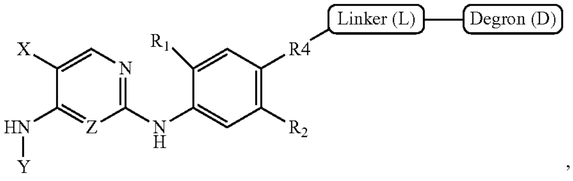

, or a pharmaceutically acceptable salt or stereoisomer thereof.

4. The bifunctional compound of claim 1, wherein X is $CF_3$;

Y is

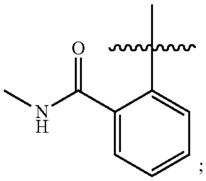 [SMILES: *c1ccccc1C(=O)NC]

;

Z is CH, $R_1$ is $OR_3$, wherein $R_3$ is methyl or isopropyl; $R_2$ is H or methyl; $R_4$ is

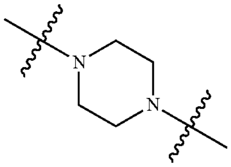

or

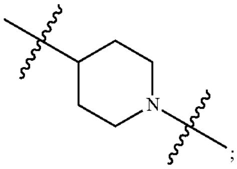

;

and $R_5$ is H, and the FAK targeting ligand is represented by structure (TL1a) or (TL1b):

(TL1a)

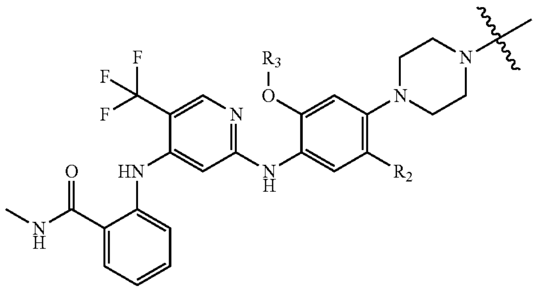

or

-continued (TL1b)

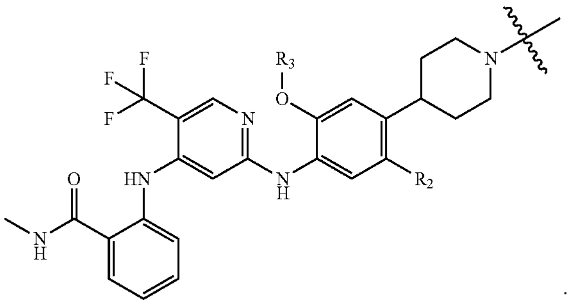

.

5. The bifunctional compound of claim 1, wherein the linker is represented by a structure selected from the group consisting of:

(L10-a)

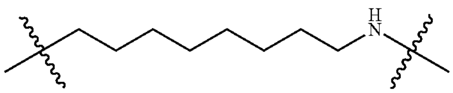

, (L10-b)

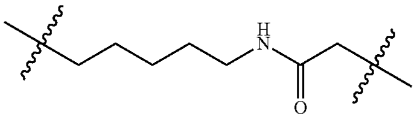

, (L10-c)

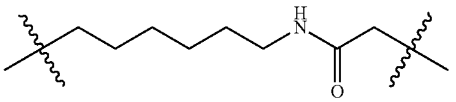

, (L10-d)

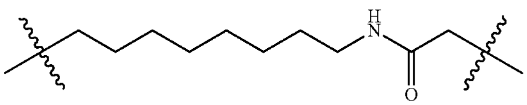

, (L10-e)

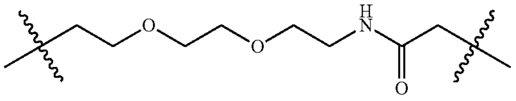

, and (L10-f)

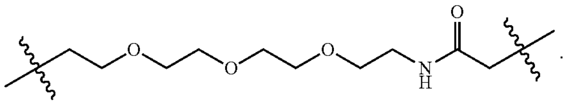

.

6. The bifunctional compound of claim 1, which is represented by a structure selected from the group consisting of:

(TL-L10a)
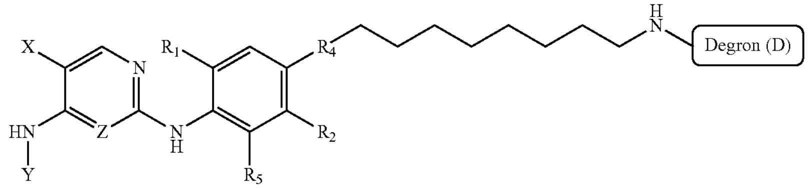
;
(TL-L10b)
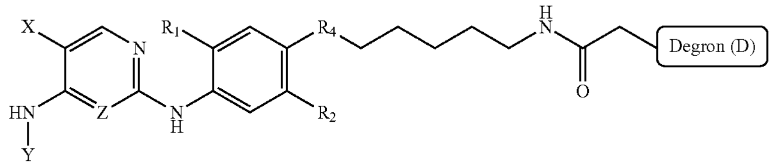
;
(TL-L10c)
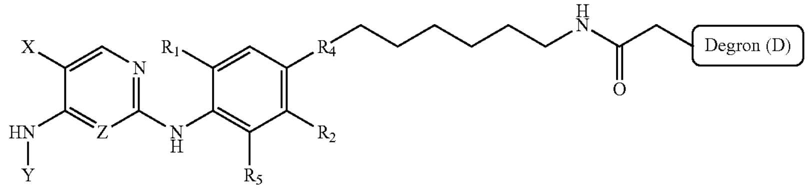
;
(TL-L10d)
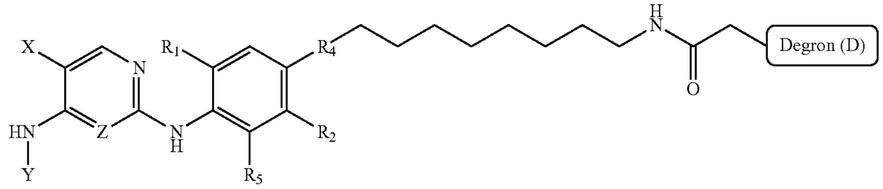
;
(TL-L10e)
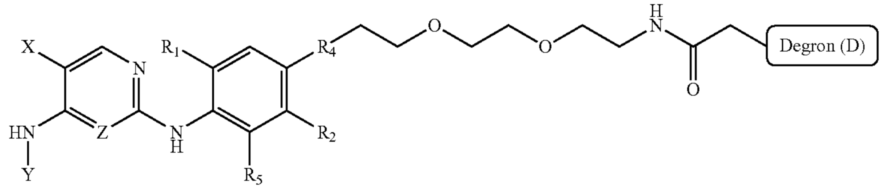
;
(TL-L10f)
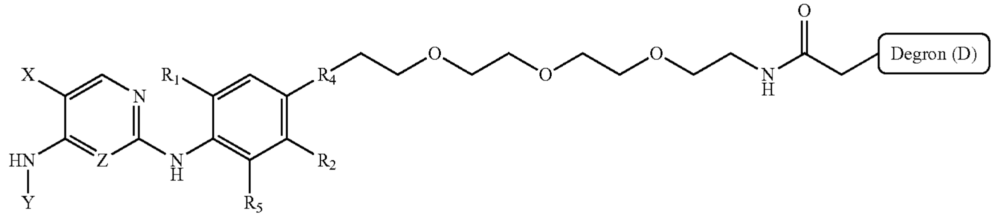
;
(TL1a-L10a)
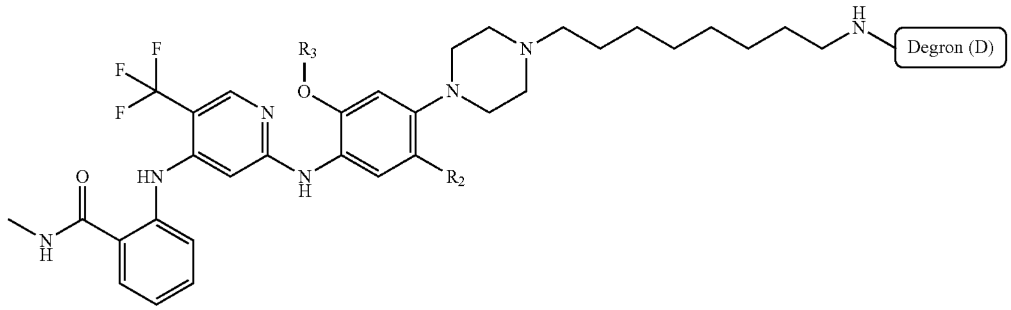
;

-continued
(TL1a-L10b)
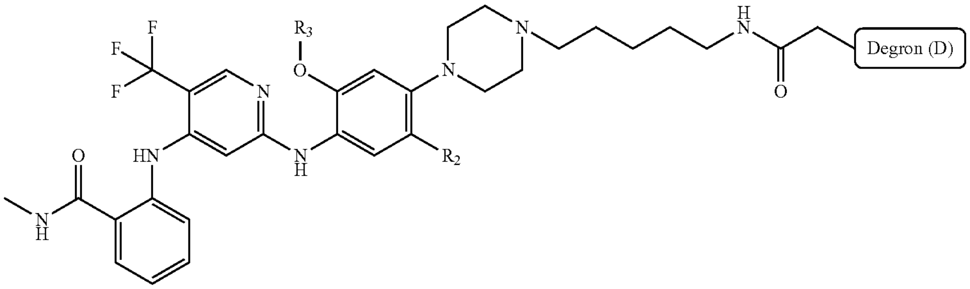
;
(TL1a-L10c)
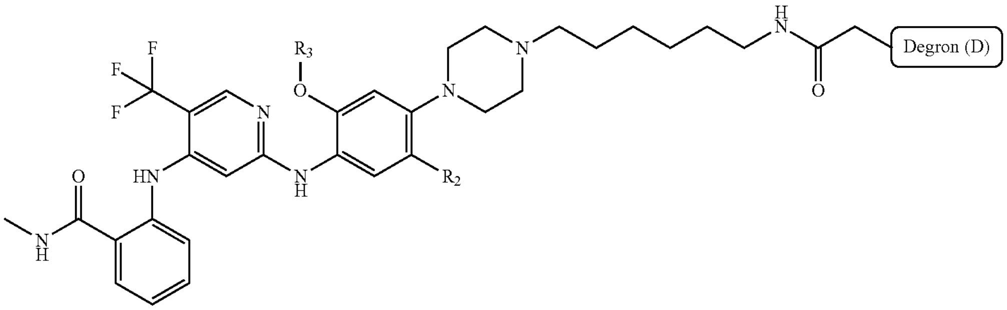
;
(TL1a-L10d)
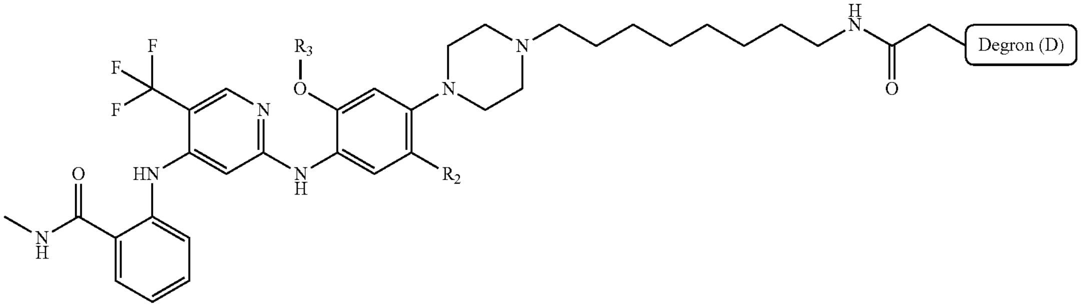
;
(TL1a-L10e)
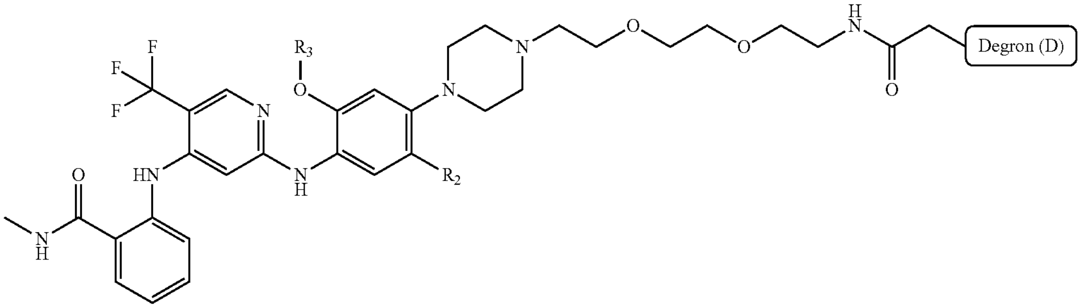
;
(TL1a-L10f)
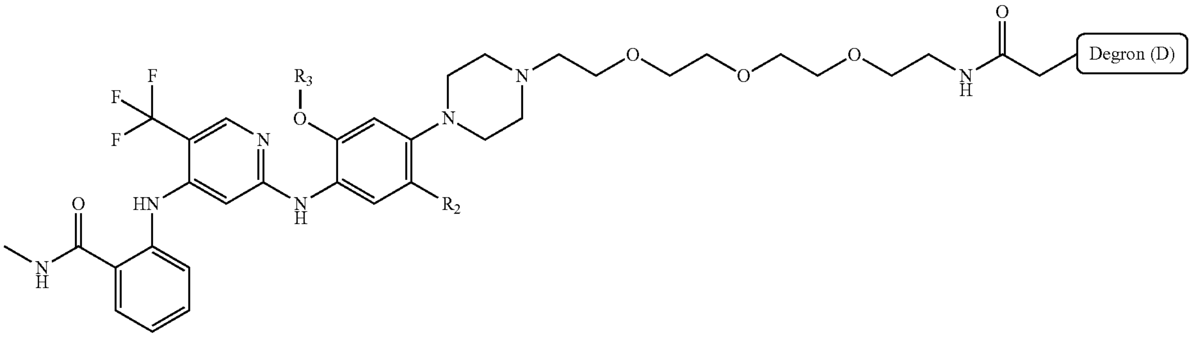
;

-continued
(TL1b-L10a)
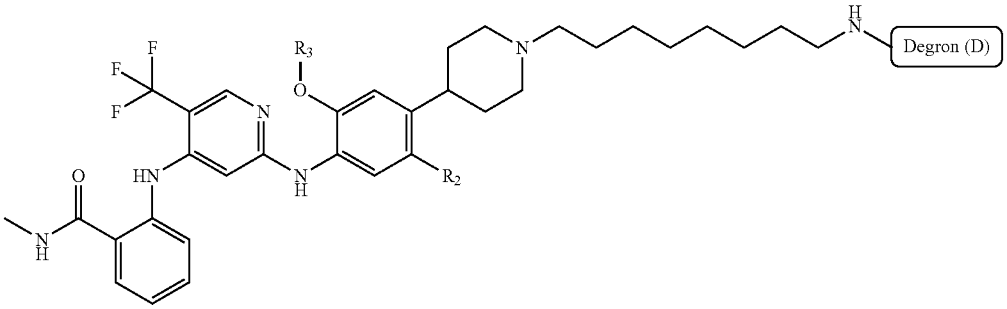
;
(TL1b-L10b)
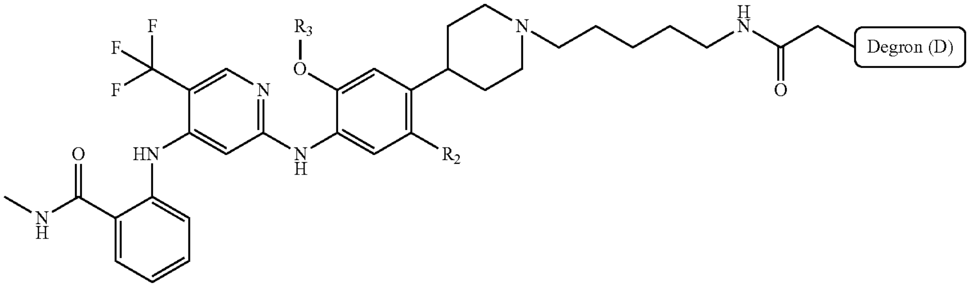
;
(TL1b-L10c)
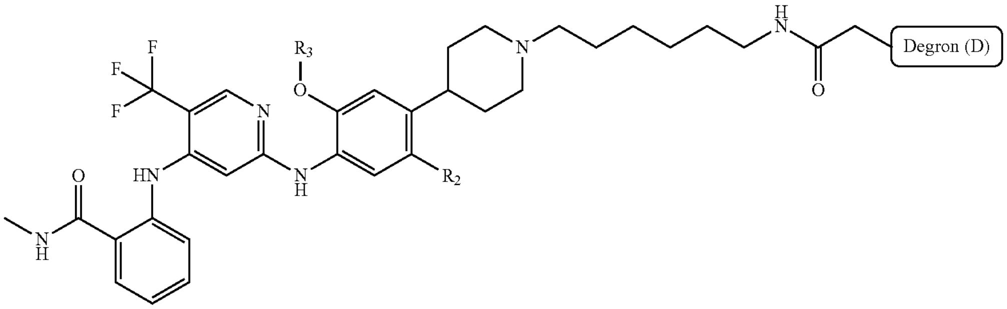
;
(TL1b-L10d)
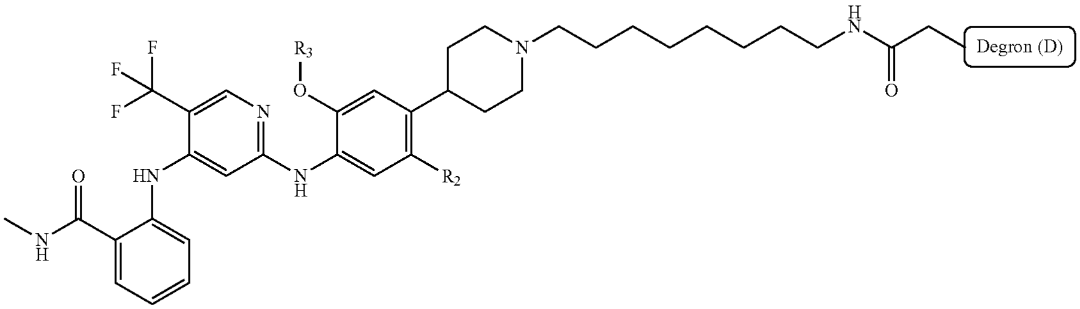
;
(TL1b-L10e)
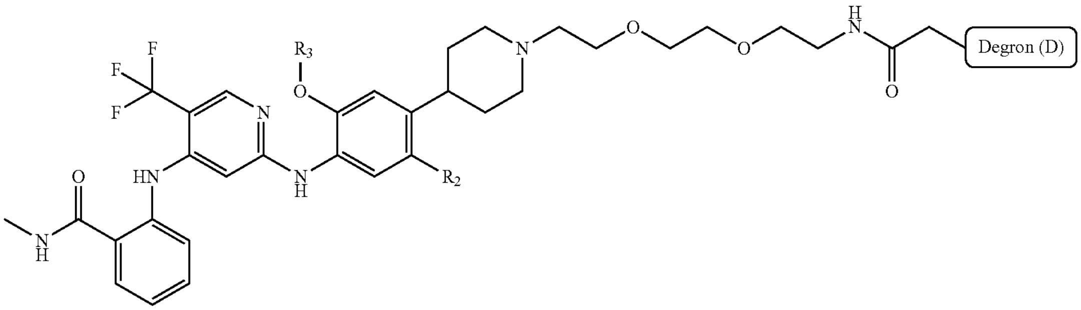
;

-continued
(TL1b-L10f)
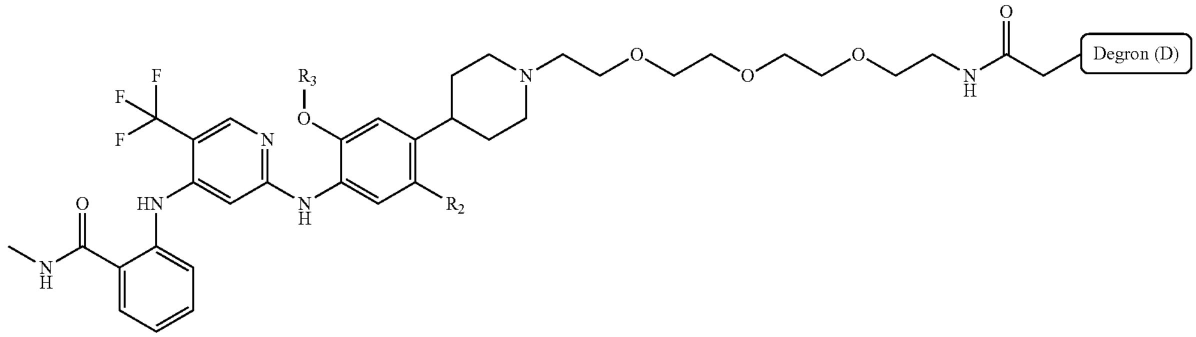
;
or a pharmaceutically acceptable salt or stereoisomer thereof.
7. The bifunctional compound of claim 1, wherein the degron is represented by any one of structures (D1-a) to (D1-d):
(D1-a)
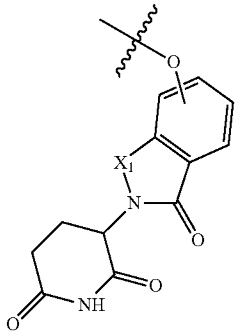
,
(D1-b)
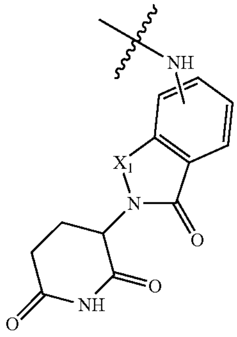
,
(D1-c)
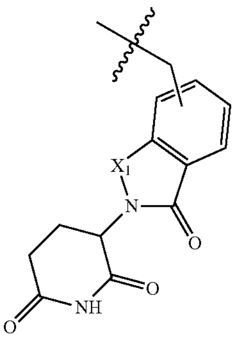
, and
-continued
(D1-d)
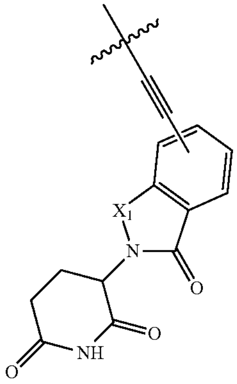
,
wherein $X_1$ is $CH_2$ or CO.
8. The bifunctional compound of claim 7, which is represented by any one of structures (Ib) to (Ie):
(Ib)
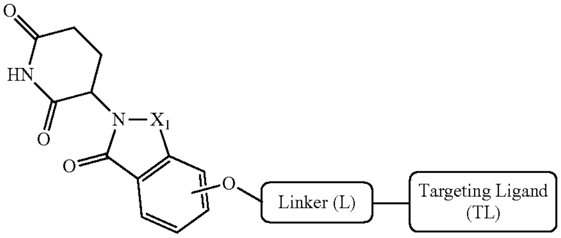
;
(Ic)
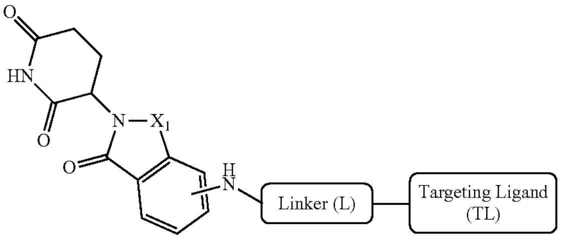
;

-continued
(Id)
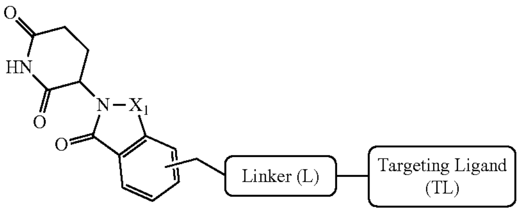
; and
(Ie)
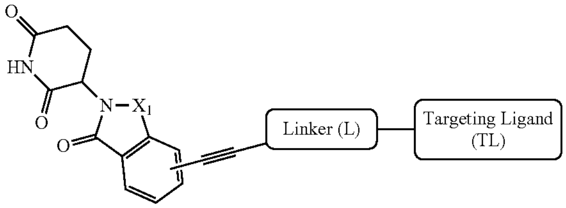
,
wherein $X_1$ is CO,
or a pharmaceutically acceptable salt or stereoisomer thereof.
9. The bifunctional compound of claim 8, which is represented by a structure selected from the group consisting of:
(Ib-1)
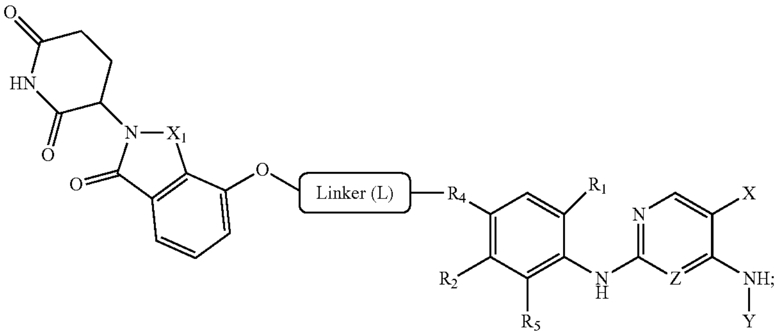
(Ib-1a1)
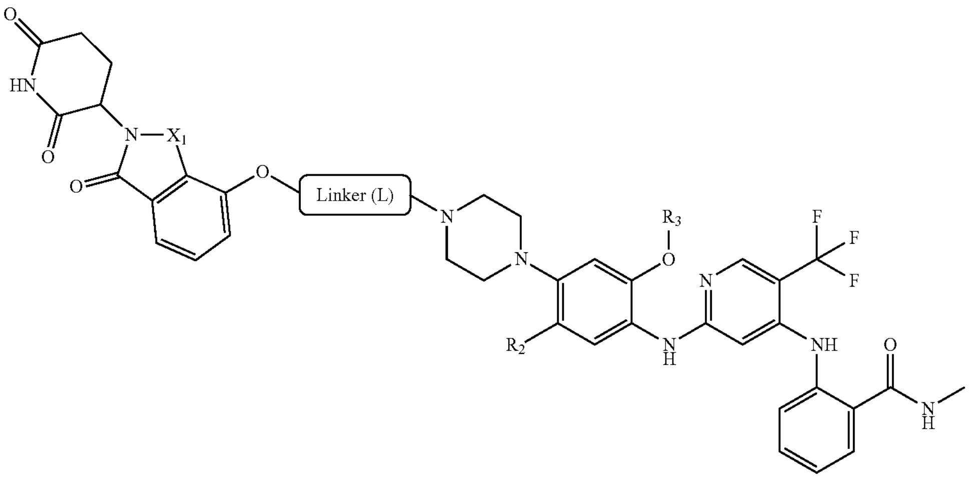
;

-continued
(Ib-1a2)
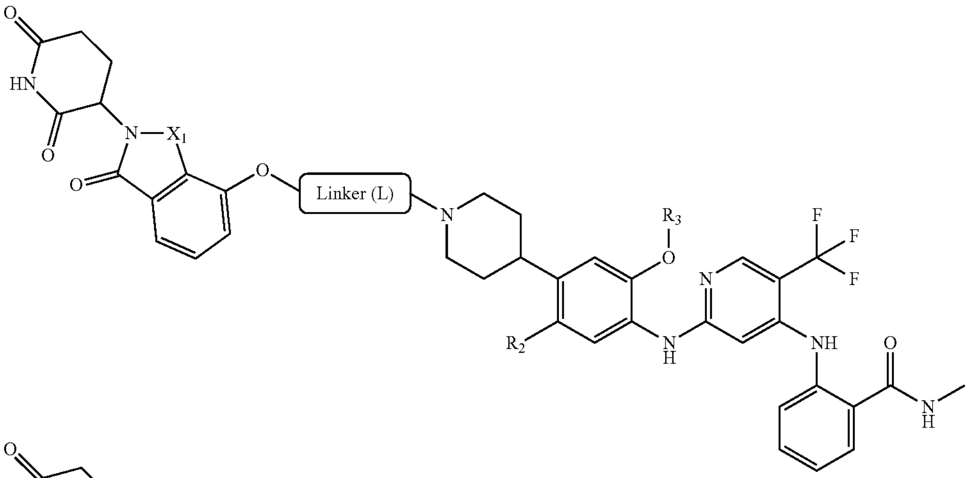
;
(Ic-1)
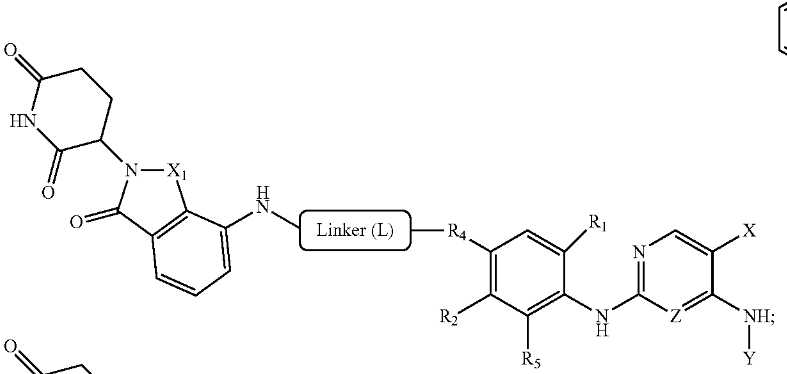
(Ic-1a1)
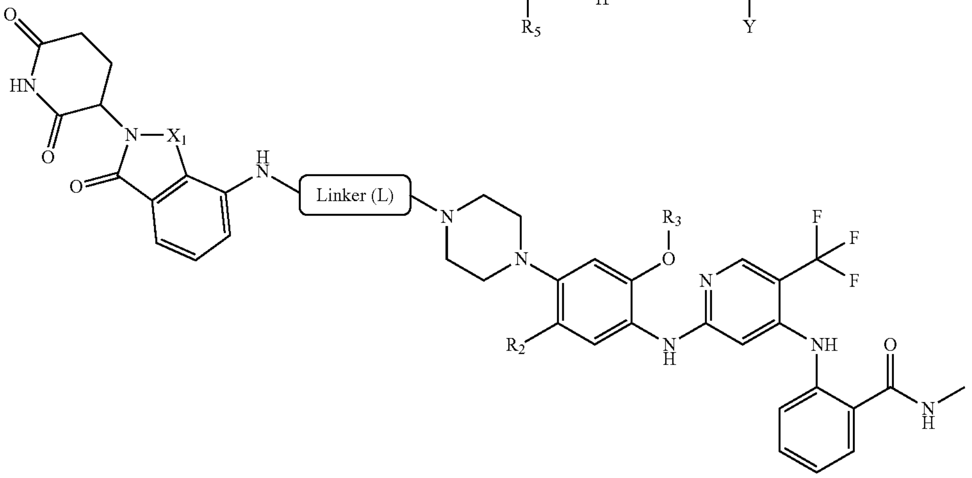
;
(Ic-1a2)
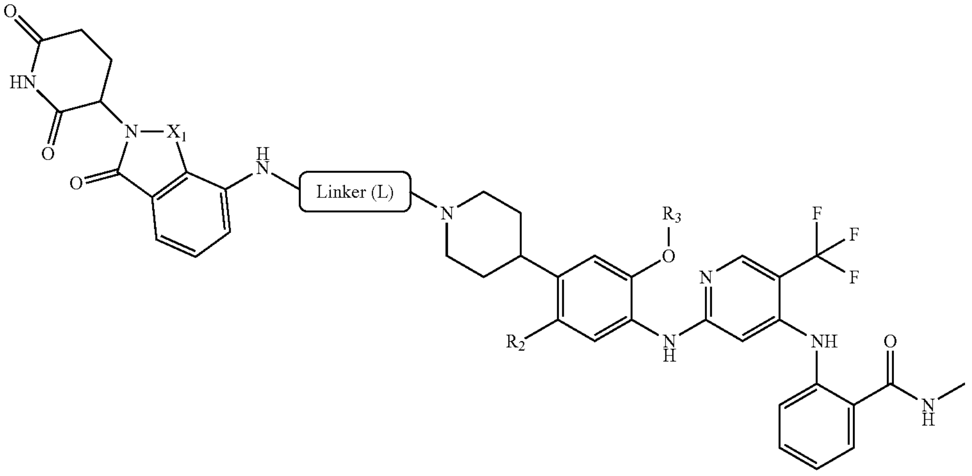
;

-continued
(Id-1)
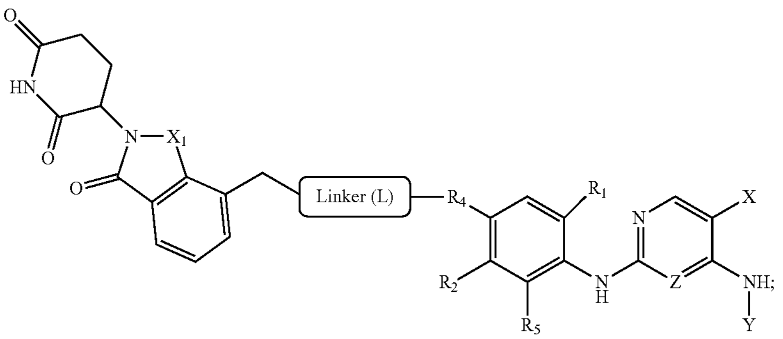
(Id-1a1)
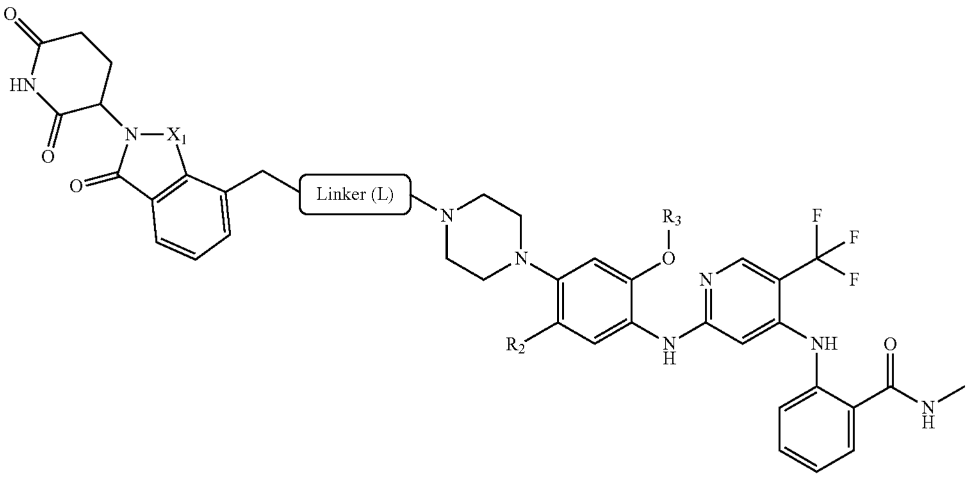
;
(Id-1a2)
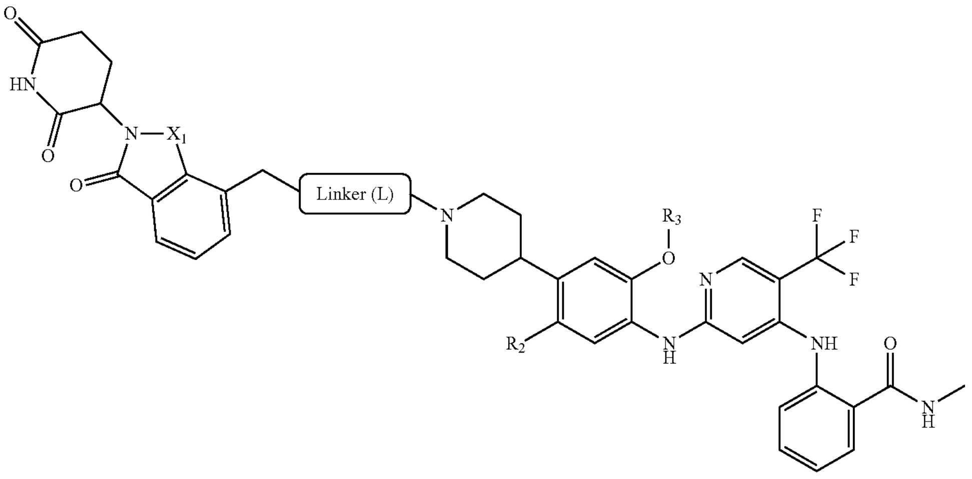
;
(Ie-1)
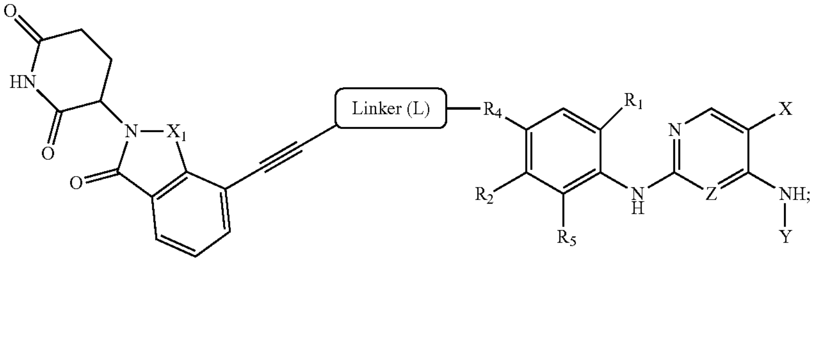

-continued
(Ie-1a1)
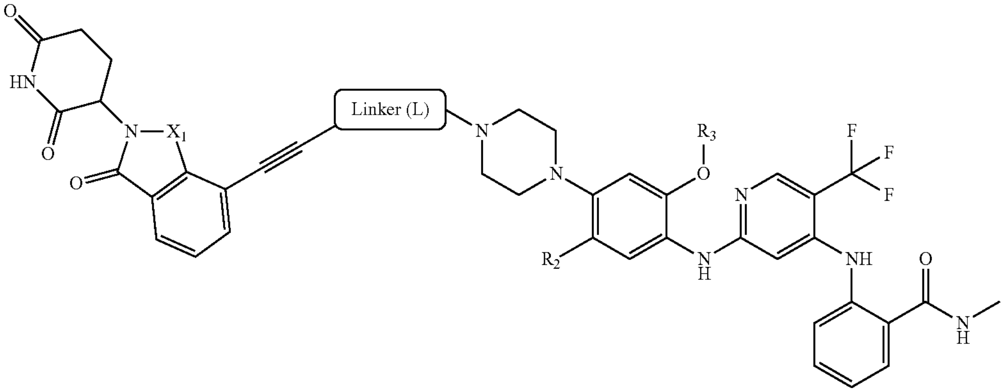
; and
(Ie-1a2)
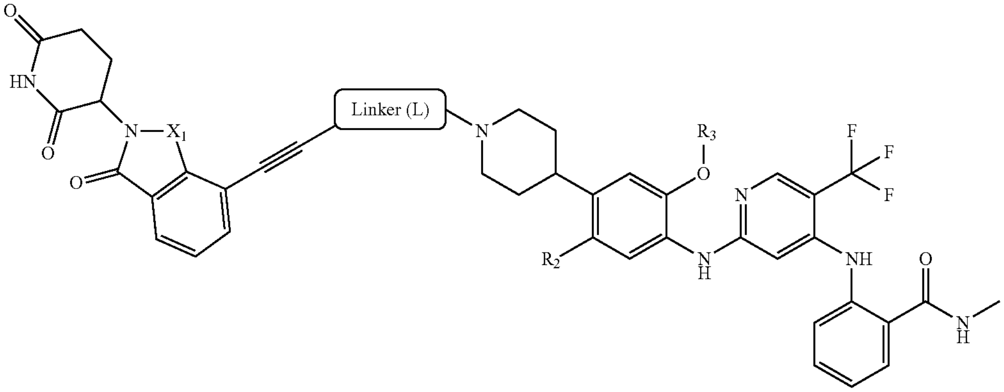
;
or a pharmaceutically acceptable salt or stereoisomer thereof.
10. The bifunctional compound of claim 1, wherein the degron has a structure represented by any one of structures (D2-a) to (D2-e):
(D2-a)
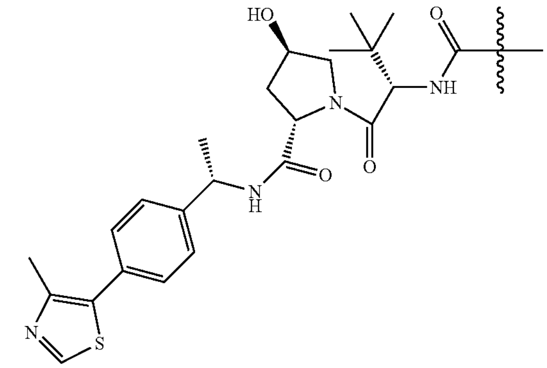
;
-continued
(D2-b)
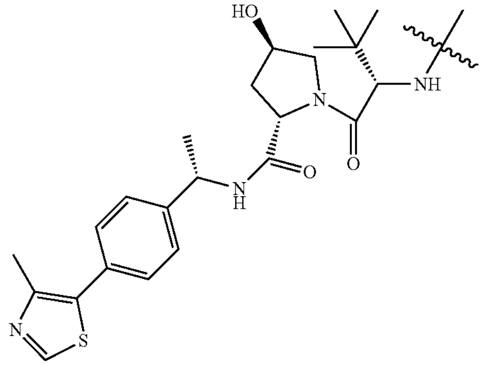
;
(D2-c)
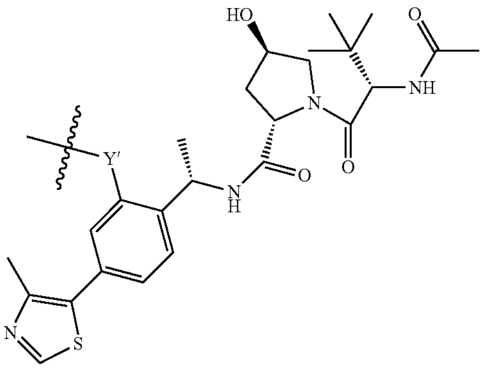
, wherein Y' is a bond or O;
(D2-d)
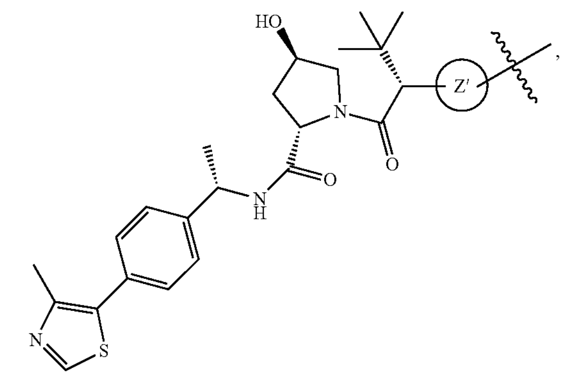
wherein Z' is a $C_5$-$C_6$ carbocyclic or heterocyclic group; and
(D2-e)
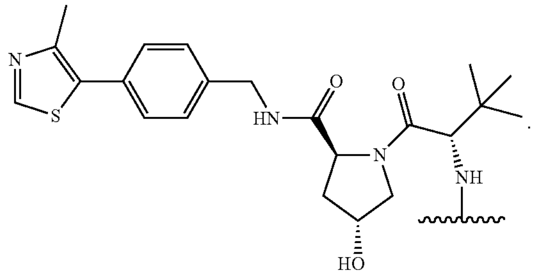
11. The bifunctional compound of claim 10, which is represented by a structure selected from the group consisting of:
(If-1)
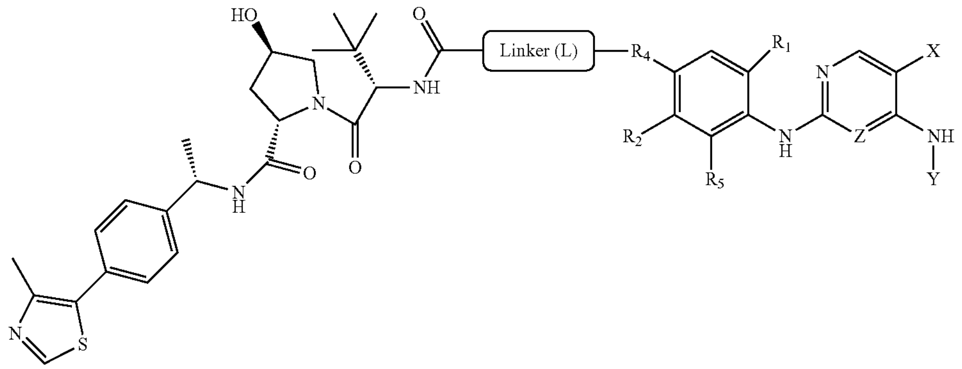
(If-1a1)
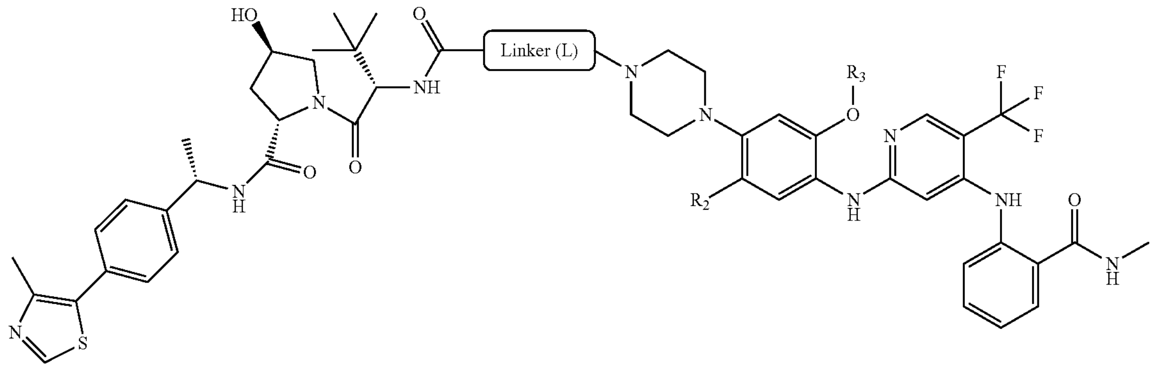
;

-continued
(If-1a2)
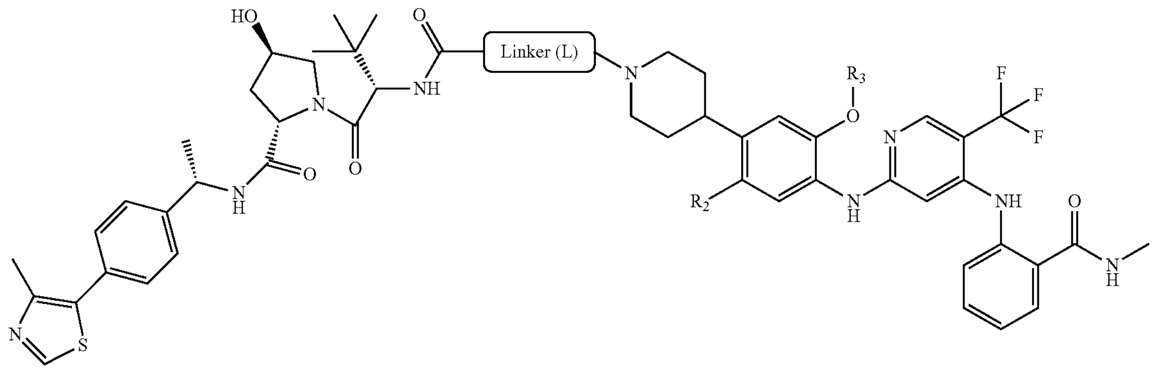
;
(Ig-1)
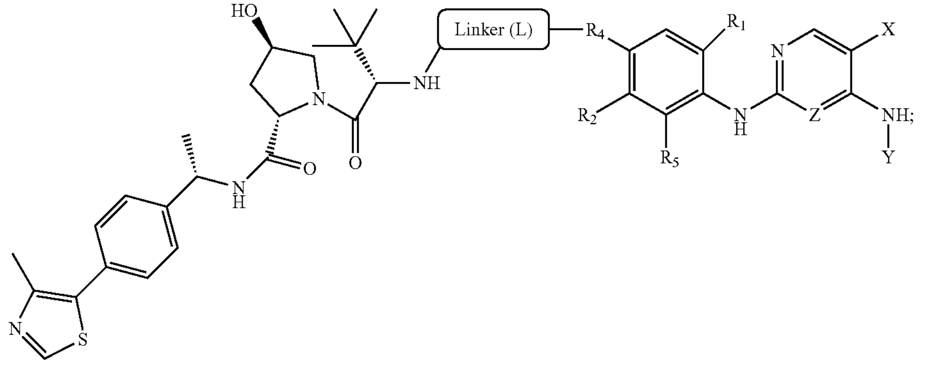
(Ig-1a1)
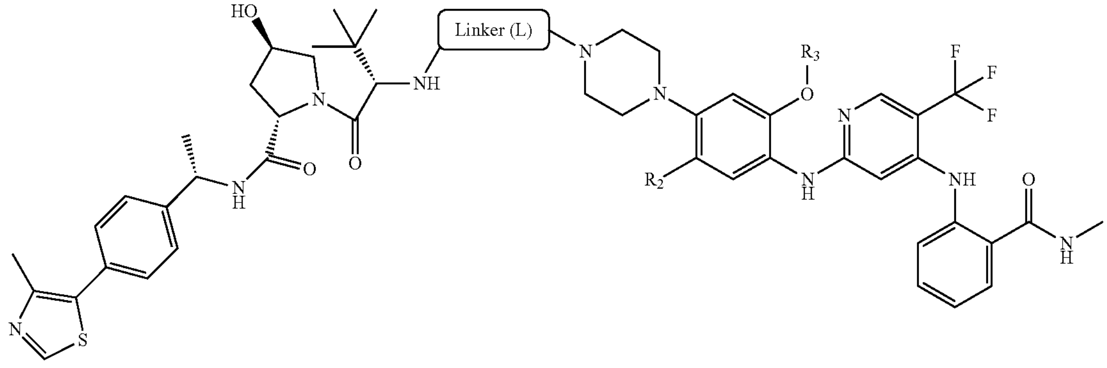
;
(Ig-1a2)
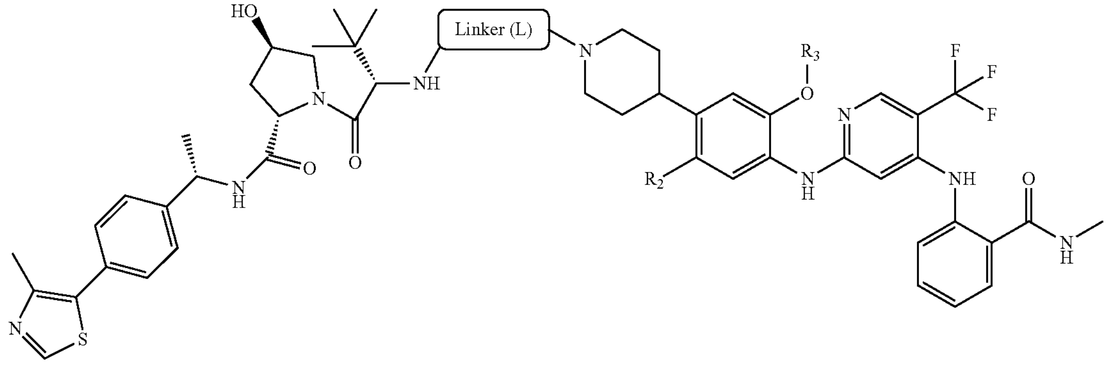
;

-continued
(Ih-1)
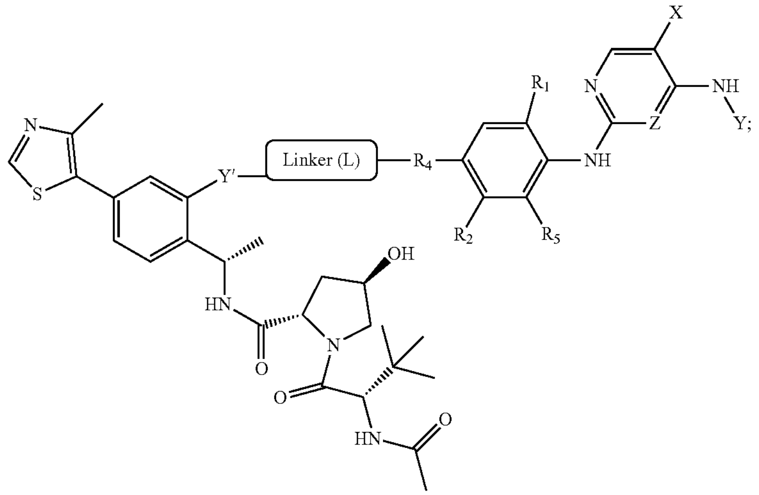
(Ih-1a1)
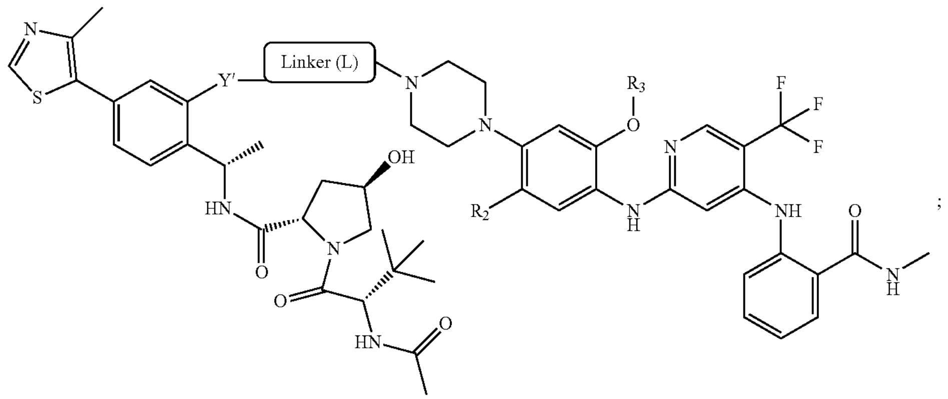
(Ih-1a2)
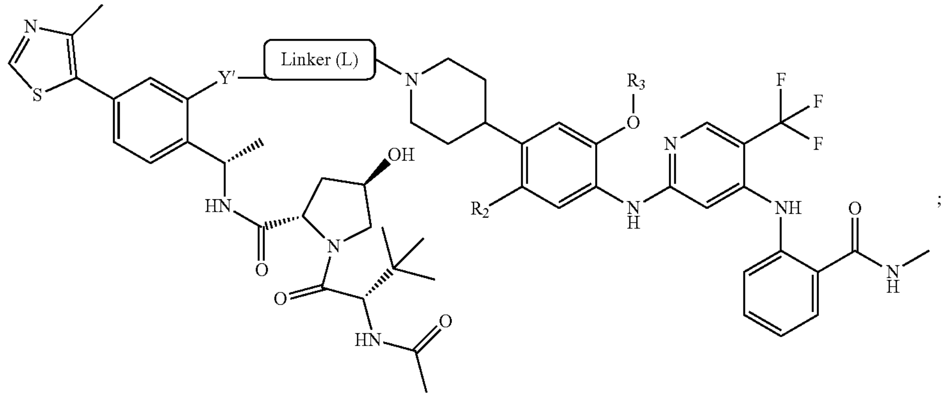

(I-1a1)
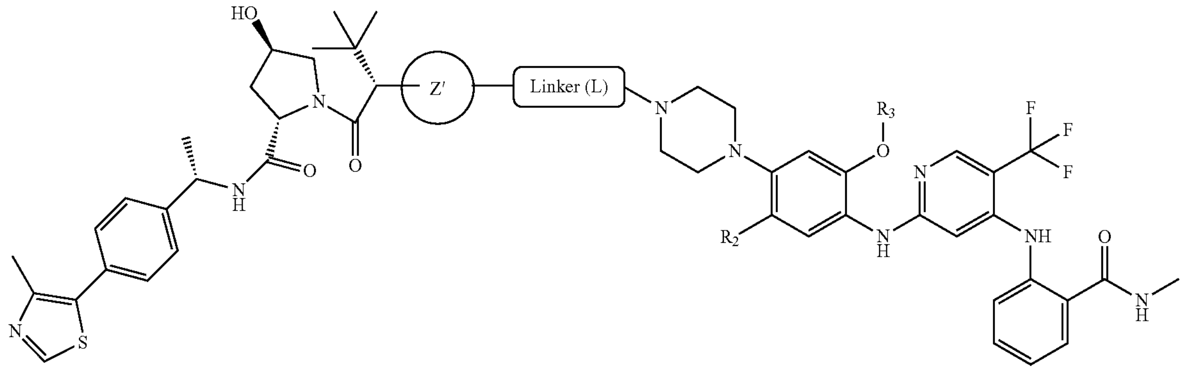
;
(I-1a2)
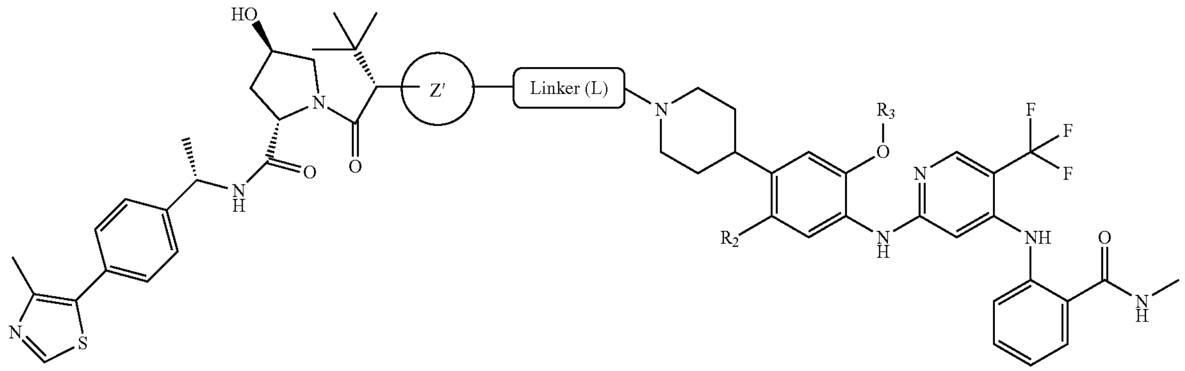
;
(Ij-1)
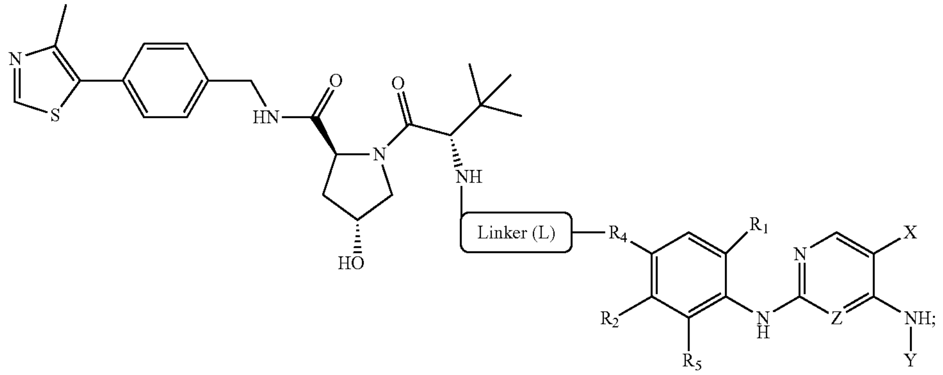

-continued
(Ij-1a1)
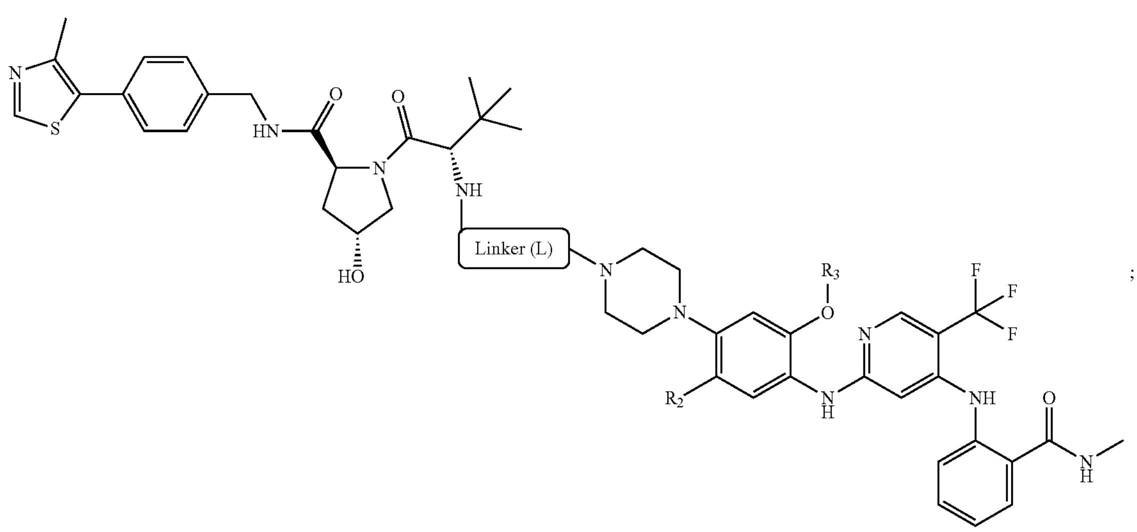
; and
(Ij-1a2)
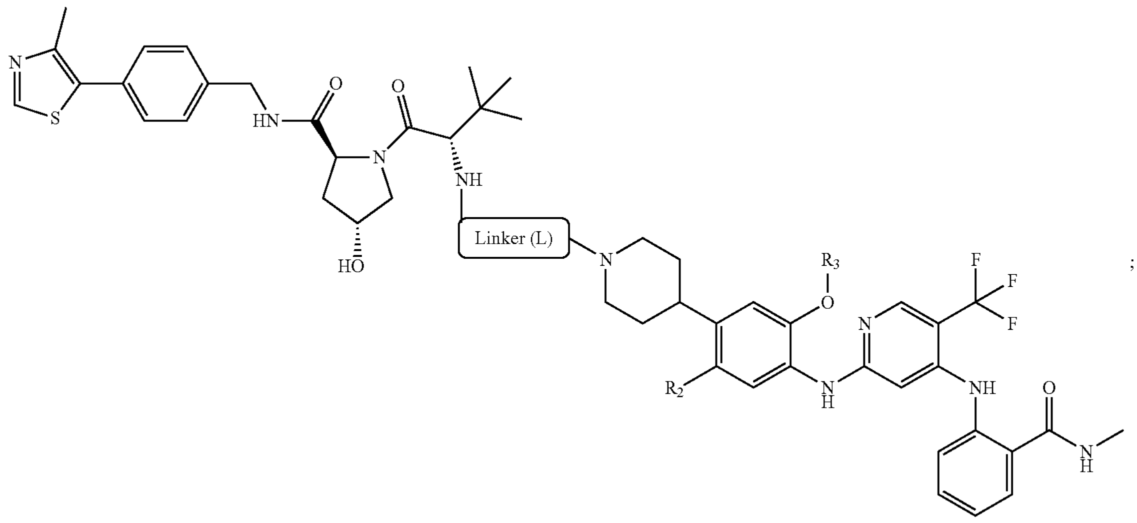
;
wherein Y' is a bond or O and Z' is a $C_5$-$C_6$ carbocyclic or heterocyclic group, or a pharmaceutically acceptable salt or stereoisomer thereof.
12. The bifunctional compound of claim 1, which is selected from the group consisting of:
(1)
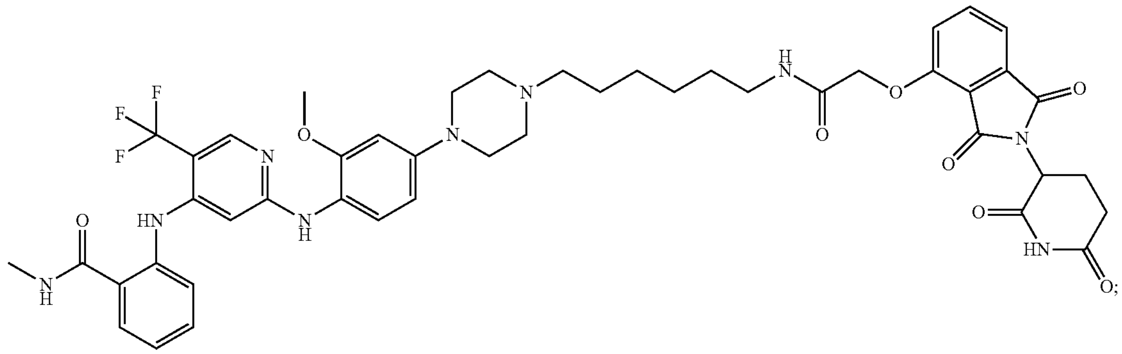
;

-continued
(3)
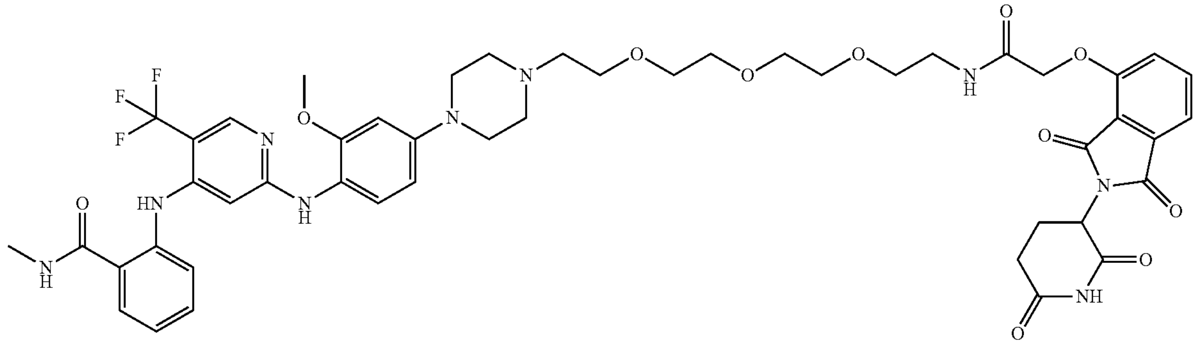
;
(4)
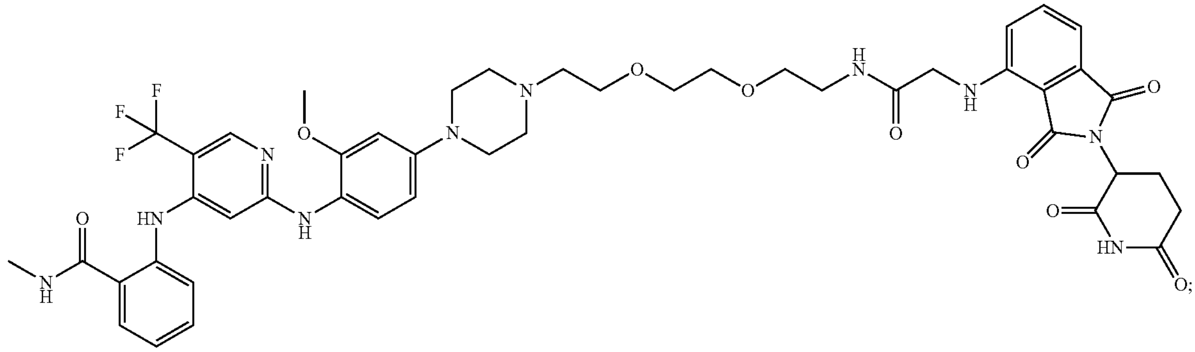
;
(5)
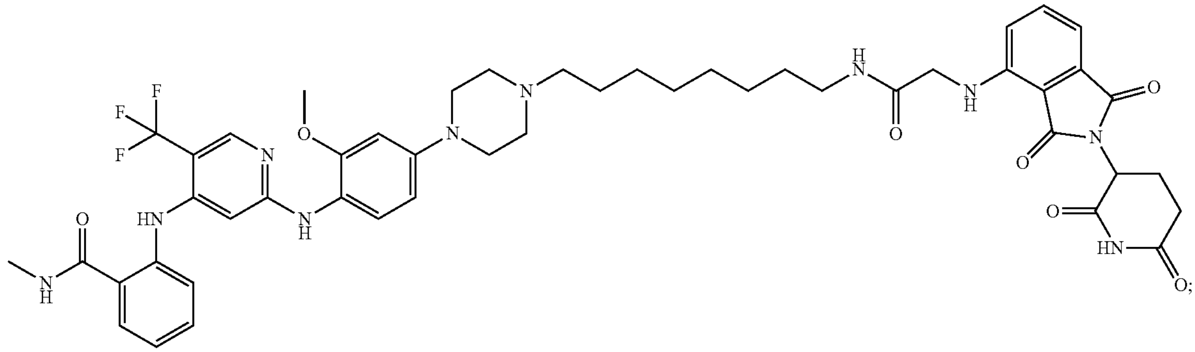
;
(6)
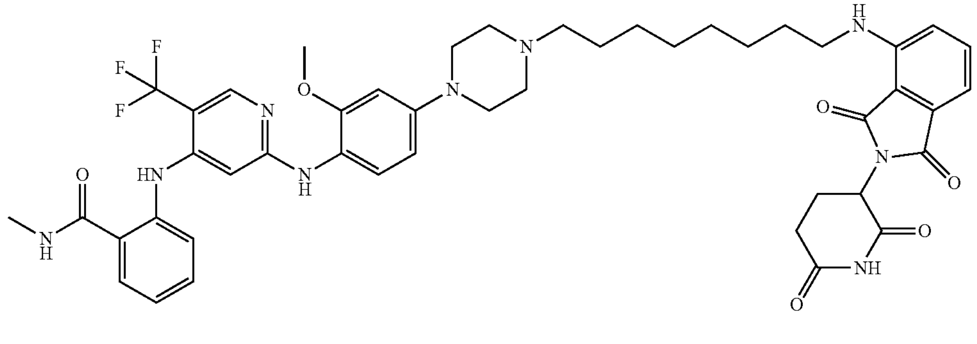
;

-continued (9)

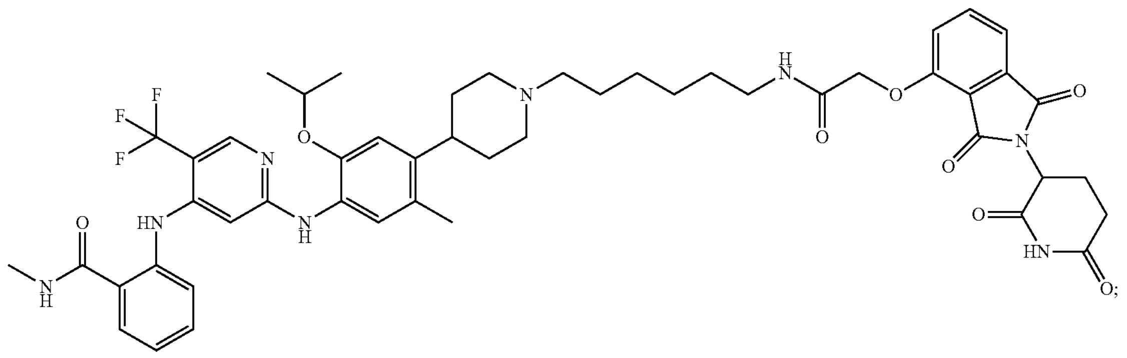

and (12)

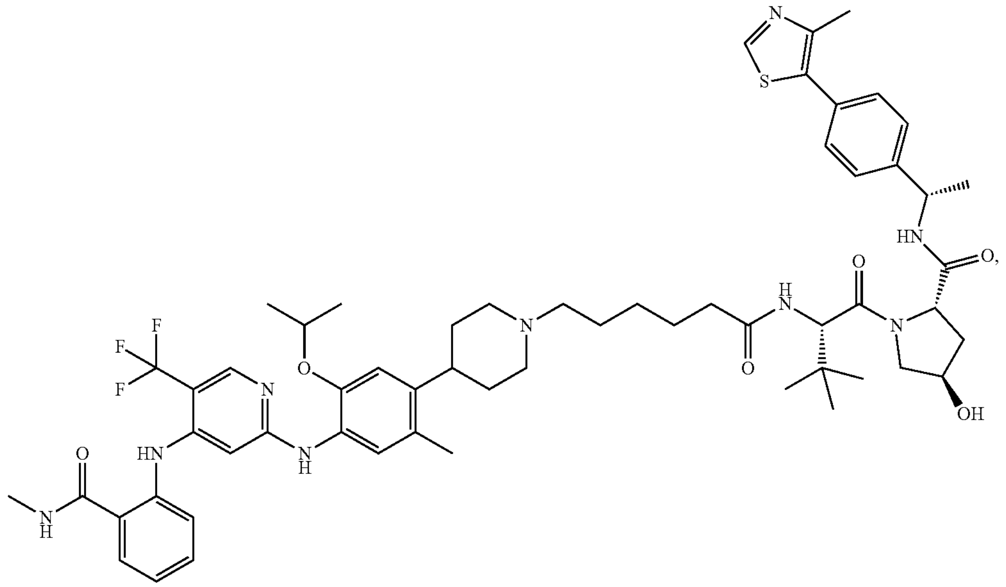

or a pharmaceutically acceptable salt or stereoisomer thereof.

13. A pharmaceutical composition containing a therapeutically effective amount of the bifunctional compound of claim 1, or a pharmaceutically acceptable salt or stereoisomer thereof, and pharmaceutically acceptable carrier.

14. The bifunctional compound of claim 4, wherein the FAK targeting ligand is represented by structure (TL1a):

(TL1a)

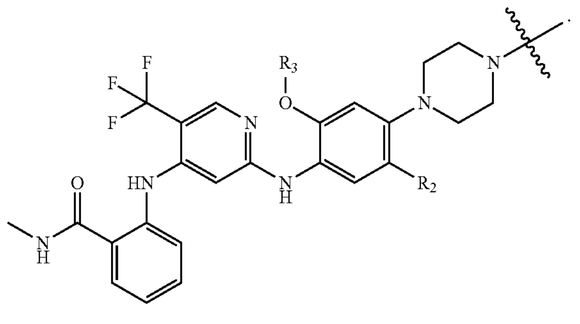

* * * * *